(12) United States Patent
Smith et al.

(10) Patent No.: US 7,662,844 B2
(45) Date of Patent: Feb. 16, 2010

(54) NAPHTHYLENE DERIVATIVES AS CYTOCHROME P450 INHIBITORS

(75) Inventors: Vanessa Smith, West Midlands (GB); Anthony Nigro, Stonypoint, NY (US); Mark Mulvihill, East Northport, NY (US); Cara Cesario, Farmingdale, NY (US); Patricia Anne Beck, Dixon, MO (US); Arlindo L. Castelhano, New City, NY (US)

(73) Assignee: OSI Pharmaceuticals, Inc., Melville, NY (US)

( * ) Notice: Subject to any disclaimer, the term of this patent is extended or adjusted under 35 U.S.C. 154(b) by 0 days.

(21) Appl. No.: 10/889,520

(22) Filed: Jul. 12, 2004

(65) Prior Publication Data

US 2006/0009645 A1    Jan. 12, 2006

(51) Int. Cl.
*A61K 31/50* (2006.01)
*A61K 31/415* (2006.01)
*C07D 231/00* (2006.01)
*C07D 233/00* (2006.01)

(52) U.S. Cl. .................. 514/385; 514/403; 548/300.1; 548/356.1

(58) Field of Classification Search ................ 514/385, 514/403; 548/300.1, 356.1
See application file for complete search history.

(56) References Cited

U.S. PATENT DOCUMENTS

| | | | |
|---|---|---|---|
| 4,734,406 A * | 3/1988 | Lau et al. .................... | 514/183 |
| 4,876,354 A | 10/1989 | Siegel | |
| 5,023,357 A | 6/1991 | Siegel | |
| 5,100,890 A | 3/1992 | Siegel | |

FOREIGN PATENT DOCUMENTS

| | | |
|---|---|---|
| GB | 909357 A1 | 10/1962 |
| GB | 1122756 A1 | 8/1968 |
| JP | 06263742 A1 | 9/1994 |
| WO | WO9408973 A1 | 4/1994 |
| WO | WO9954309 A1 | 10/1999 |
| WO | WO0102373 A1 | 1/2001 |
| WO | WO0130762 A1 | 5/2001 |
| WO | WO2005007631 A1 | 1/2005 |

OTHER PUBLICATIONS

Li, Xingshu et al. (2004) Acta Crystallographica, E59(5): 0706-0707.
Wahler, Denis et al (2002) Chemistry—European Journal, 8(14): 3211-3228.
Shibata, Tomoyuki et al. Database Caplus 'Online'—Chemical Abstracts Service, Columbus, Ohio, US. 'Preparation of (cyanobenzyl) azole derivatives as aromatase inhibitors' retreived from STN Database accession No. 1995:513524. (from International Search Report PCT/US2004/022282).
International Search Report in PCT/US2004/022282.
Written Opinion of the International Searching Authority in PCT/US2004/022282.
International Preliminary Report On Patentability in PCT/US2004/022282.

* cited by examiner

*Primary Examiner*—Golam M. M. Shameem
*Assistant Examiner*—Susannah Chung
(74) *Attorney, Agent, or Firm*—Michael J. Rafa; OSI Pharmaceuticals, Inc.

(57) ABSTRACT

Compounds of the formula

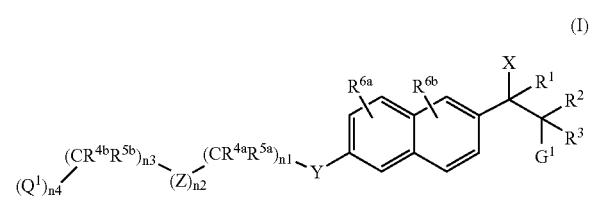

(I)

and pharmaceutically acceptable salts thereof, wherein n1, n2, n3, n4, $G^1$, $Q^1$, Z, $R^1$, $R^2$, $R^3$, $R^{4a}$, $R^{4b}$, $R^{5a}$, and $R^{5b}$ are defined herein, inhibit the cytochrome P450RAI enzyme and are useful for the treatment and/or prevention of various diseases and conditions which respond to treatment by retinoids and by naturally occurring retinoic acid.

33 Claims, No Drawings

NAPHTHYLENE DERIVATIVES AS CYTOCHROME P450 INHIBITORS

BACKGROUND OF THE INVENTION

The present invention is directed to novel heteroaryl-naphthalenyl-alkylamines, their salts, processes for their preparation, and compositions comprising them. The novel compounds of this invention are useful in inhibiting the cytochrome P450RAI enzyme (Cyp26) in animals, including humans, for the treatment and/or prevention of various diseases and conditions that respond to treatment by retinoids and by naturally occurring retinoic acid.

Retinoic acid, retinoid-like compounds, and pharmaceutical compositions comprising retinoic acid or rectinoid-like compounds as the active ingredient are known in the art to play a significant role in the regulation and differentiation of epithelial cells. Such regulatory and differentiating effects, which include the ability to promote cell differentiation, apoptosis, and the inhibition of cell proliferation, make retinoic acid and retinoid compounds useful agents in tumor therapy and in treating such conditions as skin-related diseases. Retinoids and retinoid compounds are known as agents for treating skin-related diseases such as actinic keratoses, arsenic keratoses, inflammatory and non-inflammatory acne, psoriasis, ichthyoses, keratinization and hyperproliferative disorders of the skin, eczema, atopic dermatitis, Darriers disease, lichen planus; for preventing, treating, and reversal of glucocorticoid, age, and photo damage to the skin. Retinoids and retinoid compounds are also known as topical anti-microbial and skin antipigmentation agents. Retinoids, with their ability to serve as differentiating agents, redirect cells towards their normal phenotype and therefore may reverse or suppress developing malignant lesions or prevent cancer invasions altogether. Therefore, retinoid compounds are useful for the prevention and treatment of cancerous and precancerous conditions, including, for example, premalignant and malignant hyperproliferative diseases such as cancers of the breast, skin, prostate, colon, bladder, cervix, uterus, stomach, lung, esophagus, blood and lymphatic system, larynx, oral cavity, metaplasias, dysplasias, neoplasias, leukoplakias and papillomas of the mucous membranes, and in the treatment of Kaposi's sarcoma. In addition, retinoid compounds can be used as agents to treat diseases of the eye, including, for example, proliferative vitreoretinopathy, retinal detachment, corneopathies such as dry eye, as well as in the treatment and prevention of various cardiovascular diseases, including, without limitation, diseases associated with lipid metabolism such as dyslipidemias, prevention of post-angioplasty restenosis and as an agent to increase the level of circulation tissue plasminogen activator. Other uses for retinoid compounds include the prevention and treatment of conditions and diseases associated with human papilloma virus (HPV), including warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis, restoration of hair growth, including combination therapies with the present compounds and other agents such as Minoxidil®, diseases associated with the immune systems, including use of the present compounds as immunosuppressant and immunostimulants, modulation of organ transplant rejection and facilitation of wound healing, including modulation of chelosis. Retinoid compounds have also been discovered to be useful in treating type II non-insulin dependent diabetes mellitus (NIDDM).

Several compounds having retinoid-like activity are marketed under appropriate regulatory approvals in the United States of America and elsewhere as medicants for the treatment of several diseases responsive to treatment with retinoids. Retinoic acid (RA) itself is a naturally occurring retinoid, the biologically most active metabolite of vitamin A, is biosynthesized and present in a multitude of human and mammalian tissues and is known to play a crucial role in the regulation of gene expression, cellular differentiation, proliferation of epithelial cells, and other important biological processes in mammals including humans.

Retinoids have demonstrated reversal of malignant growth in vivo and in vitro and are effective as chemopreventive agents. Retinoids could successfully be used to treat oral leukoplakia, a potentially premalignant mucosal lesion, and the occurrence of second primary tumors following head and neck squamous cell carcinoma (HNSCC) could be inhibited or delayed. These second primary tumors, which occur at an incidence rate of 2-3% per year, are a major cause of death after surgical resection of early-stage head and neck cancer. Retinoid therapy has also been explored in the treatment of glioma tumors, primary and metastatic melanoma cells, and has shown anti-metastatic activities in rat invasive prostate adenocarcinoma cells. Retinoid leukemia therapy works through terminal differentiation and the eventual apoptotic death of leukemic cells and has been shown to result in complete remission in up to 90% of patients with Acute Promyelocytic Leukemia (APL).

Although treatment with retinoids is highly successful in inducing complete remission in APL, if maintained on retinoids alone, most patients will relapse within a few months. The clinical use of retinoic acid in the treatment of cancer has been significantly hampered by the prompt emergence of resistance, which is believed to be caused by increased retinoic acid metabolism. Retinoic acid is metabolized by Cyp26A1 (Cyp26), an inducible cytochrome P450 enzyme, that inactivates RA by oxidation of RA to 4-HO-atRA, 8-HO-atRA, and 4-oxo-atRA. The tightly controlled negative feedback mechanism limits the availability of RA and thereby limits its biological activity. Compounds have been identified that inhibit Cyp26 and therefore RA metabolism and have shown to enhance the antiproliferative effects of RA and cause an increase in endogenous levels of RA in plasma and in tissues.

Cyp26 inhibitors, also known as retinoic acid metabolism-blocking agents (RAMBAs), are known and include, for example, Liarozole (Liazal™) and R116010. Such Cyp26 inhibitors have demonstrated therapeutic benefits in dermatological and cancerous conditions in vitro, in vivo, and in clinical settings. In several preclinical tumor models, Liarozole displayed antitumoral properties which correlated with decreased endogenous retinoic acid metabolism and therefore, an increase in RA accumulation within tumor cells. In cancer patients, Liarozole has been shown to increase the half-life of orally administered RA and 13-cis-RA. Unfortunately, one of the limitations of Liarozole and many Cyp26 inhibitors described in the literature was their lack of specificity. Liarozole as well as other Cyp26 inhibitors inhibit other cytochrome P450-mediated reactions and are limited due to their lack of specificity towards other cytochrome P450 enzymes. This lack of specificity might explain the limited risk benefit ratio (the activity/toxicity ratio was considered insufficient by the FDA) observed in prostate cancer patients in the Liarozole phase III clinical trials. Therefore, there is clearly a need within retinoid therapy for Cyp26 inhibitors (RAMBA's) that are highly potent and selective that have greater selectivity to other cytochrome P450 enzymes, fewer side effects, and favorable drug-like properties including sufficient water solubility, bioavailability, sufficient pharmacokinetic properties, extraction ratios, and limited toxicity to balance the activity/toxicity ratio and for use in the treatment of various dermatological and cancerous conditions.

The present invention shows highly potent and selective novel heteroaryl-naphthalenyl-alkylamines Cyp26 inhibitors that provide therapeutic benefits in the treatment or prevention of the diseases and conditions which respond to treatment by retinoids or are controlled by natural retinoic acid. The perceived mode of action of these compounds is that by inhibiting the Cyp26 enzyme (CP450RAI [cytochrome P450 retinoic acid inducible]) that has been proven in the art to catabolyze natural retinoic acid, endogenous retinoic acid level is elevated to a level where desired therapeutic benefits are attained. The endogenous levels of all natural and synthetic retinoids which are metabolized by Cyp26 would be expected to increase from inhibition of Cyp26 by the novel heteroaryl-naphthalenyl-alkylamines Cyp26 inhibitors described in this invention. Co-administration with a composition of the natural or synthetic retinoids with the compounds, or pharmaceutically acceptable salts thereof, disclosed in this invention can increase the level of retinoids. The co-administration of the natural and synthetic retinoids, which are catabolized by Cyp26, with at least one compound disclosed in this invention is a method for treating skin-related or cancerous diseases to yield higher endogenous levels of the retinoids. The compounds of this invention are active at nanomolar concentrations and selectively and potently inhibit enzymes involved in retinoic acid catabolism and therefore result in the effective modulation of desirable levels of atRA.

The following publications describe or relate to the role of Cyp26 inhibitors and their ability to slow the catabolism of retinoic acid, thereby increasing endogenous retinoic acid levels, and their potential for the treatment of dermatological diseases and cancers:

Altucci, L. et. al. "Retinoic Acid-induced Apoptosis in Leukemia Cells is Mediated by Paracrine Action of Tumor-Selective Death Ligand Trail", *Nature Med.* 2001, 7, 680-686;

Altucci, L.; Gronemeyer, H. "The Promise of Retinoids to Fight Against Cancer", Nature Reviews (Cancer), 2001, 1, 181-193;

Winum, J. Y.; et. al. "Synthesis of New Targretin® Analogues that Induce Apoptosis in Leukemia HL-60 Cells", Bioorganic & Medicinal Chemistry Letters, 2002, 12, 3529-3532.

Kuijpers, et. al. "The Effects of Oral Liarozole on Epidermal Proliferation and Differentiation in Severe Plaque Psoriasis are Comparable with Those of Acitretin", British Journal of Dermatology, 1998. 139, 380-389;

Van Wauwe, et. al. "Liarozole, an Inhibitor of Retinoic Acid Metabolism, Exerts Retinoid-Mimetic Effects in Vivo", The Journal of Pharmacology and Experimental Therapeutics, 1992, 261, 773-779.

Haque, M.; Andreola, F.; DeLuca, L. M. "The Cloning and Characterization of a Novel Cytochrome P450 Family, Cyp26, with Specificity towards Retinoic Acid", *Nutri Rev.* 1999, 56, 84-85.

Wouters, W. et. al. "Effects of Liarozole, a New Antitumoral Compound and Retinoic Acid-Induced Inhibition of Cell Growth and on Retinoic Acid Metabolism in MCF-7 Breast Cancer Cells", *Cancer Res,* 1992, 52, 2841-2846;

Freyne, E. et. al. "Synthesis of Liazal™, a Retinoic Acid Metabolism Blocking Agents (RAMBA) with Potential Clinical Applications in Oncology and Dermatology", *Bioorganic & Medicinal Chemistry Letters,* 1998, 8, 267-272;

Miller, W. H. "The Emerging Role of Retinoids and Retinoic Acid Metabolism Blocking Agents in the Treatment of Cancer", *Cancer,* 1998, 83, 1471-1482;

Van Heusden J. et. al. "Inhibition of all-TRANS-retinoic Acid Metabolism by R116010 Induces Antitumor Activity", *Br. J. Cancer,* 2002, 86(4), 605-611;

Debruyne, F. J. M. et. al. "Liarozole-A Novel Treatment Approach for Advanced Prostate Cancer: Results of a Large Randomized Trial versus Cyproterone", *Urology,* 1998, 52, 72-81;

De Coster, R. et. al. "Experimental Studies with Liarozole (R75251): An Antitumor Agent which Inhibits Retinoic Acid Breakdown", *J. Steroid Biochem. Molec. Biol.* 1992, 43, 197-201;

Njar, V. C. O.; Brodie, A. M. H. "Inhibitors of Cytochrome P450 Enzymes: Their Role in Prostate Cancer Therapy", I Drugs, 1999, 1, 495-506;

Miller, V. A.; Rigas, J. R.; Muindi, J. F. R.; Tong, W. P.; Venkatraman, E.; Kris, M. G.; Warrell Jr. R. P. "Modulation of all-trans-retinoic acid pharmacokinetics by liarozole", *Cancer Chemother. Pharmacol.* 1994, 34, 522-526;

Muindi, J.; Frankel, S. R.; Miller Jr. W. H.; Jakubowski, A.; Scheinberg, D. A.; Young, C. W.; Dmitrovski, E.; Warrell, Jr. R. P. "Continuous treatment with all-trans-retinoic acid causes a progressive reduction in plasma drug concentrations: implications for relapse and retinoid 'resistance' in patients with acute promyelocytic leukemia", *Blood.* 1992, 79, 299-303;

Muindi, J F.; Scher, H. I.; Rigas, J. R.; Warrell Jr. R. P.; Young, C. W. "Elevated plasma lipid peroxide content correlates with rapid plasma clearance of all-trans-retinoic acid in patients with advanced cancer", *Cancer Res.* 1994, 54, 2125-2128.

U.S. Pat. No. 6,303,785B1 describes inhibitors of cytochrome P450RAI. International Patent Publication No. WO 99/29674 describes inhibitors of retinoic acid metabolism. International Patent Publication No. WO 01/30762A1 describes imidazol-4-ylmethanols used as inhibitors of steroid C17-20 Lyase.

U.S. Pat. Nos. 6,291,677 and 6,124,330 and International Patent Publication No. WO 02/03912 A2 describe inhibitors of cytochrome P450RAI. International Application No. PCT/US00/11833 describes PPAR agonists or antagonists. International Patent Publication No. WO 02/06281 describes selective β3 adrenergic receptor agonists. International Patent Publication No. WO 01/068647 describes an antiviral agent. International Patent Publication No. WO 01/062234 describes a farnesyl protein transferase inhibitor. International Patent Publication No. WO 01/055155 describes compounds which have antibacterial activities. International Patent Publication No. WO 01/044170 describes adamantine derivatives. International Patent Publication No. WO 01/000615 describes benzimidazoles. International Patent Publication No. WO 00/069843 describes compounds for the treatment of inflammations. International Patent Publication No. WO 00/043384 describes aromatic heterocyclic ureas as anti-inflammatory agents. Japanese Patent Publication No. JP 01/43635 describes benzimidazole compositions and derivatives. International Patent Publication No. WO 99/40092 describes GABAa agonists, antagonists or inverse agonists. International Patent Publication No. WO 99/376609 describes virucides used against cytomegalovirus. German Patent Publication No. DE 75/6388 describes substituted 2-aryl-4-amino-quinazolines. International Patent Publication No. WO 98/54168 describes 2-oxoimidazole derivatives. International Patent Publication No. WO 98/23593 describes inhibitors of apolipoprotein B and/or microsomal triglyceride transfer protein. U.S. Pat. No. 5,852,213 describes matrix metalloproteinase inhibitors of the MMP enzyme. U.S. Pat. No. 5,834,483 and International Patent Publication No. WO 97/37665 describes endothelin antagonists. International Patent Publication No. WO 97/24117 describes substituted hydroxamic acid compounds. International Patent Publication No. WO 95/29689 describes N-carboxyalkyl derivatives. U.S. Pat. No. 5,461,162 describes N-acyl auxilliary compounds. European Patent Publication No. 611,776 describes pseudopeptides with antiviral activity. European Patent Publication No. 569,220 describes organic sulfonamides. European Patent Publication No. 545,376 describes guanidinothiazoles. German Patent No. DE 4,201,435 describes trifluoromethyl ketones. German Patent No. DE 4,138,820 describes compounds used as herbicides. International Patent Publication No. WO 91/19717 describes phosphodiesterase inhibitors. European Patent Publication No. EP 437,729 describes peptide retroviral protease inhibitors. European Patent Publication No. EP 412,350 describes peptides as renin inhibitors. International Patent Publication No. WO 89/10919 describes carbostyril derivatives. International Patent Publication No. WO 00/064888 describes diaryl carboxylic acids and derivatives. WO 99/47497 describes naphthyl and indolyl acylsulfonamides. German Patent No. DE 4304650 describes benzimidazoles, xanthines, and analogs. International Patent Application No. PCT/CA99/00212 describes compounds used for treating or preventing prostaglandin mediated diseases.

SUMMARY OF THE INVENTION

The present invention relates to compounds represented by Formula I:

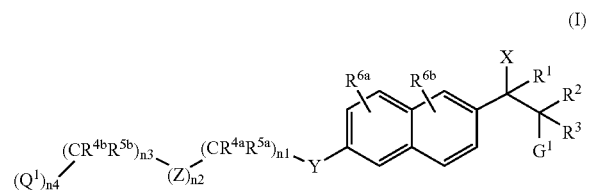

(I)

and pharmaceutically accepted salts thereof. The compounds of Formula I inhibit cytochrome P450RAI enzyme and are useful for the treatment and/or prevention of various diseases and conditions that respond to treatment by retinoids and by naturally occurring retinoic acid.

DETAILED DESCRIPTION OF THE INVENTION

The present invention relates to a compound of Formula I:

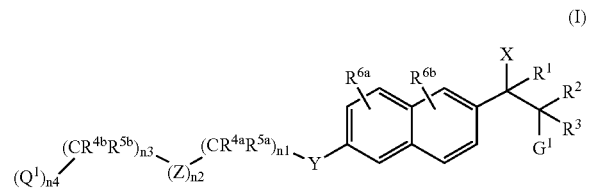

(I)

or a pharmaceutically acceptable salt thereof, wherein:

X is an unsaturated heterocycle selected from pyrrolyl, pyrazolyl, imidazolyl, triazolyl, tetrazolyl, thiazole, or pyridinyl, any of which is optionally substituted with one or more independent $R^{66}$ substituents;

$R^1$ is a $C_{0-6}$alkyl, —$OR^7$, —$SR^7$, or —$NR^7R^8$;

$R^2$ and $R^3$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —$SO_2NR^{71}R^{81}$, or —$NR^{71}R^{81}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —$OR^{71}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{71}R^{81}$, —$SO_2NR^{71}R^{81}$ or —$NR^{71}R^{81}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$OR^{71}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{71}R^{81}$, —$SO_2NR^{71}R^{81}$ or —$NR^{71}R^{81}$ substituents;

or $R^2$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $C_{1-6}$alkyl, halo, cyano, nitro, —$OR^{71}$, —$SO_2NR^{71}R^{81}$ or —$NR^{71}R^{81}$ substituents;

$G^1$ is —$OR^{72}$, —$SR^{72}$, —$NR^{72}R^{82}(R^9)_{n5}$, or $G^1$ and $R^3$ taken together with the carbon atom to which they are attached form a 3-10 membered saturated ring, unsaturated ring, heterocyclic saturated ring, or heterocyclic unsaturated ring, any of which is optionally substituted with one or more independent $R^{67}$ and an N heteroatom of the heterocyclic saturated ring or heterocyclic unsaturated ring optionally is substituted with an $R^{72}$ substituent; or in the case of —$NR^{72}R^{82}(R^9)_{n5}$, $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents;

Y is an oxygen atom, sulfur atom, —(C=O)N($R^{74}$)—, >$CR^{4c}R^{5c}$ or >$NR^{74}$;

Z is -aryl-, -arylalkyl-, -aryloxy-, -oxyaryl-, -arylalkenyl-, -alkenylaryl-, -hetaryl-, -hetarylalkyl-, -alkylhetaryl-, -hetarylalkenyl-, -alkenylhetaryl-, or -aryl-, any of which is optionally substituted with $R^{68}$;

$Q^1$ is $C_{0-6}$alkyl, —$OR^{75}$, —$NR^{75}R^{85}(R^{95})_{n6}$, —$CO_2R^{75}$, —$CONR^{75}R^{85}$, —(C=S)$OR^{75}$, —(C=O)$SR^{75}$, —$NO_2$, —CN, halo, —$S(O)_{n6}R^{75}$, —$SO_2NR^{75}R^{85}$, —$NR^{75}$(C=N$R^{775}$)$NR^{7775}R^{85}$, —$NR^{75}$(C=N$R^{775}$)$OR^{7775}$, —$NR^{75}$(C=N$R^{775}$)$SR^{7775}$, —O(C=O)$OR^{75}$, —O(C=O)$NR^{75}R^{85}$, —O(C=O)$SR^{75}$, —S(C=O)$OR^{75}$, —S(C=O)$NR^{75}R^{85}$, —S(C=O)$SR^{75}$, —$NR^{75}$(C=O)$NR^{775}R^{85}$, or —$NR^{75}$ (C=S)$NR^{775}R^{85}$; in the case of —$NR^{75}R^{85}(R^{95})_{n6}$, $R^{75}$ and $R^{85}$ taken together with the nitrogen atom to which they are attached form a 3-10 membered saturated ring, unsaturated ring, heterocyclic saturated ring, or heterocyclic unsaturated ring, any of which is optionally substituted with one or more independent halo, cyano, hydroxy, nitro, $C_{1-10}$alkoxy, —$SO_2NR^{76}R^{86}$ or —$NR^{76}R^{86}$ substituents;

$R^{4a}$, $R^{4b}$, $R^{4c}$, $R^{5a}$, $R^{5b}$ and $R^{5c}$ are each independently a $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, —$OR^{77}$, —$SO_2NR^{77}R^{87}$ or —$NR^{77}R^{87}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —$OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{77}R^{87}$, —$SO_2NR^{77}R^{87}$ or —$NR^{77}R^{87}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{77}R^{87}$, —$SO_2NR^{77}R^{87}$ or —$NR^{77}R^{87}$ substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or —N($C_{1-6}$alkyl)-$C_{1-6}$alkyl-aryl, any of which is optionally substituted with one or more independent halo, cyano, nitro, —$OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{77}R^{87}$, —$SO_2NR^{77}R^{87}$ or —$NR^{77}R^{87}$ substituents; or $R^{4a}$ with $R^{5a}$, or $R^{4b}$ with $R^{5b}$, or $R^{4c}$ with $R^{5c}$, taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$, or $R^{4c}$ with $R^{5c}$, taken together with the respective carbon atom to which they are attached, form a 3-10 membered saturated or unsaturated heterocyclic ring, wherein said ring is optionally substituted with $R^{69}$;

$R^{6a}$, $R^{6b}$, $R^{66}$, $R^{67}$, $R^{68}$, and $R^{69}$ are each independently halo, —$OR^{78}$, —SH, —$NR^{78}R^{88}(R^{98})_{n7}$, —$CO_2R^{78}$, —$CONR^{78}R^{88}$, —$NO_2$, —CN, —$S(O)_{n7}R^{78}$, —$SO_2NR^{78}R^{88}$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, —$OR^{778}$, —$SO_2NR^{778}R^{888}$ or —$NR^{778}R^{888}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{778}R^{888}$, —$SO_2NR^{778}R^{888}$ or —$NR^{778}R^{888}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{778}R^{888}$, —$SO_2NR^{778}R^{888}$ or —$NR^{778}R^{888}$ substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, —N($C_{1-6}$alkyl)-$C_{1-6}$alkyl-aryl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{778}R^{888}$, —$SO_2NR^{778}R^{888}$ or —$NR^{778}R^{888}$ substituents; or in the case of —$NR^{78}R^{88}$ $(R^{98})_{n7}$, $R^{78}$ and $R^{88}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{778}R^{888}$ or —$NR^{778}R^{888}$ substituents;

$R^7$, $R^{71}$, $R^{72}$, $R^{73}$, $R^{74}$, $R^{75}$, $R^{775}$, $R^{7775}$, $R^{76}$, $R^{77}$, $R^{78}$, $R^{778}$, $R^8$, $R^{81}$, $R^{82}$, $R^{83}$, $R^{84}$, $R^{85}$, $R^{86}$, $R^{87}$, $R^{88}$, $R^{888}$, $R^9$, $R^{95}$, and $R^{98}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —$SO_2N(C_{0-4}$alkyl$)(C_{0-4}$alkyl$)$ or —$N(C_{0-4}$alkyl$)(C_{0-4}$alkyl$)$ substituents; aryl-$C_{0-10}$alkyl, aryl-$C_{2-10}$alkenyl, or aryl-$C_{2-10}$alkynyl, any of which is optionally substituted with one or more independent halo, cyano, nitro, —$O(C_{0-4}$alkyl$)$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CON(C_{0-4}$alkyl$)(C_{0-10}$alkyl$)$, —$SO_2N(C_{0-4}$alkyl$)(C_{0-4}$alkyl$)$ or —$N(C_{0-4}$alkyl$)(C_{0-4}$alkyl$)$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$O(C_{0-4}$alkyl$)$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CON(C_{0-4}$alkyl$)(C_{0-4}$alkyl$)$, —$SO_2N(C_{0-4}$alkyl$)(C_{0-4}$alkyl$)$ or —$N(C_{0-4}$alkyl$)(C_{0-4}$alkyl$)$ substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or —N($C_{1-6}$alkyl)-$C_{1-6}$alkyl-aryl, any of which is optionally substituted with one or more independent halo, cyano, nitro, —$O(C_{0-4}$alkyl$)$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CON(C_{0-4}$alkyl$)(C_{0-4}$alkyl$)$, —$SO_2N(C_{0-4}$alkyl$)(C_{0-4}$alkyl$)$ or —$N(C_{0-4}$alkyl$)(C_{0-4}$alkyl$)$ substituents; and n1, n2, n3, n4, n5, n6, and n7 are each independently equal to 0, 1 or 2.

In an aspect of the present invention, a compound is represented by Formula I, or a pharmaceutically acceptable salt thereof, wherein X is an optionally substituted imidazolyl or optionally substituted triazolyl, and the other variables are as described above.

In an embodiment of this aspect, a compound is represented by Formula I, or a pharmaceutically acceptable salt thereof, wherein X is a substituted imidazolyl or substituted triazolyl; $R^1$ is hydrogen; and the other variables are as described above.

In a second aspect of the present invention, a compound is represented by Formula I, or a pharmaceutically acceptable salt thereof, wherein Y is oxygen, and the other variables are as described above.

In an embodiment of this second aspect, a compound of the invention is represented by Formula I-A:

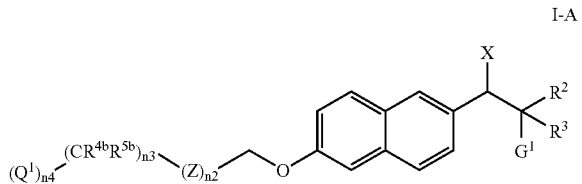

I-A or a pharmaceutically acceptable salt thereof, wherein:

X is an unsaturated heterocycle selected from pyrrolyl, pyrazolyl, imidazolyl, triazolyl, tetrazolyl, thiazole, or pyridinyl, any of which is optionally substituted with one or more independent $R^{66}$ substituents;

$R^2$ and $R^3$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{2-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —$SO_2NR^{71}R^{81}$, or —$NR^{71}R^{81}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —$OR^{71}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{71}R^{81}$, —$SO_2NR^{71}R^{81}$ or —$NR^{71}R^{81}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$OR^{71}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{71}R^{81}$, —$SO_2NR^{71}R^{81}$ or —$NR^{71}R^{81}$ substituents;

or $R^2$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $C_{1-6}$alkyl, halo, cyano, nitro, —$OR^{71}$, —$SO_2NR^{71}R^{81}$ or —$NR^{71}R^{81}$ substituents;

$G^1$ is —$OR^{72}$, —$SR^{72}$, —$NR^{72}R^{82}(R^9)_{n5}$, or $G^1$ and $R^3$ taken together with the carbon atom to which they are attached form a 3-10 membered saturated ring, unsaturated ring, heterocyclic saturated ring, or heterocyclic unsaturated ring, any of which is optionally substituted with one or more independent $R^{67}$ and an N heteroatom of the heterocyclic saturated ring or heterocyclic unsaturated ring optionally is substituted with an $R^{72}$ substituent; or in the case of —$NR^{72}R^{82}(R^9)_{n5}$, $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents;

Z is -aryl-, -arylalkyl-, -aryloxy-, -oxyaryl-, -arylalkenyl-, -alkenylaryl-, -hetaryl-, -hetarylalkyl-, -alkylhetaryl-, -hetarylalkenyl-, -alkenylhetaryl-, or -aryl-, any of which is optionally substituted with $R^{68}$;

$Q^1$ is $C_{0-6}$alkyl, —$OR^{75}$, —$NR^{75}R^{85}(R^{95})_{n6}$, —$CO_2R^{75}$, —$CONR^{75}R^{85}$, —(C=S)$OR^{75}$, —(C=O)$SR^{75}$, —$NO_2$, —CN, halo, —$S(O)_{n6}R^{75}$, —$SO_2NR^{75}R^{85}$, —$NR^{75}$(C=$NR^{775}$)$NR^{7775}R^{85}$, —$NR^{75}$(C=$NR^{775}$)$OR^{7775}$, —$NR^{75}$(C=$NR^{775}$)$SR^{7775}$, —O(C=O)$OR^{75}$, —O(C=O)$NR^{75}R^{85}$, —O(C=O)$SR^{75}$, —S(C=O)$OR^{75}$, —S(C=O)$NR^{75}R^{85}$, —S(C=O)$SR^{75}$, —$NR^{75}$(C=O)$NR^{775}R^{85}$, or —$NR^{75}$(C=S)$NR^{775}R^{85}$; in the case of —$NR^{75}R^{85}(R^{95})_{n6}$, $R^{75}$ and $R^{85}$ taken together with the nitrogen atom to which they are attached form a 3-10 membered saturated ring, unsaturated ring, heterocyclic saturated ring, or heterocyclic unsaturated ring, any of which is optionally substituted with one or more independent halo, cyano, hydroxy, nitro, $C_{1-10}$alkoxy, —$SO_2NR^{76}R^{86}$ or —$NR^{76}R^{86}$ substituents;

$R^{4b}$ and $R^{5b}$ are each independently a $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, —$OR^{77}$, —$SO_2NR^{77}R^{87}$ or —$NR^{77}R87$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —$OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{77}R^{87}$, —$SO_2NR^{77}R^{87}$ or —$NR^{77}R^{87}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{77}R^{87}$, —$SO_2NR^{77}R^{87}$ or —$NR^{77}R^{87}$ substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or —N($C_{1-6}$alkyl)-$C_{1-6}$alkyl-aryl, any of which is optionally substituted with one or more independent halo, cyano, nitro, —$OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{77}R^{87}$, —$SO_2NR^{77}R^{87}$ or —$NR^{77}R^{87}$ substituents; or $R^{4b}$ with $R^{5b}$, taken together with the respective carbon atom to which they are attached, form a 3-10 membered saturated or unsaturated ring, wherein said ring is optionally substituted with $R^{69}$; or $R^{4b}$ with $R^{5b}$, taken together with the respective carbon atom to which they are attached, form a 3-10 membered saturated or unsaturated heterocyclic ring, wherein said ring is optionally substituted with $R^{69}$;

$R^{69}$, $R^{67}$, $R^{68}$, and $R^{69}$ are each independently halo, —$OR^{78}$, —$NR^{78}R^{88}(R^{98})_{n7}$, —$CO_2R^{78}$, —$CONR^{78}R^{88}$, —$NO_2$, —CN, —$S(O)_{n7}R^{78}$, —$SO_2NR^{78}R^{88}$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{2-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, —$OR^{778}$, —$SO_2NR^{778}R^{888}$ or —$NR^{778}R^{888}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, $C_{1-4}$alkoxycarbonyl, —$CONR^{778}R^{888}$, —$SO_2NR^{778}R^{888}$ or —$NR^{778}R^{888}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{778}R^{888}$, —$SO_2NR^{778}R^{888}$ or —$NR^{778}R^{888}$ substituents; or mono($C_{1-6}$alkyl)amino $C_{1-6}$alkyl, di($C_{1-6}$alkyl)amino$C_{1-6}$alkyl, mono(aryl)amino$C_{1-6}$alkyl, di(aryl)amino$C_{1-6}$alkyl, —$N(C_{1-6}$alkyl)-$C_{1-6}$alkyl-aryl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{778}R^{888}$, —$SO_2$ $NR^{778}R^{888}$ or —$NR^{778}R^{888}$ substituents; or in the case of —$NR^{78}R^{88}$ $(R^{98})_{n7}$, $R^{78}$ and $R^{88}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{778}R^{888}$ or —$NR^{778}R^{888}$ substituents; $R^7$, $R^{71}$, $R^{72}$, $R^{73}$, $R^{75}$, $R^{775}$, $R^{7775}$, $R^{76}$, $R^{77}$, $R^{78}$, $R^{778}$, $R^8$, $R^{81}$, $R^{82}$, $R^{83}$, $R^{85}$, $R^{86}$, $R^{87}$, $R^{88}$, $R^{888}$, $R^9$, $R^{95}$, and $R^{98}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —$SO_2N(C_{0-4}$alkyl)($C_{0-4}$alkyl) or —$N(C_{0-4}$alkyl)($C_{0-4}$alkyl) substituents; aryl-$C_{0-10}$alkyl, aryl-$C_{2-10}$alkenyl, or aryl-$C_{2-10}$alkynyl, any of which is optionally substituted with one or more independent halo, cyano, nitro, —$O(C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, $C_{1-4}$alkoxycarbonyl, —CON$(C_{0-4}$alkyl)($C_{0-4}$alkyl), —$SO_2N(C_{0-4}$alkyl)($C_{0-4}$alkyl) or —$N(C_{0-4}$alkyl)($C_{0-4}$alkyl) substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$O(C_{0-4}$alkyl), $C_{1-10}$alkyl, $C_{2-10}$alkynyl, halo$C_{1-10}$alkyl, halo$C_{2-10}$alkenyl, halo $C_{2-10}$alkynyl, —COOH, $C_{1-4}$alkoxycarbonyl, —CON $(C_{0-4}$alkyl)($C_{0-4}$alkyl), —$SO_2N(C_{0-4}$alkyl)($C_{0-4}$alkyl) or —$N(C_{0-4}$alkyl)($C_{0-4}$alkyl) substituents; or mono($C_{1-6}$alkyl) amino$C_{1-6}$alkyl, di($C_{1-6}$alkyl)amino$C_{1-6}$alkyl, mono(aryl) amino$C_{1-6}$alkyl, di(aryl)amino$C_{1-6}$alkyl, or —$N(C_{1-6}$alkyl)-$C_{1-6}$alkyl-aryl, any of which is optionally substituted with one or more independent halo, cyano, nitro, —$O(C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CON$(C_{0-4}$alkyl)($C_{0-4}$alkyl), —$SO_2N(C_{0-4}$alkyl) ($C_{0-4}$alkyl) or —$N(C_{0-4}$alkyl)($C_{0-4}$alkyl) substituents; and n2, n3, n4, n5, n6, and n7 are each independently equal to 0, 1 or 2.

In another embodiment of this second aspect, a compound of the invention is represented by Formula I-B:

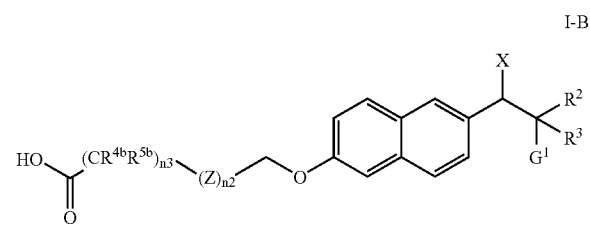

I-B or a pharmaceutically acceptable salt thereof, wherein:

X is substituted imidazolyl;

$R^2$ and $R^3$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —$SO_2NR^{71}R^{81}$, or —$NR^{71}R^{81}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —$OR^{71}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{71}R^{81}$, —$SO_2NR^{71}R^{81}$ or —$NR^{71}R^{81}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$OR^{71}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{71}R^{81}$, —$SO_2NR^{71}R^{81}$ or —$NR^{71}R^{81}$ substituents;

or $R^2$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $C_{1-6}$alkyl, halo, cyano, nitro, —$OR^{71}$, —$SO_2NR^{71}R^{81}$ or —$NR^{71}R^{81}$ substituents;

$G^1$ is $-OR^{72}$, $-SR^{72}$, $-NR^{72}R^{82}(R^9)_{n5}$, or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or in the case of $-NR^{72}R^{82}(R^9)_{n5}$, $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, $-SO_2NR^{73}R^{83}$ or $-NR^{73}R^{83}$ substituents;

Z is -aryl-, -arylalkyl-, -aryloxy-, -oxyaryl-, -arylalkenyl-, -alkenylaryl-, -hetaryl-, -hetarylalkyl-, -alkylhetaryl-, -hetarylalkenyl-, -alkenylhetaryl-, or -aryl-, any of which is optionally substituted with $R^{68}$;

$R^{4b}$ and $R^{5b}$ are each independently a $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, $-OR^{77}$, $-SO_2NR^{77}R^{87}$ or $-NR^{77}R^{87}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, $-OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CONR^{77}R^{87}$, $-SO_2NR^{77}R^{87}$ or $-NR^{77}R^{87}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, $-OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CONR^{77}R^{87}$, $-SO_2NR^{77}R^{87}$ or $-NR^{77}R^{87}$ substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or $-N(C_{1-6}$alkyl)-$C_{1-6}$alkyl-aryl, any of which is optionally substituted with one or more independent halo, cyano, nitro, $-OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CONR^{77}R^{87}$, $-SO_2NR^{77}R^{87}$ or $-NR^{77}R^{87}$ substituents; or $R^{4b}$ with $R^{5b}$, taken together with the respective carbon atom to which they are attached, form a 3-10 membered saturated or unsaturated ring, wherein said ring is optionally substituted with $R^{69}$; or $R^{4b}$ with $R^{5b}$, taken together with the respective carbon atom to which they are attached, form a 3-10 membered saturated or unsaturated heterocyclic ring optionally substituted with $R^{69}$;

$R^{67}$, $R^{68}$, and $R^{69}$ are each independently halo, $-OR^{78}$, $-NR^{78}R^{88}(R^{98})_{n7}$, $-CO_2R^{78}$, $-CONR^{78}R^{88}$, $-NO_2$, $-CN$, $-S(O)_{n7}R^{78}$, $-SO_2NR^{78}R^{88}$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, $-OR^{778}$, $-SO_2NR^{778}R^{888}$ or $-NR^{778}R^{888}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, $-OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CONR^{778}R^{888}$, $-SO_2NR^{778}R^{888}$ or $-NR^{778}R^{888}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, $-OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CONR^{778}R^{888}$, $-SO_2NR^{778}R^{888}$ or $-NR^{778}R^{888}$ substituents; or mono($C_{1-6}$alkyl)amino $C_{1-6}$alkyl, di($C_{1-6}$alkyl)amino$C_{1-6}$alkyl, mono(aryl)amino$C_{1-6}$alkyl, di(aryl)amino$C_{1-6}$alkyl, $-N(C_{1-6}$alkyl)-$C_{1-6}$alkyl-aryl, any of which is optionally substituted with one or more independent halo, cyano, nitro, $-OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CONR^{778}R^{888}$, $-SO_2NR^{778}R^{888}$ or $-NR^{778}R^{888}$ substituents; or in the case of $-NR^{78}R^{88}(R^{98})_{n7}$, $R^{78}$ and $R^{88}$ taken together with the nitrogen atom to which they are attached form a 3-10 membered saturated ring, unsaturated ring, heterocyclic saturated ring, or heterocyclic unsaturated ring, optionally substituted with one or more independent halo, cyano, hydroxy, nitro, $C_{1-10}$alkoxy, $-SO_2NR^{778}R^{888}$ or $-NR^{778}R^{888}$ substituents;

$R^7$, $R^{71}$, $R^{72}$, $R^{73}$, $R^{75}$, $R^{775}$, $R^{7775}$, $R^{76}$, $R^{77}$, $R^{78}$, $R^{778}$, $R^8$, $R^{81}$, $R^{82}$, $R^{83}$, $R^{85}$, $R^{86}$, $R^{87}$, $R^{88}$, $R^{888}$, $R^9$, $R^{95}$, and $R^{98}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, $-SO_2N(C_{0-4}$alkyl)($C_{0-4}$alkyl) or $-N(C_{0-4}$alkyl)($C_{0-4}$alkyl) substituents; aryl-$C_{0-10}$alkyl, aryl-$C_{2-10}$alkenyl, or aryl-$C_{2-10}$alkynyl, any of which is optionally substituted with one or more independent halo, cyano, nitro, $-O(C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CON(C_{0-4}$alkyl)($C_{0-10}$alkyl), $-SO_2N(C_{0-4}$alkyl)($C_{0-4}$alkyl) or $-N(C_{0-4}$alkyl)($C_{0-4}$alkyl) substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, $-O(C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CON(C_{0-4}$alkyl)($C_{0-4}$alkyl), $-SO_2N(C_{0-4}$alkyl)($C_{0-4}$alkyl) or $-N(C_{0-4}$alkyl)($C_{0-4}$alkyl) substituents; or mono($C_{1-6}$alkyl) amino$C_{1-6}$alkyl, di($C_{1-6}$alkyl)amino$C_{1-6}$alkyl, mono(aryl) amino$C_{1-6}$alkyl, di(aryl)amino$C_{1-6}$alkyl, or $-N(C_{1-6}$alkyl)-

$C_{1-6}$alkyl-aryl, any of which is optionally substituted with one or more independent halo, cyano, nitro, —O($C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CON($C_{0-4}$alkyl)($C_{0-4}$alkyl), —SO$_2$N($C_{0-4}$alkyl)($C_{0-4}$alkyl) or —N($C_{0-4}$alkyl)($C_{0-4}$alkyl) substituents; and n2, n3, n4, n5, n6, and n7 are each independently equal to 0, 1 or 2.

In a third aspect, an intermediate compound of the invention is represented by Formula II:

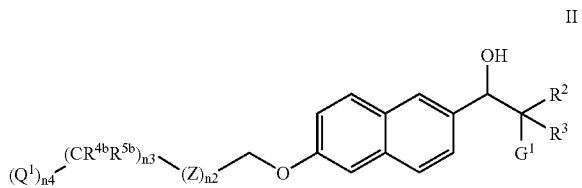

II or a pharmaceutically acceptable salt thereof, wherein:

$R^2$ and $R^3$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —SO$_2$NR$^{71}$R$^{81}$, or —NR$^{71}$R$^{81}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —OR$^{71}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CONR$^{71}$R$^{81}$, —SO$_2$NR$^{71}$R$^{81}$ or —NR$^{71}$R$^{81}$ substituents; or heteroaryl-$C_{0-10}$alkyl, heteroaryl-$C_{2-10}$alkenyl, or heteroaryl-$C_{2-10}$alkynyl, any of which is optionally substituted with one or more independent halo, cyano, nitro, —OR$^{71}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CONR$^{71}$R$^{81}$, —SO$_2$NR$^{71}$R$^{81}$ or —NR$^{71}$R$^{81}$ substituents;

or $R^2$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $C_{1-6}$alkyl, halo, cyano, nitro, —OR$^{71}$, —SO$_2$NR$^{71}$R$^{81}$ or —NR$^{71}$R$^{81}$ substituents;

$G^1$ is —OR$^{72}$, —SR$^{72}$, —NR$^{72}$R$^{82}$(R$^9$)$_{n5}$, or $G^1$ and $R^3$ taken together with the carbon atom to which they are attached form a 3-10 membered saturated ring, unsaturated ring, heterocyclic saturated ring, or heterocyclic unsaturated ring, any of which is optionally substituted with one or more independent R$^{67}$ and an N heteroatom of the heterocyclic saturated ring or heterocyclic unsaturated ring optionally is substituted with an R$^{72}$ substituent; or in the case of —NR$^{72}$R$^{82}$(R$^9$)$_{n5}$, R$^{72}$ and R$^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —SO$_2$NR$^{73}$R$^{83}$ or —NR$^{73}$R$^{83}$ substituents;

Z is -aryl-, -arylalkyl-, -aryloxy-, -oxyaryl-, -arylalkenyl-, -alkenylaryl-, -hetaryl-, -hetarylalkyl-, -alkylhetaryl-, -hetarylalkenyl-, -alkenylhetaryl-, or -aryl-, any of which is optionally substituted with R$^{68}$;

$Q^1$ is $C_{0-8}$alkyl, —OR$^{75}$, —NR$^{75}$R$^{85}$(R$^{95}$)$_{n6}$, —CO$_2$R$^{75}$, —CONR$^{75}$R$^{85}$, —(C=S)OR$^{75}$, —(C=O)SR$^{75}$, —NO$_2$, —CN, halo, —S(O)$_{n6}$R$^{75}$, —SO$_2$NR$^{75}$R$^{85}$, —NR$^{75}$(C=NR$^{775}$)NR$^{7775}$R$^{85}$, —NR$^{75}$(C=NR$^{775}$)OR$^{7775}$, —NR$^{75}$(C=NR$^{775}$)SR$^{7775}$, —O(C=O)OR$^{75}$, —O(C=O)NR$^{75}$R$^{85}$, —O(C=O)SR$^{75}$, —S(C=O)OR$^{75}$, —S(C=O)NR$^{75}$R$^{85}$, —S(C=O)SR$^{75}$, —NR$^{75}$(C=O)NR$^{775}$R$^{85}$, or —NR$^{75}$(C=S)NR$^{775}$R$^{85}$; in the case of —NR$^{75}$R$^{85}$(R$^{95}$)$_{n6}$, R$^{75}$ and R$^{85}$ taken together with the nitrogen atom to which they are attached form a 3-10 membered saturated ring, unsaturated ring, heterocyclic saturated ring, or heterocyclic unsaturated ring, any of which is optionally substituted with one or more independent halo, cyano, hydroxy, nitro, $C_{1-10}$alkoxy, —SO$_2$NR$^{76}$R$^{86}$ or —NR$^{76}$R$^{86}$ substituents;

$R^{4b}$ and $R^{5b}$ are each independently a $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, —OR$^{77}$, —SO$_2$NR$^{77}$R$^{87}$ or —NR$^{77}$R$^{87}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —OR$^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CONR$^{77}$R$^{87}$, —SO$_2$NR$^{77}$R$^{87}$ or —NR$^{77}$R$^{87}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —OR$^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CONR$^{77}$R$^{87}$, —SO$_2$NR$^{77}$R$^{87}$ or —NR$^{77}$R$^{87}$ substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or —N($C_{1-6}$alkyl)-$C_{1-6}$alkyl-aryl, any of which is optionally substituted with one or more independent halo, cyano, nitro, —OR$^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CONR$^{77}$R$^{87}$, —SO$_2$NR$^{77}$R$^{87}$ or —NR$^{77}$R$^{87}$ substituents; or R$^{4b}$ with R$^{5b}$, taken together with the respective carbon atom to which they are attached, form a 3-10 membered saturated or unsaturated ring, any of which is optionally substituted with R$^{69}$; or R$^{4b}$ with R$^{5b}$, taken together with the respective carbon atom to which they are attached, form a 3-10 membered saturated or unsaturated heterocyclic ring, any of which is optionally substituted with R$^{69}$;

$R^7$, $R^{71}$, $R^{72}$, $R^{73}$, $R^{75}$, $R^{775}$, $R^{7775}$, $R^{76}$, $R^{77}$, $R^{78}$, $R^{778}$, $R^8$, $R^{81}$, $R^{82}$, $R^{83}$, $R^{85}$, $R^{86}$, $R^{88}$, $R^{888}$, $R^9$, $R^{95}$, and $R^{98}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —SO$_2$N(C$_{0-4}$alkyl)(C$_{0-4}$alkyl) or —N(C$_{0-4}$alkyl)(C$_{0-4}$alkyl) substituents; aryl-$C_{0-10}$alkyl, aryl-$C_{2-10}$alkenyl, or aryl-$C_{2-10}$alkynyl, any of which is optionally substituted with one or more independent halo, cyano, nitro, —O(C$_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CON(C$_{0-4}$alkyl)(C$_{0-10}$alkyl), —SO$_2$N(C$_{0-4}$alkyl)(C$_{0-4}$alkyl) or —N(C$_{0-4}$alkyl)(C$_{0-4}$alkyl) substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —O(C$_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CON(C$_{0-4}$alkyl)(C$_{0-4}$alkyl), —SO$_2$N(C$_{0-4}$alkyl)(C$_{0-4}$alkyl) or —N(C$_{0-4}$alkyl)(C$_{0-4}$alkyl) substituents; or mono(C$_{1-6}$alkyl)amino$C_{1-6}$alkyl, di(C$_{1-6}$alkyl)amino$C_{1-6}$alkyl, mono(aryl)amino$C_{1-6}$alkyl, di(aryl)amino$C_{1-6}$alkyl, or —N(C$_{1-6}$alkyl)-$C_{1-6}$alkyl-aryl, any of which is optionally substituted with one or more independent halo, cyano, nitro, —O(C$_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CON(C$_{0-4}$alkyl)(C$_{0-4}$alkyl), —SO$_2$N(C$_{0-4}$alkyl)(C$_{0-4}$alkyl) or —N(C$_{0-4}$alkyl)(C$_{0-4}$alkyl) substituents; and n1, n2, n3, n4, n5, n6, and n7 are each independently equal to 0, 1 or 2.

In a fourth aspect, an intermediate compound of this invention is represented by Formula III:

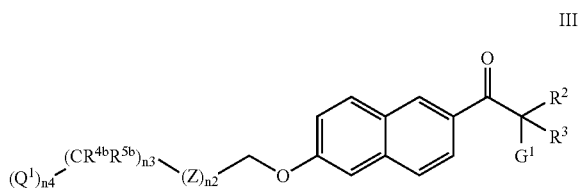

III or a pharmaceutically acceptable salt thereof, wherein:

$R^2$ and $R^3$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —SO$_2$NR$^{71}$R$^{81}$, or —NR$^{71}$R$^{81}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —OR$^{71}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CONR$^{71}$R$^{81}$, —SO$_2$NR$^{71}$R$^{81}$ or —NR$^{71}$R$^{81}$ substituents; or heteroaryl-$C_{0-10}$alkyl, heteroaryl-$C_{2-10}$alkenyl, or heteroaryl-$C_{2-10}$alkynyl, any of which is optionally substituted with one or more independent halo, cyano, nitro, —OR$^{71}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CONR$^{71}$R$^{81}$, —SO$_2$NR$^{71}$R$^{81}$ or —NR$^{71}$R$^{81}$ substituents;

or $R^2$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $C_{1-6}$alkyl, halo, cyano, nitro, —OR$^{71}$, —SO$_2$NR$^{71}$R$^{81}$ or —NR$^{71}$R$^{81}$ substituents;

$G^1$ is —OR$^{72}$, —SR$^{72}$, —NR$^{72}$R$^{82}$(R$^9$)$_{n5}$, or $G^1$ and $R^3$ taken together with the carbon atom to which they are attached form a 3-10 membered saturated ring, unsaturated ring, heterocyclic saturated ring, or heterocyclic unsaturated ring, any of which is optionally substituted one or more independent with $R^{67}$ and an N heteroatom of the heterocyclic saturated ring or heterocyclic unsaturated ring optionally is substituted with an $R^{72}$ substituent; or in the case of —NR$^{72}$R$^{82}$(R$^9$)$_{n5}$, $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —SO$_2$NR$^{73}$R$^{83}$ or —NR$^{73}$R$^{83}$ substituents;

Z is -aryl-, -arylalkyl-, -aryloxy-, -oxyaryl-, -arylalkenyl-, -alkenylaryl-, -hetaryl-, -hetarylalkyl-, -alkylhetaryl-, -hetarylalkenyl-, -alkenylhetaryl-, or -aryl-, any of which is optionally substituted with R$^{68}$;

$Q^1$ is $C_{0-6}$alkyl, —OR$^{75}$, —NR$^{75}$R$^{85}$(R$^{95}$)$_{n6}$, —CO$_2$R$^{75}$, —CONR$^{75}$R$^{85}$, —(C=S)OR$^{75}$, —(C=O)SR$^{75}$, —NO$_2$, —CN, halo, —S(O)$_{n6}$R$^{75}$, —SO$_2$NR$^{75}$R$^{85}$, —NR$^{75}$(C=NR$^{775}$)NR$^{7775}$R$^{85}$, —NR$^{75}$(C=NR$^{775}$)OR$^{7775}$, —NR$^{75}$(C=NR$^{775}$)SR$^{7775}$, —O(C=O)R$^{75}$, —O(C=O)NR$^{75}$R$^{85}$, —O(C=O)SR$^{75}$, —S(C=O)OR$^{75}$, —S(C=O)NR$^{75}$R$^{85}$, —S(C=O)SR$^{75}$, —NR$^{75}$(C=O)NR$^{775}$R$^{85}$, or —NR$^{75}$(C=S)NR$^{775}$R$^{85}$; in the case of —NR$^{75}$R$^{85}$(R$^{95}$)$_{n6}$, $R^{75}$ and $R^{85}$ taken together with the nitrogen atom to which they are attached form a 3-10 membered saturated ring, unsaturated ring, heterocyclic saturated ring, or heterocyclic unsaturated ring, any of which is optionally substituted with one or more independent halo, cyano, hydroxy, nitro, $C_{1-10}$alkoxy, —SO$_2$NR$^{76}$R$^{86}$ or —NR$^{76}$R$^{86}$ substituents;

$R^{4b}$ and $R^{5b}$ are each independently a $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, —OR$^{77}$, —SO$_2$NR$^{77}$R$^{87}$ or —NR$^{77}$R$^{87}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, $-OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CONR^{77}R^{87}$, $-SO_2NR^{77}R^{87}$ or $-NR^{77}R^{87}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, $-OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CONR^{77}R^{87}$, $-SO_2NR^{77}R^{87}$ or $-NR^{77}R^{87}$ substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or $-N(C_{1-6}$alkyl)-$C_{1-6}$alkyl-aryl, any of which is optionally substituted with one or more independent halo, cyano, nitro, $-OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CONR^{77}R^{87}$, $-SO_2NR^{77}R^{87}$ or $-NR^{77}R^{87}$ substituents; or $R^{4b}$ with $R^{5b}$, taken together with the respective carbon atom to which they are attached, form a 3-10 membered saturated or unsaturated ring, any of which is optionally substituted with $R^{69}$; or $R^{4b}$ with $R^{5b}$, taken together with the respective carbon atom to which they are attached, form a 3-10 membered saturated or unsaturated heterocyclic ring, wherein said ring is optionally substituted with $R^{69}$;

$R^{67}$, $R^{68}$, and $R^{69}$ is a halo, $-OR^{78}$, $-NR^{78}R^{88}(R^{98})_{7n}$, $-CO_2R^{78}$, $-CONR^{78}R^{88}$, $-NO_2$, $-CN$, $-S(O)_{n7}R^{78}$, $-SO_2NR^{78}R^{88}$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, $-OR^{778}$, $-SO_2NR^{778}R^{888}$ or $-NR^{778}R^{888}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, $-OR^{778}$, $C_{1-10}$alkyl, $C_{2-10}$alkenyl, $C_{2-10}$alkynyl, halo $C_{1-10}$alkyl, halo$C_{2-10}$alkenyl, halo$C_{2-10}$alkynyl, $-COOH$, $C_{1-4}$alkoxycarbonyl, $-CONR^{778}R^{888}$, $-SO_2NR^{778}R^{888}$ or $-NR^{778}R^{888}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, $-OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CONR^{778}R^{888}$, $-SO_2NR^{778}R^{888}$ or $-NR^{778}R^{888}$ substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, $-N(C_{1-6}$alkyl)-$C_{1-6}$alkyl-aryl, any of which is optionally substituted with one or more independent halo, cyano, nitro, $-OR^{778}$, $C_{1-10}$alkyl, $C_{2-10}$alkenyl, $C_{2-10}$alkynyl, halo $C_{1-10}$alkyl, halo$C_{2-10}$alkenyl, halo$C_{2-10}$alkynyl, $-COOH$, $C_{1-4}$alkoxycarbonyl, $-CONR^{778}R^{888}$, $-SO_2NR^{778}R^{888}$ or $-NR^{778}R^{888}$ substituents; or in the case of $-NR^{78}R^{88}(R^{98})_{n7}$, $R^{78}$ and $R^{88}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, $-SO_2NR^{778}R^{888}$ or $-NR^{778}R^{888}$ substituents;

$R^7$, $R^{71}$, $R^{72}$, $R^{73}$, $R^{74}$, $R^{75}$, $R^{775}$, $R^{7775}$, $R^{76}$, $R^{77}$, $R^{78}$, $R^{778}$, $R^8$, $R^{81}$, $R^{82}$, $R^{83}$, $R^{85}$, $R^{86}$, $R^{87}$, $R^{88}$, $R^{888}$, $R^9$, $R^{95}$, and $R^{98}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, $-SO_2N(C_{0-4}$alkyl)($C_{0-4}$alkyl) or $-N(C_{0-4}$alkyl)($C_{0-4}$alkyl) substituents; aryl-$C_{0-10}$alkyl, aryl-$C_{2-10}$alkenyl, or aryl-$C_{2-10}$alkynyl, any of which is optionally substituted with one or more independent halo, cyano, nitro, $-O(C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, $-COOH$, $C_{1-4}$alkoxycarbonyl, $-CON(C_{0-4}$alkyl)($C_{0-10}$alkyl), $-SO_2N(C_{0-4}$alkyl)($C_{0-4}$alkyl) or $-N(C_{0-4}$alkyl)($C_{0-4}$alkyl) substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, $-O(C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, $-COOH$, $C_{1-4}$alkoxycarbonyl, $-CON(C_{0-4}$alkyl)($C_{0-4}$alkyl), $-SO_2N(C_{0-4}$alkyl)($C_{0-4}$alkyl) or $-N(C_{0-4}$alkyl)($C_{0-4}$alkyl) substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or $-N(C_{1-6}$alkyl)-$C_{1-6}$alkyl-aryl, any of which is optionally substituted with one or more independent halo, cyano, nitro, $-O(C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CON(C_{0-4}$alkyl)($C_{0-4}$alkyl), $-SO_2N(C_{0-4}$alkyl)($C_{0-4}$alkyl) or $-N(C_{0-4}$alkyl)($C_{0-4}$alkyl) substituents; and n2, n3, n4, n5, n6, and n7 are each independently equal to 0, 1 or 2.

The compounds of the present invention include compounds represented by Formula I above, or a pharmaceutically acceptable salt thereof, and 1) wherein X is hetaryl, imidazolyl, or triazolyl, any of which is optionally substituted with one or more independent $R^{66}$ substituents; or 2) wherein X is imidazolyl or triazolyl; or 3) wherein X is hetaryl, imidazolyl, or triazolyl, any of which is optionally substituted with one or more independent $R^{66}$ substituents, and $Q^1$ is $-CO_2H$ or $-CO_2R^{75}$; or 4) wherein Y is oxygen; or 5) wherein Y is oxygen and X is hetaryl, imidazolyl, or triazolyl, any of which is optionally substituted with one or more independent $R^{66}$ substituents; or 6) wherein Y is oxygen and X is imidazolyl or triazolyl; or 7) wherein Y is oxygen and X is imidazolyl or triazolyl and $Q^1$ is $-CO_2H$ or $-CO_2R^{75}$; or 8) wherein Y is oxygen and $R^{4a}$ and $R^{5a}$ are each hydrogen; or 9) wherein X is hetaryl, imidazolyl, or triazolyl, any of which is optionally substituted with one or more independent $R^{66}$ substituents; $R^1$, $R^2$ and $R^3$ are each independently $C_{0-10}$alkyl; $G^1$ is $-NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1\text{-}10}$alkoxy, $-SO_2NR^{73}R^{83}$ or $-NR^{73}R^{83}$ substituents; Y is oxygen; $Q^1$ is $C_{0\text{-}6}$alkyl, $-CO_2R^{75}$, or $-CONR^{75}R^{85}$; $R^{4a}$, $R^{4b}$, $R^{5a}$, and $R^{5b}$ are each independently a $C_{0\text{-}10}$alkyl, any of which is optionally substituted with one or more independent halo, cyano, nitro, $-OR^{77}$, $-SO_2NR^{77}R^{87}$ or $-NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, $-OR^{78}$, $-NR^{78}R^{88}(R^{98})_{n7}$, $-CO_2R^{78}$, $-CONR^{78}R^{88}$, $-NO_2$, $-CN$, $-S(O)_{n7}R^{78}$, $-SO_2NR^{78}R^{88}$, or $C_{0\text{-}10}$alkyl; or 10) wherein X is imidazolyl or triazolyl; $R^1$ is hydrogen, $R^2$ and $R^3$ are each independently $C_{0\text{-}10}$alkyl; $G^1$ is $-NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1\text{-}10}$alkoxy, $-SO_2NR^{73}R^{83}$ or $-NR^{73}R^{83}$ substituents; Y is oxygen; $Q^1$ is $-CO_2R^{75}$ or $-CONR^{75}R^{85}$; $R^{4a}$, $R^{4b}$, $R^{5a}$, and $R^{5b}$ are each independently a $C_{0\text{-}10}$alkyl, any of which is optionally substituted with one or more independent halo, cyano, nitro, $-OR^{77}$, $-SO_2NR^{77}R^{87}$ or $-NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each hydrogen; or 11) wherein X is hetaryl, imidazolyl, or triazolyl, any of which is optionally substituted with one or more independent $R^{66}$ substituents; $R^1$, $R^2$ and $R^3$ are each independently $C_{0\text{-}10}$alkyl; $G^1$ is $-NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1\text{-}10}$alkoxy, $-SO_2NR^{73}R^{83}$ or $-NR^{73}R^{83}$ substituents; Y is oxygen; $Q^1$ is $C_{0\text{-}6}$alkyl, $-CO_2R^{75}$ or $-CONR^{75}R^{85}$; $R^{4a}$ and $R^{5a}$ are each hydrogen; $R^{4b}$ and $R^{5b}$ are each independently a $C_{0\text{-}10}$alkyl, any of which is optionally substituted with $R^{69}$; or $R^{4b}$ with $R^{5b}$ taken together with the respective carbon atom to which they are attached form a 3-10 membered saturated or unsaturated ring, wherein said ring is optionally substituted with $R^{69}$; or $R^{4b}$ with $R^{5b}$ taken together with the respective carbon atom to which they are attached form a 3-10 membered saturated or unsaturated heterocyclic ring, wherein said ring is optionally substituted with $R^{69}$; or 12) wherein X is hetaryl, imidazolyl, or triazolyl, any of which is optionally substituted with one or more independent $R^{66}$ substituents; $R^1$, $R^2$ and $R^3$ are each independently $C_{0\text{-}10}$alkyl; $G^1$ is $-NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1\text{-}10}$alkoxy, $-SO_2NR^{73}R^{83}$ or $-NR^{73}R^{83}$ substituents; Y is oxygen; $Q^1$ is $C_{0\text{-}6}$alkyl, $-CO_2R^{75}$, or $-CONR^{75}R^{85}$; $R^{4b}$ and $R^{5b}$ are each independently $C_{0\text{-}6}$alkyl, or $R^{4b}$ with $R^{5b}$ taken together with the respective carbon atom to which they are attached form a 3-10 membered saturated ring; $R^{4a}$ and $R^{5a}$ are each independently a $C_{0\text{-}10}$alkyl, any of which is optionally substituted with one or more independent halo, cyano, nitro, $-OR^{77}$, $-SO_2NR^{77}R^{87}$ or $-NR^{77}R^{87}$ substituents; or $R^{4a}$ with $R^{5a}$, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, $-OR^{78}$, $-NR^{78}R^{88}(R^{98})_{n7}$, $-CO_2R^{78}$, $-CONR^{78}R^{88}$, $-NO_2$, $-CN$, $-S(O)_{n7}R^{78}$, $-SO_2NR^{78}R^{88}$, or $C_{0\text{-}10}$alkyl; or 13) wherein X is hetaryl, imidazolyl, or triazolyl, any of which is optionally substituted with one or more independent $R^{66}$ substituents; $R^1$, $R^2$ and $R^3$ are each independently $C_{0\text{-}10}$alkyl; $G^1$ is $-NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1\text{-}10}$alkoxy, $-SO_2NR^{73}R^{83}$ or $-NR^{73}R^{83}$ substituents; Y is oxygen; $Q^1$ is $C_{0\text{-}6}$alkyl, $-CO_2R^{75}$, or $-CONR^{75}R^{85}$; $R^{4a}$ and $R^{5a}$ are each independently a $C_{0\text{-}10}$alkyl, any of which is optionally substituted with one or more independent halo, cyano, nitro, $-OR^{77}$, $-SO_2NR^{77}R^{87}$ or $-NR^{77}R^{87}$ substituents; or $R^{4a}$ with $R^{5a}$, wherein said ring is optionally substituted with $R^{69}$; or $R^{4a}$ with $R^{5a}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —$CN$, —$S(O)_{n7}R^{78}$, —$SO_2NR^{78}R^{88}$, or $C_{0-10}$alkyl; and $R^{4b}$ with $R^{5b}$ taken together with the respective carbon atom to which they are attached form a cyclopropyl, cyclobutyl, cyclopentyl, or cyclohexyl ring; or 14) wherein X is hetaryl, imidazolyl, or triazolyl, any of which is optionally substituted with one or more independent $R^{66}$ substituents; $R^1$, $R^2$ and $R^3$ are each independently $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $Q^1$ is $C_{0-6}$alkyl, —$CO_2R^{75}$ or —$CONR^{75}R^{85}$; $R^{4a}$ and $R^{5a}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, wherein said ring is optionally substituted with $R^{69}$; or $R^{4a}$ with $R^{5a}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{7n}$, —$CO_2R^{78}$, —$CONR^{78}R^{88}$, —$NO_2$, —$CN$, —$S(O)_{n7}R^{78}$, —$SO_2NR^{78}R^{88}$, or $C_{0-10}$alkyl; and $R^{4b}$ and $R^{5b}$ are both ethyl or are both methyl or are independently ethyl or methyl; or 15) wherein X is hetaryl, imidazolyl, or triazolyl, any of which is optionally substituted with one or more independent $R^{66}$ substituents; $R^1$, $R^2$ and $R^3$ are each independently $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —$CN$, —$S(O)_{n7}R^{78}$, —$SO_2NR^{78}R^{88}$, or $C_{0-10}$alkyl; and $Q^1$ is —$CO_2R^{75}$; or 16) wherein X is hetaryl, imidazolyl, or triazolyl, any of which is optionally substituted with one or more independent $R^{66}$ substituents; $R^1$, $R^2$ and $R^3$ are each independently $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$ or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —$CN$, —$S(O)_{n7}R^{78}$, —$SO_2NR^{78}R^{88}$, or $C_{0-10}$alkyl; and $Q^1$ is —$CO_2H$; or 17) wherein X is hetaryl, imidazolyl, or triazolyl, any of which is optionally substituted with one or more independent $R^{66}$ substituents; $R^1$, $R^2$ and $R^3$ are each independently $C_{0-10}$alkyl; Y is oxygen; $Q^1$ is $C_{0-6}$alkyl, —$CO_2R^{75}$, or —$CONR^{75}R^{85}$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —$CN$, —$S(O)_{n7}R^{78}$, —$SO_2NR^{78}R^{88}$, or $C_{0-10}$alkyl; and $G^1$ is di($C_{1-6}$alkyl)amino; or 18) wherein X is hetaryl, imidazolyl, or triazolyl, any of which is optionally substituted with one or more independent $R^{66}$ substituents; $R^1$, $R^2$ and $R^3$ are each independently $C_{0-10}$alkyl; Y is oxygen; $Q^1$ is $C_{0-6}$alkyl, —$CO_2R^{75}$, or —$CONR^{75}R^{85}$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —$CN$, —$S(O)_{n7}R^{78}$, —$SO_2NR^{78}R^{88}$, or $C_{0-10}$alkyl; and $G^1$ is dimethylamino, ethylmethylamino, diethylamino, or iso-propylmethylamino; or 19) wherein X is hetaryl, imidazolyl, or triazolyl, any of which is optionally substituted with one or more independent $R^{66}$ substituents; $R^1$ is $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $Q^1$ is $C_{0-6}$alkyl, —$CO_2R^{75}$, or —$CONR^{75}R^{85}$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —$CN$, —$S(O)_{n7}R^{78}$, —$SO_2NR^{78}R^{88}$, or $C_{0-10}$alkyl; and $R^2$ and $R^3$ are each independently hydrogen, methyl, or ethyl; or 20) wherein X is hetaryl, imidazolyl, or triazolyl, any of which is optionally substituted with one or more independent $R^{66}$ substituents; $R^1$ and $R^3$ are each independently $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $Q^1$ is $C_{0-6}$alkyl, —$CO_2R^{75}$, or —$CONR^{75}R^{85}$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$,
—$CN$, —$S(O)_{n7}R^{78}$, —$SO_2NR^{78}R^{88}$, or $C_{0-10}$alkyl; $R^2$ is hydrogen; and $G^1$ and $R^3$ taken together with the carbon atom to which they are attached form

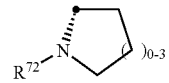

wherein ● is the carbon to which they are attached;

or $G^1$ and $R^3$ taken together with the carbon atom to which they are attached form

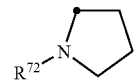

wherein ● is the carbon to which they are attached, any of which is optionally substituted by 1-10 independent $R^{67}$ substituents; or 21) wherein X is imidazole; or 22) wherein X is hetaryl, imidazolyl, or triazolyl, any of which is optionally substituted with one or more independent $R^{66}$ substituents; $R^1$ is $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $Q^1$ is $C_{0-6}$alkyl, —$CO_2R^{75}$, or —$CONR^{75}R^{85}$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —$CN$, —$S(O)_{n7}R^{78}$, —$SO_2NR^{78}R^{88}$, or $C_{0-10}$alkyl; and $R^2$ is hydrogen and $R^3$ is methyl; or 23) wherein X is hetaryl, imidazolyl, or triazolyl, any of which is optionally substituted with one or more independent $R^{66}$ substituents; $R^1$ is $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $Q^1$ is $C_{0-6}$alkyl, —$CO_2R^{75}$, or —$CONR^{75}R^{85}$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —$CN$, —$S(O)_{n7}R^{78}$, —$SO_2NR^{78}R^{88}$, or $C_{0-10}$alkyl; and $R^2$ is hydrogen and $R^3$ is ethyl; or 24) wherein X is hetaryl, imidazolyl, or triazolyl, any of which is optionally substituted with one or more independent $R^{66}$ substituents; $R^1$ is $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $Q^1$ is $C_{0-6}$alkyl, —$CO_2R^{75}$, or —$CONR^{75}R^{85}$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —$CN$, —$S(O)_{n7}R^{78}$, —$SO_2NR^{78}R^{88}$, or $C_{0-10}$alkyl; and $R^2$ is hydrogen and $R^3$ are both methyl; or 25) wherein X is hetaryl, imidazolyl, or triazolyl, any of which is optionally substituted with one or more independent $R^{66}$ substituents; $R^1$ and $R^3$ are each independently $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $Q^1$ is $C_{0-6}$alkyl, —$CO_2R^{75}$, or —$CONR^{75}R^{85}$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —$CN$, —$S(O)_{n7}R^{78}$, —$SO_2NR^{78}R^{88}$, or $C_{0-10}$alkyl; $R^2$ is hydrogen; and $G^1$ and $R^3$ taken together with the carbon atom to which they are attached form

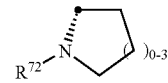

wherein ● is the carbon to which they are attached, or $G^1$ and $R^3$ taken together with the carbon atom to which they are attached form

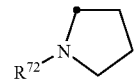

wherein ● is the carbon to which they are attached, any of which is optionally substituted by 1-10 independent $R^{67}$ substituents; and n2, n3, and n4 are each 1 and Z is aryl; or 26) wherein X is hetaryl, imidazolyl, or triazolyl, any of which is optionally substituted with one or more independent $R^{66}$ substituents; $R^1$ and $R^3$ are each independently $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $Q^1$ is $C_{0-6}$alkyl, —$CO_2R^{75}$, or —$CONR^{75}R^{85}$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —CN, —$S(O)_{n7}R^{78}$, —$SO_2NR^{78}R^{88}$, or $C_{0-10}$alkyl; $R^2$ is hydrogen; and $G^1$ and $R^3$ taken together with the carbon atom to which they are attached form

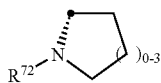

wherein ● is the carbon to which they are attached, or $G^1$ and $R^3$ taken together with the carbon atom to which they are attached form

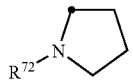

wherein ● is the carbon to which they are attached, any of which is optionally substituted by 1-10 independent $R^{67}$ substituents; n2 is 1; n3 and n4 are each 0; and Z is aryl; or 27) wherein Z is aryl or aryloxy or oxyaryl; or 28) wherein X is hetaryl, imidazolyl, or triazolyl, any of which is optionally substituted with one or more independent $R^{66}$ substituents; $R^1$ and $R^3$ are each independently $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $Q^1$ is —$CO_2R^{75}$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —CN, —$S(O)_{n7}R^{78}$, —$SO_2NR^{78}R^{88}$, or $C_{0-10}$alkyl; $R^2$ is hydrogen; and $G^1$ and $R^3$ taken together with the carbon atom to which they are attached form

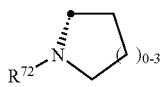

wherein ● is the carbon to which they are attached, or $G^1$ and $R^3$ taken together with the carbon atom to which they are attached form

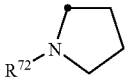

wherein ● is the carbon to which they are attached, any of which is optionally substituted by 1-10 independent $R^{67}$ substituents; and n2, n3, and n4 are each 1 and Z is aryl; and n3 is 0; or 29) wherein X is hetaryl, imidazolyl, or triazolyl, any of which is optionally substituted with one or more independent $R^{66}$ substituents; $R^1$ and $R^3$ are each independently $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $Q^1$ is —$CO_2H$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —CN, —$S(O)_{n7}R^{78}$, —$SO_2NR^{78}R^{88}$, or $C_{0-10}$alkyl; $R^2$ is hydrogen; and $G^1$ and $R^3$ taken together with the carbon atom to which they are attached form

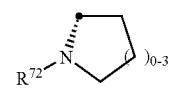

wherein ● is the carbon to which they are attached, or or $G^1$ and $R^3$ taken together with the carbon atom to which they are attached form

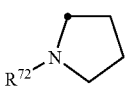

wherein ● is the carbon to which they are attached, any of which is optionally substituted by 1-10 independent $R^{67}$ substituents; and n2, n3, and n4 are each 1 and Z is aryl; and n3 is 0; or 30) wherein X is imidazolyl or triazolyl; $R^1$ is hydrogen; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $Q^1$ is —$CO_2R^{75}$ or —$CONR^{75}R^{85}$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each hydrogen; $R^2$ is hydrogen; and $R^3$ is methyl; or 31) wherein X is imidazolyl or triazolyl; $R^1$ is hydrogen; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $Q^1$ is —$CO_2R^{75}$ or —$CONR^{75}R^{85}$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each hydrogen; $R^2$ is hydrogen; and $R^3$ is ethyl; or 32) wherein X is imidazolyl or triazolyl; $R^1$ is hydrogen; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $Q^1$ is —$CO_2R^{75}$ or —$CONR^{75}R^{85}$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each hydrogen; and $R^2$ and $R^3$ are methyl; or 33) wherein X is hetaryl, imidazolyl, or triazolyl, any of which is optionally substituted with one or more independent $R^{66}$ substituents; $R^1$ and $R^3$ are each independently $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $Q^1$ is $C_{0-6}$alkyl, —$CO_2R^{75}$, or —$CONR^{75}R^{85}$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —CN, —$S(O)_{n7}R^{78}$, —$SO_2NR^{78}R^{88}$, or $C_{0-10}$alkyl; $R^2$ is hydrogen; and $G^1$ and $R^3$ taken together with the carbon atom to which they are attached form

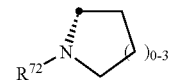

wherein ● is the carbon to which they are attached, or $G^1$ and $R^3$ taken together with the carbon atom to which they are attached form

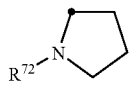

wherein ● is the carbon to which they are attached, any of which is optionally substituted by 1-10 independent $R^{67}$ substituents; n1 and n2 are each 1; and Z is aryl; or 34) wherein X is hetaryl, imidazolyl, or triazolyl, any of which is optionally substituted with one or more independent $R^{66}$ substituents; $R^1$ and $R^3$ are each independently $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $Q^1$ is $C_{0-6}$alkyl, —$CO_2R^{75}$, or —$CONR^{75}R^{85}$; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —$CN$, —$S(O)_{n7}R^{78}$, —$SO_2NR^{78}R^{88}$, or $C_{0-10}$alkyl; $R^2$ is hydrogen; and $G^1$ and $R^3$ taken together with the carbon atom to which they are attached form

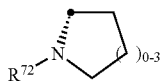

wherein ● is the carbon to which they are attached, or $G^1$ and $R^3$ taken together with the carbon atom to which they are attached form

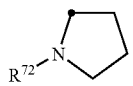

wherein ● is the carbon to which they are attached, any of which is optionally substituted by 1-10 independent $R^{67}$ substituents; n1 and n2 are each 1; n3 and n4 are each 0; and Z is aryl; or 35) wherein X is hetaryl, imidazolyl, or triazolyl, any of which is optionally substituted with one or more independent $R^{66}$ substituents; $R^1$ and $R^3$ are each independently $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —$CN$, —$S(O)_{n7}R^{78}$, —$SO_2NR^{78}R^{88}$, or $C_{0-10}$alkyl; $R^2$ is hydrogen; and $G^1$ and $R^3$ taken together with the carbon atom to which they are attached form

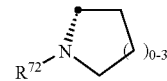

wherein ● is the carbon to which they are attached, or $G^1$ and $R^3$ taken together with the carbon atom to which they are attached form

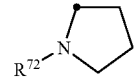

wherein ● is the carbon to which they are attached, any of which is optionally substituted by 1-10 independent $R^{67}$ substituents; n1 and n2 are each 1; Z is aryl; and $Q^1$ is —$CO_2R^{75}$; or 36) wherein X is hetaryl, imidazolyl, or triazolyl, any of which is optionally substituted with one or more independent $R^{66}$ substituents; $R^1$ and $R^3$ are each independently $C_{0-10}$alkyl; $G^1$ is —$NR^{72}R^{82}$; or $G^1$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $R^{67}$ and an N heteroatom of the heterocyclic saturated ring or heterocyclic unsaturated ring optionally is substituted with an $R^{72}$ substituent; or $R^{72}$ and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{73}R^{83}$ or —$NR^{73}R^{83}$ substituents; Y is oxygen; $R^{4a}$, $R^{4b}$, $R^{5a}$, and $R^{5b}$ are each independently a $C_{0-10}$alkyl, any of which is optionally substituted with one or more independent halo, cyano, nitro, $-OR^{77}$, $-SO_2NR^{77}R^{87}$ or $-NR^{77}R^{87}$ substituents; or $R^{4a}$ with $R^{5a}$, or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, $-OR^{78}$, $-NR^{78}R^{88}(R^{98})_{n7}$, $-CO_2R^{78}$, $-CONR^{78}R^{88}$, $-NO_2$, $-CN$, $-S(O)_{n7}R^{78}$, $-SO_2NR^{78}R^{88}$, or $C_{0-10}$alkyl; $R^2$ is hydrogen; and $G^1$ and $R^3$ taken together with the carbon atom to which they are attached form

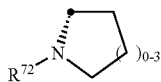

wherein ● is the carbon to which they are attached, or $G^1$ and $R^3$ taken together with the carbon atom to which they are attached form

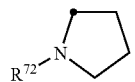

wherein ● is the carbon to which they are attached, any of which is optionally substituted by 1-10 independent $R^{67}$ substituents; n1 and n2 are each 1; Z is aryl; and $Q^1$ is $-CO_2H$;

and wherein, in each case, the other variables are as defined above for Formula I.

The compounds of the present invention include:
3-[6-(2-Dimethylamino-1-imidazol-1-yl-propyl)-naphthalen-2-yloxy]-2,2-dimethyl-propionic acid;
2-[6-(2-Dimethylamino-1-imidazol-1-yl-propyl)-naphthalen-2-yloxymethyl]-2-ethyl-butyric acid;
1-[6-(2-Dimethylamino-1-imidazol-1-yl-propyl)-naphthalen-2-yloxymethyl]-cyclopropanecarboxylic acid;
1-[6-(2-Dimethylamino-1-imidazol-1-yl-propyl)-naphthalen-2-yloxymethyl]-cyclobutanecarboxylic acid;
1-[6-(2-Dimethylamino-1-imidazol-1-yl-propyl)-naphthalen-2-yloxymethyl]-cyclopentanecarboxylic acid;
1-[6-(2-Dimethylamino-1-imidazol-1-yl-propyl)-naphthalen-2-yloxymethyl]-cyclohexanecarboxylic acid;
1-{6-[1-Imidazol-1-yl-2-(isopropylmethylamino)-propyl]-naphthalen-2-yloxymethyl}-cyclopentanecarboxylic acid;
3-[6-(2-Diethylamino-1-imidazol-1-yl-propyl)-naphthalen-2-yloxy]-2,2-dimethyl-propionic acid;
3-{6-[1-Imidazol-1-yl-2-(isopropylmethylamino)-propyl]-naphthalen-2-yloxy}-2,2-dimethyl-propionic acid;
3-{6-[2-(Ethyl-methyl-amino)-1-imidazol-1-yl-propyl]-naphthalen-2-yloxy}-2,2-dimethyl-propionic acid;
3-[6-(2-Dimethylamino-1-imidazol-1-yl-propyl)-naphthalen-2-yloxy]-2,2-dimethyl-propionamide;
3-[6-(2-Dimethylamino-1-imidazol-1-yl-propyl)-naphthalen-2-yloxy]-2,2,N-trimethyl-propionamide;
3-[6-(2-Dimethylamino-1-imidazol-1-yl-propyl)-naphthalen-2-yloxy]-2,2,N,N-tetramethyl-propionamide;
3-[6-(2-Dimethylamino-1-imidazol-1-yl-butyl)-naphthalen-2-yloxy]-2,2-dimethyl-propionic acid;
4-[6-(2-Dimethylamino-1-imidazol-1-yl-propyl)-naphthalen-2-yloxymethyl]-benzoic acid;
3-[6-(2-Dimethylamino-1-imidazol-1-yl-propyl)-naphthalen-2-yloxymethyl]-benzoic acid;
4-[6-(2-Dimethylamino-1-imidazol-1-yl-propyl)-naphthalen-2-yloxymethyl]-benzamide;
4-[6-(2-Dimethylamino-1-imidazol-1-yl-propyl)-naphthalen-2-yloxymethyl]-N-methyl-benzamide;
4-[6-(2-Dimethylamino-1-imidazol-1-yl-propyl)-naphthalen-2-yloxymethyl]-N,N-dimethyl-benzamide; and
1-[(6-Benzyloxy-naphthalen-2-yl)-(1-methyl-pyrrolidin-2-yl)-methyl]-1H-imidazole.

Unless otherwise stated, the connections of compound name moieties are at the rightmost recited moiety. That is, the substituent name starts with a terminal moiety, continues with any bridging moieties, and ends with the connecting moiety. For example, hetarylthio$C_{1-4}$alkyl has a heteroaryl group connected through a thio sulfur to a $C_{1-4}$ alkyl that connects to the chemical species bearing the substituent.

As used herein, for example, "$C_{0-4}$alkyl" is used to mean an alkyl having 0-4 carbons—that is, 0, 1, 2, 3, or 4 carbons in a straight or branched configuration. An alkyl having no carbon is hydrogen when the alkyl is a terminal group. An alkyl having no carbon is a direct bond when the alkyl is a bridging (connecting) group.

In all embodiments of this invention, the term "alkyl" includes both branched and straight chain alkyl groups. Typical alkyl groups are methyl, ethyl, n-propyl, isopropyl, n-butyl, sec-butyl, isobutyl, tert-butyl, n-pentyl, isopentyl, n-hexyl, n-heptyl, isooctyl, nonyl, decyl, undecyl, dodecyl, tetradecyl, hexadecyl, octadecyl, eicosyl and the like.

The term "halo" refers to fluoro, chloro, bromo or iodo.

The term "haloalkyl" refers to an alkyl group substituted with one or more halo groups, for example chloromethyl, 2-bromoethyl, 3-iodopropyl, trifluoromethyl, perfluoropropyl, 8-chlorononyl and the like.

The term "cycloalkyl" refers to a cyclic aliphatic ring structure, optionally substituted with alkyl, hydroxy and halo, such as cyclopropyl, methylcyclopropyl, cyclobutyl, cyclopentyl, 2-hydroxycyclopentyl, cyclohexyl, 4-chlorocyclohexyl, cycloheptyl, cyclooctyl and the like.

The term "alkylcarbonyloxyalkyl" refers to an ester moiety, for example acetoxymethyl, n-butyryloxyethyl and the like.

The term "alkynylcarbonyl" refers to an alkynylketo functionality, for example propynoyl and the like.

The term "hydroxyalkyl" refers to an alkyl group substituted with one or more hydroxy groups, for example hydroxymethyl, 2,3-dihydroxybutyl and the like.

The term "alkylsulfonylalkyl" refers to an alkyl group substituted with an alkylsulfonyl moiety, for example mesylmethyl, isopropylsulfonylethyl and the like.

The term "alkylsulfonyl" refers to a sulfonyl moiety substituted with an alkyl group, for example mesyl, n-propylsulfonyl and the like.

The term "acetylaminoalkyl" refers to an alkyl group substituted with an amide moiety, for example acetylaminomethyl and the like.

The term "acetylaminoalkenyl" refers to an alkenyl group substituted with an amide moiety, for example 2-(acetylamino)vinyl and the like.

The term "alkenyl" refers to an ethylenically unsaturated hydrocarbon group, straight or branched chain, having 1 or 2 ethylenic bonds, for example vinyl, allyl, 1-butenyl, 2-butenyl, isopropenyl, 2-pentenyl and the like.

The term "haloalkenyl" refers to an alkenyl group substituted with one or more halo groups.

The term "cycloalkenyl" refers to a cyclic aliphatic ring structure, optionally substituted with alkyl, hydroxy and halo, having 1 or 2 ethylenic bonds such as methylcyclopropenyl, trifluoromethylcyclopropenyl, cyclopentenyl, cyclohexenyl, 1,4-cyclohexadienyl and the like.

The term "alkynyl" refers to an unsaturated hydrocarbon group, straight or branched, having 1 or 2 acetylenic bonds, for example ethynyl, propargyl and the like.

The term "haloalkynyl" refers to an alkynyl group substituted with one or more halo groups.

The term "alkylcarbonyl" refers to an alkylketo functionality, for example acetyl, n-butyryl and the like.

The term "alkenylcarbonyl" refers to an alkenylketo functionality, for example, propenoyl and the like.

The term "aryl" refers to phenyl or naphthyl which may be optionally substituted. Typical aryl substituents include, but are not limited to, phenyl, 4-chlorophenyl, 4-fluorophenyl, 4-bromophenyl, 3-nitrophenyl, 2-methoxyphenyl, 2-methylphenyl, 3-methyphenyl, 4-methylphenyl, 4-ethylphenyl, 2-methyl-3-methoxyphenyl, 2,4-dibromophenyl, 3,5-difluorophenyl, 3,5-dimethylphenyl, 2,4,6-trichlorophenyl, 4-methoxyphenyl, naphthyl, 2-chloronaphthyl, 2,4-dimethoxyphenyl, 4-(trifluoromethyl)phenyl and 2-iodo-4-methylphenyl.

The terms "heteroaryl" or "hetaryl" refer to a substituted or unsubstituted 3-10 membered unsaturated ring containing one, two, three or four heteroatoms, preferably one or two heteroatoms independently selected from oxygen, nitrogen and sulfur or to a bicyclic unsaturated ring system containing up to 10 atoms including at least one one heteroatom selected from oxygen, nitrogen and sulfur. Examples of hetaryls include, but are not limited to, 2-, 3- or 4-pyridinyl, pyrazinyl, 2-, 4-, or 5-pyrimidinyl, pyridazinyl, triazolyl, tetrazolyl, imidazolyl, 2- or 3-thienyl, 2- or 3-furyl, pyrrolyl, oxazolyl, isoxazolyl, thiazolyl, isothiazolyl, oxadiazolyl, thiadiazolyl, quinolyl, isoquinolyl, benzimidazolyl, benzotriazolyl, benzofuranyl, and benzothienyl. The heterocyclic ring may be optionally substituted with up to two substituents.

The terms "aryl-alkyl" or "arylalkyl" are used to describe a group wherein the alkyl chain can be branched or straight chain with the aryl portion, as defined hereinbefore, forming a bridging portion of the aryl-alkyl moiety. Examples of aryl-alkyl groups include, but are not limited to, optionally substituted benzyl, phenethyl, phenpropyl and phenbutyl such as 4-chlorobenzyl, 2,4-dibromobenzyl, 2-methylbenzyl, 2-(3-fluorophenyl)ethyl, 2-(4-methylphenyl)ethyl, 2-(4-(trifluoromethyl)phenyl)ethyl, 2-(2-methoxyphenyl)ethyl, 2-(3-nitrophenyl)ethyl, 2-(2,4-dichlorophenyl)ethyl, 2-(3,5-dimethoxyphenyl)ethyl, 3-phenylpropyl, 3-(3-chlorophenyl)propyl, 3-(2-methylphenyl)propyl, 3-(4-methoxyphenyl)propyl, 3-(4-(trifluoromethyl)phenyl)propyl, 3-(2,4-dichlorophenyl)propyl, 4-phenylbutyl, 4-(4-chlorophenyl)butyl, 4-(2-methylphenyl)butyl, 4-(2,4-dichlorophenyl)butyl, 4-(2-methoxphenyl)butyl and 10-phenyldecyl.

The terms "aryl-cycloalkyl" or "arylcycloalkyl" are used to describe a group wherein the aryl group is attached to a cycloalkyl group, for example phenylcyclopentyl and the like.

The terms "aryl-alkenyl" or "arylalkenyl" are used to describe a group wherein the alkenyl chain can be branched or straight chain with the aryl portion, as defined hereinbefore, forming a bridging portion of the aralkenyl moiety, for example styryl(2-phenylvinyl), phenpropenyl and the like.

The terms "aryl-alkynyl" or "arylalkynyl" are used to describe a group wherein the alkynyl chain can be branched or straight chain with the aryl portion, as defined hereinbefore, forming a bridging portion of the aryl-alkynyl moiety, for example 3-phenyl-1-propynyl and the like.

The terms "aryl-oxy" or "aryloxy" are used to describe a terminal aryl group attached to a bridging oxygen atom. Typical aryl-oxy groups include phenoxy, 3,4-dichlorophenoxy and the like.

The terms "aryl-oxyalkyl" or "aryloxyalkyl" are used to describe a group wherein an alkyl group is substituted with an aryl-oxy group, for example pentafluorophenoxymethyl and the like.

The terms "hetaryl-oxy" or "heteroaryl-oxy" or "hetaryloxy" or "heteroaryloxy" are used to describe a terminal hetaryl group attached to a bridging oxygen atom. Typical hetaryl-oxy groups include 4,6-dimethoxypyrimidin-2-yloxy and the like.

The terms "hetarylalkyl" or "heteroarylalkyl" or "hetarylalkyl" or "heteroaryl-alkyl" are used to describe a group wherein the alkyl chain can be branched or straight chain with the heteroaryl portion, as defined hereinbefore, forming a bridging portion of the heteroaralkyl moiety, for example 3-furylmethyl, thenyl, furfuryl and the like.

The terms "hetarylalkenyl" or "heteroarylalkenyl" or "hetaryl-alkenyl" or "heteroaryl-alkenyl" are used to describe a group wherein the alkenyl chain can be branched or straight chain with the heteroaryl portion, as defined hereinbefore, forming a bridging portion of the heteroaralkenyl moiety, for example 3-(4-pyridyl)-1-propenyl.

The terms "hetarylalkynyl" or "heteroarylalkynyl" or "hetaryl-alkynyl" or "heteroaryl-alkynyl" are used to describe a group wherein the alkynyl chain can be branched or straight chain with the heteroaryl portion, as defined hereinbefore, forming a bridging portion of the heteroaralkynyl moiety, for example 4-(2-thienyl)-1-butynyl.

The term "heterocyclyl" refers to a substituted or unsubstituted 3-10 membered saturated ring containing one, two or three heteroatoms, preferably one or two heteroatoms independently selected from oxygen, nitrogen and sulfur or to a bicyclic ring system containing up to 10 atoms including at least one heteroatom selected from oxygen, nitrogen and sulfur wherein the ring containing the heteroatom is saturated. Examples of heterocyclyls include, but are not limited to, tetrahydrofuranyl, tetrahydrofuryl, pyrrolidinyl, piperidinyl, 4-pyranyl, tetrahydropyranyl, thiolanyl, morpholinyl, piperazinyl, dioxolanyl, dioxanyl, indolinyl and 5-methyl-6-chromanyl.

The terms "heterocyclylalkyl" or "heterocyclyl-alkyl" are used to describe a group wherein the alkyl chain can be branched or straight chain with the heterocyclyl portion, as defined hereinabove, forming a bridging portion of the heterocyclylalkyl moiety, for example 3-piperidinylmethyl and the like.

The terms "heterocyclylalkenyl" or "heterocyclyl-alkenyl" are used to describe a group wherein the alkenyl chain can be branched or straight chain with the heterocyclyl portion, as defined hereinbefore, forming a bridging portion of the heterocyclylalkenyl moiety, for example 2-morpholinyl-1-propenyl.

The terms "heterocyclylalkynyl" or "heterocyclyl-alkynyl" are used to describe a group wherein the alkynyl chain can be branched or straight chain with the heterocyclyl portion, as defined hereinbefore, forming a bridging portion of the heterocyclylalkynyl moiety, for example 2-pyrrolidinyl-1-butynyl.

The term "carboxylalkyl" includes both branched and straight chain alkyl groups as defined hereinbefore attached to a carboxyl (—COOH) group.

The term "carboxylalkenyl" includes both branched and straight chain alkenyl groups as defined hereinbefore attached to a carboxyl (—COOH) group.

The term "carboxylalkynyl" includes both branched and straight chain alkynyl groups as defined hereinbefore attached to a carboxyl (—COOH) group.

The term "carboxylcycloalkyl" refers to a carboxyl (—COOH) group attached to a cyclic aliphatic ring structure as defined hereinbefore.

The term "carboxylcycloalkenyl" refers to a carboxyl (—COOH) group attached to a cyclic aliphatic ring structure having 1 or 2 ethylenic bonds as defined hereinbefore.

The terms "cycloalkylalkyl" or "cycloalkyl-alkyl" refer to a cycloalkyl group as defined hereinbefore attached to an alkyl group, for example cyclopropylmethyl, cyclohexylethyl and the like.

The terms "cycloalkylalkenyl" or "cycloalkyl-alkenyl" refer to a cycloalkyl group as defined hereinbefore attached to an alkenyl group, for example cyclohexylvinyl, cycloheptylallyl and the like.

The terms "cycloalkylalkynyl" or "cycloalkyl-alkynyl" refer to a cycloalkyl group as defined hereinbefore attached to an alkynyl group, for example cyclopropylpropargyl, 4-cyclopentyl-2-butynyl and the like.

The terms "cycloalkenylalkyl" or "cycloalkenyl-alkyl" refer to a cycloalkenyl group as defined hereinbefore attached to an alkyl group, for example 2-(cyclopenten-1-yl)ethyl and the like.

The terms "cycloalkenylalkenyl" or "cycloalkenyl-alkenyl" refer to a cycloalkenyl group as defined hereinbefore attached to an alkenyl group, for example 1-(cyclohexen-3-yl)allyl and the like.

The terms "cycloalkenylalkynyl" or "cycloalkenyl-alkynyl" refer to a cycloalkenyl group as defined hereinbefore attached to an alkynyl group, for example 1-(cyclohexen-3-yl)propargyl and the like.

The term "carboxylcycloalkylalkyl" refers to a carboxyl (—COOH) group attached to the cycloalkyl ring portion of a cycloalkylalkyl group as defined hereinbefore.

The term "carboxylcycloalkylalkenyl" refers to a carboxyl (—COOH) group attached to the cycloalkyl ring portion of a cycloalkylalkenyl group as defined hereinbefore.

The term "carboxylcycloalkylalkynyl" refers to a carboxyl (—COOH) group attached to the cycloalkyl ring portion of a cycloalkylalkynyl group as defined hereinbefore.

The term "carboxylcycloalkenylalkyl" refers to a carboxyl (—COOH) group attached to the cycloalkenyl ring portion of a cycloalkenylalkyl group as defined hereinbefore.

The term "carboxylcycloalkenylalkenyl" refers to a carboxyl (—COOH) group attached to the cycloalkenyl ring portion of a cycloalkenylalkenyl group as defined hereinbefore.

The term "carboxylcycloalkenylalkynyl" refers to a carboxyl (—COOH) group attached to the cycloalkenyl ring portion of a cycloalkenylalkynyl group as defined hereinbefore.

The term "alkoxy" includes both branched and straight chain terminal alkyl groups attached to a bridging oxygen atom. Typical alkoxy groups include methoxy, ethoxy, n-propoxy, isopropoxy, tert-butoxy and the like.

The term "haloalkoxy" refers to an alkoxy group substituted with one or more halo groups, for example chloromethoxy, trifluoromethoxy, difluoromethoxy, perfluoroisobutoxy and the like.

The term "alkoxyalkoxyalkyl" refers to an alkyl group substituted with an alkoxy moiety which is in turn substituted with a second alkoxy moiety, for example methoxymethoxymethyl, isopropoxymethoxyethyl and the like.

The term "alkylthio" includes both branched and straight chain alkyl groups attached to a bridging sulfur atom, for example methylthio.

The term "haloalkylthio" refers to an alkylthio group substituted with one or more halo groups, for example trifluoromethylthio.

The term "alkoxyalkyl" refers to an alkyl group substituted with an alkoxy group, for example isopropoxymethyl.

The term "alkoxyalkenyl" refers to an alkenyl group substituted with an alkoxy group, for example 3-methoxyallyl.

The term "alkoxyalkynyl" refers to an alkynyl group substituted with an alkoxy group, for example 3-methoxypropargyl.

The term "alkoxycarbonylalkyl" refers to a straight chain or branched alkyl substituted with an alkoxycarbonyl, for example ethoxycarbonylmethyl, 2-(methoxycarbonyl)propyl and the like.

The term "alkoxycarbonylalkenyl" refers to a straight chain or branched alkenyl as defined hereinbefore substituted with an alkoxycarbonyl, for example 4-(ethoxycarbonyl)-2-butenyl and the like.

The term "alkoxycarbonylalkynyl" refers to a straight chain or branched alkynyl as defined hereinbefore substituted with an alkoxycarbonyl, for example 4-(ethoxycarbonyl)-2-butynyl and the like.

The term "haloalkoxyalkyl" refers to a straight chain or branched alkyl as defined hereinbefore substituted with a haloalkoxy, for example 2-chloroethoxymethyl, trifluoromethoxymethyl and the like.

The term "haloalkoxyalkenyl" refers to a straight chain or branched alkenyl as defined hereinbefore substituted with a haloalkoxy, for example 4-(chloromethoxy)-2-butenyl and the like.

The term "haloalkoxyalkynyl" refers to a straight chain or branched alkynyl as defined hereinbefore substituted with a haloalkoxy, for example 4-(2-fluoroethoxy)-2-butynyl and the like.

The term "alkylthioalkyl" refers to a straight chain or branched alkyl as defined hereinbefore substituted with an alkylthio group, for example methylthiomethyl, 3-(isobutylthio)heptyl and the like.

The term "alkylthioalkenyl" refers to a straight chain or branched alkenyl as defined hereinbefore substituted with an alkylthio group, for example 4-(methylthio)-2-butenyl and the like.

The term "alkylthioalkynyl" refers to a straight chain or branched alkynyl as defined hereinbefore substituted with an alkylthio group, for example 4-(ethylthio)-2-butynyl and the like.

The term "haloalkylthioalkyl" refers to a straight chain or branched alkyl as defined hereinbefore substituted with an haloalkylthio group, for example 2-chloroethylthiomethyl, trifluoromethylthiomethyl and the like.

The term "haloalkylthioalkenyl" refers to a straight chain or branched alkenyl as defined hereinbefore substituted with an haloalkylthio group, for example 4-(chloromethylthio)-2-butenyl and the like.

The term "haloalkylthioalkynyl" refers to a straight chain or branched alkynyl as defined hereinbefore substituted with a haloalkylthio group, for example 4-(2-fluoroethylthio)-2-butynyl and the like.

The term "dialkoxyphosphorylalkyl" refers to two straight chain or branched alkoxy groups as defined hereinbefore attached to a pentavalent phosphorous atom, containing an oxo substituent, which is in turn attached to an alkyl, for example diethoxyphosphorylmethyl.

The term "oligomer" refers to a low-molecular weight polymer, whose number average molecular weight is typically less than about 5000 g/mol, and whose degree of polymerization (average number of monomer units per chain) is greater than one and typically equal to or less than about 50.

Compounds described herein contain one or more asymmetric centers and may thus give rise to diastereomers and optical isomers. The present invention includes all such possible diastereomers as well as their racemic mixtures, their substantially pure resolved enantiomers, all possible geometric isomers, and pharmaceutically acceptable salts thereof. The above Formula I is shown without a definitive stereochemistry at certain positions. The present invention includes all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

Within the enantiomers of the compounds, both the syn and anti isomers involving the X and $G^1$ substituent show activity. It was found that the syn isomer is more active than the anti isomer and thus, is the preferred isomer. Furthermore, it is preferable that there be dual chiral centers at the X and $G^1$ attachment positions.

The invention also encompasses a pharmaceutical composition that is comprised of a compound of Formula I in combination with a pharmaceutically acceptable carrier.

Preferably the composition is comprised of a pharmaceutically acceptable carrier and a non-toxic therapeutically effective amount of a compound of Formula I as described above (or a pharmaceutically acceptable salt thereof).

Moreover, within this preferred embodiment, the invention encompasses a pharmaceutical composition for the treatment of disease by inhibiting the cytochrome P450RAI enzyme, resulting in regulation and differentiating of epithelial cells, comprising a pharmaceutically acceptable carrier and a non-toxic therapeutically effective amount of compound of Formula I as described above (or a pharmaceutically acceptable salt thereof).

The term "pharmaceutically acceptable salts" refers to salts prepared from pharmaceutically acceptable non-toxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium slats. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosphoric, sulfuric and tartaric acids. Particularly preferred are formic and hydrochloric acid.

The pharmaceutical compositions of the present invention comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration. e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

For example, a formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, dermatological diseases and cancers may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

Biological Assays

The efficacy of the Examples of the invention, compounds of Formula I, as inhibitors of Cyp26 were demonstrated and confirmed by a number of pharmacological in vitro assays. The following assays and their respective methods have been carried out with the compounds according to the invention. Activity possessed by compounds of Formula I may be demonstrated in vivo.

In vitro Biochemical Assay

The compounds of Formula I can inhibit CYP26 activity. In vitro biochemical assay was performed using microsomal preparations from T47D cells induced to express CYP26. Enzymatic activity was measured as the conversion of the radiolabeled substrate to its metabolites, 4-OH RA (4-hydroxy all trans retinoic acid) and 4-oxo RA (4-oxy retinoic acid) by separation on a C18 HPLC column. Inhibition of CYP26 activity in the presence of variable naphthalene analog concentrations was used to determine the $IC_{50}$'s.

Methods

Microsomal Preparation from T47D Cells

T47D cells were grown in RPMI 1640 containing 10% FBS and 1% P/S, plated and treated 16-25 hours later with 5 uM atRA and allowed to incubate for an additional 48 hours before cell harvest. Cells were washed twice with 1×PBS and scraped from plates. Cells were pelleted and resuspended in homogenization buffer (0.1M Tris-Cl, pH7.4, 0.1M DTT, 0.2 mM EDTA, 1.15% w/v KCl, 0.1 mM PMSF and 20% v/v glycerol). Microsomes were prepared by differential centrifugation of homogenized cells. Homogenate was spun at 17,000 g and the supernatant spun again at 100,000 g. The pellet was resuspended in 25 mM potassium phosphate, pH7.4, 20% v/v glycerol and stored at −80° C.

HPLC Biochemical CYP26 Assay

Enzymatic assays were performed in a total volume of 100 μL in a reaction mixture composed of 100 mM Tris pH7.4, 150 mM KCl, 10 mM $MgCl_2$, 2 mM NADPH, 40 nM 3H-atRA, and varying concentrations of novel compound dissolved in DMSO such that the concentration in the reaction is 1% final, and 20 μg of T47D microsomes. The reactions were incubated at 37° C. for 30 min in the dark. The reaction was stopped by the addition of 125 μL of acetonitrile, mixed and spun at 10,000 g for 10 min. The supernatant was removed and atRA and metabolites were separated on a C18 Waters Spherisorb column with an in line radiometric detector with a flow rate of 1 m/min at detected at 350 nM. The gradient used was the mixture of 60 mM Ammonium Acetate, pH 5.2/30%$CH_3OH$, solvent A and solvent B ($CH_3OH$). A 30-50% gradient of $CH_3OH$ was run for 8 min followed by a 50-99% $CH_3OH$ gradient for 4 min and 99% $CH_3OH$ for 2 min.

Inhibition of Cell Proliferation In vitro

The novel naphthalene analogs inhibit the proliferation of breast cancer and prostate cells in vitro. Experiments were conducted on T47D breast cancer cell line and on the AT6.1 rat prostate adenocarcinoma cell line.

Methods

T47D cells were grown in RPMI 1640 containing 10% FBS and 1% P/S. Cells were plated into 96 well culture plates (2000 cells per well) in 100 μL of same medium. After attachment for 16-24 h, the vehicle (DMSO), or atRA alone (at concentrations of 1 nM to 1 μM), or atRA at these concentrations in combination with varying concentration of novel compound were added to triplicate wells (*J. Biol. Chem.* 1997, 272(29), 17921-17928). Medium/treatments were repeated 3 days after the first treatment and measure of the decrease in cell proliferation was measured 48 hours later using CellTiter-Glo™ (Promega).

The method described above was also used for AT6.1 cells except that cells were plated at 1500 cells per well and treatment was performed once with measure of the decrease in cell proliferation 72 h post treatment. AT6.1 cells were grown in RPMI 1640 containing 10% FBS, 1% P/S and 250 nM Dexamethasone.

CYP3A4 Assay

Enzymatic assays to measure the inhibition of CYP3A4 activity was determined in 100 ul volume in a 96 well plate by the use of a fluorescence substrate (BD, Gentest). Compounds were tested at various concentrations in a reaction that contained 200 mM Potassium Phosphate buffer, pH 7.4, 200 mM NADPH and 50 uM 7-benzyloxy-4-(trifluoromethyl)-coumarin. The reaction was incubated at 37° C. for 45 minutes followed by the addition of 37 ul of 0.5M Tris Base to terminate the reaction. The plates were read at excitation/emission of 405/535 nm, respectively.

All Examples showed inhibition of Cyp26. The following Examples showed efficacy and activity by inhibiting Cyp26 in the biochemical assay in the range from about 5 μM to below 10 nM. The most preferred Examples are selective towards Cyp26. It is preferred that the ratio of the $IC_{50}$ value of Cyp3A4 activity to the $IC_{50}$ value of Cyp26 activity of 10:1 or greater, or 100:1 or greater.

EXPERIMENTAL

In Schemes 1-29 below showing how to synthesize compounds of this invention and Tables 1-5 below listing various representative compounds of this invention, the following abbreviations are used: Me for methyl, Et for ethyl, $^i$Pr or $^i$Pr for isopropyl, n-Bu for n-butyl, t-Bu for tert-butyl, Ac for acetyl, Ph for phenyl, 4Cl-Ph or (4Cl)Ph for 4-chlorophenyl, 4Me-Ph or (4Me)Ph for 4-methylphenyl, (p-$CH_3O$)Ph for p-methoxyphenyl, (p-$NO_2$)Ph for p-nitrophenyl, 4Br-Ph or (4Br)Ph for 4-bromophenyl, 2-$CF_3$-Ph or (2$CF_3$)Ph for 2-trifluoromethylphenyl, DMAP for 4-(dimethylamino)pyridine, DCC for 1,3-dicyclohexylcarbodiimide, EDC for 1-(3-dimethylaminopropyl)-3-ethylcarbodiimide hydrochloride, HOBt for 1-hydroxybenzotriazole, HOAt for 1-hydroxy-7-azabenzotriazole, CDI for 1,1'-carbonyldiimidazole, CDT for 1,1'-carbonyldi(1,2,4-triazole), DEAD for diethyl azodicarboxylate, DIAD for diisopropyl azodicarboxylate, DBAD for di-tert-butyl azodicarboxylate, FBS for fetal bovine serum, P/S for Penicillin/Streptomycin, DTT for dithiothreitol, EDTA for ethylenediaminetetraacetic acid, PMSF for phenylmethanesulfonyl fluoride, Tris for trimethamine, NADPH for beta nicotinamide adenine dinucleotide phosphate reduced, and Bn for benzyl.

The following schematic processes show certain compounds which are useful as intermediates in the formation of Cyp26 inhibiting Examples. Such intermediates are included in the present invention.

The compounds of Formula I of this invention and the intermediates used in the synthesis of the compounds of this invention were prepared according to the following methods. Method A was used when preparing compounds of Formula I-A [compounds of Formula I where $R^1$ equals H; $R^{4a}$, $R^{5a}$, $R^{6a}$ and $R^{6b}$ equal H; and Y equals O] as shown below in Scheme 1:

Method A:

Scheme 1

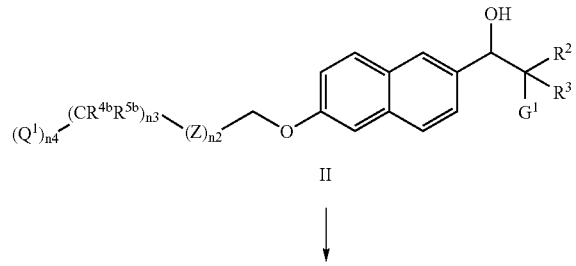

II

-continued

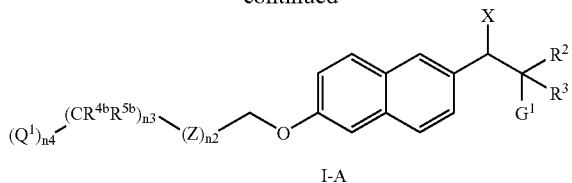

I-A where X, $R^2$, $R^3$, $G^1$, $(Z)_{n2}$, $(CR^{4b}R^{5b})_{3n}$, and $(Q^1)_{n4}$, are as defined previously for compound of Formula I.

In a typical preparation, a compound of Formula II was reacted with CDI or CDT in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; and chlorinated solvents such as methylene chloride ($CH_2Cl_2$) or chloroform ($CHCl_3$). If desired, mixtures of these solvents were used. The preferred solvent was dependent upon the substrates employed and was selected according to the properties of the substrates. The above process was carried out at temperatures between about −78° C. and about 100° C. Preferably, the reaction was carried out between 22° C. and about 80° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula II of Scheme 1 were prepared as shown below in Scheme 2.

Scheme 2

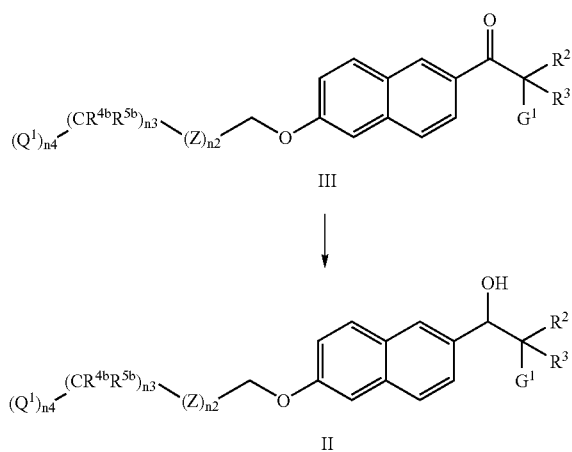

where $R^2$, $R^3$, $G^1$, $(Z)_{n2}$, $(CR^{4b}R^{5b})_{n3}$, and $(Q^1)_{n4}$, are as defined previously for compound of Formula I.

In a typical preparation of a compound of Formula II, a compound of Formula III was treated with a suitable reducing agent in a suitable solvent, where the suitable reducing agents included boron-derived reducing agents such as, but not limited to, sodium borohydride, lithium borohydride, borane, and the like; aluminum-derived reducing agents such as lithium aluminum hydride, alane, lithium tri-tert-butoxy-aluminum hydride, and the like; hydrogenation over a metal catalyst such as palladium on carbon. The preferred reducing agent was sodium borohydride. Suitable solvents for use in the above process included, but were not limited to, ethers such as tetrahydrofuran (THF), glyme, and the like; alcoholic solvents such as methanol, ethanol, isopropanol, and the like; however, the reactions were normally in methanol. The above process was carried out at temperatures between about −78° C. and about 100° C. Preferably, the reaction was carried out between 0° C. and about 20° C. The above process to produce compounds of the present invention was preferably carried out at about atmospheric pressure although higher or lower pressures could be used if desired. Substantially, equimolar amounts of reactants were preferably used although higher or lower amounts could be used if desired.

The compounds of Formula III of Scheme 2 were prepared as shown below in Scheme 3:

Scheme 3

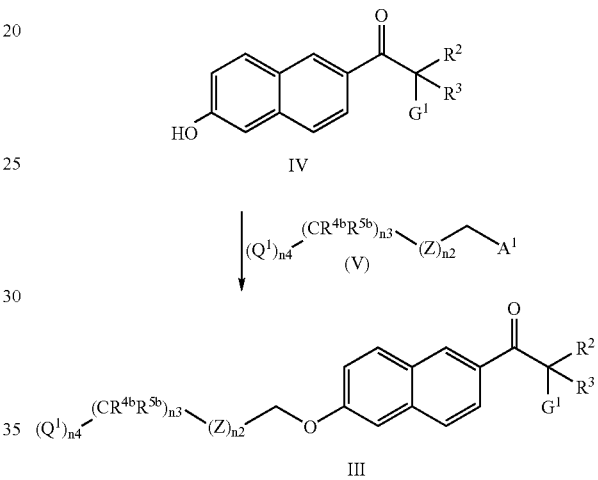

where $R^2$, $R^3$, $G^1$, $(Z)_{n2}$, $(CR^{4b}R^{5b})_{n3}$, and $(Q^1)_{n4}$, are as defined previously for compound of Formula I, and $A^1$=OH, OTs, OMs or halo.

In a typical preparation of a compound of Formula III (when $A^1$=halo in compound of Formula V), a compound of Formula IV was reacted with a compound of Formula V (where $A^1$=halo) in a suitable solvent in the presence of a suitable base. Suitable solvents for use in the above process include, but are not limited to, ethers such as tetrahydrofuran (THF), glyme, and the like; dimethylformamide (DMF); dimethyl sulfoxide (DMSO); acetonitrile ($CH_3CN$); chlorinated solvents such as methylene chloride ($CH_2Cl_2$) or chloroform ($CHCl_3$). If desired, mixtures of these solvents may be used. The preferred solvent was DMF or $CH_3CN$. Suitable bases for use in the above process included, but were not limited to, metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases were used. The preferred base was sodium hydride or potassium tert-butoxide. The above process was carried out at temperatures between about −78° C. and about 100° C. Preferably, the reaction was carried out between 0° C. and about 50° C. The above process to produce compounds of the present invention was preferably carried out at about atmospheric pressure although higher or lower pressures could be used if desired. Substantially, equimolar amounts of reactants were preferably used although higher or lower amounts were used if desired. Generally, one equivalent of base was used per equivalent of starting material of compound of Formula IV.

In a typical preparation of a compound of Formula III (when $A^1$=OH in compound of Formula V), a compound of Formula IV was reacted with a compound of Formula V (where $A^1$=OH) in a suitable solvent in the presence suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); chlorinated solvents such as methylene chloride ($CH_2Cl_2$) or chloroform ($CHCl_3$). If desired, mixtures of these solvents were used, however, the preferred solvent was THF. Suitable reactants for use in the above process included, but were not limited to, triphenylphosphine and an azodicarboxylate (DIAD, DEAD, DBAD). The desired reactants were triphenylphosphine and DIAD. The above process was carried out at temperatures between about $-78°$ C. and about $100°$ C. Preferably, the reaction was carried out between $0°$ C. and about $50°$ C. The above process to produce compounds of the present invention was preferably carried out at about atmospheric pressure although higher or lower pressures were used if desired. Substantially, equimolar amounts of reactants were preferably used although higher or lower amounts were used if desired. Generally, one equivalent of triphenylphosphine, DIAD and compound of formula V was used per equivalent of starting material of compound of Formula IV. The compounds of Formula V were generally commercially available or were prepared according to known procedures (*Tetrahedron Letters*, 1999, 40, 5467-5470).

The compounds of Formula IV of Scheme 3 were prepared as shown below in Scheme 4:

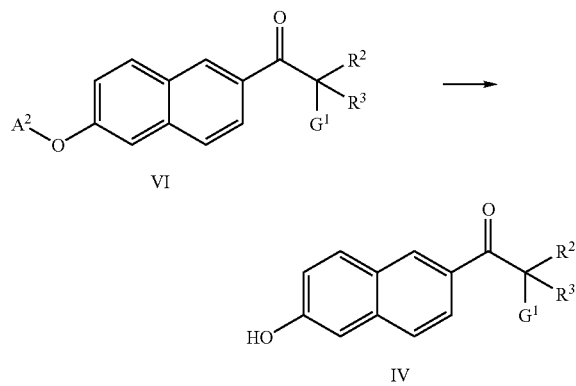

where $R^2$, $R^3$, and $G^1$ are as defined previously for compound of Formula I, and $A^2$=$C_{1-6}$alkyl or aryl-$C_{1-6}$alkyl.

In a typical preparation of a compound of Formula IV, a compound of Formula VI was reacted with suitable conditions to afford the conversion of $A^2$ to H. Suitable reagents for use in the conversion of $A^2$ to H in the above process included but were not limited to, pyridine-HCl, $BBr_3$, $AlCl_3$, and HBr/Acetic acid. The preferred condition was treatment of compound of Formula VI with 48% $_{aq}$HBr/acetic acid. The above process was carried out at temperatures between about $50°$ C. and about $150°$ C. Preferably, the reaction was carried out between $100°$ C. and about $120°$ C. The above process to produce compounds of the present invention was preferably carried out at about atmospheric pressure although higher or lower pressures were used if desired. Substantially, equimolar amounts of reactants were preferably used although higher or lower amounts were used if desired. Generally, an excess of 48% $_{aq}$HBr/acetic acid was used per equivalent of starting material of compound of Formula VIII.

The compounds of Formula VI of Scheme 4 were prepared as shown below in Scheme 5:

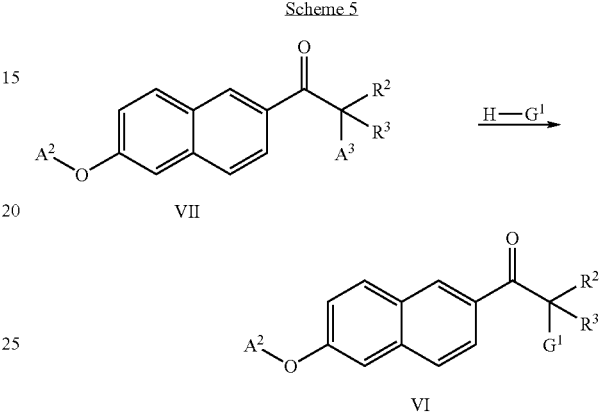

where $R^2$, $R^3$, and $G^1$ are as defined previously for compound of Formula I, $A^2$=$C_{1-6}$alkyl or aryl-$C_{1-6}$alkyl, and $A^3$=suitable leaving group such as halo.

In a typical preparation of a compound of Formula VI, a compound of Formula VII was reacted with H-$G^1$ in a suitable solvent in the presence of a suitable base. Suitable solvents for use in the above process included, but were not limited to, ethers such as tetrahydrofuran (THF), glyme, diethyl ether, dioxane and the like; aromatic solvents such as benzene and toluene; acetonitrile; chlorinated solvents such as methylene chloride ($CH_2Cl_2$), carbon tetrachloride ($CCl_4$) or chloroform ($CHCl_3$). If desired, mixtures of these solvents were used, however the preferred solvent was a mixture of methanol/chloroform. Suitable catalysts for use in the above process included, but were not limited to, tetrabutylammonium iodide or NaI. If desired, mixtures of these catalysts were used, however, the preferred catalyst was NaI. Suitable bases for use in the above process included, but were not limited to, metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases were used, however, the preferred base was diisopropylethylamine or H-$G^1$ when $G^1$=$NR^7R^8$. The above process were carried out at temperatures between about $-78°$ C. and about $100°$ C. Preferably, the reaction was carried out between $0°$ C. and about $100°$ C. The above process to produce compounds of the present invention was preferably carried out at about atmospheric pressure although higher or lower pressures were used if desired. Substantially, equimolar amounts of reactants were preferably used although higher or lower amounts were used if desired. The catalyst was normally used in lower amounts than that of both compounds of Formula VII and H-$G^1$. H-$G^1$ is generally commercially available or was prepared according to known procedures.

Compound of Formula VII was prepared according to known literature procedures (Sonawane, H. R.; et. al. *Tetrahedron*, 1994, 50 (4), 1243-1260).

The compounds of Formula VII of Scheme 5 were prepared as shown below in Scheme 6a:

Scheme 6a

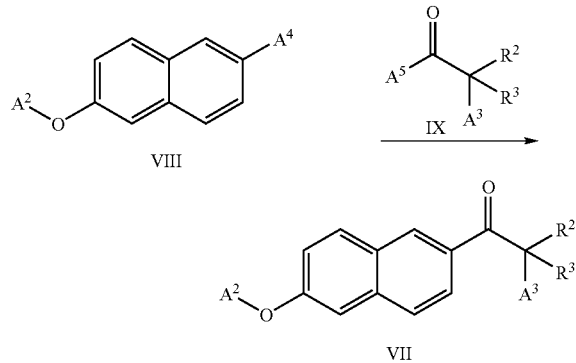

wherein $R^2$ and $R^3$ are as defined previously for compound of Formula I, $A^2=C_{1-6}$alkyl or aryl-$C_{1-6}$alkyl, and $A^3$ and $A^5$=suitable leaving groups such as halo, and $A^4$=halo or OTf.

In a typical preparation of a compound of Formula VII, a compound of Formula VIII was reacted with a suitable organolithium reagent or metal catalyst followed by reaction with a compound of Formula IX in a suitable solvent. Suitable solvents for use in the above process included, but were not limited to, ethers such as tetrahydrofuran (THF), glyme, diethyl ether, dioxane and the like; aromatic solvents such as benzene and toluene. If desired, mixtures of these solvents were used, however the preferred solvent was THF. Suitable organolithium or metal species for use in the above process included, but were not limited to organolithium species such as n-butyl lithium or tert-butyl lithium; magnesium. The preferred metal catalyst was magnesium. The above process was carried out at temperatures between about −78° C. and about 100° C. Preferably, the reaction was carried out between 0° C. and about 100° C. The above process to produce compounds of the present invention was preferably carried out at about atmospheric pressure although higher or lower pressures could used if desired. Substantially, equimolar amounts of reactants were preferably used although higher or lower amounts were used if desired. The magnesium was normally used in excess amounts than that of compounds of Formula VIII. Compounds of Formula VIII and IX were generally commercially available or were prepared according to known procedures.

Alternatively, the compounds of Formula VI of Scheme 5 were prepared as shown below in Scheme 6b:

Scheme 6b

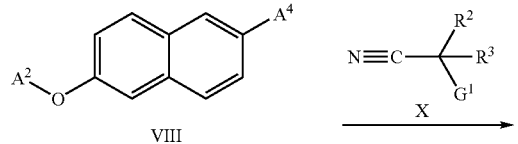

-continued

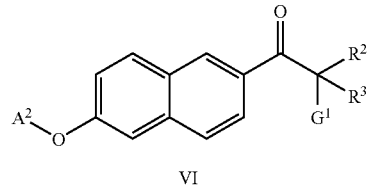

where $R^2$, $R^3$ and $G^1$ are as defined previously for compound of Formula I, $A^2=C_{1-6}$alkyl or aryl-$C_{1-6}$alkyl, and $A^4$=halo or OTf.

In a typical preparation of a compound of Formula VI, a compound of Formula VIII was reacted with a suitable organolithium reagent or metal catalyst followed by reaction with a compound of Formula X in a suitable solvent. Suitable solvents for use in the above process included, but were not limited to, ethers such as tetrahydrofuran (THF), glyme, diethyl ether, dioxane and the like; aromatic solvents such as benzene and toluene. If desired, mixtures of these solvents were used, however the preferred solvent was THF. Suitable organolithium or metal species for use in the above process included, but were not limited to organolithium species such as n-butyl lithium or tert-butyl lithium; magnesium. The preferred organolithium species was tert-butyl lithium. The above process was carried out at temperatures between about −78° C. and about 100° C. Preferably, the reaction was carried out between −78° C. and about 50° C. The above process to produce compounds of the present invention was preferably carried out at about atmospheric pressure although higher or lower pressures were used if desired. Substantially, equimolar amounts of reactants were preferably used although higher or lower amounts were used if desired. Compounds of Formula VIII and X were generally commercially available or were prepared according to known procedures.

The compounds of Formula III of this invention and the intermediates used in the synthesis of the compounds of this invention were prepared according to the following methods.

Method B was used when preparing compounds of Formula III as shown below in Scheme 7:

Method B:

Scheme 7

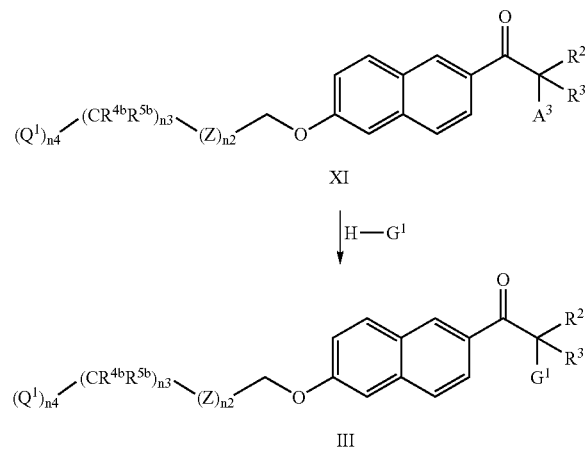

where $R^2$, $R^3$, $G^1$, $(Z)_{n2}$, $(CR^{4b}R^{5b})_{n3}$, and $(Q^1)_{n4}$, are as defined previously for compound of Formula I, and $A^3$=halo.

In a typical preparation, according to Method B, Scheme 7, of a compound of Formula III, a compound of Formula XI was reacted with H-$G^1$ in a suitable solvent in the presence of a suitable base. Suitable solvents for use in the above process included, but were not limited to, ethers such as tetrahydrofuran (THF), glyme, diethyl ether, dioxane and the like; aromatic solvents such as benzene and toluene; acetonitrile; chlorinated solvents such as methylene chloride ($CH_2Cl_2$), carbon tetrachloride ($CCl_4$) or chloroform ($CHCl_3$). If desired, mixtures of these solvents were used, however the preferred solvent was a mixture of acetonitrile. Suitable catalysts for use in the above process include, but are not limited to, tetrabutylammonium iodide or NaI. If desired, mixtures of these catalysts were used, however, the preferred catalyst was NaI. Suitable bases for use in the above process included, but were not limited to, metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases were used, however, the preferred base was diisopropylethylamine or H-$G^1$ when $G^1$=$NR^7R^8$. The above process was carried out at temperatures between about −78° C. and about 100° C. Preferably, the reaction was carried out between 0° C. and about 100° C. The above process to produce compounds of the present invention was preferably carried out at about atmospheric pressure although higher or lower pressures were used if desired. Substantially, equimolar amounts of reactants were preferably used although higher or lower amounts were used if desired. The catalyst was normally used in lower amounts than that of both compounds of Formula XI and H-$G^1$. H-$G^1$ is generally commercially available or was prepared according to known procedures.

The compounds of Formula XI of Scheme 7 was prepared as shown below in Scheme 8:

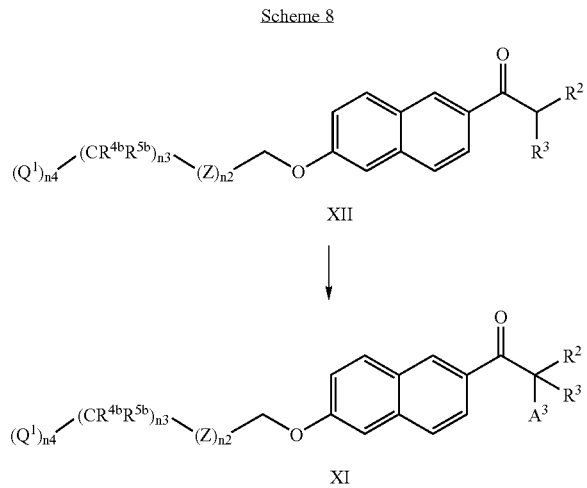

where $R^2$, $R^3$, $(Z)_{n2}$, $(CR^{4b}R^{5b})_{n3}$, and $(Q^1)_{n4}$, are as defined previously for compound of Formula I, and $A^3$=halo.

In a typical preparation of a compound of Formula XI, a compound of Formula XII was reacted with a suitable halogenating agent in a suitable solvent. Suitable halogenating agents include $Br_2$, $Cl_2$, N-bromosuccinimide, N-chlorosuccinimide, sulfuryl chloride, and $CuBr_2$. Suitable solvents for use in the above process included, but were not limited to, ethers such as tetrahydrofuran (THF), dioxane, glyme, diethyl ether, and the like; acetonitrile; chlorinated solvents such as methylene chloride ($CH_2Cl_2$) or chloroform ($CHCl_3$). If desired, mixtures of these solvents were used, however, the preferred solvent was dioxane. The above process was carried out at temperatures between about −78° C. and about 150° C. Preferably, the reaction was carried out between 80° C. and about 150° C. The above process to produce compounds of the present invention was preferably carried out at about atmospheric pressure although higher or lower pressures were used if desired. Substantially, equimolar amounts of reactants were preferably used although higher or lower amounts were used if desired. Generally, two equivalents of $CuBr_2$ were used per equivalent of starting material of compound of Formula XII.

The compounds of Formula XII of Scheme 8 were prepared as shown below in Scheme 9:

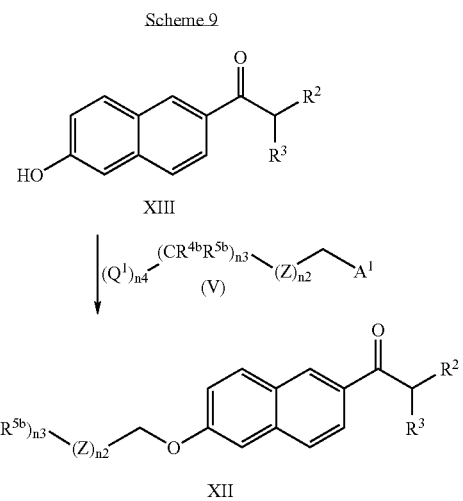

where $R^2$, $R^3$, $(Z)_{n2}$, $(CR^{4b}R^{5b})_{n3}$, and $(Q^1)_{n4}$, are as defined previously for compound of Formula I, and $A^1$=halo or OH.

In a typical preparation of a compound of Formula XII (when $A^1$ in compound of Formula V equals halo), a compound of Formula XIII was reacted with a compound of Formula V (where $A^1$=halo) in a suitable solvent in the presence of a suitable base. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); chlorinated solvents such as methylene chloride ($CH_2Cl_2$) or chloroform ($CHCl_3$). If desired, mixtures of these solvents were used. The preferred solvent was DMF or $CH_3CN$. Suitable bases for use in the above process included, but were not limited to, metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases were used. The preferred base was sodium hydride or potassium tert-butoxide. The above process was carried out at temperatures between about −78° C. and about 100° C. Preferably, the reaction was carried out between 0° C. and about 50° C. The above process to produce compounds of the present invention was preferably carried out at about atmospheric pressure although higher or lower pressures were used if desired. Substantially, equimolar amounts of reactants were preferably used although higher or lower amounts were used if desired. Generally, one equivalent of base was used per equivalent of starting material of compound of Formula XIII.

In a typical preparation of a compound of Formula XII (when $A^1$=OH in compound of Formula V), a compound of Formula XIII was reacted with a compound of Formula V (where $A^1$=OH) in a suitable solvent in the presence suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); chlorinated solvents such as methylene chloride ($CH_2Cl_2$) or chloroform ($CHCl_3$). If desired, mixtures of these solvents were used, however, the preferred solvent was THF. Suitable reactants for use in the above process included, but were not limited to, triphenylphosphine and an azodicarboxylate (DIAD, DEAD, DBAD). The desired reactants were triphenylphosphine and DIAD. The above process may be carried out at temperatures between about –78° C. and about 100° C. Preferably, the reaction was carried out between 0° C. and about 50° C. The above process to produce compounds of the present invention was preferably carried out at about atmospheric pressure although higher or lower pressures were used if desired. Substantially, equimolar amounts of reactants were preferably used although higher or lower amounts were used if desired. Generally, one equivalent of triphenylphosphine, DIAD and compound of formula V was used per equivalent of starting material of compound of Formula XIII. The compounds of Formula V and XIII were generally commercially available or were prepared according to known procedures.

Method C was used when preparing compounds of Formula I-B [compounds of Formula I where $R^1$ equals H, $n^1$=1, $R^{4a}$, $R^{5a}$, $R^{6a}$ and $R^{6b}$ equal H, Y equals O, $n^4$=1, and $Q^1$=$CO_2H$] as shown below in Scheme 10:

Method C:

Scheme 10

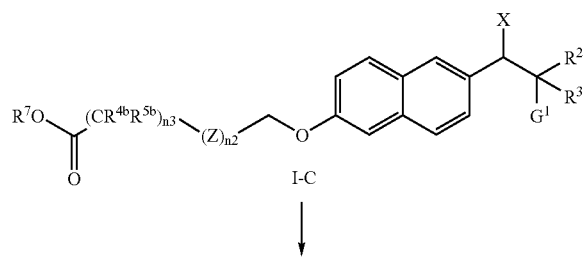

I-C

↓

-continued

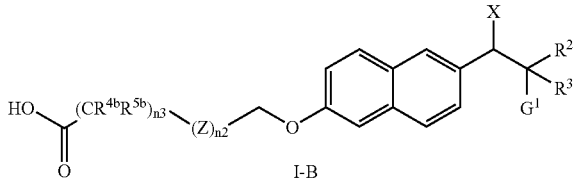

I-B where X, $R^2$, $R^3$, $G^1$, $(Z)_{n2}$, and $(CR^{4b}R^{5b})_{n3}$ are as defined previously for compound of Formula I, and $R^7$=alkyl.

In a typical preparation, according to Method C, of a compound of Formula I-B [compounds of Formula I where $R^1$ equals H, $n^1$=1, $R^{4a}$, $R^{5a}$, $R^{6a}$ and $R^{6b}$ equal H, Y equals O, $n^4$=1, and $Q^1$=$CO_2H$], a compound of Formula I-A [compounds of Formula I where $R^1$ equals H, $n^1$=1, $R^{4a}$, $R^{5a}$, $R^{6a}$ and $R^{6b}$ equal H, Y equals O, $n^4$=1, and $Q^1$=$CO_2R^7$] was reacted under basic or acidic conditions in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; alcoholic solvents such as methanol, ethanol, and the like. If desired, mixtures of these solvents were used, however the preferred solvent was a mixture of water, THF, and methanol. The basic conditions for use in the above process included alkoxides such as sodium or potassium alkoxides and alkali metal hydroxides such as sodium or potassium hydroxide in water. The acidic conditions for use in the above process included HCl in water. The above process was carried out at temperatures between about 0° C. and about 80° C. Preferably, the reaction was carried out between 22° C. and about 70° C. The above process to produce compounds of the present invention was preferably carried out at about atmospheric pressure although higher or lower pressures was used if desired. Substantially, equimolar amounts of reactants was preferably used although higher or lower amounts were used if desired.

Method D was used when preparing salts of compounds of Formula I-$(HA^6)_{n7}$ as shown below in Scheme 11:

Method D:

Scheme 11

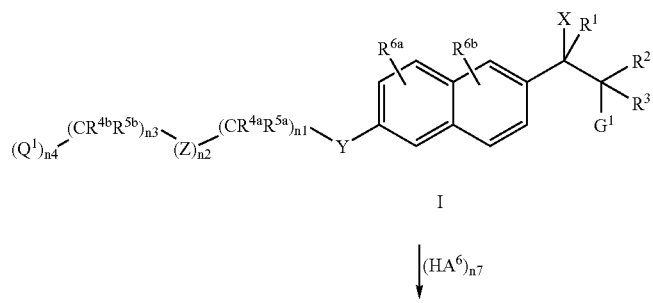

I

↓ $(HA^6)_{n7}$

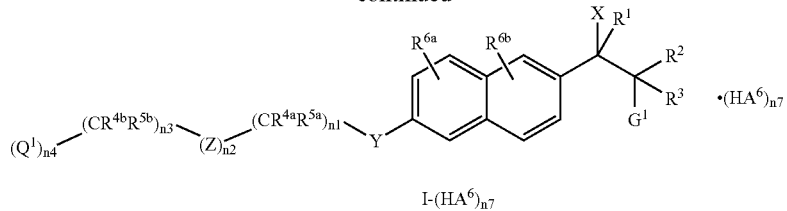

I-(HA$^6$)$_{n7}$ where X, R$^1$, R$^2$, R$^3$, G$^1$, Y, (CR$^{4a}$R$^{5a}$)$_{n1}$, (Z)$_{n2}$, (CR$^{4b}$R$^{5b}$)$_{n3}$, (Q$^1$)$_{n4}$, R$^{6a}$ and R$^{6b}$ are as defined previously for compound of Formula I, n$^7$=1 or 2, and A$^6$=counteranion to H including, for example, chloride or formate.

In a typical preparation, according to Method D, of a compound of Formula I-(HA$^6$)$_{n7}$, a compound of Formula I was reacted with a suitable acid, HA$^6$, in a suitable solvent. Suitable solvents for use in the above process included, but were not limited to, ethers such as tetrahydrofuran (THF), glyme, diethyl ether and the like; acetonitrile; water; alcoholic solvents such as methanol, ethanol, and the like. If desired, mixtures of these solvents were used, however, the preferred solvents were either diethyl ether, methanol, or water. HA$^6$ is a suitable pharmaceutically acceptable acid from which the respective mono or disalt of compound of Formula I-(HA$^6$)$_{n7}$ was formed. The above process was carried out at temperatures between about 0° C. and about 60° C. Preferably, the reaction was carried out between 0° C. and about 25° C. The above process to produce compounds of the present invention was preferably carried out at about atmospheric pressure although higher or lower pressures were used if desired. Substantially, equimolar amounts of reactants were preferably used although higher or lower amounts were used if desired. Acids HA$^6$ were generally commercially available or was be prepared according to known procedures.

Method E was used when preparing compounds of Formula I-D [compounds of Formula I where R$^1$ equals H, n$^1$=1, R$^{4a}$, R$^{5a}$, R$^{6a}$ and R$^{6b}$ equal H, Y equals O, n$^4$=1, and Q$^1$=CONR$^7$R$^8$] as shown below in Scheme 12:

Method E:

Scheme 12

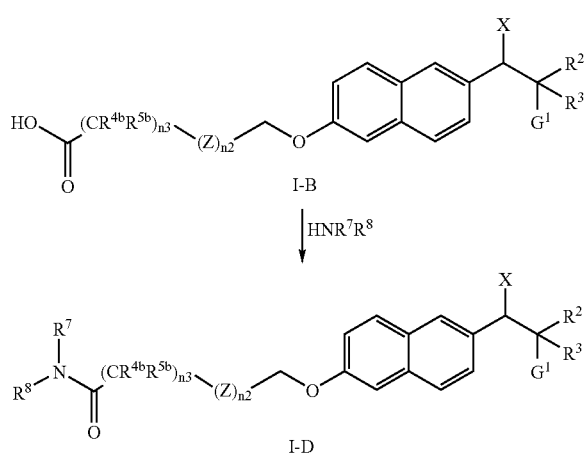

where X, R$^2$, R$^3$, G$^1$, (Z)$_{n2}$, R$^7$, R$^8$ and (CR$^{4b}$R$^{5b}$)$_{n3}$ are as defined previously for compound of Formula I.

In a typical preparation, according to Method E, of a compound of Formula I-D [compounds of Formula I where R$^1$ equals H, n$^1$=1, R$^{4a}$, R$^{5a}$, R$^{6a}$ and R$^{6b}$ equal H, Y equals O, n$^4$=1, and Q$^1$=CONR$^7$R$^8$], a compound of Formula I-B [compounds of Formula I where R$^1$ equals H, n$^1$=1, R$^{4a}$, R$^{5a}$, R$^{6a}$ and R$^{6b}$ equal H, Y equals O, n$^4$=1, and Q$^1$=CO$_2$H] was reacted under suitable conditions with HNR$^7$R$^8$ to afford compound of formula I-D. Suitable conditions included but were not limited to treating compound of Formula I-B with thionyl chloride, triphenylphosphine/carbon tetrachloride, CDI, or diphenylphosphorylazide to afford activated carbonyl species followed by treatment with HNR$^7$R$^8$. The preferred reaction condition was reaction of compound of Formula I-B with CDI followed by treatment with HNR$^7$R$^8$. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was acetonitrile. The above process was carried out at temperatures between about 0° C. and about 80° C. Preferably, the reaction was carried out between 22° C. and about 80° C. The above process to produce compounds of the present invention was preferably carried out at about atmospheric pressure although higher or lower pressures were used if desired. Substantially, equimolar amounts of reactants were preferably used although higher or lower amounts were used if desired.

Additionally, a typical preparation, according to Method E, of a compound of Formula I-D [compounds of Formula I where R$^1$ equals H, n$^1$=1, R$^{4a}$, R$^{5a}$, R$^{6a}$ and R$^{6b}$ equal H, Y equals O, n$^4$=1, and Q$^1$=CONR$^7$R$^8$], a compound of Formula I-B [compounds of Formula I where R$^1$ equals H, n$^1$=1, R$^{4a}$, R$^{5a}$, R$^{6a}$ and R$^{6b}$ equal H, Y equals O, n$^4$=1, and Q$^1$=CO$_2$H] was reacted under typical amide formation conditions to afford compound of Formula I-D. Suitable conditions include but are not limited to treating compound of Formula I-B and HNR$^7$R$^8$ with coupling reagents such as DCC or EDC in conjunction with DMAP, HOBt, HOAt and the like. Suitable solvents for use in the above process included, but were not limited to, ethers such as tetrahydrofuran (THF), glyme, and the like; dimethylformamide (DMF); dimethyl sulfoxide (DMSO); acetonitrile; halogenated solvents such as chloroform or methylene chloride. If desired, mixtures of these solvents were used, however the preferred solvent was DMF. The above process was carried out at temperatures between about 0° C. and about 80° C. Preferably, the reaction was carried out between 22° C. and about 80° C. The above process to produce compounds of the present invention was preferably carried out at about atmospheric pressure although higher or lower pressures were used if desired. Substantially, equimolar amounts of reactants were preferably used although higher or lower amounts were used if desired. Additionally, other suitable reaction conditions for the conversion of CO$_2$H to CONR$^7$R$^8$ can be found in Larock, R. C. *Comprehensive Organic Transformations*, 2$^{nd}$ ed.; Wiley and Sons: New York, 1999, pp 1941-1949.

Alternatively, the compounds of Formula II of Scheme 1 was prepared as shown in Scheme 13.

Scheme 13

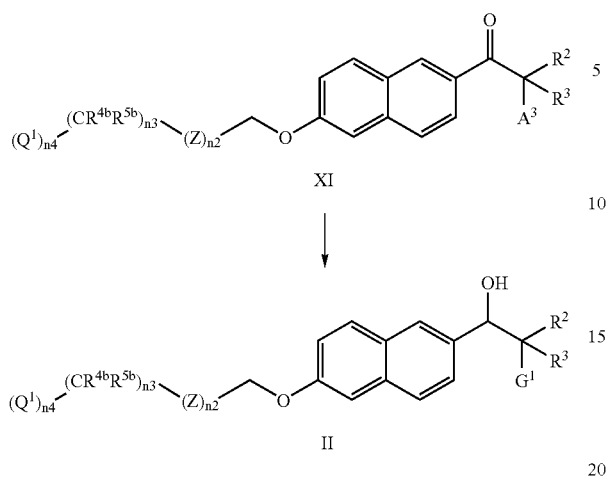

where $R^2$, $R^3$, $A^3$, $G^1$, $(Z)_{n2}$, $(CR^{4b}R^{5b})_{n3}$, and $(Q^1)_{n4}$, are as defined previously for compound of Formula I.

In a typical preparation of a compound of Formula II, a compound of Formula XI was treated with a suitable reducing agent in a suitable solvent, where the suitable reducing agents included boron-derived reducing agents such as but not limited to sodium borohydride, lithium borohydride, borane, and the like; aluminum-derived reducing agents such as lithium aluminum hydride, alane, lithium tri-tert-butoxy-aluminum hydride, and the like; hydrogenation over a metal catalyst such as palladium on carbon. However, the preferred reducing agent was sodium borohydride. Suitable solvents for use in the above process included, but were not limited to, ethers such as tetrahydrofuran (THF), glyme, and the like; alcoholic solvents such as methanol, ethanol, isopropanol, and the like; however, the reactions are normally in methanol. The above process was carried out at temperatures between about −78° C. and about 100° C. Preferably, the reaction was carried out between 0° C. and about 20° C. The above process to produce compounds of the present invention was preferably carried out at about atmospheric pressure although higher or lower pressures were used if desired. Substantially, equimolar amounts of reactants were preferably used although higher or lower amounts were used if desired. Once the reduction of the ketone to the alcohol was deemed complete, the reaction was then charged with $HNR^7R^8$ in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); chlorinated solvents such as methylene chloride ($CH_2Cl_2$) or chloroform ($CHCl_3$); alcoholic solvents such as methanol, ethanol, isopropanol, and the like. If desired, mixtures of these solvents were used; however, the reactions were normally in methanol. The above process was carried out at temperatures between about −78° C. and about 100° C. Preferably, the reaction was carried out between 0° C. and about 60° C. The above process to produce compounds of the present invention was preferably carried out at about atmospheric pressure although higher or lower pressures were used if desired. Substantially, equimolar amounts of reactants were preferably used although higher or lower amounts were used if desired. $HNR^7R^8$ was used in excess in relation to compound of Formula XI and was generally commercially available or was prepared according to known procedures.

Alternatively, Method F was used when preparing compounds of Formula I-A [compounds of Formula I where $R^1$ equals H, $R^{4a}$, $R^{5a}$, $R^{6a}$ and $R^{6b}$ equal H, and Y equals O] as shown below in Scheme 14.

Method F

Scheme 14

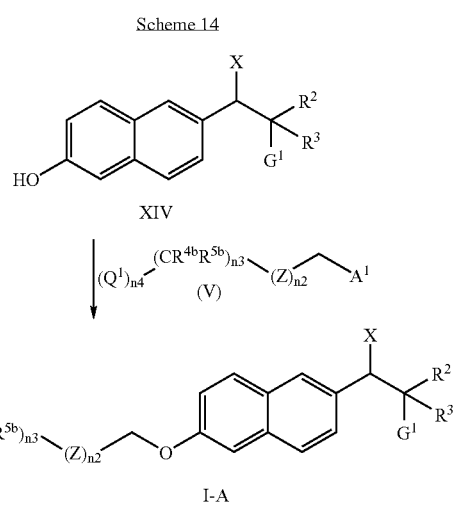

where X, $R^2$, $R^3$, $G^1$, $(Z)_{n2}$, $(CR^{4b}R^{5b})_{n3}$, and $(Q^1)_{n4}$, are as defined previously for compound of Formula I, and $A^1$=OH, OTs, OMs or halo.

In a typical preparation, according to Method F, of a compound of Formula I-A [compound of Formula I where $R^1$ equals H, $R^{4a}$, $R^{5a}$, $R^{6a}$ and $R^{6b}$ equal H, and Y equals O), a compound of Formula XIV was reacted with a compound of Formula V (where $A^1$=halo) in a suitable solvent in the presence of a suitable base. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); chlorinated solvents such as methylene chloride ($CH_2Cl_2$) or chloroform ($CHCl_3$). If desired, mixtures of these solvents were used. The preferred solvent was DMF or $CH_3CN$. Suitable bases for use in the above process included, but were not limited to, metal hydrides such as sodium or potassium hydride; metal alkoxides such as sodium or potassium alkoxides; alkali metal hydroxides such as sodium or potassium hydroxide; tertiary amines such as triethylamine or diisopropylethylamine; an alkali metal carbonate such as sodium or potassium carbonate; or pyridine. If desired, mixtures of these bases were used. The preferred base was sodium hydride or potassium tert-butoxide. The above process was carried out at temperatures between about −78° C. and about 100° C. Preferably, the reaction was carried out between 0° C. and about 50° C. The above process to produce compounds of the present invention was preferably carried out at about atmospheric pressure although higher or lower pressures were used if desired. Substantially, equimolar amounts of reactants were preferably used although higher or lower amounts were used if desired. Generally, one equivalent of base was used per equivalent of starting material of compound of Formula XIV.

In a typical preparation of a compound of Formula I-A [compound of Formula I where $R^1$ equals H, $R^{4a}$, $R^{5a}$, $R^{6a}$ and $R^{6b}$ equal H, and Y equals O], a compound of Formula XIV was reacted with a compound of Formula V (where $A^1$=OH) in a suitable solvent in the presence suitable reactants. Suitable solvents for use in the above process included, but were not limited to, ethers such as tetrahydrofuran (THF), glyme, and the like; dimethylformamide (DMF); dimethyl sulfoxide (DMSO); acetonitrile ($CH_3CN$); chlorinated solvents such as methylene chloride ($CH_2Cl_2$) or chloroform ($CHCl_3$). If desired, mixtures of these solvents were used, however, the preferred solvent was THF. Suitable reactants for use in the above process included, but were not limited to, triphenylphosphine and an azodicarboxylate (DIAD, DEAD, DBAD). The desired reactants were triphenylphosphine and DIAD. The above process was carried out at temperatures between about −78° C. and about 100° C. Preferably, the reaction was carried out between 0° C. and about 50° C. The above process to produce compounds of the present invention was preferably carried out at about atmospheric pressure although higher or lower pressures were used if desired. Substantially, equimolar amounts of reactants were preferably used although higher or lower amounts were used if desired. Generally, one equivalent of triphenylphospine, DIAD and compound of formula V was used per equivalent of starting material of compound of Formula XIV. The compounds of Formula V were generally commercially available or were prepared according to known procedures.

The compounds of Formula XIV of Scheme 14 were prepared as shown below in Scheme 15:

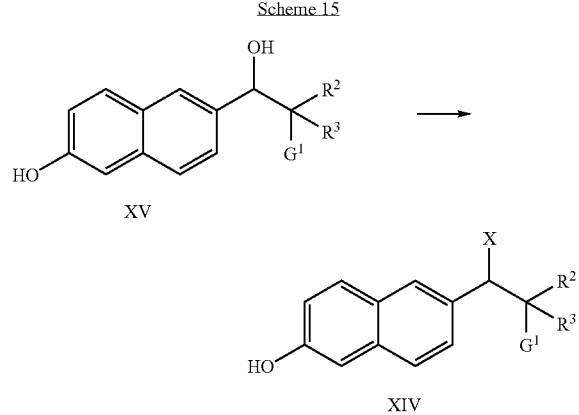

where X, $R^2$, $R^3$, and $G^1$ are as defined previously for compound of Formula I.

In a typical preparation of a compound of Formula XIV, a compound of Formula XV was reacted with CDI or CDT in a suitable solvent. Suitable solvents for use in the above process included, but were not limited to, ethers such as tetrahydrofuran (THF), glyme, and the like; dimethylformamide (DMF); dimethyl sulfoxide (DMSO); acetonitrile; chlorinated solvents such as methylene chloride ($CH_2Cl_2$) or chloroform ($CHCl_3$). If desired, mixtures of these solvents were used. The preferred solvent was dependent upon the substrates employed and was selected according to the properties of the substrates. The above process was carried out at temperatures between about −78° C. and about 100° C. Preferably, the reaction was carried out between 22° C. and about 80° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula XV of Scheme 15 were prepared as shown in Scheme 16.

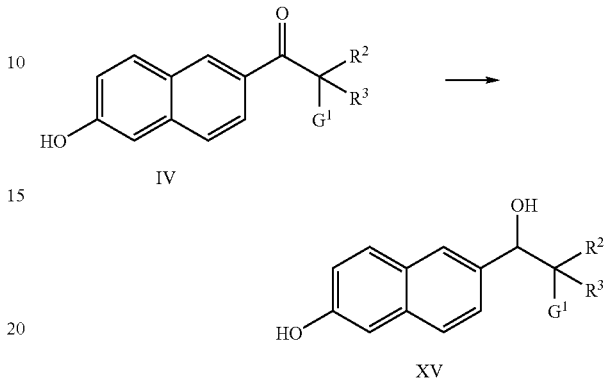

where $R^2$, $R^3$, and $G^1$ are as defined previously for compound of Formula I.

In a typical preparation of a compound of Formula XV, a compound of Formula IV was treated with a suitable reducing agent in a suitable solvent, where the suitable reducing agents included boron-derived reducing agents such as but not limited to sodium borohydride, lithium borohydride, borane, and the like; aluminum-derived reducing agents such as lithium aluminum hydride, alane, lithium tri-tert-butoxy-aluminum hydride, and the like; hydrogenation over a metal catalyst such as palladium on carbon. The preferred reducing agent was sodium borohydride. Suitable solvents for use in the above process included, but were not limited to, ethers such as tetrahydrofuran (THF), glyme, and the like; alcoholic solvents such as methanol, ethanol, isopropanol, and the like; however, the reactions were normally performed in methanol. The above process was carried out at temperatures between about −78° C. and about 100° C. Preferably, the reaction was carried out between 0° C. and about 20° C. The above process to produce compounds of the present invention was preferably carried out at about atmospheric pressure although higher or lower pressures were used if desired. Substantially, equimolar amounts of reactants were preferably used although higher or lower amounts were used if desired.

The compounds of Formula I-Z (compound of Formula I where $R^1$=OH, X=heteroaryl, Y=O, n1 =1, and $R^{6a}$, $R^{6b}$, $R^{4a}$ and $R^{5a}$=H) are prepared as shown in Scheme 17 following Reactions A-C.

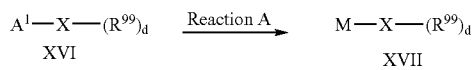

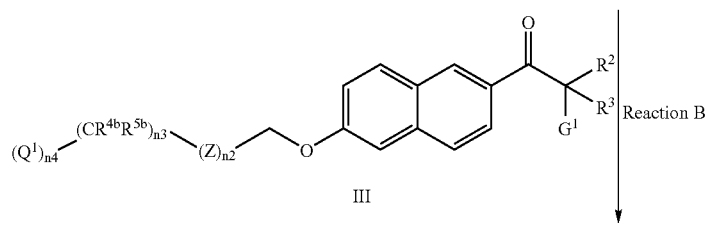

-continued

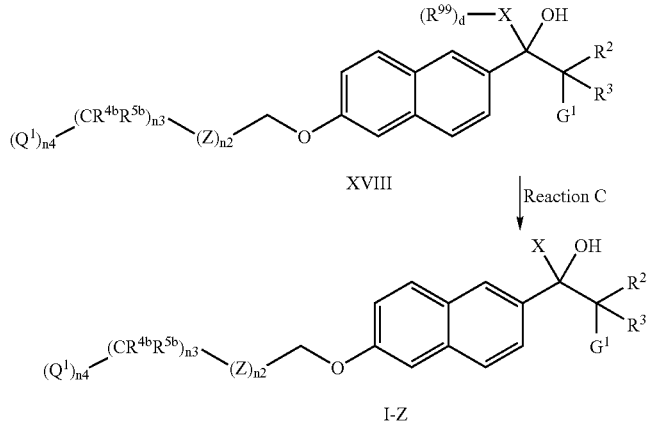

XVIII

Reaction C

I-Z where X, $R^2$, $R^3$, $G^1$, $(Z)_{n2}$, $(CR^{4b}R^{5b})_{n3}$, and $(Q^1)_{n4}$, are as defined previously for compound of Formula I and $A^1$=suitable exchangeable group such as halo or triflate or a deprotonateable hydrogen atom, d=0 or 1, $R^{99}$=suitable protecting group such as benzyl or trityl, and M=metal including lithium and magnesium; the salt of the metal shown by M can include for example, a metal halide such as magnesium chloride, magnesium bromide, or magnesium triflate.

In a typical preparation of an intermediate of Formula XVII via Reaction A, a compound of Formula XVI is treated with a suitable alkyl-lithium species or magnesium metal. Examples of such alkyl-lithium species include n-butyllithium, sec-butyllithium, or tert-butyllithium. Examples of the alkyl-magnesium halide include ethylmagnesium bromide or methylmagnesium chloride. Suitable solvents for use in the above process include, but are not limited to, ethers such as tetrahydrofuran (THF), diethyl ether, dioxane and the like; saturated hydrocarbons such as hexane, pentane, and the like; aromatic hydrocarbons such as benzene or toluene. The above process is carried out at temperatures between about −40° C. and about 70° C. The above process to produce compounds of the present invention is preferably carried out at about atmospheric pressure although higher or lower pressures are used if desired. Substantially, equimolar amounts of reactants are used although higher or lower amounts are used if desired. In the case of the alkyl-lithium, the alkyl-lithium is used in an amount of 1 to 3 moles, preferably 1 to 1.5 moles per one mole of the starting material XVI.

Following Reaction B, in a typical preparation of a compound of Formula XVIII, the intermediate of Formula XVII is allowed to react with a compound of Formula III. Suitable solvents for use in the above process include, but are not limited to, ethers such as tetrahydrofuran (THF), diethyl ether, dioxane and the like; saturated hydrocarbons such as hexane, pentane, and the like; an aromatic hydrocarbon such as benzene or toluene. The above process is carried out at temperatures between about −40° C. and about 70° C. The above process to produce compounds of the present invention is preferably carried out at about atmospheric pressure although higher or lower pressures are used if desired. Substantially, equimolar amounts of reactants are used although higher or lower amounts are used if desired.

According to Reaction C, in a typical preparation of compound of Formula I-Z, compound of Formula XVIII is treated under suitable deprotection conditions to afford the transformation of $R^{99}$ into a hydrogen atom. For example, when d=1 and $R^{99}$ is a trityl group, deprotection is afforded under acidic or hydrogenolysis conditions. Examples of acidic conditions include the use of organic acids such as formic, acetic, or trifluoroacetic acid or the use of inorganic acids such as hydrochloric acid. Suitable solvents include alcohols, ethers, or halogenated solvents. The above process is carried out at temperatures between about −40° C. and about 70° C. The above process to produce compounds of the present invention is preferably carried out at about atmospheric pressure although higher or lower pressures are used if desired. Substantially, equimolar amounts of reactants are used although higher or lower amounts are used if desired. Examples of $A^1$-X—$(R^{99})_d$ include, but are not limited to, the following heteroaryl groups:

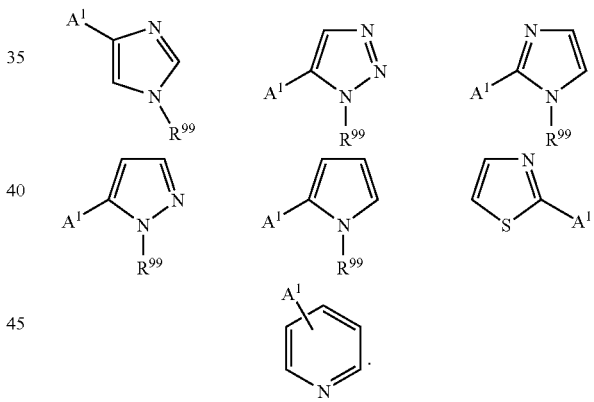

Alternatively, the compounds of Formula XVII of Scheme 17 are prepared as shown below in Scheme 18:

Scheme 18

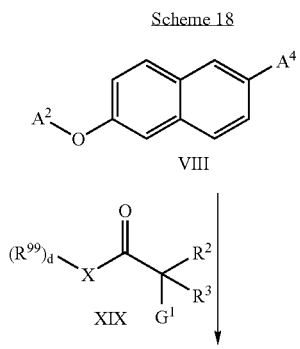

VIII

XIX

-continued

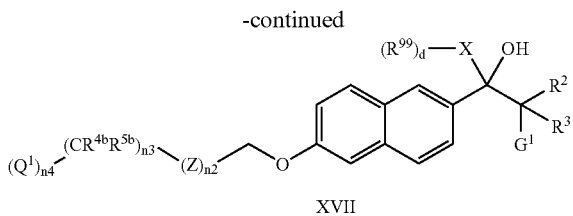

XVII where X, $R^2$, $R^3$, $G^1$, $(Z)_{n2}$, $(CR^{4b}R^{5b})_{n3}$, and $(Q^1)_{n4}$ are as defined previously for compound of Formula I and $A^2$=$C_{1-6}$alkyl or aryl-$C_{1-6}$alkyl, and $A^4$=halo or OTf, d=0 or 1, $R^{99}$=suitable protecting group such as benzyl or trityl.

In a typical preparation of a compound of Formula XVII, a compound of Formula VIII is first reacted with a suitable organolithium reagent or metal catalyst followed by reaction with a compound of Formula XIX in a suitable solvent. Suitable solvents for use in the above process included, but were not limited to, ethers such as tetrahydrofuran (THF), glyme, diethyl ether, dioxane and the like; aromatic solvents such as benzene and toluene. Suitable organolithium or metal species for use in the above process included, but were not limited to organolithium species such as n-butyl lithium or tert-butyl lithium; magnesium. The above process is carried out at temperatures between about −78° C. and about 70° C. The above process to produce compounds of the present invention is preferably carried out at about atmospheric pressure although higher or lower pressures were used if desired. Substantially, equimolar amounts of reactants are used although higher or lower amounts were used if desired. Compounds of Formula VIII and XIX are generally commercially available or is prepared according to known procedures. For example, compounds of Formula XIX is prepared according to the methods described in Scheme 6b by replacing compound of Formula VIII with compound of Formula XVI.

The optically pure isomers, compounds of Formula I' and I", are prepared as shown in Scheme 19 from (±)-syn-isomer, compound of Formula (±)-I-syn:

Scheme 19

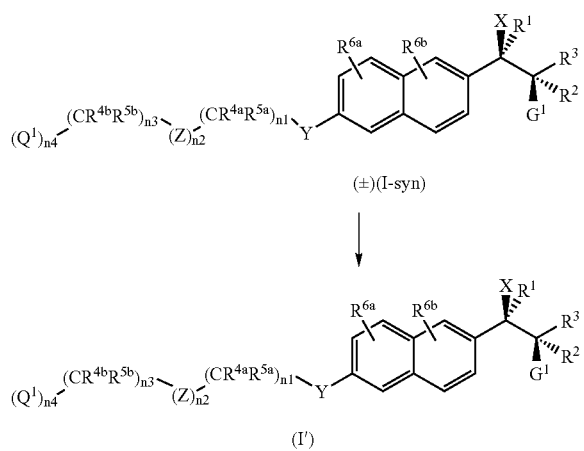

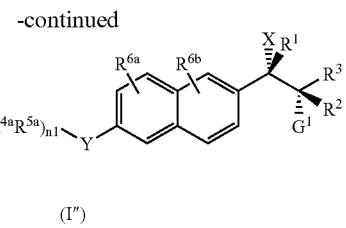

(I")

where X, $R^1$, $R^2$, $R^3$, $G^1$, $(CR^{4a}R^{5a})_{n1}$, $(Z)_{n2}$, $(CR^{4b}R^{5b})_{n3}$, $R^{6a}$, $R^{6b}$, and $(Q^1)_{n4}$ are as defined previously for compound of Formula I.

In a typical preparation of optically resolved syn-compounds of Formula I' and I", (±)-syn-compound of Formula I is subjected to liquid chromatography method equipped with a chiral column or diastereomer salt method using an optically active acid or optically active base. When the desired enantiomers of Formula I' or I" are obtained in their respective diastereomeric salt form (compounds of Formula I-$(HA^6)_{n7}$) from the diastereomer salt method where $HA^6$=optically pure acid such as tartaric or mandelic acid), the enantiomers of Formula I' and I" are obtained in their respective free forms by neutralization of the reaction mixture. Additionally, compounds of Formula I' and I" as diastereomeric salts are treated with HCl under suitable conditions to afford compounds of Formula I-$(HA^6)_{n7}$ where n7=2 and $HA^6$=HCl.

The optically pure isomers, compounds of Formula I''' and I'''', are prepared as shown in Scheme 20 from (±)-anti-compound of Formula I:

Scheme 20

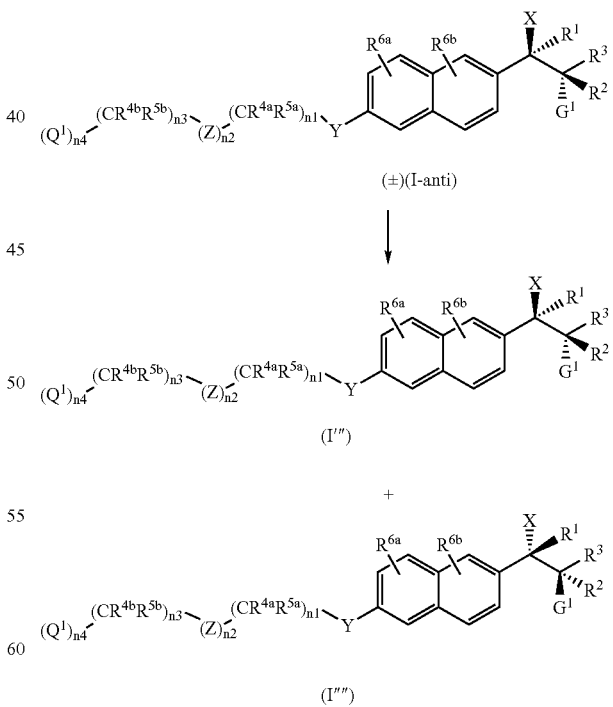

where X, $R^1$, $R^2$, $R^3$, $G^1$, $(CR^{4a}R^{5a})_{n1}$, $(Z)_{n2}$, $(CR^{4b}R^{5b})_{n3}$, $R^{6a}$, $R^{6b}$, and $(Q^1)_{n4}$ are as defined previously for compound of Formula I.

In a typical preparation of optically resolved anti-compounds of Formula I''' and I'''', (±)-anti-compound of Formula I is subjected to liquid chromatography method equipped with a chiral column or diastereomer salt method using an optically active acid or optically active base. When the desired enantiomers of Formula I''' and I'''' are obtained in their respective diastereomeric salt form (compounds of Formula I-(HA⁶)$_{n7}$ from the diastereomer salt method where HA⁶=optically pure acid such as tartaric or mandelic acid), the enantiomers of Formula I''' and I'''' are obtained in their respective free forms by neutralization of the reaction mixture. Additionally, compounds of Formula I''' and I'''' as diastereomeric salts are treated with HCl under suitable conditions to afford compounds of Formula I-(HA⁶)$_{n7}$ where n7=2 and HA⁶=HCl.

The optically pure isomers, compounds of Formula III' and III'', are prepared as shown in Scheme 21 from (±)-compound of Formula III.

Scheme 21

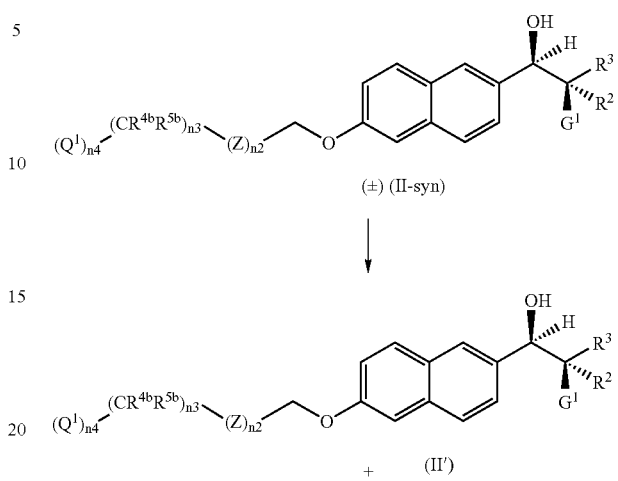

where $R^2$, $R^3$, $(Z)_{n2}$, $(CR^{4b}R^{5b})_{n3}$, and $(Q^1)_{n4}$ are as defined previously for compound of Formula I and $G^1=NR^{72}R^{82}$.

In a typical preparation of optically resolved compounds of Formula III' and III'', (±)-compound of Formula III is subjected to liquid chromatography method equipped with a chiral column or diastereomer salt method using an optically active acid. When the desired enantiomers of Formula III' and III'' are obtained in their respective diastereomeric salt form, compounds of Formula III' and III'' are obtained in their respective free non-salt forms by neutralization of the reaction mixture followed by extraction into a suitable organic solvent such as EtOAc or methylene chloride.

The optically pure isomers, compounds of Formula II' and II'', are prepared as shown in Scheme 22 from (±)-syn-compound of Formula II.

Scheme 22

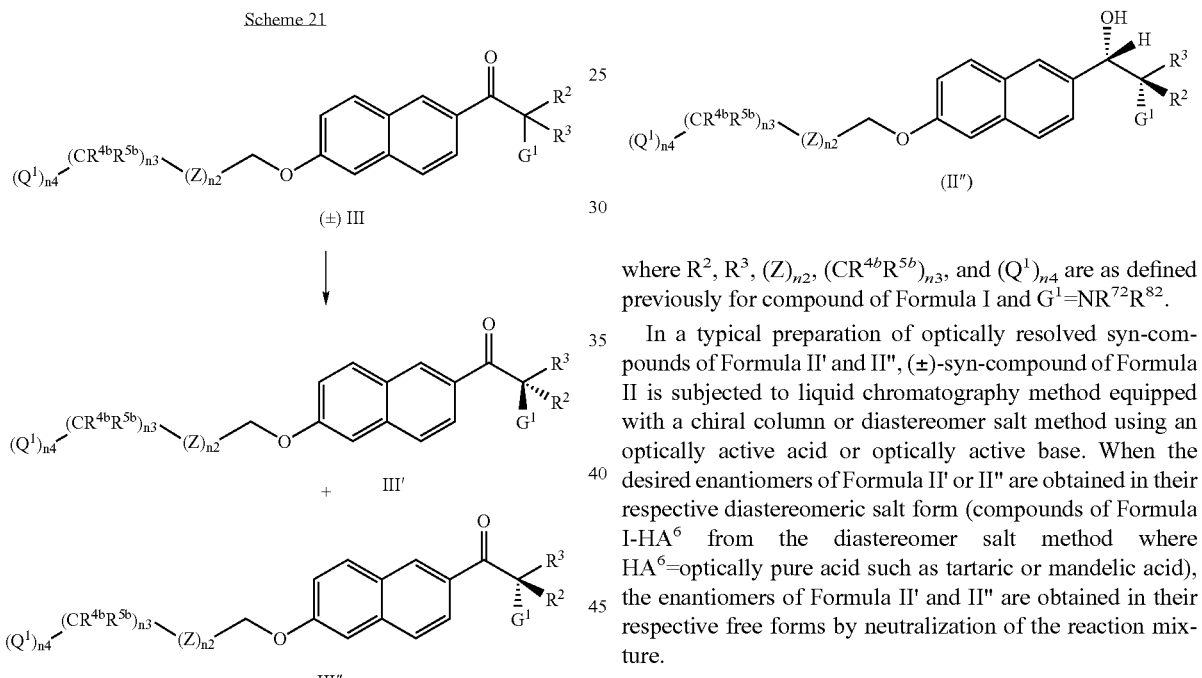

where $R^2$, $R^3$, $(Z)_{n2}$, $(CR^{4b}R^{5b})_{n3}$, and $(Q^1)_{n4}$ are as defined previously for compound of Formula I and $G^1=NR^{72}R^{82}$.

In a typical preparation of optically resolved syn-compounds of Formula II' and II'', (±)-syn-compound of Formula II is subjected to liquid chromatography method equipped with a chiral column or diastereomer salt method using an optically active acid or optically active base. When the desired enantiomers of Formula II' or II'' are obtained in their respective diastereomeric salt form (compounds of Formula I-HA⁶ from the diastereomer salt method where HA⁶=optically pure acid such as tartaric or mandelic acid), the enantiomers of Formula II' and II'' are obtained in their respective free forms by neutralization of the reaction mixture.

The optically pure isomers, compounds of Formula II''' and II'''', are prepared as shown in Scheme 23 from (±)-anti-compound of Formula II.

Scheme 23

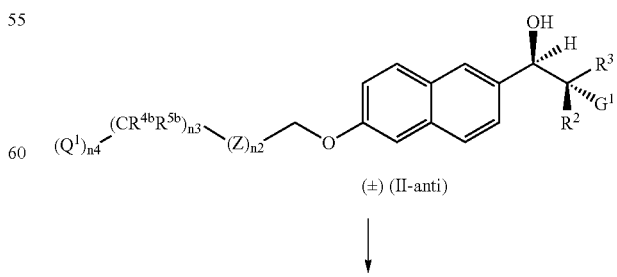

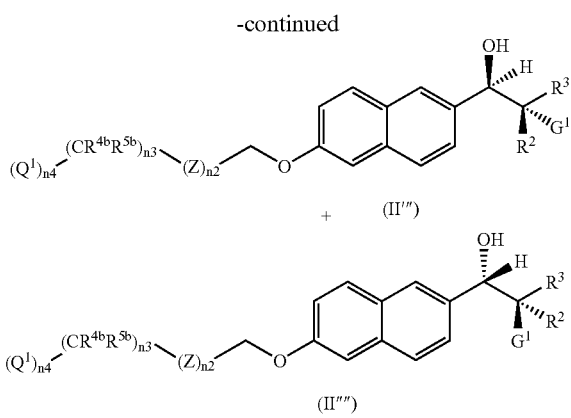

where $R^2$, $R^3$, $(Z)_{n2}$, $(CR^{4b}R^{5b})_{n3}$, and $(Q^1)_{n4}$ are as defined previously for compound of Formula I and $G^1=NR^{72}R^{82}$.

In a typical preparation of optically resolved anti-compounds of Formula II''' and II'''', (±)-anti-compound of Formula II is subjected to liquid chromatography method equipped with a chiral column or diastereomer salt method using an optically active acid or optically active base. When the desired enantiomers of Formula II''' and II'''' are obtained in their respective diastereomeric salt form (compounds of Formula I-HA⁶ from the diastereomer salt method where HA⁶=optically pure acid such as tartaric or mandelic acid), the enantiomers of Formula II''' and II'''' are obtained in their respective free forms by neutralization of the reaction mixture.

The compounds of Formula II', II'', II''', and II'''' of this invention and the intermediates used in the synthesis of the compounds of this invention were prepared according Method G as shown below in Schemes 24-27. The optically pure compound of Formula II' is prepared as shown in Scheme 24 from optically pure compound of Formula IIa':

Method G:

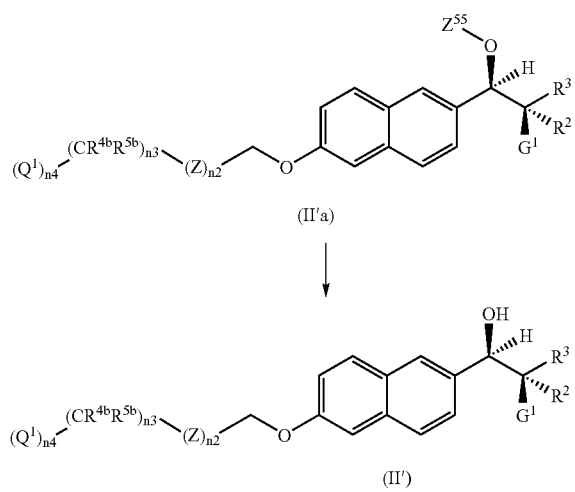

where $R^2$, $R^3$, $(Z)_{n2}$, $(CR^{4b}R^{5b})_{n3}$, and $(Q^1)_{n4}$ are as defined previously for compound of Formula I; $G^1=NR^{72}R^{82}$ and $Z^{55}$=chiral auxiliary.

In a typical preparation of compound of Formula II', a compound of Formula IIa' (where $OZ^{55}$ is taken together to equal O—(C=O)—R*, where R* is the chiral auxiliary) is reacted under typical reaction conditions to afford hydrolysis of an ester to an alcohol. Typical hydrolysis conditions involve HCl in water or NaOH, KOH, or LiOH in water. Suitable solvents include water, THF, acetonitrile, or an alcohol such as methanol or ethanol. The above processes are carried out at temperatures between about −5° C. and about 100° C. The above processes to produce compounds of the present invention are carried out at about atmospheric pressure although higher or lower pressures are used if desired. Substantially, equimolar amounts of reactants are used, however, an excess of HCl or NaOH are used if desired.

The optically pure compound of Formula II'' is prepared as shown in Scheme 25 from optically pure compound of Formula IIa'':

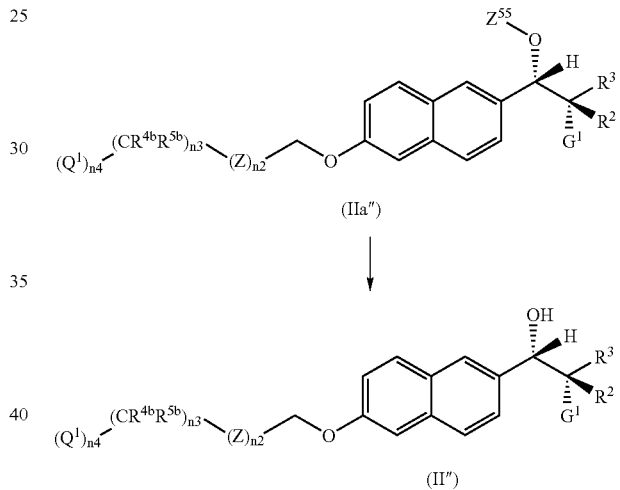

where $R^2$, $R^3$, $(Z)_{n2}$, $(CR^{4b}R^{5b})_{n3}$, and $(Q^1)_{n4}$ are as defined previously for compound of Formula I; $G^1=NR^{72}R^{82}$ and $Z^{55}$=chiral auxiliary.

In a typical preparation of compound of Formula II'', a compound of Formula IIa'' (where $OZ^{55}$ is taken together to equal O—(C=O)—R*, where R* is the chiral auxiliary) is reacted under typical reaction conditions to afford hydrolysis of an ester to an alcohol. Typical hydrolysis conditions involve HCl in water or NaOH, KOH, or LiOH in water. Suitable solvents include water, THF, acetonitrile, or an alcohol such as methanol or ethanol. The above processes are carried out at temperatures between about −5° C. and about 100° C. The above processes to produce compounds of the present invention are carried out at about atmospheric pressure although higher or lower pressures are used if desired. Substantially, equimolar amounts of reactants are used, however, an excess of HCl or NaOH are used if desired.

The optically pure compound of Formula II''' is prepared as shown in Scheme 26 from optically pure compound of Formula IIb':

Scheme 26

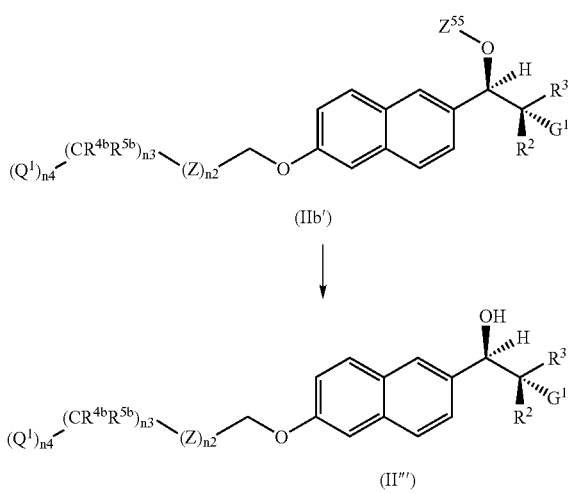

where $R^2$, $R^3$, $(Z)_{n2}$, $(CR^{4b}R^{5b})_{n3}$, and $(Q^1)_{n4}$ are as defined previously for compound of Formula I; $G^1=NR^{72}R^{82}$ and $Z^{55}$=chiral auxiliary.

In a typical preparation of compound of Formula II''', a compound of Formula IIb' (where $OZ^{55}$ is taken together to equal O—(C=O)—R*, where R* is the chiral auxiliary) is reacted under typical reaction conditions to afford hydrolysis of an ester to an alcohol. Typical hydrolysis conditions involve HCl in water or NaOH, KOH, or LiOH in water. Suitable solvents include water, THF, acetonitrile, or an alcohol such as methanol or ethanol. The above processes are carried out at temperatures between about −5° C. and about 100° C. The above processes to produce compounds of the present invention are carried out at about atmospheric pressure although higher or lower pressures are used if desired. Substantially, equimolar amounts of reactants are used, however, an excess of HCl or NaOH are used if desired.

The optically pure compound of Formula II'''' is prepared as shown in Scheme 27 from optically pure compound of Formula IIb'':

Scheme 27

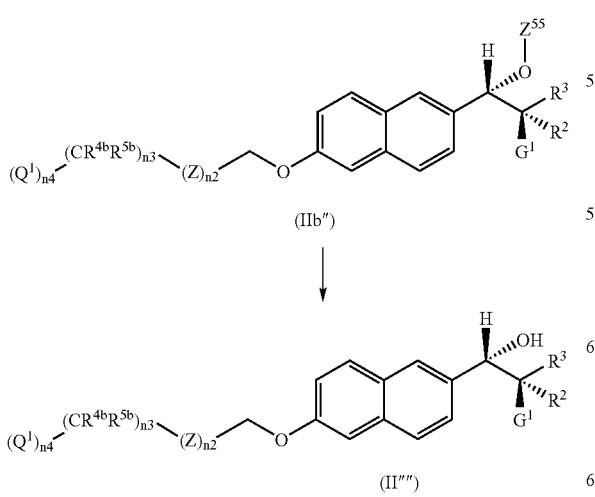

where $R^2$, $R^3$, $(Z)_{n2}$, $(CR^{4b}R^{5b})_{n3}$, and $(Q^1)_{n4}$ are as defined previously for compound of Formula I; $G^1=NR^{72}R^{82}$ and $Z^{55}$=chiral auxiliary.

In a typical preparation of compound of Formula II'''', a compound of Formula IIb'' (where $OZ^{55}$ is taken together to equal O—(C=O)—R*, where R* is the chiral auxiliary) is reacted under typical reaction conditions to afford hydrolysis of an ester to an alcohol. Typical hydrolysis conditions involve HCl in water or NaOH, KOH, or LiOH in water. Suitable solvents include water, THF, acetonitrile, or an alcohol such as methanol or ethanol. The above processes are carried out at temperatures between about −5° C. and about 100° C. The above processes to produce compounds of the present invention are carried out at about atmospheric pressure although higher or lower pressures are used if desired. Substantially, equimolar amounts of reactants are used, however, an excess of HCl or NaOH are used if desired.

The optically pure compounds of Formula IIa' and IIa'' are prepared as shown in Scheme 28 from the transformation of (±)-syn-compound of Formula II, into diastereomeric compounds of Formula IIa' and IIa'', respectively:

Scheme 28

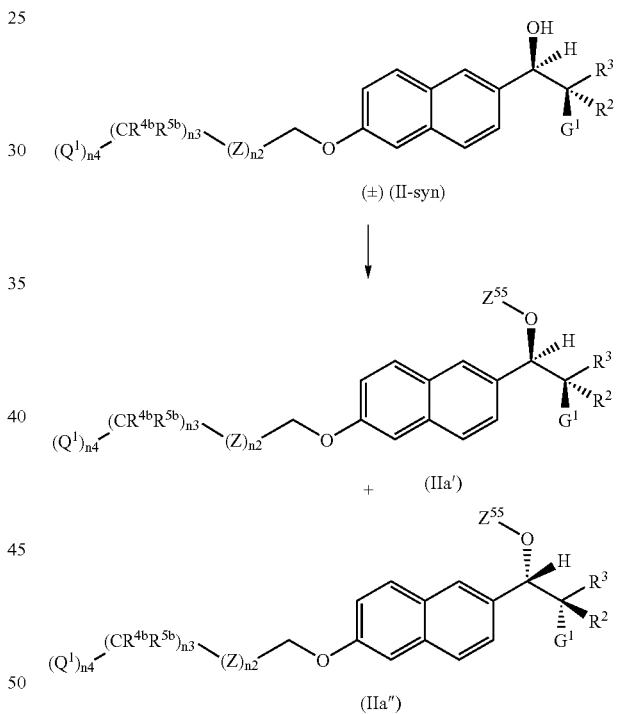

where $R^2$, $R^3$, $(Z)_{n2}$, $(CR^{4b}R^{5b})_{n3}$, and $(Q^1)_{n4}$ are as defined previously for compound of Formula I; $G^1=NR^{72}R^{82}$ and $Z^{55}$=chiral auxiliary.

In a typical preparation of diastereomerically resolved syn-compounds of Formula IIa' and IIa'', (±)-syn-compound of Formula II is reacted with a suitable chiral auxiliary and then the respective diastereomers, compounds of Formula IIa' and IIa'', are separated by known methods such as recrystallization or chromatography. A typical reaction involves the treatment of (±)-syn-compound of Formula II with a suitable chiral auxiliary which contained a carboxylic acid or acid chloride moiety. Treatment of (±)-syn-compound of Formula II with an acid-based chiral auxiliary involves typical conditions for transforming an alcohol into an ester. These coupling conditions include, but are not limited to, DCC or EDC with a suitable catalyst such as DMAP, HOAT, or HOBT in a suitable solvent in the presence of a suitable base such as triethylamine or diisopropylamine. Treatment of (±)-syn-compound of Formula II with an acid chloride-based chiral auxiliary involves typical conditions for transforming an alcohol into an ester with an acid chloride such as an inert solvent and base. Typical chiral auxiliaries include, but are not limited to, suitably protected amino acid such as N-(tert-butoxycarbonyl)-L-proline, N-(tert-butoxycarbonyl)-D-proline, (R)-(+)-α-methoxy-α-(trifluoromethyl)phenylacetic acid, (S)-(−)-α-methoxy-α-(trifluoromethyl)phenylacetic acid, (R)-(+)-α-methoxy-α-(trifluoromethyl)phenylacetyl chloride, (S)-(−)-α-methoxy-α-(trifluoromethyl)phenylacetyl chloride, (1R)-(+)-camphanic acid, (1S)-(−)camphanic acid, and (1S)-(−)-camphanic chloride. Suitable solvents for use in both of the above processes include, but are not limited to, ethers such as tetrahydrofuran (THF), glyme, and the like; dimethyl formamide; dimethyl sulfoxide; halogenated solvents such as methylene chloride or chloroform. The above processes are carried out at temperatures between about −5° C. and about 100° C. The above processes to produce compounds of the present invention are preferably carried out at about atmospheric pressure although higher or lower pressures are used if desired. Substantially, equimolar amounts of reactants are used if desired.

The optically pure compounds of Formula IIb' and IIb" are prepared as shown in Scheme 29 from the transformation of (±)-anti-compound of Formula II, into diastereomeric compounds of Formula IIb' and IIb", respectively:

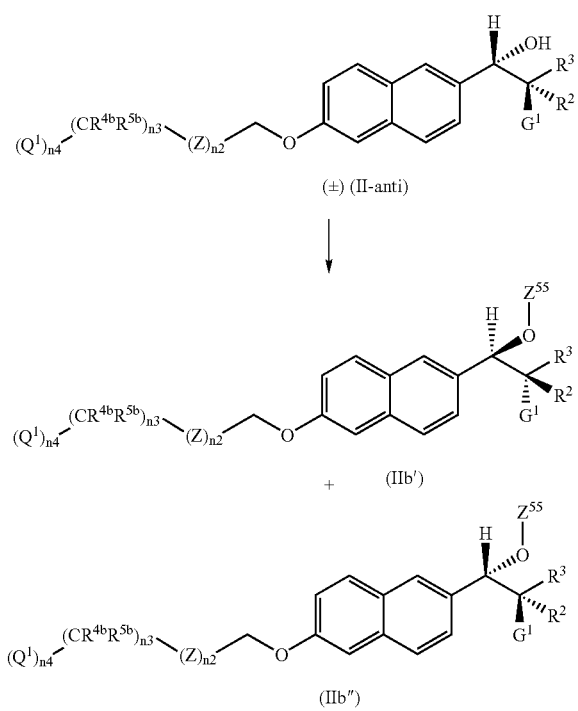

Scheme 29 where $R^2$, $R^3$, $(Z)_{n2}$, $(CR^{4b}R^{5b})_{n3}$, and $(Q^1)_{n4}$ are as defined previously for compound of Formula I; $G^1$=$NR^{72}R^{82}$ and $Z^{55}$=chiral auxiliary.

In a typical preparation of diastereomerically resolved anti-compounds of Formula IIb' and IIb", (±)-anti-compound of Formula II is reacted with a suitable chiral auxiliary and then the respective diastereomers, compounds of Formula IIb' and IIb", are separated by known methods such as by recrystallization or by chromatography. A typical reaction involves the treatment of (±)-anti-compound of Formula II with a suitable chiral auxiliary which contained a carboxylic acid or acid chloride moiety. Treatment of (±)-anti-compound of Formula II with an acid-based chiral auxiliary involves typical conditions for transforming an alcohol into an ester. These coupling conditions include, but are not limited to, DCC or EDC with a suitable catalyst such as DMAP, HOAT, or HOBT in a suitable solvent in the presence of a suitable base such as triethylamine or diisopropylamine. Treatment of (±)-anti-compound of Formula II with an acid chloride-based chiral auxiliary involves typical conditions for transforming an alcohol into an ester with an acid chloride such as an inert solvent and base. Typical chiral auxiliaries include, but are not limited to, suitably protected amino acid such as N-(tert-butoxycarbonyl)-L-proline, N-(tert-butoxycarbonyl)-D-proline, (R)-(+)-α-methoxy-α-(trifluoromethyl)phenylacetic acid, (S)-(−)-α-methoxy-α-(trifluoromethyl)phenylacetic acid, (R)-(+)-α-methoxy-α-(trifluoromethyl)phenylacetyl chloride, (S)-(−)-α-methoxy-α-(trifluoromethyl)phenylacetyl chloride, (1R)-(+)-camphanic acid, (1S)-(−)camphanic acid, and (1S)-(−)-camphanic chloride. Suitable solvents for use in both of the above processes include, but are not limited to, ethers such as tetrahydrofuran (THF), glyme, and the like; dimethyl formamide; dimethyl sulfoxide; halogenated solvents such as methylene chloride or chloroform. The above processes are carried out at temperatures between about −5° C. and about 100° C. The above processes to produce compounds of the present invention are preferably carried out at about atmospheric pressure although higher or lower pressures are used if desired. Substantially, equimolar amounts of reactants are used if desired.

The following examples are intended to illustrate and not to limit the scope of the present invention.

Analytical HPLC Conditions:

Unless otherwise stated, all HPLC analyses were run on a Micromass system with a XTERRA MS C 18 5μ 4.6×50 mm column and detection at 254 nm. Table A below lists the mobile phase, flow rate, and pressure.

TABLE A

| Time (min) | % CH$_3$CN | 0.01% HCOOH in H$_2$O % | Flow (mL/min) | Pressure (psi) |
| --- | --- | --- | --- | --- |
| 0.00 | 5 | 95 | 1.3 | 400 |
| 4.00 | 100 | 0 | 1.3 | 400 |
| 5.50 | 100 | 0 | 1.3 | 400 |
| 6.00 | 5 | 95 | 1.3 | 400 |
| 7.00 | 5 | 95 | 1.3 | 400 |

Semipreparative HPLC Conditions:

Where indicated as "purified by Gilson HPLC", the compounds of interest were purified by a preparative/semipreparative Gilson HPLC workstation with a Phenomenex Luna 5μ C18 (2) 60×21 20 MM 5μ column and Gilson 215 liquid handler (806 manometric module, 811C dynamic mixer, detection at 254 nm). Table B lists the gradient, flow rate, time, and pressure.

TABLE B

| Time (min) | % CH$_3$CN | 0.01% HCOOH in H$_2$O % | Flow (mL/min) | Pressure (psi) |
|---|---|---|---|---|
| 0.00 | 5 | 95 | 15 | 1000 |
| 15.00 | 60 | 40 | 15 | 1000 |
| 15.10 | 100 | 0 | 15 | 1000 |
| 19.00 | 100 | 0 | 15 | 1000 |
| 20.00 | 5 | 95 | 15 | 1000 |

Intermediate A-1 (compound of Formula VI where $R^2$=CH$_3$, $R^3$=H, $G^1$=N(CH$_3$)$_2$, and $A^2$=CH$_3$): A solution of 2-iodo-1-(6-methoxy-naphthalen-2-yl)-propan-1-one (compound of Formula VII, where $R^2$=CH$_3$, $R^3$=H, $A^3$=I, and $A^2$=CH$_3$) (54 g, 161 mmol), dimethylamine (161 mL of a 2M solution in MeOH, 322 mmol), and diisopropylamine (28 mL, 161 mmol) in 500 mL of CHCl$_3$ and 500 mL of MeOH was stirred at rt for 16 h. The reaction mixture was concentrated in-vacuo and partitioned between Na$_2$CO$_3$ (sat) and CH$_2$Cl$_2$. The aqueous phase was extracted with CH$_2$Cl$_2$ (4×), dried over Na$_2$SO$_4$ and concentrated in-vacuo. Intermediate A-1 was deemed pure by $^1$HNMR and taken directly onto the next reaction. $^1$HNMR (CDCl$_3$, 200 MHz) δ 1.31 (d, 3H, J=7.0 Hz), 2.35 (s, 6H), 3.94 (s, 3H), 4.16 (q, 1H, J=8.0 Hz), 7.15-8.56 (m, 6H); MS (ES) 258.0 (M+1).

Intermediate A-2 (compound of Formula IV where $R^2$=CH$_3$, $R^3$=H, and $G^1$=N(CH$_3$)$_2$): A 2L rbf equipped with a reflux condensor, was charged with intermediate A-1 (38 g, 148 mmol), 48% HBr$_{aq}$ (800 mL) and glacial acetic acid (800 mL) and heated in an oil bath at 120° C. with stirring for 16 h. The reaction mixture was concentrated in-vacuo to as small a volume as possible, cooled in an ice bath and quenched with 8M NaOH. The cooled slurry was then extracted with CH$_2$Cl$_2$ (7×). The organic layers were combined and filtered through a pad of celite. The filtrate was concentrated in-vacuo and the product was further purified by silica gel column chromatography (gradient of 5% CH$_3$OH:CH$_2$Cl$_2$ with 1% Et$_3$N per 100 mL of solvent to 10% CH$_3$OH:CH$_2$Cl$_2$ with 1% Et$_3$N per 100 mL of solvent) to afford the desired intermediate A-2 as a foamy brown solid. $^1$HNMR (CDCl$_3$, 200 MHz) δ 1.34 (d, 3H, J=8.0 Hz), 2.39 (s, 6H), 4.22 (q, 1H, J=8.0 Hz), 7.09-7.13 (m, 2H), 7.66 (d, 1H, J=8.0 Hz), 7.82 (d, 1H, J=8.0 Hz), 8.02 (dd, 11H, J=2.0, 10.0 Hz), 8.52 (d, 1H, J=2.0 Hz).

Intermediate A-3 (compound of Formula VI where $R^2$=CH$_3$, $R^3$=CH$_3$, $A^2$=CH$_3$, and $G^1$=N(CH$_3$)$_2$): To a solution of the 2-bromo-6-methoxynaphthelene (2.37 g, 10 mmol) in THF (30 mL) at −78° C., was charged with tBuLi (1.7 M, 11.76 mL, 20 mmol) over a period of 20 min. The reaction mixture was stirred at −78° C. for 20 min, upon which time, neat 2-dimethylamino-2-methylpropionitrile (1.23 g, 11.1 mmol) was added. The mixture was allowed to stir for an additional 30 min and then allowed to warm to rt. The mixture was charged with 2N H$_2$SO$_4$ (50 mL) and stirred for 10 min. The THF layer was separated and the aqueous layer was extracted with ethyl acetate (2×40 mL). The aqueous layer was basified using 2N NaOH to pH 8.0 and was extracted with CH$_2$Cl$_2$ (3×40 mL). The CH$_2$Cl$_2$ extract was washed with water, brine, dried over anhydrous sodium sulfate and concentrated in vacuo to give Intermediate A-3 as a pale yellow oil. MS (ES): m/z 271.96 [M$^+$]; $^1$H NMR (CDCl$_3$, 400 MHz): δ 9.09 (d, J=1.2 Hz, 1H), 8.35 (dd, J=8.8, 4.0 Hz, 1H), 7.76 (d, J=8.8 Hz, 1H), 7.62 (d, J=8.8 Hz, 1H), 7.07 (dd, J=8.8, 2.8 Hz, 1H), 7.03 (d, J=2.8 Hz, 1H), 3.83 (s, 3H), 2.21 (s, 6H), 1.25 (s, 6H).

Intermediate A4 (compound of Formula IV where $R^2$=CH$_3$, $R^3$=CH$_3$, and $G^1$=N(CH$_3$)$_2$): A mixture of Intermediate A-3 (1.92 g, 7.11 mmol) and aq. HBr (48%, 30 mL) was charged with glacial acetic acid (30 mL) and heated to 120° C. for 16 h. The reaction mixture was cooled to rt and neutralized with 2N NaOH (up to pH 5.0) and saturated NaHCO$_3$ (up to pH 7.0). The aqueous mixture was extracted with CH$_2$Cl$_2$ (4×40 mL) and the combined organics were washed with water, brine, dried over anhydrous sodium sulfate and concentrated in vacuo to give the crude product as a brown oil. Purification of the crude product by column chromatography (10% MeOH/CH$_2$Cl$_2$) afforded Intermediate A-4. MS (ES): m/z 258.22 [M+H$^+$]; $^1$H NMR (CDCl$_3$, 400 MHz) δ 9.17 (s, 1H), 8.39 (dd, J=8.8, 2.0 Hz, 1H), 7.86 (d, J=8.4 Hz, 1H), 7.63 (d, J=8.8 Hz, 1H), 7.15 (s, 1H), 7.12 (dd, J=8.4, 2.4 Hz, 1H), 2.29 (s, 6H), 1.34 (s, 6H).

Intermediate A-5 (compound of Formula XII where $R^2$=CH$_3$, $R^3$=H, $n^2$=0, $n^3$=1, $R^{4b}$ and $R^{5b}$=CH$_3$, $n^4$=1, and $Q^1$=CO$_2$CH$_3$): A THF (160 mL) solution of 1-(6-hydroxynaphthalen-2-yl)propan-1-one (10.0 g, 50.0 mmol), triphenylphosphine (20.0 g, 76.0 mmol), and methyl 2,2-dimethyl-3-hydroxypropionate (7.0 mL, 55.0 mmol) was evacuated, placed under a N$_2$ atm, cooled in an ice bath and charged with DIAD (15.0 mL, 76.0 mmol) portionwise over 5 min. The mixture was allowed to warm to rt and then heated to 45° C. for 16 h. The reaction mixture was concentrated in vacuo to a dark oil and purified by silica gel column chromatography (5 to 10% EtOAc/Hexanes). The white solids were recrystallized from hot hexanes to afford the desired Intermediate A-5. $^1$HNMR (CDCl$_3$, 400 MHz) δ 1.28 (t, 3H, J=7.2 Hz), 2.33 (s, 6H), 1.38 (s, 6H), 3.12 (q, 1H, J=7.2 Hz), 3.72 (s, 3H), 4.12 (s, 2H), 7.16 (m, 2H), 7.20 (dd, 1H, J=2.5, 8.8 Hz), 7.76 (d, 1H, J=8.6 Hz), 7.84 (d, 1H, J=8.8 Hz), 8.01 (dd, 1H, J=2.0, 8.6 Hz), 8.41 (s, 1H).

Intermediate A-6 (compound of Formula XI where $R^2$=CH$_3$, $R^3$=H, $n^2$=0, $n^3$=1, $R^{4b}$ and $R^{5b}$=CH$_3$, $n^4$=1, $A^3$=Br, and $Q^1$=CO$_2$CH$_3$): A 250 mL rbf containing Intermediate A-5 (8.60 g, 27.4 mmol) and CuBr$_2$ (12.2 g, 54.7 mmol) was charged with dioxane (55 mL), evacuated, placed under a N$_2$ atm, and heated to 110° C. for 16 h. The reaction mixture was concentrated in vacuo to a dark slurry and purified by silica gel column chromatography (5-10% EtOAc/Hexanes). The off white solids were recrystallized from hexanes/EtOAc to afford 9.36 g of Intermediate A-6 as off white solids. $^1$HNMR (CDCl$_3$, 400 MHz) δ 1.38 (s, 6H), 1.95 (d, 3H, J=6.6 Hz), 3.77 (s, 3H), 4.12 (s, 2H), 5.44 (q, 1H, J=6.6 Hz), 7.16 (m, 2H), 7.21 (dd, 1H, J=2.4, 8.8 Hz), 7.77 (d, 1H, J=8.0 Hz), 7.86 (d, 1H, J=8.8 Hz), 8.03 (dd, 1H, J=2.4, 8.8 Hz), 8.49 (s, 1H).

Intermediate A-7 (compound of Formula XII where $R^2$=H, $R^3$=H, $n^2$=0, $n^3$=1, $R^{4b}$ and $R^{5b}$=CH$_3$, $n^4$=1, and $Q^1$=CO$_2$CH$_3$): The title compound was prepared according to the procedures described in Intermediate A-5 above except for the substitution of 1-(6-hydroxynaphthalen-2-yl)propan-1-one with 1-(6-hydroxynaphthalen-2-yl)ethanone. MS (ES) 301.0 (M+1).

Intermediate A-8 (compound of Formula XI where $R^2$=H, $R^3$=H, $n^2$=0, $n^3$=1, $R^{4b}$ and $R^{5b}$=CH$_3$, $n^4$=1, $A^3$=Br, and $Q^1$=CO$_2$CH$_3$): Intermediate A-7 (3.0 g, 9.99 mmol) and CuBr$_2$ (4.9 g, 21.97 mmol) were dissolved in dioxane (35 ml) and heated at 100° C. for 20 h. The crude mixture was concentrated in vacuo, and water was added and extracted with CH$_2$Cl$_2$ (3×). The organic layers were dried over Na$_2$SO$_4$, filtered, and concentrated in vacuo. The crude product was purified by silica gel column chromatography (10% EtOAc: Hexanes) to yield the desired product as a yellow solid. $^1$H NMR (CDCl$_3$, 400 MHz) δ 1.38 (s, 6H), 3.72 (s, 3H), 4.12 (s, 2H), 4.56 (s, 2H), 7.17-7.23 (m, 2H), 7.78 (d, 1H, J=8.8 Hz), 7.86 (d, 1H, J=9.2 Hz), 7.99 (dd, 1H, J=2.0, 6.4 Hz), 8.43 (s, 1H).

Intermediate A-9 (compound of Formula XII where $R^2=CH_3$, $R^3=H$, $n^2=0$, $n^3=1$, $R^{4b}$ and $R^{5b}$ along with the carbon to which they are attached form a cyclopentyl ring, $n^4=1$, and $Q^1=CO_2Et$): The title compound was prepared according to the procedures described for Intermediate A-5 above except for the substitution of methyl 2,2-dimethyl-3-hydroxypropionate with 1-hydroxymethyl cyclopentanecarboxylic acid ethyl ester. $^1H$ NMR (CDCl$_3$, 400 MHz) δ 1.22 (t, 3H, J=8.0 Hz), 1.28 (t, 3H, J=8.0 Hz), 1.72-1.82 (m, 6H), 2.19-2.22 (m, 2H), 3.11 (q, 2H, J=8.0 Hz), 4.18 (m, 4H), 7.16-7.21 (m, 2H), 7.75 (d, 1H, J=8.8 Hz), 7.83 (d, 1H, J=8.8 Hz), 8.00 (dd, 1H, J=2.0, 6.4 Hz), 8.40 (s, 1H).

Intermediate A-10 (compound of Formula XI where $R^2=CH_3$, $R^3=H$, $n^2=0$, $n^3=1$, $R^{4b}$ and $R^{5b}$ along with the carbon to which they are attached form a cyclopentyl ring, $n^4=1$, $A^3=Br$, and $Q^1=CO_2Et$): The title compound was prepared according to the procedures described for Intermediate A-6 above except for the substitution of Intermediate 5 with Intermediate A-9. $^1H$ NMR (CDCl$_3$, 400 MHz) δ 1.22 (t, 3H, J=8.0 Hz), 1.72-1.75 (m, 6H), 1.95 (d, 3H, J=6.4 Hz), 2.19-2.23 (m, 2H), 4.18 (q, 2H, J=8.0 Hz), 5.44 (q, 1H, J=6.4 Hz), 7.11-7.21 (m, 2H), 7.77 (d, 1H, J=8.8 Hz), 7.85 (d, 1H, J=8.8 Hz), 8.03 (dd, 1H, J=2.0, 6.4 Hz), 8.48 (s, 1H).

Intermediate A-i 1 (compound of Formula VII where $R^2=CH_2CH_3$, $R^3=H$, $A^3=Cl$, $A^2=CH_3$): The title compound was prepared as follows: A 1 L, three necked rbf, equipped with a $N_2$ inlet and a reflux condenser, was charged with Mg turnings (7.70 g, 317 mmol) and dry THF (300 mL). 6-Bromo-2-methoxynaphthalene (compound of Formula VIII where $A^4=Br$ and $A^2=CH_3$) (60.0 g, 253 mmol) was added portionwise over a period of 20 min. The reaction was evacuated and placed under a $N_2$ atm and warmed gradually to 50° C. for 1 h. In another three necked flask equipped with a $N_2$ inlet, dropping funnel and a septum was placed 2-chlorobutyryl chloride (compound of Formula IX where $R^2=CH_2CH_3$, $R^3=H$, $A^3=Cl$, $A^5=Cl$) (64.0 g, 505 mmol) and dry THF (70 mL). The reaction mixture was cooled to −50° C. and the Grignard reagent as prepared above, was transferred by a cannula to the dropping funnel, under $N_2$ pressure. The Grignard reagent was then added dropwise over 30 min. The reaction mixture was allowed to warm to room temperature (rt) and stirred for 16 h. The reaction mixture was charged with 5% HCl, the volume of THF was reduced in-vacuo, and water was added and the product was extracted with $CH_2Cl_2$ (3×). The combined organic layers were washed with water, brine, dried over MgSO$_4$ and concentrated in-vacuo. The crude solid was purified by silica gel chromatography (9:1 EtOAc:Hexanes), and recrystallized from MeOH to yield the title compound. $^1H$ NMR (CDCl$_3$, 400 MHz) δ 1.11 (t, 3H, J=7.2 Hz), 2.04-2.15 (m, 1H), 2.18-2.29 (m, 1H), 3.93 (s, 3H), 5.18-5.22 (m, 1H), 7.16 (d, 1H, J=2.4 Hz), 7.22 (dd, 1H, J=6.0, 8.8 Hz), 7.79 (d, 1H, J=8.8 Hz), 7.87 (d, 1H, J=8.8 Hz), 8.02 (dd, 1H, J=1.6, 8.8 Hz), 8.46 (s, 1H).

Intermediate A-12 (compound of Formula VI where $R^2=CH_2CH_3$, $R^3=H$, $G^1=N(CH_3)_2$, and $A^2=CH_3$) was prepared according to the procedures described for Intermediate A-1 above except for the substitution of 2-iodo-1-(6-methoxy-naphthalen-2-yl)-propan-1-one with intermediate A-11. MS (ES) 271.7 (M+1). $^1H$ NMR (CDCl$_3$, 400 MHz) δ 0.89 (t, 3H, J=7.4 Hz), 1.72-1.84 (m, 1H), 1.91-2.02 (m, 1H), 2.38 (s, 6H), 3.96 (s, 3H), 3.99-4.03 (m, 1H), 7.15-7.21 (m, 2H), 7.77 (d, 1H, J=9.0 Hz), 7.87 (d, 1H, J=9.0 Hz), 8.07 (dd, 1H, J=1.8, 9.6 Hz), 8.53 (s, 1H).

Intermediate A-13 (compound of Formula IV where $R^2=CH_2CH_3$, $R^3=H$, and $G^1=N(CH_3)_2$) was prepared according to the procedures described for Intermediate A-2 above except for the substitution of intermediate A-1 with intermediate A-12. MS (ES) 258.3 (M+1).

Following the general methods described hereinbefore, the following intermediates of Formula III as listed in Table 1 were prepared.

TABLE 1

Listing of Intermediates of Formula III

| Compound | $R^2$ | $R^3$ | $G^1$ | n2 | Z | n3 | $R^{4b}$ | $R^{5b}$ | n4 | $Q^1$ |
|---|---|---|---|---|---|---|---|---|---|---|
| 1-1 | CH$_3$ | H | N(CH$_3$)$_2$ | 0 | — | 1 | CH$_3$ | CH$_3$ | 1 | CO$_2$CH$_3$ |
| 1-2 | CH$_3$ | H | N(CH$_3$)$_2$ | 1 | 4 Ph | 0 | — | — | 1 | CO$_2$CH$_3$ |
| 1-3 | CH$_3$ | H | N(CH$_3$)$_2$ | 1 | 3 Ph | 0 | — | — | 1 | CO$_2$CH$_3$ |
| 1-4 | CH$_3$ | H | N(CH$_3$)$_2$ | 1 | 4 Ph | 1 | H | H | 1 | CO$_2$CH$_3$ |
| 1-5 | CH$_3$ | H | N(CH$_3$)$_2$ | 0 | — | 1 | CH$_3$ | CH$_3$ | 1 | CH$_3$ |
| 1-6 | CH$_3$ | H | N(CH$_3$)$_2$ | 1 | 4 Ph | 0 | — | — | 1 | OtBu |
| 1-7 | CH$_3$ | H | N(CH$_3$)$_2$ | 1 | 4 PhO | 1 | H | H | 1 | CO$_2$CH$_3$ |
| 1-8 | CH$_3$ | H | N(CH$_3$)$_2$ | 0 | — | 2 | H | H | 1 | OCH$_3$ |
| 1-9 | CH$_3$ | H | N(CH$_3$)$_2$ | 1 | 4 Ph | 0 | — | — | 1 | OCH$_3$ |
| 1-10 | CH$_3$ | H | N(CH$_3$)$_2$ | 1 | trans-CH=CHPh | 0 | — | — | 0 | — |
| 1-11 | CH$_3$ | H | N(CH$_3$)$_2$ | 1 | 4 Ph | 0 | — | — | 1 | CN |
| 1-12 | CH$_3$ | H | N(CH$_3$)$_2$ | 1 | 4 Ph | 0 | — | — | 1 | NO$_2$ |
| 1-13 | CH$_3$ | H | N(CH$_3$)$_2$ | 0 | — | 1 | Et | Et | 1 | CO$_2$Et |
| 1-14 | CH$_3$ | H | N(CH$_3$)$_2$ | 0 | — | 1 | CH$_2$CH$_2$ ring | | 1 | CO$_2$Et |
| 1-15 | CH$_3$ | H | N(CH$_3$)$_2$ | 0 | — | 1 | CH$_2$CH$_2$CH$_2$ ring | | 1 | CO$_2$Et |
| 1-16 | CH$_3$ | H | N(CH$_3$)$_2$ | 0 | — | 1 | CH$_2$CH$_2$OCH$_2$CH$_2$ ring | | 1 | CO$_2$Et |
| 1-17 | CH$_3$ | H | N(CH$_3$)$_2$ | 0 | — | 1 | CH$_2$(CH$_2$)$_3$CH$_2$ ring | | 1 | CO$_2$CH$_3$ |
| 1-18 | CH$_3$ | H | N(CH$_3$)$_2$ | 0 | — | 1 | CH$_2$(CH$_2$)$_2$CH$_2$ ring | | 1 | CO$_2$Et |
| 1-19 | CH$_3$ | H | N(CH$_3$)$_2$ | 1 | Ph | 0 | — | — | 0 | — |
| 1-20 | CH$_3$ | H | N(CH$_2$)$_2$O(CH$_2$)$_2$ ring | 0 | — | 1 | CH$_3$ | CH$_3$ | 1 | CO$_2$CH$_3$ |
| 1-21 | CH$_3$ | H | N(Et)$_2$ | 0 | — | 1 | CH$_3$ | CH$_3$ | 1 | CO$_2$CH$_3$ |

TABLE 1-continued

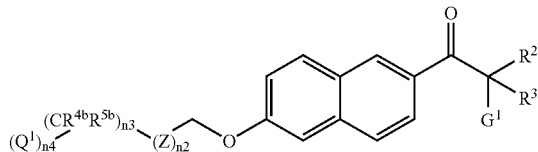

III

Listing of Intermediates of Formula III

| Compound | R² | R³ | G¹ | n2 | Z | n3 | R⁴ᵇ | R⁵ᵇ | n4 | Q¹ |
|---|---|---|---|---|---|---|---|---|---|---|
| 1-22 | CH₃ | H | N(CH₃)cyclohexyl | 0 | — | 1 | CH₃ | CH₃ | 1 | CO₂CH₃ |
| 1-23 | CH₃ | H | N(CH₃)n-butyl | 0 | — | 1 | CH₃ | CH₃ | 1 | CO₂CH₃ |
| 1-24 | CH₃ | H | N(CH₃)iPr | 0 | — | 1 | CH₃ | CH₃ | 1 | CO₂CH₃ |
| 1-25 | CH₃ | H | N(CH₃)Ph | 0 | — | 1 | CH₃ | CH₃ | 1 | CO₂CH₃ |
| 1-26 | CH₃ | H | N(CH₂)₄ | 0 | — | 1 | CH₃ | CH₃ | 1 | CO₂CH₃ |
| 1-27 | CH₃ | CH₃ | N(CH₃)₂ | 0 | — | 1 | CH₃ | CH₃ | 1 | CO₂CH₃ |
| 1-28 | CH₃ | H | N(CH₃)Et | 0 | — | 1 | CH₃ | CH₃ | 1 | CO₂CH₃ |
| 1-29 | CH₃ | H | N(CH₃)₂ | 0 | — | 0 | — | — | 1 | CO₂tBu |
| 1-30 | | | A* | 1 | Ph | 0 | — | — | 0 | — |
| 1-31 | Et | H | N(CH₃)₂ | 0 | — | 1 | CH₃ | CH₃ | 1 | CO₂CH₃ |
| 1-32 | CH₃ | H | N(CH₃)iPr | 0 | — | 1 | CH₂(CH₂)₂CH₂ ring | | 1 | CO₂Et | wherein A* = R²R³G¹ taken together with the carbon atom to which they are attached form:

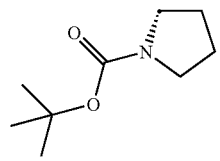

where • is the carbon to which they are attached.

General Synthetic Method A for the preparation of compounds of the Formula III: A THF (0.4 M) solution of compound of Formula IV (1 eq) (Intermediate A-2, A-4, or A-13), triphenylphosphine (1.1 eq), and compound of Formula V (1 eq) was evacuated, placed under a $N_2$ atm, cooled in an ice bath and charged with DIAD (1 eq) portionwise over 5 min. The mixture was allowed to warm to rt and then heated to 45° C. for 16 h. The reaction mixture was concentrated in vacuo and purified by silica gel column chromatography (gradient of 6:1 $CH_2Cl_2$: 10% $CH_3OH$ in $CH_2Cl_2$ (1% $Et_3N$) to 3:1 $CH_2Cl_2$: 10% $CH_3OH$ in $CH_2Cl_2$ (1% $Et_3N$)).

General Synthetic Method B for the preparation of compounds of the Formula III: An acetonitrile solution (0.5 M) of compound of Formula XI (1 eq) (Intermediate A-8 or A-10) was charged with 1 eq. NaI and 3 eq. HG¹ and allowed to stir at 40° C. for 16 h. The reaction mixture was concentrated in vacuo to a slurry and partitioned between $CH_2Cl_2$ and $NaHCO_3$ (sat), and the aqueous layer extracted with $CH_2Cl_2$ (5×). The combined organic layers were dried over $Na_2SO_4$, filtered, and concentrated in vacuo. The resulting residue was purified by silica gel chromatography (gradient of 6:1 $CH_2Cl_2$:10% $CH_3OH$ in $CH_2Cl_2$ (1% $Et_3N$) to 3:1 $CH_2Cl_2$: 10% $CH_3OH$ in $CH_2Cl_2$ (1% $Et_3N$)) to afford the desired compound of Formula III.

COMPOUND 1-1 (Compound of Formula III where $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CO_2CH_3$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=0$, $n^3=1$, $R^{4b}$ and $R^{5b}=CH_3$, $n^4=1$, and $Q^1=CO_2CH_3$. ¹HNMR (CDCl₃, 200 MHz) δ 1.18-1.35 (m, 9H), 3.68 (s, 3H), 4.10 (s, 1H), 7.14-7.20 (m, 2H), 7.74 (d, 1H, J=8.0 Hz), 7.84 (d, 1H, J=8.0 Hz), 7.74 (dd, 1H, J=0.6, 4.4 Hz), 8.55 (s, 1H).

COMPOUND 1-2 (Compound of Formula III where $R^2=CH_3$, $R^3=H$, $G^1=N(CH_3)_2$, $n^2=1$, Z=4-phenyl, $n^3=0$, $n^4=1$, and $Q^1=CO_2CH_3$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=1$, Z=4-phenyl, $n^3=0$, $n^4=1$, and $Q^1=CO_2CH_3$. ¹HNMR (CDCl₃, 200 MHz) δ 1.30 (d, 3H, J=6.0 Hz), 2.33 (s, 6H), 3.91 (s, 3H), 4.15 (q, 1H , J=6.0 Hz), 5.27 (s, 2H), 7.20-7.31 (m, 1H), 7.56 (d, 2H, J=8.0 Hz), 7.74 (d, 1H, J=8.4 Hz), 7.89 (d, 1H, J=8.8 Hz), 8.06-8.10 (m, 4H), 8.57 (s, 1H); MS (ES) 391.9 (M+1).

COMPOUND 1-3 (Compound of Formula III where $R^2=CH_3$, $R^3=H$, $G^1=N(CH_3)_2$, $n^2=1$, Z=3-phenyl, $n^3=0$, $n^4=1$, and $Q^1=CO_2CH_3$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=1$, Z=3-phenyl, $n^3=0$, $n^4=1$, and $Q^1=CO_2CH_3$. ¹HNMR (CDCl₃, 200 MHz) δ 1.32 (d, 3H, J=7.0 Hz), 2.36 (s, 6H), 3.94 (s, 3H), 4.18 (q, 1H, J=6.6 Hz), 5.25 (s, 2H), 7.20-7.31 (m, 1H), 7.44-7.52 (m, 2H), 7.68-7.78 (m, 2H), 7.89 (d, 1H, J=10.0 Hz), 8.00-8.09 (m, 2H), 8.18 (s, 1H), 8.56 (s, 1H); MS (ES) 392.0 (M+1).

COMPOUND 1-4 (Compound of Formula III where $R^2=CH_3$, $R^3=H$, $G^1=N(CH_3)_2$, $n^2=1$, Z=4-phenyl, $n^3=1$, $R^{4b}$ and $R^{5b}=H$, $n^4=1$, and $Q^1=CO_2CH_3$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=1$, Z=4-phenyl, $n^3=1$, $R^{4b}$ and $R^{5b}=H$, $n^4=1$, and $Q^1=CO_2CH_3$. $^1$H NMR (CDCl$_3$, 200 MHz) δ 1.30 (d, 3H, J=8.0 Hz), 2.35 (s, 6H), 3.64 (s, 2H), 3.68 (s, 3H), 4.17 (q, 1H, J=8.0 Hz), 5.16 (s, 2H), 7.11-8.08 (m, 9H), 8.56 (s, 1H); MS (ES) 405.9 (M+1).

COMPOUND 1-5 (Compound of Formula III where $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CH_3$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=0$, $n^3=1$, $R^{4b}$ and $R^{5b}=CH_3$, $n^4=1$, and $Q^1=CH_3$. $^1$H NMR (CDCl$_3$, 200 MHz) δ 1.07 (s, 9H), 1.40 (d, 3H, J=6.2 Hz), 2.37 (s, 6H), 3.73 (s, 2H), 4.20 (q, 1H, J=7.0 Hz), 7.11 (d, 1H, J=2.2 Hz), 7.20 (dd, 1H, J=2.6, 9.2 Hz). 7.47-7.58 (m, 1H), 7.84 (d, 1H, J=8.8 Hz), 7.88 (dd, 1H, J=1.4, 8.2 Hz); 8.55 (s, 1H).

COMPOUND 1-6 (Compound of Formula III where $R^2=CH_3$, $R^3=H$, $G^1=N(CH_3)_2$, $n^2=1$, Z=4-phenyl, $n^3=0$, $n^4=1$, and $Q^1=OtBu$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=1$, Z=4-phenyl, $n^3=0$, $n^4=1$, and $Q^1=OtBu$. $^1$HNMR (CDCl$_3$, 200 MHz) δ 1.30-1.36 (m, 12H), 2.35 (s, 6H), 4.17 (q, 1H, J=6.0 Hz), 5.14 (s, 2H), 7.01-7.07 (m, 2H), 7.24-7.30 (m, 2H), 7.36-7.41 (m, 2H), 7.73-7.90 (m, 2H), 8.05-8.10 (m, 1H), 8.58 (s, 1H); MS (ES) 406.0 (M+1).

COMPOUND 1-7 (Compound of Formula III where $R^2=CH_3$, $R^3=H$, $G^1=N(CH_3)_2$, $n^2=1$, Z=4-PhO, $n^3=1$, $R^{4b}$ and $R^{5b}=H$, $n^4=1$, and $Q^1=CO_2CH_3$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=1$, Z=4-PhO, $n^3=1$, $R^{4b}$ and $R^{5b}=H$, $n^4=1$, and $Q^1=CO_2CH_3$. $^1$HNMR (CDCl$_3$, 200 MHz) δ 1.31 (d, 3H, J=6.0 Hz), 2.34 (s, 6H), 3.80 (s, 3H), 4.17 (q, 1H, J=6.0 Hz), 4.66 (s, 2H), 5.13 (s, 2H), 6.92-6.98 (m, 2H), 7.23-7.44 (m, 4H), 7.72-8.10 (m, 3H), 8.57 (s, 1H); MS (ES) 422.0 (M+1).

COMPOUND 1-8 (Compound of Formula III where $R^2=CH_3$, $R^3=H$, $G^1=N(CH_3)_2$, $n^2=0$, $n^3=2$, $R^{4b}$ and $R^{5b}=H$. $n^4=1$, and $Q^1=OCH_3$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=0$, $n^3=2$, $R^{4b}$ and $R^{5b}=H$, $n^4=1$, and $Q^1=OCH_3$. MS (ES) 302.3 (M+1).

COMPOUND 1-9 (Compound of Formula III where $R^2=CH_3$, $R^3=H$, $G^1=N(CH_3)_2$, $n^2=1$, Z=4-phenyl, $n^3=0$, $n^4=1$, and $Q^1=OCH_3$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=1$, Z=4-phenyl, $n^3=0$, $n^4=1$, and $Q^1=OCH_3$. MS (ES) 364.3 (M+1).

COMPOUND 1-10 (Compound of Formula III where $R^2=CH_3$, $R^3=H$, $G^1=N(CH_3)_2$, $n^2=1$, Z equals trans-CH=CHPh, $n^3$ and $n^4=0$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=1$, Z equals trans-CH=CHPh, $n^3$ and $n^4=0$. MS (ES) 360.3 (M+1).

COMPOUND 1-11 (Compound of Formula III where $R^2=CH_3$, $R^3=H$, $G^1=N(CH_3)_2$, $n^2=1$, Z=4-phenyl, $n^3=0$, $n^4=1$, and $Q^1=CN$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=1$, Z=4-phenyl, $n^3=0$, $n^4=1$, and $Q^1=CN$. MS (ES) 359.3 (M+1).

COMPOUND 1-12 (Compound of Formula III where $R^2=CH_3$, $R^3=H$, $G^1=N(CH_3)_2$, $n^2=1$, Z=4-phenyl, $n^3=0$, $n^4=1$, and $Q^1=NO_2$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=1$, Z=4-phenyl, $n^3=0$, $n^4=1$, and $Q^1=NO_2$. MS (ES) 381.3 (M+1).

COMPOUND 1-13 (Compound of Formula III where $R^2=CH_3$, $R^3=H$, $G^1=N(CH_3)_2$, $n^2=0$, $n^3=1$, $R^{4b}$ and $R^{5b}=CH_2CH_3$, $n^4=1$, and $Q^1=CO_2Et$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=0$, $n^3=1$, $R^{4b}$ and $R^{5b}=CH_2CH_3$, $n^4=1$, and $Q^1=CO_2Et$. MS (ES) 400.3 (M+1).

COMPOUND 1-14 (Compound of Formula III where $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclopropyl ring, $n^4=1$, and $Q^1=CO_2Et$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=0$, $n^3=1$, $R^{4b}$ and $R^{5b}$ are taken together with the carbon to which they are attached to equal a cyclopropyl ring, $n^4=1$, and $Q^1=CO_2Et$. MS (ES) 370.3 (M+1).

COMPOUND 1-15 (Compound of Formula III where $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclobutyl ring, $n^4=1$, and $Q^1=CO_2Et$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=0$, $n^3=1$, $R^{4b}$ and $R^{5b}$ are taken together with the carbon to which they are attached to equal a cyclobutyl ring, $n^4=1$, and $Q^1=CO_2Et$. MS (ES) 384.3 (M+1).

COMPOUND 1-16 (Compound of Formula III where $R^2=CH_3$, $R^3=H$, $G^1=N(CH_3)_2$, $n^2=0$, $n^3=1$, $R^{4b}$ and $R^{5b}$ are taken together with the carbon to which they are attached to equal a 4-pyranyl ring, $n^4=1$, and $Q^1=CO_2CH_3$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=0$, $n^3=1$, $R^{4b}$ and $R^{5b}$ are taken together with the carbon to which they are attached to equal a 4-pyranyl ring, $n^4=1$, and $Q^1=CO_2CH_3$. MS (ES) 400.3 (M+1).

COMPOUND 1-17 (Compound of Formula III where $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclohexyl ring, $n^4=1$, and $Q^1=CO_2Et$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=0$, $n^3=1$, $R^{4b}$ and $R^{5b}$ are taken together with the carbon to which they are attached to equal a cyclohexyl ring, $n^4=1$, and $Q^1=CO_2Et$. MS (ES) 412.3 (M+1).

COMPOUND 1-18 (Compound of Formula III where $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclopentyl ring, $n^4=1$, and $Q^1=CO_2Et$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=0$, $n^3=1$, $R^{4b}$ and $R^{5b}$ are taken together with the carbon to which they are attached to equal a cyclopentyl ring, $n^4=1$, and $Q^1=CO_2Et$. MS (ES) 398.2 (M+1).

COMPOUND 1-19 (Compound of Formula III where $R^2=CH_3$, $R^3=H$, $G^1=N(CH_3)_2$, $n^2=1$, $Z=Ph$, $n^3$ and $n^4=0$): The title compound was prepared according to the General Synthetic Method A as described above wherein compound of Formula IV, $R^2=CH_3$, $R^3=H$, and $G^1=N(CH_3)_2$ and compound of Formula V, $A^1=OH$, $n^2=1$, $Z=Ph$, $n^3$ and $n^4=0$. $^1H$ NMR (CDCl$_3$, 200 MHz) δ 1.32 (d, 3H, J=6.0 Hz), 2.37 (s, 6H), 4.21 (q, 1H, J=6.0 Hz), 5.50 (s, 2H), 7.24-7.50 (m, 3H), 7.75 (d, 2H, J=10.0 Hz), 7.88 (d, 2H, J=8.0 Hz ), 8.04-8.09 (m, 2H), 8.58 (s, 2H); MS (ES) 334.2 (M+1).

COMPOUND 1-20 (Compound of Formula III where $R^2=CH_3$, $R^3=H$, $G^1=N(CH_2)_2O(CH_2)_2$ring, $n^2=0$, $n^3=1$, $R^{4b}$ and $R^{5b}=CH_3$, $n^4=1$, and $Q^1=CO_2CH_3$): The title compound was prepared according to the General Synthetic Method B as described above wherein compound of Formula XI, $R^2=CH_3$, $R^3=H$, $A^3=Br$, $n^2=0$, $n^3=1$, $R^{4b}$ and $R^{5b}=CH_3$, $n^4=1$, and $Q^1=CO_2CH_3$ and $HG^1=HN(CH_2)_2O(CH_2)_2$. MS (ES) 400.2 (M+1).

COMPOUND 1-21 (Compound of Formula III where $R^2=CH_3$, $R^3=H$. $G^1=N(Et)_2$, $n^2=0$, $n^3=1$, $R^{4b}$ and $R^{5b}=CH_3$, $n^4=1$, and $Q^1=CO_2CH_3$): The title compound was prepared according to the General Synthetic Method B as described above wherein compound of Formula XI, $R^2=CH_3$, $R^3=H$, $A^3=Br$, $n^2=0$, $n^3=1$, $R^{4b}$ and $R^{5b}=CH_3$, $n^4=1$, and $Q^1=CO_2CH_3$ and $HG^1=HN(Et)_2$. MS (ES) 386.2 (M+1).

COMPOUND 1-22 (Compound of Formula III where $R^2=CH_3$, $R^3=H$, $G^1=N(CH_3)$cyclohexyl, $n^2=0$, $n^3=1$, $R^{4b}$ and $R^{5b}=CH_3$, $n^4=1$, and $Q^1=CO_2CH_3$): The title compound was prepared according to the General Synthetic Method B as described above wherein compound of Formula XI, $R^2=CH_3$, $R^3=H$, $A^3=Br$, $n^2=0$, $n^3=1$, $R^{4b}$ and $R^{5b}=CH_3$, $n^4=1$, and $Q^1=CO_2CH_3$ and $HG^1=HN(CH_3)$cyclohexyl. MS (ES) 426.2 (M+1).

COMPOUND 1-23 (Compound of Formula III where $R^2=CH_3$, $R^3=H$, $G^1=N(CH_3)$n-butyl, $n^2=0$, $n^3=1$, $R^{4b}$ and $R^{5b}=CH_3$, $n^4=1$, and $Q^1=CO_2CH_3$): The title compound was prepared according to the General Synthetic Method B as described above wherein compound of Formula XI, $R^2=CH_3$, $R^3=H$, $A^3=Br$, $n^2=0$, $n^3=1$, $R^{4b}$ and $R^{5b}=CH_3$, $n^4=1$, and $Q^1=CO_2CH_3$ and $HG^1=HN(CH_3)$n-butyl. MS (ES) 400.2 (M+1).

COMPOUND 1-24 (Compound of Formula III where $R^2=CH_3$, $R^3=Hp$ $G^1=N(CH_3)$iPr, $n^2=0$, $n^3=1$, $R^{4b}$ and $R^{5b}=CH_3$, $n^4=1$, and $Q^1=CO_2CH_3$): The title compound was prepared according to the General Synthetic Method B as described above wherein compound of Formula XI, $R^2=CH_3$, $R^3=H$, $A^3=Br$, $n^2=0$, $n^3=1$, $R^{4b}$ and $R^{5b}=CH_3$, $n^4=1$, and $Q^1=CO_2CH_3$ and $HG^1=HN(CH_3)$iPr. MS (ES) 386.3 (M+1).

COMPOUND 1-25 (Compound of Formula III where $R^2=CH_3$, $R^3=H$, $G^1=N(CH_3)$Ph, $n^2=0$, $n^3=1$, $R^{4b}$ and $R^{5b}=CH_3$, $n^4=1$, and $Q^1=CO_2CH_3$): The title compound was prepared according to the General Synthetic Method B as described above wherein compound of Formula XI, $R^2=CH_3$, $R^3=H$, $A^3=Br$, $n^2=0$, $n^3=1$, $R^{4b}$ and $R^{5b}=CH_3$, $n^4=1$, and $Q^1=CO_2CH_3$ and $HG^1=HN(CH_3)$Ph. MS (ES) 420.2 (M+1).

COMPOUND 1-26 (Compound of Formula III where $R^2=CH_3$, $R^3=H$, $G^1=N(CH_2)_4$, $n^2=0$, $n^3=1$, $R^{4b}$ and $R^{5b}=CH_3$, $n^4=1$, and $Q^1=CO_2CH_3$): The title compound was prepared according to the General Synthetic Method B as described above wherein compound of Formula XI, $R^2=CH_3$, $R^3=H$, $A^3=Br$, $n^2=0$, $n^3=1$, $R^{4b}$ and $R^{5b}=CH_3$, $n^4=1$, and $Q^1=CO_2CH_3$ and $HG^1=HN(CH_2)_4$. MS (ES) 384.3 (M+1).

COMPOUND 1-27 (Compound of Formula III where $R^2=CH_3$, $R^3=CH_3$, $G^1=N(CH_3)_2$, $n^2=0$, $n^3=1$, $R^{4b}$ and $R^{5b}=CH_3$, $n^4=1$, and $Q^1=CO_2CH_3$): The title compound was prepared according to the General Synthetic Method A as described above wherein compound of Formula IV, $R^2=CH_3$, $R^3=CH_3$, and $G^1=N(CH_3)_2$ and compound of Formula V, $A^1=OH$, $n^2=0$, $n^3=1$, $R^{4b}$ and $R^{5b}=CH_3$, and $n^4=1$, and $Q^1=CO_2CH_3$. $^1HNMR$ (CDCl$_3$, 400 MHz) δ 1.31 (d, 6H, J=7.6 Hz), 1.37 (s, 6H), 2.29 (s, 6H), 3.70 (s, 3H), 4.10 (s, 2H), 7.12-7.26 (m, 2H), 7.68 (d, 1H, J=8.8 Hz), 7.83 (d, 1H, J=8.8 Hz), 8.41 (dd, 1H, J=2.0, 8.8 Hz), 9.14 (s, 1H).

COMPOUND 1-28 (Compound of Formula III where $R^2=CH_3$, $R^3=H$, $G^1=N(CH_3)Et$, $n^2=0$, $n^3=1$, $R^{4b}$ and $R^{5b}=CH_3$, $n^4=1$, and $Q^1=CO_2CH_3$): The title compound was prepared according to the General Synthetic Method A as described above wherein compound of Formula IV, $R^2=CH_3$, $R^3=H$, and $G^1=N(CH_3)Et$ and compound of Formula V, $A^1=OH$, $n^2=0$, $n^3=1$, $R^{4b}$ and $R^{5b}=CH_3$, $n^4=1$, and $Q^1=CO_2CH_3$. MS (ES) 372.2 (M+1).

COMPOUND 1-29 (Compound of Formula III where $R^2=CH_3$, $R^3=H$, $G^1=N(CH_3)_2$, $n^2=0$, $n^3=0$, $n^4=1$, and $Q^1=CO_2tBu$): The title compound was prepared as follows: An N,N-dimethylformamide (25 mL) solution of intermediate A-2 (3.00 g, 12.33 mmol) was charged with potassium tert-butoxide (1.52 g, 13.56 mmol) and allowed to stir at rt for 30 min. tert-Butyl bromoacetate (2.64 g, 13.56 mmol), compound of Formula V where $A^1=Br$, $n^2=0$, $n^3=0$, $n^4=1$, and $Q^1=CO_2tBu$, was added dropwise and the reaction was allowed to stir for 24 h. The mixture was dissolved in EtOAc, washed with Na$_2$CO$_3$(sat) 2×, water 2×, and brine 1×. The organic layer was dried over Na$_2$SO$_4$, filtered, and concentrated in vacuo as a brown oil. Silica gel column chromatography (gradient of CH$_2$Cl$_2$ to 5% CH$_3$OH:CH$_2$Cl$_2$ (containing 1 mL Et$_3$N/100 mL of solvent) afforded the desired product as a brown oil. $^1HNMR$ (CDCl$_3$, 200 MHz) δ 1.32 (d, 3H, J=6.0 Hz), 1.50 (s, 9H), 2.36 (s, 6H), 4.17 (q, 1H, J=8.0 Hz), 4.66 (s, 2H), 7.08 (d, 2H, J=2.0 Hz), 7.28 (dd, 1H, J=4.0, 8.0 Hz), 7.73 (d, 1H, J=8.0 Hz), 7.89 (d, 1H, J=8.0 Hz), 8.08 (dd, 1H, J=4.0, 8.0 Hz), 8.58 (s, 1H); MS (ES) 358.0 (M+1).

COMPOUND 1-30 (Compound of Formula III where $R^2$, $R^3$, and $G^1$ are taken together to equal A* (see Table 1), $n^2=1$, $Z=Ph$, $n^3=0$, and $n^4=0$): The title compound was prepared as follows: A 0° C. solution of N-(tert-butoxycarbonyl)-L-proline (1.65 g, 7.66 mmol) in DCM (25 mL) was charged with triethylamine (1.07 mL, 7.66 mmol) and diphenylphosphinic chloride (1.44 mL, 7.66 mmol), and allowed to warm to rt over 2 h. The solvent was removed in-vacuo, and the residual was partitioned between ethyl ether and H$_2$O. The organic layer was subsequently washed with Na$_2$CO$_3$ (2×) and brine (1×), dried over Na$_2$SO$_4$, filtered, and concentrated in-vacuo. The residual was dissolved in THF (25 mL) and cooled to −78° C. Separately, a suspension of 2-bromo-6-benzyloxynaphthelene (1.20 g, 3.83 mmol) and Mg (0.140 g, 5.75 mmol) in THF (4.8 mL) was heated to 50° C. for 30 min, charged with CH$_3$I (1 drop), maintained at 50° C. for an additional 30 min, heated to reflux for 30 min, cooled to rt, and added dropwise to the cooled mixed anhydride solution, which subsequently was allowed to warm to rt overnight with stirring. The solvent was removed in-vacuo, and the residual was partitioned between CH$_2$Cl$_2$ and 1:1 phosphate buffer: 1 M citric acid. The organic layer was subsequently washed with Na$_2$CO$_3$ (2×) and brine (1×), dried over Na$_2$SO$_4$, filtered, and concentrated in-vacuo. The residual was subjected to chromatography (gradient of 95% hexanes:5% EtOAc to 80% hexanes:20% EtOAc) to afford the title compound as a white solid; mp 102-104° C.; MS (ES) 432.13 (M+1).

COMPOUND 1-31 (compound of Formula III where $R^2=CH_2CH_3$, $R^3=H$, $G^1=N(CH_3)_2$, $n^2=0$, $n^3=1$, $R^{4b}$ and $R^{5b}=CH_3$, $n^4=1$, and $Q^1=CO_2CH_3$. The title compound was prepared according to the General Synthetic Method A as described above wherein compound of Formula IV, $R^2=CH_2CH_3$, $R^3=H$, and $G^1=N(CH_3)_2$ and compound of Formula V, $A^1=OH$, $n^2=0$, $n^3=1$, $R^{4b}$ and $R^{5b}=CH_3$, $n^4=1$, and $Q^1=CO_2CH_3$. $^1H$ NMR (CDCl$_3$, 400 MHz) δ 0.89 (t, 3H, 7.4 Hz), 1.38 (s, 6H), 1.78-1.79 (m, 1H), 1.92-1.98 (m, 1H), 2.38 (s, 6H), 3.71 (s, 3H), 3.97-4.01 (m, 1H), 4.12 (s, 2H), 7.15 (d, 1H, J=2.3 Hz), 7.18 (dd, 1H, J=2.5, 8.9 Hz), 7.76 (d, 1H, J=8.0 Hz), 7.86 (d, 1H, J=8.0 Hz), 8.06 (dd, 1H, J=1.7, 8.6 Hz), 8.52 (s, 1H).

COMPOUND 1-32 (Compound of Formula III where $R^2=CH_3$, $R^3=H$, $G^1=N(CH_3)iPr$, $n^2=0$, $n^3=1$, $R^{4b}$ and $R^{5b}$ are taken together with the carbon to which they are attached to equal a cyclopentyl ring, $n^4=1$, and $Q^1=CO_2Et$): The title compound was prepared according to the General Synthetic Method A as described above wherein compound of Formula IV, $R^2=CH_3$, $R^3=H$, and $G^1=N(CH_3)iPr$ and compound of Formula V, $A^1=OH$, $n^2=0$, $n^3=1$, $R^{4b}$ and $R^{5b}$ are taken together with the carbon to which they are attached to equal a cyclopentyl ring, $n^4=1$, and $Q^1=CO_2Et$. MS (ES) 426.1 (M+1).

Following the general methods described hereinbefore, the following intermediates of Formula II as listed in Table 2 were prepared. In the intermediate numbers, "a" denotes the syn amino alcohol and "b" denotes the anti amino alcohol with respect to $G^1$.

TABLE 2

Listing of Intermediates of Formula II

| Compound | $R^2$ | $R^3$ | $G^1$ | n2 | Z | n3 | $R^{4b}$ | $R^{5b}$ | n4 | $Q^1$ |
|---|---|---|---|---|---|---|---|---|---|---|
| 2-1a | CH$_3$ | H | N(CH$_3$)$_2$ | 0 | — | 1 | CH$_3$ | CH$_3$ | 1 | CO$_2$CH$_3$ |
| 2-1b | CH$_3$ | H | N(CH$_3$)$_2$ | 0 | — | 1 | CH$_3$ | CH$_3$ | 1 | CO$_2$CH$_3$ |
| 2-2a | CH$_3$ | H | N(CH$_3$)$_2$ | 1 | 4 Ph | 0 | — | — | 1 | CO$_2$CH$_3$ |
| 2-2b | CH$_3$ | H | N(CH$_3$)$_2$ | 1 | 4 Ph | 0 | — | — | 1 | CO$_2$CH$_3$ |
| 2-3a | CH$_3$ | H | N(CH$_3$)$_2$ | 1 | 3 Ph | 0 | — | — | 1 | CO$_2$CH$_3$ |
| 2-3b | CH$_3$ | H | N(CH$_3$)$_2$ | 1 | 3 Ph | 0 | — | — | 1 | CO$_2$CH$_3$ |
| 2-4a | CH$_3$ | H | N(CH$_3$)$_2$ | 1 | 4 Ph | 1 | H | H | 1 | CO$_2$CH$_3$ |
| 2-4b | CH$_3$ | H | N(CH$_3$)$_2$ | 1 | 4 Ph | 1 | H | H | 1 | CO$_2$CH$_3$ |
| 2-5a | CH$_3$ | H | N(CH$_3$)$_2$ | 0 | — | 1 | CH$_3$ | CH$_3$ | 1 | CH$_3$ |
| 2-5b | CH$_3$ | H | N(CH$_3$)$_2$ | 0 | — | 1 | CH$_3$ | CH$_3$ | 1 | CH$_3$ |
| 2-6a | CH$_3$ | H | N(CH$_3$)$_2$ | 1 | 4 Ph | 0 | — | — | 1 | OtBu |
| 2-6b | CH$_3$ | H | N(CH$_3$)$_2$ | 1 | 4 Ph | 0 | — | — | 1 | OtBu |
| 2-7a | CH$_3$ | H | N(CH$_3$)$_2$ | 1 | 4 PhO | 1 | H | H | 1 | CO$_2$CH$_3$ |
| 2-7b | CH$_3$ | H | N(CH$_3$)$_2$ | 1 | 4 PhO | 1 | H | H | 1 | CO$_2$CH$_3$ |
| 2-8a | CH$_3$ | H | N(CH$_3$)$_2$ | 0 | — | 2 | H | H | 1 | OCH$_3$ |
| 2-8b | CH$_3$ | H | N(CH$_3$)$_2$ | 0 | — | 2 | H | H | 1 | OCH$_3$ |
| 2-9a | CH$_3$ | H | N(CH$_3$)$_2$ | 1 | 4 Ph | 0 | — | — | 1 | OCH$_3$ |
| 2-9b | CH$_3$ | H | N(CH$_3$)$_2$ | 1 | 4 Ph | 0 | — | — | 1 | OCH$_3$ |
| 2-10a | CH$_3$ | H | N(CH$_3$)$_2$ | 1 | trans-CH=CHPh | 0 | — | — | 0 | — |
| 2-10b | CH$_3$ | H | N(CH$_3$)$_2$ | 1 | trans-CH=CHPh | 0 | — | — | 0 | — |
| 2-11a | CH$_3$ | H | N(CH$_3$)$_2$ | 1 | 4 Ph | 0 | — | — | 1 | CN |
| 2-11b | CH$_3$ | H | N(CH$_3$)$_2$ | 1 | 4 Ph | 0 | — | — | 1 | CN |
| 2-12a | CH$_3$ | H | N(CH$_3$)$_2$ | 1 | 4 Ph | 0 | — | — | 1 | NO$_2$ |
| 2-12b | CH$_3$ | H | N(CH$_3$)$_2$ | 1 | 4 Ph | 0 | — | — | 1 | NO$_2$ |
| 2-13a | CH$_3$ | H | N(CH$_3$)$_2$ | 0 | — | 1 | Et | Et | 1 | CO$_2$Et |
| 2-13b | CH$_3$ | H | N(CH$_3$)$_2$ | 0 | — | 1 | Et | Et | 1 | CO$_2$Et |
| 2-14a | CH$_3$ | H | N(CH$_3$)$_2$ | 0 | — | 1 | CH$_2$CH$_2$ ring | | 1 | CO$_2$Et |
| 2-14b | CH$_3$ | H | N(CH$_3$)$_2$ | 0 | — | 1 | CH$_2$CH$_2$ ring | | 1 | CO$_2$Et |
| 2-15a | CH$_3$ | H | N(CH$_3$)$_2$ | 0 | — | 1 | CH$_2$CH$_2$CH$_2$ ring | | 1 | CO$_2$Et |
| 2-15b | CH$_3$ | H | N(CH$_3$)$_2$ | 0 | — | 1 | CH$_2$CH$_2$CH$_2$ ring | | 1 | CO$_2$Et |
| 2-16a | CH$_3$ | H | N(CH$_3$)$_2$ | 0 | — | 1 | CH$_2$CH$_2$OCH$_2$CH$_2$ ring | | 1 | CO$_2$CH$_3$ |
| 2-16b | CH$_3$ | H | N(CH$_3$)$_2$ | 0 | — | 1 | CH$_2$CH$_2$OCH$_2$CH$_2$ ring | | 1 | CO$_2$CH$_3$ |
| 2-17a | CH$_3$ | H | N(CH$_3$)$_2$ | 0 | — | 1 | CH$_2$(CH$_2$)$_3$CH$_2$ ring | | 1 | CO$_2$Et |
| 2-17b | CH$_3$ | H | N(CH$_3$)$_2$ | 0 | — | 1 | CH$_2$(CH$_2$)$_3$CH$_2$ ring | | 1 | CO$_2$Et |
| 2-18a | CH$_3$ | H | N(CH$_3$)$_2$ | 0 | — | 1 | CH$_2$(CH$_2$)$_2$CH$_2$ ring | | 1 | CO$_2$Et |
| 2-18b | CH$_3$ | H | N(CH$_3$)$_2$ | 0 | — | 1 | CH$_2$(CH$_2$)$_2$CH$_2$ ring | | 1 | CO$_2$Et |
| 2-19a | CH$_3$ | H | N(CH$_3$)$_2$ | 1 | Ph | 0 | — | — | 0 | — |
| 2-19b | CH$_3$ | H | N(CH$_3$)$_2$ | 1 | Ph | 0 | — | — | 0 | — |
| 2-20a | CH$_3$ | H | N(CH$_2$)$_2$O(CH$_2$)$_2$ ring | 0 | — | 1 | CH$_3$ | CH$_3$ | 1 | CO$_2$CH$_3$ |
| 2-20b | CH$_3$ | H | N(CH$_2$)$_2$O(CH$_2$)$_2$ ring | 0 | — | 1 | CH$_3$ | CH$_3$ | 1 | CO$_2$CH$_3$ |
| 2-21a | CH$_3$ | H | N(Et)$_2$ | 0 | — | 1 | CH$_3$ | CH$_3$ | 1 | CO$_2$CH$_3$ |
| 2-21b | CH$_3$ | H | N(Et)$_2$ | 0 | — | 1 | CH$_3$ | CH$_3$ | 1 | CO$_2$CH$_3$ |
| 2-22a | CH$_3$ | H | N(CH$_3$)cyclohexyl | 0 | — | 1 | CH$_3$ | CH$_3$ | 1 | CO$_2$CH$_3$ |
| 2-22b | CH$_3$ | H | N(CH$_3$)cyclohexyl | 0 | — | 1 | CH$_3$ | CH$_3$ | 1 | CO$_2$CH$_3$ |
| 2-23a | CH$_3$ | H | N(CH$_3$)n-butyl | 0 | — | 1 | CH$_3$ | CH$_3$ | 1 | CO$_2$CH$_3$ |
| 2-23b | CH$_3$ | H | N(CH$_3$)n-butyl | 0 | — | 1 | CH$_3$ | CH$_3$ | 1 | CO$_2$CH$_3$ |
| 2-24a | CH$_3$ | H | N(CH$_3$)iPr | 0 | — | 1 | CH$_3$ | CH$_3$ | 1 | CO$_2$CH$_3$ |
| 2-24b | CH$_3$ | H | N(CH$_3$)iPr | 0 | — | 1 | CH$_3$ | CH$_3$ | 1 | CO$_2$CH$_3$ |
| 2-25a | CH$_3$ | H | N(CH$_3$)Ph | 0 | — | 1 | CH$_3$ | CH$_3$ | 1 | CO$_2$CH$_3$ |

TABLE 2-continued

Listing of Intermediates of Formula II

II

| Compound | $R^2$ | $R^3$ | $G^1$ | n2 | Z | n3 | $R^{4b}$ | $R^{5b}$ | n4 | $Q^1$ |
|---|---|---|---|---|---|---|---|---|---|---|
| 2-26a | $CH_3$ | H | $N(CH_2)_4$ ring | 0 | — | 1 | $CH_3$ | $CH_3$ | 1 | $CO_2CH_3$ |
| 2-26b | $CH_3$ | H | $N(CH_2)_4$ ring | 0 | — | 1 | $CH_3$ | $CH_3$ | 1 | $CO_2CH_3$ |
| 2-27 | $CH_3$ | $CH_3$ | $N(CH_3)_2$ | 0 | — | 1 | $CH_3$ | $CH_3$ | 1 | $CO_2CH_3$ |
| 2-28a | $CH_3$ | H | $N(CH_3)Et$ | 0 | — | 1 | $CH_3$ | $CH_3$ | 1 | $CO_2CH_3$ |
| 2-28b | $CH_3$ | H | $N(CH_3)Et$ | 0 | — | 1 | $CH_3$ | $CH_3$ | 1 | $CO_2CH_3$ |
| 2-29a | $CH_3$ | H | $N(CH_3)_2$ | 0 | — | 0 | — | — | 1 | $CO_2tBu$ |
| 2-29b | $CH_3$ | H | $N(CH_3)_2$ | 0 | — | 0 | — | — | 1 | $CO_2tBu$ |
| 2-30 | H | H | $N(CH_3)_2$ | 0 | — | 1 | $CH_3$ | $CH_3$ | 1 | $CO_2CH_3$ |
| 2-31a | | | A2* | 1 | Ph | 0 | — | — | 0 | — |
| 2-31b | | | A2* | 1 | Ph | 0 | — | — | 0 | — |
| 2-32a | Et | H | $N(CH_3)_2$ | 0 | — | 1 | $CH_3$ | $CH_3$ | 1 | $CO_2CH_3$ |
| 2-32b | Et | H | $N(CH_3)_2$ | 0 | — | 1 | $CH_3$ | $CH_3$ | 1 | $CO_2CH_3$ |
| 2-33a | $CH_3$ | H | $N(CH_3)iPr$ | 0 | — | 1 | $CH_2(CH_2)_2CH_2$ ring | | 1 | $CO_2Et$ |
| 2-33b | $CH_3$ | H | $N(CH_3)iPr$ | 0 | — | 1 | $CH_2(CH_2)_2CH_2$ ring | | 1 | $CO_2Et$ | wherein A2* = $R^2R^3G^1$ taken together with the carbon to which they are attached form:

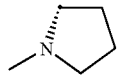

where • is the carbon to which they are attached.

General Synthetic Method C for the preparation of compounds of the Formula IIa/b: A solution of compound of Formula II (1 eq) in $CH_3OH$ (0.3M) was cooled to 0° C. Sodium borohydride (1 eq) was added portionwise at 0° C. and the reaction mixture was allowed to warm to rt and stir for 1.5 h. The reaction mixture was concentrated in vacuo, partitioned between $NaHCO_3$ and $CH_2Cl_2$, and the aqueous layer was extracted 5× with $CH_2Cl_2$. The combined organic layers were dried over $Na_2SO_4$, filtered, and concentrated in vacuo. The crude product was purified by silica gel column chromatography (gradient of $CH_2Cl_2$ to 5% $CH_3OH:CH_2Cl_2$ with 1% $Et_3N$) to afford the desired syn and anti isomers, a and b respectively, of compound of Formula II.

COMPOUND 2-1a (Compound of Formula II where $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CO_2CH_3$): The title compound was prepared according to the General Synthetic Method C as described above wherein compound of Formula III, $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CO_2CH_3$. $^1$HNMR (CDCl$_3$, 200 MHz) δ 0.72 (d, 3H, J=6.6 Hz), 1.36 (s, 6H), 2.34 (s, 6H), 2.63-2.68 (m, 1H), 3.71 (s, 3H), 4.08 (s, 2H), 4.32 (d, 1H, J=9.8 Hz), 7.11-7.14 (m, 2H), 7.26 (s, 1H), 7.66-7.74 (m, 3H); MS (ES) 360.0 (M+1).

COMPOUND 2-1b (Compound of Formula II where $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CO_2CH_3$): The title compound was prepared according to the General Synthetic Method C as described above wherein compound of Formula III, $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CO_2CH_3$. $^1$HNMR (CDCl$_3$, 200 MHz) δ 0.85 (d, 3H, J=6.6 Hz), 1.36 (s, 6H), 2.34 (s, 6H), 2.63-2.68 (m, 1H), 3.71 (s, 3H), 4.08 (s, 2H), 5.13 (d, 1H, J=3.6 Hz), 7.11-7.14 (m, 2H), 7.26 (s, 1H), 7.66-7.74 (m, 3H); MS (ES) 360.0 (M+1).

COMPOUND 2-2a (Compound of Formula II where $R^2=CH_3$, $R^3=H$, $G^1=N(CH_3)_2$, $n^2=1$, Z=4-phenyl, $n^3=0$, $n^4=1$, and $Q^1=CO_2CH_3$): The title compound was prepared according to the General Synthetic Method C as described above wherein compound of Formula III, $R^2=CH_3$, $R^3=H$, $G^1=N(CH_3)_2$, $n^2=1$, Z=4-phenyl, $n^3=0$, $n^4=1$, and $Q^1=CO_2CH_3$. $^1$HNMR (CDCl$_3$, 200 MHz) δ 0.73 (d, 3H, J=6.8 Hz), 2.33 (s, 6H), 2.61-2.68 (m, 1H), 3.93 (s, 31H), 4.33 (d, 1H, J=9.6 Hz), 5.24 (s, 2H), 7.16-7.24 (m, 2H), 7.37 (dd, 1H, J=8.4 Hz, 1.2 Hz), 7.56 (d, 2H, J=4.0 Hz), 7.66-7.77 (m, 3H), 8.06-8.08 (m, 2H); MS (ES) 393.9 (M+1).

COMPOUND 2-2b (Compound of Formula II where $R^2=CH_3$, $R^3=H$, $G^1=N(CH_3)_2$, $n^2=1$, Z=4-phenyl, $n^3=0$, $n^4=1$, and $Q^1=CO_2CH_3$): The title compound was prepared according to the General Synthetic Method C as described above wherein compound of Formula III, $R^2=CH_3$, $R^3=H$, $G^1=N(CH_3)_2$, $n^2=1$, Z=4-phenyl, $n^3=0$, $n^4=1$, and $Q^1=CO_2CH_3$. $^1$HNMR (CDCl$_3$, 200 MHz) δ 0.83 (d, 3H, J=6.8 Hz), 2.39 (s, 6H), 2.61-2.68 (m, 1H), 3.93 (s, 3H), 5.10 (d, 1H, J=3.2 Hz), 5.24 (s, 2H), 7.17-7.24 (m, 2H), 7.47 (dd, 1H, J=2.0, 8.8 Hz), 7.56 (d, 2H, J=8.0 Hz), 7.66-7.77 (m, 3H), 8.06-8.08 (m, 2H); MS (ES) 393.9 (M+1).

COMPOUND 2-3a (Compound of Formula II where $R^2=CH_3$, $R^3=H$, $G^1=N(CH_3)_2$, $n^2=1$, Z=3-phenyl, $n^3=0$, $n^4=1$, and $Q^1=CO_2CH_3$): The title compound was prepared according to the General Synthetic Method C as described above wherein compound of Formula II, $R^2=CH_3$, $R^3=H$, $G^1=N(CH_3)_2$, $n^2=1$, Z=3-phenyl, $n^3=0$, $n^4=1$, and $Q^1=CO_2CH_3$. $^1$H NMR (CDCl$_3$, 200 MHz) δ0.73 (d, 3H, J=6.6 Hz), 2.34 (s, 6H), 2.63-2.71 (m, 1H), 3.93 (s, 3H), 4.33 (d, 1H, J=9.4 Hz), 5.21 (s, 2H), 7.20 (s, 1H), 7.24 (s, 1H), 7.35-7.52 (m, 2H), 7.66-7.73 (m, 3H), 7.77 (s, 1H), 8.00-8.04 (m, 1H), 8.17 (s, 1H); MS (ES) 394.0 (M+1).

COMPOUND 2-3b (Compound of Formula II where $R^2=CH_3$, $R^3=H$, $G^1=N(CH_3)_2$, $n^2=1$, $Z$=3-phenyl, $n^3=0$, $n^4=1$, and $Q^1=CO_2CH_3$): The title compound was prepared according to the General Synthetic Method C as described above wherein compound of Formula III, $R^2=CH_3$, $R^3=H$, $G^1=N(CH_3)_2$, $n^2=1$, $Z$=3-phenyl, $n^3=0$, $n^4=1$, and $Q^1=CO_2CH_3$. $^1H$ NMR (CDCl$_3$, 200 MHz) δ 0.89 (d, 3H, J=6.6 Hz), 2.45 (s, 6H), 2.94-3.02 (m, 11H), 3.93 (s, 3H), 4.33 (d, 1H, J=9.4 Hz), 5.21 (s, 2H), 7.20 (s, 1H), 7.24 (s, 1H), 7.35-7.52 (m, 2H), 7.66-7.73 (m, 3H), 7.77 (s, 1H), 8.00-8.04 (m, 1H), 8.17 (s, 1H); MS (ES) 394.0 (M+1).

COMPOUND 2-4a (Compound of Formula II where $R^2=CH_3$, $R^3=H$, $G^1=N(CH_3)_2$, $n^2=1$, $Z$=4-phenyl, $n^3=1$, $R^{4b}$ and $R^{5b}=H$, $n^4=1$, and $Q^1=CO_2CH_3$): The title compound was prepared according to the General Synthetic Method C as described above wherein compound of Formula III, $R^2=CH_3$, $R^3=H$, $G^1=N(CH_3)_2$, $n^2=1$, $Z$=4-phenyl, $n^3=1$, $R^{4b}$ and $R^{5b}=H$, $n^4=1$, and $Q^1=CO_2CH_3$. $^1H$ NMR (CDCl$_3$, 200 MHz) δ 0.73 (d, 3H, J=6.6 Hz), 2.34 (s, 6H), 2.58-2.75 (m, 1H), 3.65 (s, 2H), 3.70 (s, 3H), 4.35 (d, 1H, J =10.0 Hz), 5.16 (s, 2H), 7.18-7.34 (m, 4H), 7.38-7.50 (m, 3H), 7.67-7.76 (m, 3H).

COMPOUND 2-4b (Compound of Formula II where $R^2=CH_3$, $R^3=H$, $G^1=N(CH_3)_2$, $n^2=1$, $Z$=4-phenyl, $n^3=1$, $R^{4b}$ and $R^{5b}=H$, $n^4=1$, and $Q^1=CO_2CH_3$): The title compound was prepared according to the General Synthetic Method C as described above wherein compound of Formula III, $R^2=CH_3$, $R^3=H$, $G^1=N(CH_3)_2$, $n^2=1$, $Z$=4-phenyl, $n^3=1$, $R^{4b}$ and $R^{5b}=H$, $n^4=1$, and $Q^1=CO_2CH_3$. $^1H$ NMR (CDCl$_3$, 200 MHz) δ 0.65 (d, 3H, J=6.6 Hz), 2.39 (s, 6H), 2.58-2.75 (m, 1H), 3.65 (s, 2H), 3.70 (s, 3H), 4.35 (d, 1H, J=10.0 Hz), 5.16 (s, 2H), 7.18-7.34 (m, 4H), 7.38-7.50 (m, 3H), 7.67-7.76 (m, 3H); MS (ES) 408.0 (M+1).

COMPOUND 2-5a (Compound of Formula II where $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CH_3$): The title compound was prepared according to the General Synthetic Method C as described above wherein compound of Formula III, $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CH_3$. $^1H$ NMR (CDCl$_3$, 200 MHz) δ 0.73 (d, 3H, J=3.6 Hz), 1.08 (s, 9H), 2.34 (s, 6H), 2.66-2.69 (m, 1H), 3.71 (s, 1H), 4.32 (d, 1H, J=10.0 Hz), 5.12 (s, 2H), 7.11 (s, 1H), 7.16 (d, 1H, J=8.8 Hz), 7.35 (d, 1H, J=7.4 Hz), 7.45 (d, 1H, J=8.4 Hz), 7.67-7.75 (m, 2H); MS (ES) 316.0 (M+1).

COMPOUND 2-5b (Compound of Formula II where $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CH_3$): The title compound was prepared according to the General Synthetic Method C as described above wherein compound of Formula III, $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CH_3$. $^1H$ NMR (CDCl$_3$, 200 MHz) δ 0.85 (d, 3H, J=3.6 Hz), 1.08 (s, 9H), 2.41 (s, 6H), 2.66-2.69 (m, 1H), 3.71 (s, 1H), 4.32 (d, 1H, J=10.0 Hz), 5.12 (s, 2H), 7.11 (s, 1H), 7.16 (d, 1H, J=8.8 Hz), 7.35 (d, 1H, J=7.4 Hz), 7.45 (d, 1H, J=8.4 Hz), 7.67-7.75 (m, 2H); MS (ES) 316.0 (M+1).

COMPOUND 2-6a (Compound of Formula II where $R^2=CH_3$, $R^3=H$, $G^1=N(CH_3)_2$, $n^2=1$, $Z$=4-phenyl, $n^3=0$, $n^4=1$, and $Q^1$=OtBu): The title compound was prepared according to the General Synthetic Method C as described above wherein compound of Formula III, $R^2=CH_3$, $R^3=H$, $G^1=N(CH_3)_2$, $n^2=1$, $Z$=4-phenyl, $n^3=0$, $n^4=1$, and $Q^1$=OtBu. $^1H$ NMR (CDCl$_3$, 200 MHz) δ 0.73 (d, 3H, J=6.0 Hz), 1.36 (s, 9H), 2.34 (s, 6H), 2.63-2.72 (m, 1H), 4.33 (d, 1H, J=8.0 Hz), 5.11 (s, 2H), 7.00-7.04 (m, 2H), 7.20-7.23 (m, 2H), 7.36-7.49 (m, 3H), 7.69-7.75 (m, 3H); MS (ES) 408.0 (M+1).

COMPOUND 2-6b (Compound of Formula II where $R^2=CH_3$, $R^3=H$, $G^1=N(CH_3)_2$, $n^2=1$, $Z$=4-phenyl, $n^3=0$, $n^4=1$, and $Q^1$=OtBu): The title compound was prepared according to the General Synthetic Method C as described above wherein compound of Formula III, $R^2=CH_3$, $R^3=H$, $G^1=N(CH_3)_2$, $n^2=1$, $Z$=4-phenyl, $n^3=0$, $n^4=1$, and $Q^1$=OtBu. $^1H$ NMR (CDCl$_3$, 200 MHz) δ 0.87 (d, 3H, J=6.0 Hz), 1.36 (s, 9H), 2.43 (s, 6H), 2.63-2.72 (m, 1H), 5.11 (s, 2H), 5.16 (d, 1H, J=4.0 Hz), 7.00-7.04 (m, 2H), 7.20-7.23 (m, 2H), 7.36-7.49 (m, 3H), 7.69-7.75 (m, 3H); MS (ES) 408.0 (M+1).

COMPOUND 2-7a (Compound of Formula II where $R^2=CH_3$, $R^3=H$, $G^1=N(CH_3)$ $n^2=1$, $Z$=4-PhO, $n^3=1$, $R^{4b}$ and $R^{5b}=H$, $n^4=1$, and $Q^1=CO_2CH_3$): The title compound was prepared according to the General Synthetic Method C as described above wherein compound of Formula III, $R^2=CH_3$, $R^3=H$, $G^1=N(CH_3)_2$, $n^2=1$, $Z$=4-PhO, $n^3=1$, $R^{4b}$ and $R^{5b}=H$, $n^4=1$, and $Q^1=CO_2CH_3$. $^1H$ NMR (CDCl$_3$, 200 MHz) δ 0.73 (d, 3H, J=6.0 Hz), 2.34 (s, 6H), 2.64-2.72 (m, 1H), 3.81 (s, 3H), 4.34 (d, 1H, J=8.0 Hz), 4.65 (s, 2H), 5.10 (s, 2H) 6.92-6.96 (m, 2H), 7.17-7.21 (m, 2H), 7.39-7.46 (m, 3H), 7.68-7.75 (m, 3H); MS (ES) 424.0 (M+1).

COMPOUND 2-7b (Compound of Formula II where $R^2=CH_3$, $R^3=H$, $G^1=N(CH_3)$ $n^2=1$, $Z$=4-PhO, $n^3=1$, $R^{4b}$ and $R^{5b}=H$, $n^4=1$, and $Q^1=CO_2CH_3$): The title compound was prepared according to the General Synthetic Method C as described above wherein compound of Formula III, $R^2=CH_3$, $R^3=H$, $G^1=N(CH_3)_2$, $n^2=1$, $Z$=4-PhO, $n^3=1$, $R^{4b}$ and $R^{5b}=H$, $n^4=1$, and $Q^1=CO_2CH_3$. $^1H$ NMR (CDCl$_3$, 200 MHz) δ 0.90 (d, 3H, J=6.0 Hz), 2.46 (s, 6H), 2.64-2.72 (m, 1H), 3.81 (s, 3H), 4.65 (s, 2H), 5.10 (s, 2H), 5.22 (d, 1H, J=4.0 Hz), 6.92-6.96 (m, 2H), 7.17-7.21 (m, 2H), 7.39-7.46 (m, 3H), 7.68-7.75 (m, 3H); MS (ES) 424.0 (M+1).

COMPOUND 2-8a (Compound of Formula II where $R^2=CH_3$, $R^3=H$, $G^1=N(CH_3)_2$, $n^2=0$, $n^3=2$, $R^{4b}$ and $R^{5b}=H$, $n^4=1$, and $Q^1=OCH_3$): The title compound was prepared according to the General Synthetic Method C as described above wherein compound of Formula III, $R^2=CH_3$, $R^3=H$, $G^1=N(CH_3)_2$, $n^2=0$, $n^3=2$, $R^{4b}$ and $R^{5b}=H$, $n^4=1$, and $Q^1=OCH_3$. MS (ES) 304.3 (M+1).

COMPOUND 2-8b (Compound of Formula II where $R^2=CH_3$, $R^3=H$, $G^1=N(CH_3)_2$, $n^2=0$, $n^3=2$, $R^{4b}$ and $R^{5b}=H$, $n^4=1$, and $Q^1=OCH_3$): The title compound was prepared according to the General Synthetic Method C as described above wherein compound of Formula III, $R^2=CH_3$, $R^3=H$, $G^1=N(CH_3)_2$, $n^2=0$, $n^3=2$, $R^{4b}$ and $R^{5b}=H$, $n^4=1$, and $Q^1=OCH_3$. MS (ES) 304.3 (M+1).

COMPOUND 2-9a (Compound of Formula II where $R^2=CH_3$, $R^3=H$, $G^1=N(CH_3)_2$, $n^2=1$, $Z$=4-phenyl, $n^3=0$, $n^4=1$, and $Q^1=OCH_3$): The title compound was prepared according to the General Synthetic Method C as described above wherein compound of Formula III, $R^2=CH_3$, $R^3=H$, $G^1=N(CH_3)_2$, $n^2=1$, $Z$=4-phenyl, $n^3=0$, $n^4=1$, and $Q^1=OCH_3$. MS (ES) 366.4 (M+1).

COMPOUND 2-9b (Compound of Formula II where $R^2=CH_3$, $R^3=H$, $G^1=N(CH_3)_2$, $n^2=1$, $Z$=4-phenyl, $n^3=0$, $n^4=1$, and $Q^1=OCH_3$): The title compound was prepared according to the General Synthetic Method C as described above wherein compound of Formula III, $R^2=CH_3$, $R^3=H$, $G^1=N(CH_3)_2$, $n^2=1$, $Z$=4-phenyl, $n^3=0$, $n^4=1$, and $Q^1=OCH_3$. MS (ES) 366.4 (M+1).

COMPOUND 2-10a (Compound of Formula II where $R^2=CH_3$, $R^3=H$, $G^1=N(CH_3)_2$, $n^2=1$, $Z$ equals trans-CH=CHPh, $n^3$ and $n^4=0$): The title compound was prepared according to the General Synthetic Method C as described above wherein compound of Formula III, $R^2=CH_3$, $R^3=H$, $G=N(CH_3)_2$, $n^2=1$, $Z$ equals trans-CH=CHPh, $n^3$ and $n^4=0$. MS (ES) 362.3 (M+1).

COMPOUND 2-10b (Compound of Formula II where $R^2=CH_3$, $R^3=H$, $G^1=N(CH_3)_2$, $n^2=1$, $Z$ equals trans-CH=CHPh, $n^3$ and $n^4=0$): The title compound was prepared according to the General Synthetic Method C as described above wherein compound of Formula III, $R^2=CH_3$, $R^3=H$, $G^1=N(CH_3)_2$, $n^2=1$, Z equals trans-CH=CHPh, $n^3$ and $n^4=0$. MS (ES) 362.3 (M+1).

COMPOUND 2-11a/b (Compound of Formula II where $R^2=CH_3$, $R^3=H$, $G^1=N(CH_3)_2$, $n^2=1$, Z=4-phenyl, $n^3=0$, $n^4=1$, and $Q^1=CN$): The title compounds were prepared as a mixture of syn and anti isomers according to the General Synthetic Method C as described above wherein compound of Formula III, $R^2=CH_3$, $R^3=H$, $G^1=N(CH_3)_2$, $n^2=1$, Z=4-phenyl, $n^3=0$, $n^4=1$, and $Q^1CN$. MS (ES) 361.2 (M+1).

COMPOUND 2-12a (Compound of Formula II where $R^2=CH_3$, $R^3=H$, $G^1=N(CH_3)_2$, $n^2=1$, Z=4-phenyl, $n^3=0$, $n^4=1$, and $Q^1=NO_2$): The title compound was prepared according to the General Synthetic Method C as described above wherein compound of Formula III, $R^2=CH_3$, $R^3=H$, $G^1=N(CH_3)_2$, $n^2=1$, Z=4-phenyl, $n^3=0$, $n^4=1$, and $Q^1=NO_2$. $^1H$ NMR (CDCl$_3$, 400 MHz) δ 0.73 (d, 3H, J=6.4 Hz), 2.33 (s, 6H), 2.63-2.70 (m, 1H), 4.33 (d, 1H, J=12.0 Hz), 5.28 (s, 2H), 7.15 (d, 1H, J=2.0 Hz), 7.21 (dd, 1H, J=2.8, 8.8 Hz), 7.38-7.52 (m, 2H), 7.60 (d, 2H, J=8.4 Hz), 7.67-7.70 (m, 2H), 7.74 (s, 1H), 7.75-7.78 (m, 1H).

COMPOUND 2-12b (Compound of Formula II where $R^2=CH_3$, $R^3=H$, $G^1=N(CH_3)_2$, $n^2=1$, Z=4-phenyl, $n^3=0$, $n^4=1$, and $Q^1=NO_2$): The title compound was prepared according to the General Synthetic Method C as described above wherein compound of Formula III, $R^2=CH_3$, $R^3=H$, $G^1=N(CH_3)_2$, $n^2=1$, Z=4-phenyl, $n^3=0$, $n^4=1$, and $Q^1=NO_2$. $^1H$ NMR (CDCl$_3$, 400 MHz) δ 0.73 (d, 3H, J=6.4 Hz), 2.33 (s, 6H), 2.63-2.70 (m, 1H), 4.33 (d, 1H, J=12.0 Hz), 5.28 (s, 2H), 7.15 (d, 1H, J=2.0 Hz), 7.21 (dd, 1H, J=2.8, 8.8 Hz), 7.38-7.52 (m, 2H), 7.60 (d, 2H, J=8.4 Hz), 7.67-7.70 (m, 2H), 7.74 (s, 1H), 7.75-7.78 (m, 1H).

COMPOUND 2-13a (Compound of Formula II where $R^2=CH_3$, $R^3=H$, $G^1=N(CH_3)_2$, $n^2=0$, $n^3=1$, $R^{4b}$ and $R^{5b}=CH_2CH_3$, $n^4=1$, and $Q^1=CO_2Et$): The title compound was prepared according to the General Synthetic Method C as described above wherein compound of Formula III, $R^2=CH_3$, $R^3=H$, $G^1=N(CH_3)_2$, $n^2=0$, $n^3=1$, $R^{4b}$ and $R^{5b}=CH_2CH_3$, $n^4=1$, and $Q^1=CO_2Et$. $^1H$ NMR (CDCl$_3$, 400 MHz) δ 0.72 (d, 3H, J=6.8 Hz), 0.85 (t, 6H, J=7.6 Hz), 1.26 (t, 3H, J=7.2 Hz), 1.78-1.83 (m, 4H), 2.33 (s, 6H), 2.63-2.71 (m, 1H), 4.15 (s, 2H), 4.20 (q, 2H, J=6.4 Hz, 14.0 Hz), 4.33 (d, 1H, J=9.6 Hz), 7.12 (dd, 1H, J=2.8 Hz, 8.8 Hz), 7.19 (d, 1H, J=2.4 Hz), 7.46 (d, 1H, J=8.8 Hz), 7.69-7.73 (m, 3H); MS (ES) 402.3 (M+1).

COMPOUND 2-13b (Compound of Formula II where $R^2=CH_3$, $R^3=H$, $G^1=N(CH_3)_2$, $n^2=0$, $n^3=1$, $R^{4b}$ and $R^{5b}=CH_2CH_3$, $n^4=1$, and $Q^1=CO_2Et$): The title compound was prepared according to the General Synthetic Method C as described above wherein compound of Formula III, $R^2=CH_3$, $R^3=H$, $G^1=N(CH_3)_2$, $n^2=0$, $n^3=1$, $R^{4b}$ and $R^{5b}=CH_2CH_3$, $n^4=1$, and $Q^1=CO_2Et$. MS (ES) 402.3 (M+1).

COMPOUND 2-14a (Compound of Formula II where $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclopropyl ring, $n^4=1$, and $Q^1=CO_2Et$): The title compound was prepared according to the General Synthetic Method C as described above wherein compound of Formula III, $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclopropyl ring, $n^4=1$, and $Q^1=CO_2Et$. $^1H$ NMR (CDCl$_3$, 400 MHz) δ 0.73 (d, 3H, J=6.4 Hz), 1.09 (q, 2H, J=3.2 Hz), 1.22 (t, 3H, J=7.6 Hz), 1.39 (q, 2H, J=2.8 Hz), 2.34 (s, 6H), 2.63-2.71 (m, 1H), 4.17 (q, 2H, J=7.2 Hz), 4.25 (s, 2H), 4.33 (d, 1H, J=8.0 Hz), 7.13 (s, 1H), 7.15 (d, 1H), 7.45 (d, 1H, J=8.4 Hz), 7.69-7.72 (m, 3H).

COMPOUND 2-14b (Compound of Formula II where $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclopropyl ring, $n^4=1$, and $Q^1=CO_2Et$): The title compound was prepared according to the General Synthetic Method C as described above wherein compound of Formula III, $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclopropyl ring, $n^4=1$, and $Q^1=CO_2Et$. MS (ES) 372.0 (M+1).

COMPOUND 2-15a (Compound of Formula II where $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclobutyl ring, $n^4=1$, and $Q^1=CO_2Et$): The title compound was prepared according to the General Synthetic Method C as described above wherein compound of Formula III, $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclobutyl ring, $n^4=1$, and $Q^1=CO_2Et$. $^1H$ NMR (CDCl$_3$, 400 MHz) δ 0.74 (d, 3H, J=6.6 Hz), 1.23-1.30 (m, 3H), 2.03-2.07 (m, 2H), 2.19-2.21 (m, 2H), 2.35 (s, 6H), 2.55-2.58 (m, 2H), 2.60-2.75 (m, 1H), 4.17-4.24 (m, 2H), 4.31-4.38 (m, 3H), 7.15 (dd, 1H, J=2.5 Hz, 8.8 Hz), 7.18 (d, 1H, J=2.4 Hz), 7.48 (dd, 1H, J=1.6 Hz, 8.6 Hz), 7.71-7.74 (m, 3H).

COMPOUND 2-15b (Compound of Formula II where $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclobutyl ring, $n^4=1$, and $Q^1=CO_2Et$): The title compound was prepared according to the General Synthetic Method C as described above wherein compound of Formula III, $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclobutyl ring, $n^4=1$, and $Q^1=CO_2Et$. MS (ES) 386.3 (M+1).

COMPOUND 2-16a (Compound of Formula II where $R^2=CH_3$, $R^3=H$, $G^1=N(CH_3)_2$, $n^2=0$, $n^3=1$, $R^{4b}$ and $R^{5b}$ are taken together with the carbon to which they are attached to equal a 4-pyranyl ring, $n^4=1$, and $Q^1=CO_2CH_3$): The title compound was prepared according to the General Synthetic Method C as described above wherein compound of Formula III, $R^2=CH_3$, $R^3=H$, $G^1=N(CH_3)_2$, $n^2=0$, $n^3=1$, $R^{4b}$ and $R^{5b}$ are taken together with the carbon to which they are attached to equal a 4-pyranyl ring, $n^4=1$, and $Q^1=CO_2CH_3$. $^1H$ NMR (CDCl$_3$, 400 MHz) δ 0.73 (d, 3H), 1.75-1.82 (m, 2H), 2.23-2.29 (m, 2H), 2.34 (s, 6H), 2.66 (m, 1H), 3.57-3.64 (m, 2H), 3.75 (s, 3H), 3.86-3.93 (m, 2H), 4.12 (s, 2H), 4.34 (d, 1H, J=9.8 Hz), 7.10 (s, 1H), 7.13 (d, 1H, J=2.6 Hz), 7.48 (dd, 1H, J=1.4 Hz, 8.5 Hz), 7.68-7.76 (m, 3H).

COMPOUND 2-16b (Compound of Formula II where $R^2=CH_3$, $R^3=H$, $G^1=N(CH_3)_2$, $n^2=0$, $n^3=1$, $R^{4b}$ and $R^{5b}$ are taken together with the carbon to which they are attached to equal a 4-pyranyl ring, $n^4=1$, and $Q^1=CO_2CH_3$): The title compound was prepared according to the General Synthetic Method C as described above wherein compound of Formula III, $R^2=CH_3$, $R^3=H$, $G^1=N(CH_3)_2$, $n^2=0$, $n^3=1$, $R^{4b}$ and $R^{5b}$ are taken together with the carbon to which they are attached to equal a 4-pyranyl ring, $n^4=1$, and $Q^1=CO_2CH_3$. MS (ES) 402.2 (M+1).

COMPOUND 2-17a (Compound of Formula II where $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclohexyl ring, $n^4=1$, and $Q^1=CO_2Et$): The title compound was prepared according to the General Synthetic Method C as described above wherein compound of Formula III, $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclohexyl ring, $n^4$=1, and $Q^1$=$CO_2$Et. $^1$H NMR (CDCl$_3$, 400 MHz) δ 0.71 (d, 3H, 9.9 Hz), 1.23 (t, 3H, J=2.10), 1.30-1.36 (m, 2H), 1.47-1.51 (m, 3H), 1.52-1.64 (m, 3H), 2.20-2.23 (m, 2H), 2.35 (s, 6H), 2.67-2.71 (m, 1H), 4.09 (s, 2H), 4.20 (q, 2H, J=7.1 Hz, 7.10), 4.34 (d, 1H, 9.7 Hz), 7.11 (s, 1H), 7.13 (d, 1H, J=2.5 Hz), 7.47 (dd, 1H, J=1.6 Hz, 8.5 Hz), 7.69-7.72 (m, 3H).

COMPOUND 2-17b (Compound of Formula II where $R^2$=$CH_3$, $R^3$=H, $G^1$=N($CH_3$)$_2$, $n^2$=0, $n^3$=1, $R^{4b}$ and $R^{5b}$ are taken together with the carbon to which they are attached to equal a cyclohexyl ring, $n^4$=1, and $Q^1$=$CO_2$Et): The title compound was prepared according to the General Synthetic Method C as described above wherein compound of Formula III, $R^2$=$CH_3$, $R^3$=H, $G^1$=N($CH_3$)$_2$, $n^2$=0, $n^3$=1, $R^{4b}$ and $R^{5b}$ are taken together with the carbon to which they are attached to equal a cyclohexyl ring, $n^4$=1, and $Q^1$=$CO_2$Et. MS (ES) 414.3 (M+1).

COMPOUND 2-18a (Compound of Formula II where $R^2$=$CH_3$, $R^3$=H, $G^1$=N($CH_3$)$_2$, $n^2$=0, $n^3$=1, $R^{4b}$ and $R^{5b}$ are taken together with the carbon to which they are attached to equal a cyclopentyl ring, $n^4$=1, and $Q^1$=$CO_2$Et): The title compound was prepared according to the General Synthetic Method C as described above wherein compound of Formula III, $R^2$=$CH_3$, $R^3$=H, $G^1$=N($CH_3$)$_2$, $n^2$=0, $n^3$=1, $R^{4b}$ and $R^{5b}$ are taken together with the carbon to which they are attached to equal a cyclopentyl ring, $n^4$=1, and $Q^1$=$CO_2$Et. $^1$H NMR (CDCl$_3$, 400 MHz) δ 0.72 (d, 3H, J=6.6 Hz), 1.21 (t, 3H, J=7.1 Hz), 1.63-1.82 (m, 6H), 2.16-2.21 (m, 2H), 2.34 (s, 6H), 2.65-2.69 (m, 1H), 4.09-4.21 (m, 4H), 4.33 (d, 1H, J=9.7 Hz), 7.10 (d, 1H, J=2.5 Hz), 7.13 (s, 1H), 7.46 (dd, 1H, J=1.6 Hz, 8.4 Hz), 7.64-7.71 (m, 3H).

COMPOUND 2-18b (Compound of Formula II where $R^2$=$CH_3$, $R^3$=H, $G^1$=N($CH_3$)$_2$, $n^2$=0, $n^3$=1, $R^{4b}$ and $R^{5b}$ are taken together with the carbon to which they are attached to equal a cyclopentyl ring, $n^4$=1, and $Q^1$=$CO_2$Et): The title compound was prepared according to the General Synthetic Method C as described above wherein compound of Formula III, $R^2$=$CH_3$, $R^3$=H, $G^1$=N($CH_3$)$_2$, $n^2$=0, $n^3$=1, $R^{4b}$ and $R^{5b}$ are taken together with the carbon to which they are attached to equal a cyclopentyl ring, $n^4$=1, and $Q^1$=$CO_2$Et. MS (ES) 400.3 (M+1).

COMPOUND 2-19a (Compound of Formula II where $R^2$=$CH_3$, $R^3$=H, $G^1$=N($CH_3$)$_2$, $n^2$=1, Z=Ph, $n^3$ and $n^4$=0): The title compound was prepared according to the General Synthetic Method C as described above wherein compound of Formula III, $R^2$=$CH_3$, $R^3$=H, $G^1$=N($CH_3$)$_2$, $n^2$=1, Z=Ph, $n^3$ and $n^4$=0. $^1$H NMR (CDCl$_3$, 200 MHz) δ 0.74 (d, 3H, J=6.0 Hz), 2.35 (s, 6H), 2.68-2.76 (m, 1H), 4.35 (d, 1H, J=10.0 Hz), 5.16 (s, 2H), 7.18-7.78 (m, 11H); MS (ES) 336.1 (M+1).

COMPOUND 2-19b (Compound of Formula II where $R^2$=$CH_3$, $R^3$=H, $G^1$=N($CH_3$)$_2$, $n^2$=1, Z=Ph, $n^3$ and $n^4$=0): The title compound was prepared according to the General Synthetic Method C as described above wherein compound of Formula III, $R^2$=$CH_3$, $R^3$=H, $G^1$=N($CH_3$)$_2$, $n^2$=1, Z=Ph, $n^3$ and $n^4$=0. $^1$H NMR (CDCl$_3$, 200 MHz) δ 0.98 (d, 3H, J=8.0 Hz), 2.62 (s, 6H), 2.68-2.76 (m, 1H), 5.16 (s, 2H), 5.45 (broad d, 1H), 7.18-7.78 (m, I 1H); MS (ES) 336.1 (M+1).

COMPOUND 2-20a (Compound of Formula II where $R^2$=$CH_3$, $R^3$=H, $G^1$=N($CH_2$)$_2$O($CH_2$)$_2$ ring, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=H, $G^1$=N($CH_2$)$_2$O($CH_2$)$_2$ ring, $n^2$=0, $n^3$=1, $R^{4b}$ and $R^{5b}$=$CH_3$, $n^4$=1, and $Q^1$=$CO_2CH_3$. $^1$H NMR (CDCl$_3$, 400 MHz) δ 0.79 (d, 3H, J=6.8 Hz), 1.36 (s, 3H), 2.49-2.54 (m, 2H), 2.64-2.70 (m, 1H), 2.74-2.79 (m, 2H), 3.75 (s, 3H), 3.76-3.85 (m, 4H), 4.08 (s, 2H), 4.39 (d, 1H, J=10.0 Hz), 7.11-7.14 (m, 2H), 7.44 (dd, 1H, J=8.8 Hz, 1.6 Hz), 7.70-7.72 (m, 3H).

COMPOUND 2-20b (Compound of Formula II where $R^2$=$CH_3$, $R^3$=H, $G^1$=N($CH_2$)$_2$O($CH_2$)$_2$ ring, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=H, $G^1$=N($CH_2$)$_2$O($CH_2$)$_2$ ring, $n^2$=0, $n^3$=1, $R^{4b}$ and $R^{5b}$=$CH_3$, $n^4$=1, and $Q^1$=$CO_2CH_3$. $^1$H NMR (CDCl$_3$, 400 MHz) δ 0.83 (d, 3H, J=6.8 Hz), 1.36 (s, 3H), 2.49-2.54 (m, 2H), 2.64-2.70 (m, 1H), 2.74-2.79 (m, 2H), 3.75 (s, 3H), 3.76-3.85 (m, 4H), 4.08 (s, 2H), 4.93 (d, 1H, J=4.0 Hz), 7.11-7.14 (m, 2H), 7.44 (dd, 1H, J=8.8 Hz, 1.6 Hz), 7.70-7.72 (m, 3H).

COMPOUND 2-21a (Compound of Formula II where $R^2$=$CH_3$, $R^3$=H, $G^1$=N(Et)$_2$, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=H, $G^1$=N(Et)$_2$, $n^2$=0, $n^3$=1, $R^{4b}$ and $R^{5b}$=$CH_3$, $n^4$=1, and $Q^1$=$CO_2CH_3$. $^1$HNMR (CDCl$_3$, 400 MHz) δ 0.77 (d, 3H, J=6.8 Hz), 1.16 (t, 6H, J=7.2 Hz), 1.37 (s, 6H), 2.38-2.46 (m, 2H), 2.69-2.78 (m, 2H), 2.79-2.86 (m, 1H), 3.71 (s, 3H), 4.08 (s, 2H), 4.32 (d, 1H, J=10.0 Hz), 7.12-7.15 (m, 2H), 7.47 (dd, 1H, J=8.4 Hz, 1.6 Hz), 7.70-7.72 (m, 3H).

COMPOUND 2-21b (Compound of Formula II where $R^2$=$CH_3$, $R^3$=H, $G^1$=N(Et)$_2$, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=H, $G^1$=N(Et)$_2$, $n^2$=0, $n^3$=1, $R^{4b}$ and $R^{5b}$=$CH_3$, $n^4$=1, and $Q^1$=$CO_2CH_3$. $^1$HNMR (CDCl$_3$, 400 MHz) δ 0.92 (d, 3H, J=6.8 Hz), 1.05 (t, 6H, J=7.2 Hz), 1.36 (s, 6H), 2.53-2.54 (m, 4H), 3.09-3.17 (m, 1H), 3.07 (s, 3H), 4.08 (s, 2H), 4.89 (s, 1H), 7.11-7.14 (m, 2H), 7.38 (dd, 1H, J=8.8 Hz, 1.2 Hz), 7.67-7.72 (m, 3H).

COMPOUND 2-22a (Compound of Formula II where $R^2$=$CH_3$, $R^3$=H, $G^1$=N($CH_3$)cyclohexyl, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=H, $G^1$=N($CH_3$)cyclohexyl, $n^2$=0, $n^3$=1, $R^{4b}$ and $R^{5b}$=$CH_3$, $n^4$=1, and $Q^1$=$CO_2CH_3$. $^1$HNMR (CDCl$_3$, 400 MHz) δ 0.76 (d, 3H, J=6.8 Hz), 1.13-1.16 (m, 1H), 1.24-1.31 (m, 3H), 1.39 (s, 6H), 1.45-1.49 (m, 1H), 1.64-1.69 (m, 1H), 1.82-1.85 (m, 3H), 1.96-1.98 (m, 1H), 2.32 (s, 3H), 2.51-2.57 (m, 1H), 2.86-2.94 (m, 1H), 3.72 (s, 3H), 4.10 (s, 2H), 4.27 (d, 1H, J=9.2 Hz), 7.13-7.16 (m, 2H), 7.48 (dd, 1H, J=8.4 Hz, 2.0 Hz), 7.71-7.74 (m, 3H).

COMPOUND 2-22b (Compound of Formula II where $R^2$=$CH_3$, $R^3$=H, $G^1$=N($CH_3$)cyclohexyl, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=H, $G^1$=N($CH_3$)cyclohexyl, $n^2$=0, $n^3$=1, $R^{4b}$ and $R^{5b}$=$CH_3$, $n^4$=1, and $Q^1$=$CO_2CH_3$. $^1$HNMR (CDCl$_3$, 400 MHz) δ 0.89 (d, 3H, J=6.8 Hz), 1.08-1.15 (m, 1H), 1.22-1.33 (m, 3H), 1.39 (s, 6H), 1.44-1.49 (m, 1H), 1.64-1.67 (m, 1H), 1.75-1.87 (m, 4H), 2.23 (s, 3H), 2.59-2.65 (m, 1H), 3.09-3.13 (m, 1H), 3.72 (s, 3H), 4.10 (s, 2H), 4.92 (s, 1H), 7.13-7.16 (m, 2H), 7.39 (dd, 1H, J=8.4 Hz, 1.6 Hz), 7.68-7.75 (m, 3H).

COMPOUND 2-23a (Compound of Formula II where $R^2$=$CH_3$, $R^3$=H, $G^1$=N($CH_3$)n-butyl, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=H, $G^1$=N($CH_3$)n-butyl, $n^2$=0, $n^3$=1, $R^{4b}$ and $R^{5b}$=$CH_3$, $n^4$=1, and $Q^1$=$CO_2CH_3$. $^1$HNMR (CDCl$_3$, 400 MHz) δ 0.76 (d, 3H, J=6.8 Hz), 0.99 (t, 3H, J=6.8 Hz), 1.39 (s, 6H), 1.40-1.45 (m, 2H), 1.52-1.61 (m, 3H), 2.31 (s, 3H), 2.38-2.43 (m, 1H), 2.56-2.63 (m, 1H), 2.70-2.76 (m, 1H), 3.73 (s, 3H), 4.10 (s, 2H), 4.37 (d, 1H, J=9.6 Hz), 7.13-7.16 (m, 2H), 7.48 (dd, 1H, J=2.0, 8.8 Hz), 7.71-7.74 (m, 3H).

COMPOUND 2-23b (Compound of Formula II where $R^2$=$CH_3$, $R^3$=H, $G^1$=N($CH_3$)n-butyl, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=H, $G^1$=N($CH_3$)n-butyl, $n^2$=0, $n^3$=1, $R^{4b}$ and $R^{5b}$=$CH_3$, $n^4$=1, and $Q^1$=$CO_2CH_3$. $^1$HNMR (CDCl$_3$, 400 MHz) δ 0.89 (d, 3H, J=7.2 Hz), 0.93 (t, 3H, J=7.2 Hz), 1.27-1.34 (m, 2H), 1.39 (s, 6H), 1.47-1.55 (m, 2H), 2.30 (s, 3H), 2.47-2.58 (m, 2H), 2.90-2.94 (m, 1H), 3.73 (s, 3H), 4.10 (s, 2H), 4.99 (d, 1H, J=3.6 Hz), 7.13-7.16 (m, 2H), 7.39 (dd, 1H, J=1.6, 8.4 Hz), 7.69-7.76 (m, 3H).

COMPOUND 2-24a (Compound of Formula II where $R^2$=$CH_3$, $R^3$=H, $G^1$=N($CH_3$)iPr, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=H, $G^1$=N($CH_3$)iPr, $n^2$=0, $n^3$=1, $R^{4b}$ and $R^{5b}$=$CH_3$, $n^4$=1, and $Q^1$=$CO_2CH_3$. $^1$HNMR (CDCl$_3$, 400 MHz) δ 0.82 (d, 3H, J=6.8 Hz), 1.11 (d, 3H, J=7.6 Hz), 1.14 (d, 3H, J=8.4 Hz), 1.36 (s, 6H), 2.26 (s, 3H), 2.84-2.88 (m, 1H), 2.96-3.02 (m, 1H), 3.71 (s, 3H), 4.08 (s, 2H), 4.25 (d, 1H, J=9.2 Hz), 7.13-7.16 (m, 2H), 7.46 (dd, 1H, J=8.4 Hz, 1.6 Hz), 7.69-7.75 (m, 3H).

COMPOUND 2-24b (Compound of Formula II where $R^2$=$CH_3$, $R^3$=H, $G^1$=N($CH_3$)iPr, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=H, $G^1$=N($CH_3$)iPr, $n^2$=0, $n^3$=1, $R^{4b}$ and $R^{5b}$=$CH_3$, $n^4$=1, and $Q^1$=$CO_2CH_3$. $^1$HNMR (CDCl$_3$, 400 MHz) δ 0.86 (d, 3H, J=6.8 Hz), 1.07 (d, 3H, J=6.4 Hz), 1.12 (d, 3H, J=6.4 Hz), 1.39 (s, 6H), 2.21 (s, 3H), 2.99-3.02 (m, 1H), 3.15-3.18 (m, 1H), 3.70 (s, 3H), 4.10 (s, 2H), 4.95 (d, 1H, J=4.0 Hz), 7.13-7.16 (m, 2H), 7.39 (dd, 1H, J=8.4 Hz, 1.6 Hz), 7.69-7.75 (m, 3H).

COMPOUND 2-25a (Compound of Formula II where $R^2$=$CH_3$, $R^3$=H, $G^1$=N($CH_3$)Ph, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=H, $G^1$=N($CH_3$)Ph, $n^2$=0, $n^3$=1, $R^{4b}$ and $R^{5b}$=$CH_3$, $n^4$=1, and $Q^1$=$CO_2CH_3$. $^1$H NMR (CDCl$_3$, 400 MHz) δ 0.86 (d, 3H, J=6.8 Hz), 1.36 (s, 6H), 2.84 (s, 3H), 3.70 (s, 3H), 3.88-3.92 (m, 1H), 4.68 (d, 1H, J=9.6 Hz), 6.86-6.90 (m, 1H), 7.05-7.08 (m, 2H), 7.13-7.16 (m, 2H), 7.28-7.33 (m, 2H), 7.56 (dd, 1H, J=8.4 Hz, 1.6 Hz), 7.72-7.76 (m, 2H), 7.80 (s, 1H).

COMPOUND 2-26a (Compound of Formula II where $R^2$=$CH_3$, $R^3$=H, $G^1$=N($CH_2$)$_4$ ring, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=H, $G^1$=N($CH_2$)$_4$ ring $n^2$=0, $n^3$=1, $R^{4b}$ and $R^{5b}$=$CH_3$, $n^4$=1, and $Q^1$=$CO_2CH_3$. $^1$HNMR (CDCl$_3$, 400 MHz) δ 0.78 (d, 3H, J=6.4 Hz), 1.36 (s, 6H), 1.78-1.87 (m, 4H), 2.67-2.78 (m, 4H), 2.97-3.05 (m, 1H), 3.70 (s, 3H), 4.08 (s, 2H), 4.36 (d, 1H, J=10.0 Hz), 7.11-7.14 (m, 2H), 7.47 (dd, 1H, J=8.4 Hz, 1.6 Hz), 7.69-7.73 (m, 3H).

COMPOUND 2-26b (Compound of Formula II where $R^2$=$CH_3$, $R^3$=H, $G^1$=N($CH_2$)$_4$ ring, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=H, $G^1$=N($CH_2$)$_4$ ring, $n^2$=0, $n^3$=1, $R^{4b}$ and $R^{5b}$=$CH_3$, $n^4$=1, and $Q^1$=$CO_2CH_3$. $^1$HNMR (CDCl$_3$, 400 MHz) δ 0.81 (d, 3H, J=6.4 Hz), 1.36 (s, 6H), 1.82-1.89 (m, 4H), 2.58-2.61 (m, 1H), 2.66-3.72 (m, 2H), 2.80-2.88 (m, 2H), 3.71 (s, 3H), 4.08 (s, 2H), 5.15 (d, 1H, J=2.4 Hz), 7.12-7.14 (m, 2H), 7.36 (dd, 1H, J=8.4 Hz, 1.6 Hz), 7.67-7.74 (m, 2H), 7.77 (s, 1H).

COMPOUND 2-27 (Compound of Formula II where $R^2$=$CH_3$, $R^3$=$CH_3$, $G^1$=N($CH_3$)$_2$, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=$CH_3$, $G^1$=N($CH_3$)$_2$, $n^2$=0, $n^3$=1, $R^{4b}$ and $R^{5b}$=$CH_3$, $n^4$=1, and $Q^1$=$CO_2CH_3$. MS (ES) 374.3 (M+1).

COMPOUND 2-28a (Compound of Formula II where $R^2$=$CH_3$, $R^3$=H, $G^1$=N($CH_3$)Et, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=H, $G^1$=N($CH_3$)Et, $n^2$=0, $n^3$=1, $R^{4b}$ and $R^{5b}$=$CH_3$, $n^4$=1, and $Q^1$=$CO_2CH_3$. $^1$HNMR (CDCl$_3$, 400 MHz) δ 0.74 (d, 3H, J=6.8 Hz), 1.16 (t, 3H, J=6.8 Hz), 1.36 (s, 6H), 2.29 (s, 3H), 2.41-2.49 (m, 1H), 2.61-2.69 (m, 1H), 2.71-2.78 (m, 1H), 3.71 (s, 3H), 4.08 (s, 2H), 4.34 (d, 1H, J=9.6 Hz), 7.11-7.14 (m, 2H), 7.46 (dd, 1H, J=8.0 Hz, 1.6 Hz), 7.69-7.71 (m, 3H).

COMPOUND 2-28b (Compound of Formula II where $R^2$=$CH_3$, $R^3$=H, $G^1$=N($CH_3$)Et, $n^2$=0, $n^3$=1, $R^{4b}$ and $R^{5b}$=$CH_3$, $n^4$=1, and $Q^1$=$CO_2CH_3$): The title compound was prepared according to the General Synthetic Method C as described above wherein compound of Formula III, $R^2$=$CH_3$, $R^3$=H, $G^1$=N($CH_3$)Et, $n^2$=0, $n^3$=1, $R^{4b}$ and $R^{5b}$=$CH_3$, $n^4$=1, and $Q^1$=$CO_2CH_3$. $^1$HNMR (CDCl$_3$, 400 MHz) δ 1.04 (d, 3H, J=7.2 Hz), 1.30 (t, 3H, J=7.2 Hz), 1.36 (s, 6H), 2.65 (s, 3H), 2.88-2.93 (m, 1H), 3.04-3.07 (m, 1H), 3.23-3.27 (m, 1H), 3.70 (s, 3H), 4.07 (s, 2H), 5.58 (s, 1H), 7.09-7.13 (m, 2H), 7.44 (dd, 1H, J=8.4 Hz, 1.6 Hz), 7.63-7.70 (m, 2H), 7.79 (s, 1H).

COMPOUND 2-29a (Compound of Formula II where $R^2$=$CH_3$, $R^3$=H, $G^1$=N($CH_3$)$_2$, $n^2$=0, $n^3$=0, $n^4$=1, and $Q^1$=$CO_2$tBu): The title compound was prepared according to the General Synthetic Method C as described above wherein compound of Formula III, $R^2$=$CH_3$, $R^3$=H, $G^1$=N($CH_3$)$_2$, $n^2$=0, $n^3$=0, $n^4$=1, and $Q^1$=$CO_2$tBu. $^1$HNMR (CDCl$_3$, 200 MHz) δ 0.71 (d, 3H, J=6.6 Hz), 1.49 (s, 9H), 2.33 (s, 6H), 4.32 (d, 1H, J=9.4 Hz), 4.62 (s, 2H), 7.04-7.06 (m, 1H), 7.18-7.24 (m, 1H), 7.34-7.49 (m, 1H), 7.64-7.77 (m, 3H) MS (ES) 360.0 (M+1).

COMPOUND 2-29b (Compound of Formula II where $R^2$=$CH_3$, $R^3$=H, $G^1$=N($CH_3$)$_2$, $n^2$=0, $n^3$=0, $n^4$=1, and $Q^1$=$CO_2$tBu): The title compound was prepared according to the General Synthetic Method C as described above wherein compound of Formula III, R =$CH_3$, $R^3$=H, $G^1$=N($CH_3$)$_2$, $n^2$=0, $n^3$=0, $n^4$=1, and $Q^1$=$CO_2$tBu. $^1$HNMR (CDCl$_3$, 200 MHz) δ 0.82 (d, 3H, J=6.6 Hz), 1.49 (s, 9H), 2.38 (s, 6H), 4.75 (s, 2H), 5.07 (d, 1H, J=3.6 Hz), 7.04-7.06 (m, 1H), 7.18-7.24 (m, 1H), 7.34-7.49 (m, 1H), 7.64-7.77 (m, 3H); MS (ES) 360.0 (M+1).

COMPOUND 2-30 (Compound of Formula II where $R^2$=H, $R^3$=H, $G^1$=N($CH_3$)$_2$, $n^2$=0, $n^3$=1, $R^{4b}$ and $R^{5b}$=$CH_3$, $n^4$=1, and $Q^1$=$CO_2CH_3$): The title compound was prepared as follows: Intermediate A-8 (200 mg, 0.53 mmol) was dissolved in a 1:1 mixture of $CH_2Cl_2$:$CH_3OH$ (2 mL) and cooled to 0° C. The solution was charged with NaBH$_4$ (30 mg, 0.79 mmol) and allowed to warm to rt. After 4 h, the reaction mixture was charged with 2M HN($CH_3$)$_2$ in $CH_3OH$ (10 eq., 5.3 mmol) at rt. After 24 h, the reaction was concentrated in vacuo, partitioned between $CH_2Cl_2$ and sat. aq. $NaHCO_3$, and the aqueous layer was extracted with $CH_2Cl_2$ (3×). The organic layers were dried over $Na_2SO_4$ and concentrated in vacuo. The crude product was purified by silica gel chromatography (2% $CH_3OH:CH_2Cl_2$) to yield the desired product as a yellow gum. MS (ES) 346.0 (M+1).

COMPOUNDS 2-31a and 2-31b (Compounds of Formula II where $R^2$, $R^3$, and $G^1$ are taken together to equal A2* (see Table 2), $n^2=1$, Z=Ph, and $n^3$ and $n^4=0$): The title compounds were prepared as follows: A 0° C. solution of compound 1-30 (0.43 g, 1.0 mmol) in THF (6 mL) was charged with $LiAlH_4$ (0.11 g, 3.0 mmol), heated to 50° C. for 3 h, cooled to rt, poured over ice, and extracted with EtOAc (3×). The organic layer was subsequently dried over $Na_2SO_4$, filtered, and concentrated in-vacuo. The residual was subjected to silica gel column chromatography (gradient of 100% $CHCl_3$ to 99% $CHCl_3$:1% $CH_3OH$ ($NH_3$ sat.)) to afford the title compounds 2-31a and 2-31b. Compound 2-31a: white solid, mp 108-110° C.; $^1$HNMR ($CDCl_3$, 400 MHz) δ 1.25-1.32 (m, 1H), 1.61-1.77 (m, 3H), 2.34-2.40 (m, 1H), 2.51 (s, 3H), 2.60-2.64 (m, 1H), 3.15-3.19 (m, 1H), 5.00 (d, 1H, J=2.8 Hz), 5.18 (s, 2H), 7.22-7.26 (m, 2H), 7.34-7.43 (m, 3H), 7.49 (d, 2H, J=7.6 Hz), 7.69 (d, 1H, J=8.4 Hz), 7.76 (d, 1H, J=8.8 Hz), 7.82 (s, 1H); MS (ES) 348.31 (M+1), 330.28 (M-18, loss of —OH). Compound 2-31b: White solid, mp 84-87° C.; $^1$H NMR ($CDCl_3$, 400 MHz) δ 1.76-1.81 (m, 3H), 1.82-1.94 (m, 1H), 2.25 (s, 3H), 2.41-2.51 (m, 1H), 2.84-87 (m, 1H), 3.14-3.17 (m, 1H), 4.49 (d, 1H, J=5.2 Hz), 5.18 (s, 2H), 7.21-7.24 (m, 2H), 7.34 (d, 1H, J=7.6 Hz), 7.40-7.50 (m, 5H), 7.70 (d, 1H, J=8.8 Hz), 7.75 (d, 1H, J=10.0 Hz), 7.78 (s, 1H); MS (ES) 348.31 (M+1), 330.26 (M-18, loss of —OH).

COMPOUND 2-32a (Compound of Formula II where $R^2=CH_2CH_3$, $R^3=H$, $G^1=N(CH_3)_2$, $n^2=0$, $n^3=1$, $R^{4b}$ and $R^{5b}=CH_3$, $n^4=1$, and $Q^1=CO_2CH_3$): The title compound was prepared according to the General Synthetic Method C as described above wherein compound of Formula III, $R^2=CH_2CH_3$, $R^3=H$, $G^1=N(CH_3)_2$, $n^2=0$, $n^3=1$, $R^{4b}$ and $R^{5b}=CH_3$, $n^4=1$, and $Q^1=CO_2CH_3$. $^1$H NMR ($CDCl_3$, 400 MHz) δ 0.58 (t, 3H, 7.6 Hz), 1.13-1.24 (m, 1H), 1.36 (s, 6H), 1.50-1.61 (m, 1H), 2.47 (s, 6H), 2.47-2.53 (m, 1H), 3.71 (s, 3H), 4.08 (s, 2H), 4.27 (d, 1H, J=9.6 Hz), 7.11-7.14 (m, 2H), 7.48 (dd, 1H, J=1.5, 8.4 Hz), 7.69-7.72 (m, 3H).

COMPOUND 2-32b (Compound of Formula II where $R^2=CH_2CH_3$, $R^3=H$, $G^1=N(CH_3)_2$, $n^2=0$, $n^3=1$, $R^{4b}$ and $R^{5b}=CH_3$, $n^4=1$, and $Q^1=CO_2CH_3$): The title compound was prepared according to the General Synthetic Method C as described above wherein compound of Formula III, $R^2=CH_2CH_3$, $R^3=H$, $G^1=N(CH_3)_2$, $n^2=0$, $n^3=1$, $R^{4b}$ and $R^{5b}=CH_3$, $n^4=1$, and $Q^1=CO_2CH_3$. $^1$H NMR ($CDCl_3$, 400 MHz) δ 0.81 (t, 3H, 7.5 Hz), 1.36 (s, 6H), 1.49-1.67 (m, 1H), 2.59 (s, 6H), 2.84-2.89 (m, 1H), 3.71 (s, 3H), 4.08 (s, 2H), 5.33 (d, 1H, J=3.1 Hz), 7.13 (s, 1H), 7.15 (d, 1H, J=2.4 Hz), 7.39 (dd, 1H, J=1.6, 8.5 Hz), 7.70 (q, 2H, J=8.6 Hz), 7.8 (s, 1H).

COMPOUND 2-33a (Compound of Formula II where $R^2=CH_3$, $R^3=H$, $G^1=N(CH_3)iPr$, $n^2=0$, $n^3=1$, $R^{4b}$ and $R^{5b}$ are taken together with the carbon to which they are attached to equal a cyclopentyl ring, $n^4=1$, and $Q^1=CO_2Et$): The title compound was prepared according to the General Synthetic Method C as described above wherein compound of Formula III, $R^2=CH_3$, $R^3=H$, $G^1=N(CH_3)iPr$, $n^2=0$, $n^3=1$, $R^{4b}$ and $R^{5b}$ are taken together with the carbon to which they are attached to equal a cyclopentyl ring, $n^4=1$, and $Q^1=CO_2Et$. $^1$H NMR ($CDCl_3$, 400 MHz) δ 0.84 (d, 3H, J=6.6 Hz), 1.12 (d, 3H, J=6.5 Hz), 1.16 (d, 3H, J=6.5 Hz), 1.21 (t, 3H, J=7.1 Hz), 1.67-1.84 (m, 6H), 2.16-2.21 (m, 2H), 2.28 (s, 3H), 2.83-2.90 (m, 1H), 2.94-3.04 (m, 1H), 4.14-4.19 (m, 4H), 4.24 (d, 1H, J=9.4 Hz), 7.10-7.13 (m, 2H), 7.46 (dd, 1H, J=1.5 Hz, 8.6 Hz), 7.69 (s, 1H), 7.71 (s, 1H).

COMPOUND 2-33b (Compound of Formula II where $R^2=CH_3$, $R^3=H$, $G^1=N(CH_3)iPr$, $n^2=0$, $n^3=1$, $R^{4b}$ and $R^{5b}$ are taken together with the carbon to which they are attached to equal a cyclopentyl ring, $n^4=1$, and $Q^1=CO_2Et$): The title compound was prepared according to the General Synthetic Method C as described above wherein compound of Formula III, $R^2=CH_3$, $R^3=H$, $G^1=N(CH_3)iPr$, $n^2=0$, $n^3=1$, $R^{4b}$ and $R^{5b}$ are taken together with the carbon to which they are attached to equal a cyclopentyl ring, $n^4=1$, and $Q^1=CO_2Et$. MS (ES) 428.0 (M+1).

Following the general methods described hereinbefore, the following compounds of Formula I (where $R^1=H$, $n^1=1$, $R^{6a}=H$, $R^{6b}=H$, Y=O, $R^{4a}=H$, $R^{5a}=H$) as listed in Table 3 were prepared. In the EXAMPLE numbers, "a" denotes the syn isomer and "b" denotes the anti isomer, with respect to X and $G^1$. X1=imidazol-1-yl, X2=triazol-1-yl, and X3=triazol-3-yl.

TABLE 3

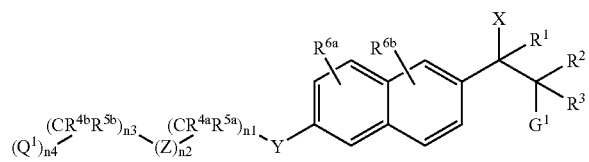

Listing of Compounds of Formula I

| EX. | $R^2$ | $R^3$ | $G^1$ | n2 | Z | n3 | $R^{4b}$ | $R^{5b}$ | n4 | $Q^1$ | X |
|---|---|---|---|---|---|---|---|---|---|---|---|
| 3-1a | $CH_3$ | H | $N(CH_3)_2$ | 0 | — | 1 | $CH_3$ | $CH_3$ | 1 | $CO_2CH_3$ | X1 |
| 3-1b | $CH_3$ | H | $N(CH_3)_2$ | 0 | — | 1 | $CH_3$ | $CH_3$ | 1 | $CO_2CH_3$ | X1 |
| 3-2a | $CH_3$ | H | $N(CH_3)_2$ | 1 | 4 Ph | 0 | — | — | 1 | $CO_2CH_3$ | X1 |
| 3-2b | $CH_3$ | H | $N(CH_3)_2$ | 1 | 4 Ph | 0 | — | — | 1 | $CO_2CH_3$ | X1 |
| 3-3a | $CH_3$ | H | $N(CH_3)_2$ | 1 | 3 Ph | 0 | — | — | 1 | $CO_2CH_3$ | X1 |

TABLE 3-continued

Listing of Compounds of Formula I

| EX. | R² | R³ | G¹ | n2 | Z | n3 | R⁴ᵇ | R⁵ᵇ | n4 | Q¹ | X |
|---|---|---|---|---|---|---|---|---|---|---|---|
| 3-3b | CH₃ | H | N(CH₃)₂ | 1 | 3 Ph | 0 | — | — | 1 | CO₂CH₃ | X1 |
| 3-4a | CH₃ | H | N(CH₃)₂ | 1 | 4 Ph | 1 | H | H | 1 | CO₂CH₃ | X1 |
| 3-4b | CH₃ | H | N(CH₃)₂ | 1 | 4 Ph | 1 | H | H | 1 | CO₂CH₃ | X1 |
| 3-5a | CH₃ | H | N(CH₃)₂ | 0 | — | 1 | CH₃ | CH₃ | 1 | CH₃ | X1 |
| 3-5b | CH₃ | H | N(CH₃)₂ | 0 | — | 1 | CH₃ | CH₃ | 1 | CH₃ | X1 |
| 3-6a | CH₃ | H | N(CH₃)₂ | 1 | 4 Ph | 0 | — | — | 1 | OtBu | X1 |
| 3-6b | CH₃ | H | N(CH₃)₂ | 1 | 4 Ph | 0 | — | — | 1 | OtBu | X1 |
| 3-7a | CH₃ | H | N(CH₃)₂ | 1 | 4 PhO | 1 | H | H | 1 | CO₂CH₃ | X1 |
| 3-7b | CH₃ | H | N(CH₃)₂ | 1 | 4 PhO | 1 | H | H | 1 | CO₂CH₃ | X1 |
| 3-8a | CH₃ | H | N(CH₃)₂ | 0 | — | 2 | H | H | 1 | OCH₃ | X1 |
| 3-8b | CH₃ | H | N(CH₃)₂ | 0 | — | 2 | H | H | 1 | OCH₃ | X1 |
| 3-9a | CH₃ | H | N(CH₃)₂ | 1 | 4 Ph | 0 | — | — | 1 | OCH₃ | X1 |
| 3-10a | CH₃ | H | N(CH₃)₂ | 1 | trans-CH=CHPh | 0 | — | — | 0 | — | X1 |
| 3-10b | CH₃ | H | N(CH₃)₂ | 1 | trans-CH=CHPh | 0 | — | — | 0 | — | X1 |
| 3-11a | CH₃ | H | N(CH₃)₂ | 1 | 4 Ph | 0 | — | — | 1 | CN | X1 |
| 3-11b | CH₃ | H | N(CH₃)₂ | 1 | 4 Ph | 0 | — | — | 1 | CN | X1 |
| 3-12a | CH₃ | H | N(CH₃)₂ | 1 | 4 Ph | 0 | — | — | 1 | NO₂ | X1 |
| 3-13a | CH₃ | H | N(CH₃)₂ | 0 | — | 1 | Et | Et | 1 | CO₂Et | X1 |
| 3-14a | CH₃ | H | N(CH₃)₂ | 0 | — | 1 | CH₂CH₂ ring | | 1 | CO₂Et | X1 |
| 3-15a | CH₃ | H | N(CH₃)₂ | 0 | — | 1 | CH₂CH₂CH₂ ring | | 1 | CO₂Et | X1 |
| 3-16a | CH₃ | H | N(CH₃)₂ | 0 | — | 1 | CH₂CH₂OCH₂CH₂ ring | | 1 | CO₂CH₃ | X1 |
| 3-17a | CH₃ | H | N(CH₃)₂ | 0 | — | 1 | CH₂(CH₂)₃CH₂ ring | | 1 | CO₂Et | X1 |
| 3-18a | CH₃ | H | N(CH₃)₂ | 0 | — | 1 | CH₂(CH₂)₂CH₂ ring | | 1 | CO₂Et | X1 |
| 3-19a | CH₃ | H | N(CH₃)₂ | 1 | Ph | 0 | — | — | 0 | — | X1 |
| 3-19b | CH₃ | H | N(CH₃)₂ | 1 | Ph | 0 | — | — | 0 | — | X1 |
| 3-20a | CH₃ | H | N(CH₂)₂O(CH₂)₂ ring | 0 | — | 1 | CH₃ | CH₃ | 1 | CO₂CH₃ | X1 |
| 3-21a | CH₃ | H | N(Et)₂ | 0 | — | 1 | CH₃ | CH₃ | 1 | CO₂CH₃ | X1 |
| 3-22a | CH₃ | H | N(CH₃)cyclohexyl | 0 | — | 1 | CH₃ | CH₃ | 1 | CO₂CH₃ | X1 |
| 3-23a | CH₃ | H | N(CH₃)n-butyl | 0 | — | 1 | CH₃ | CH₃ | 1 | CO₂CH₃ | X1 |
| 3-24a | CH₃ | H | N(CH₃)iPr | 0 | — | 1 | CH₃ | CH₃ | 1 | CO₂CH₃ | X1 |
| 3-25a | CH₃ | H | N(CH₂)₄ ring | 0 | — | 1 | CH₃ | CH₃ | 1 | CO₂CH₃ | X1 |
| 3-26a | CH₃ | H | N(CH₃)Et | 0 | — | 1 | CH₃ | CH₃ | 1 | CO₂CH₃ | X1 |
| 3-27a | CH₃ | H | N(CH₃)₂ | 0 | — | 0 | — | — | 1 | CO₂tBu | X1 |
| 3-27b | CH₃ | H | N(CH₃)₂ | 0 | — | 0 | — | — | 1 | CO₂tBu | X1 |
| 3-28 | CH₃ | CH₃ | N(CH₃)₂ | 0 | — | 1 | CH₃ | CH₃ | 1 | CO₂CH₃ | X1 |
| 3-29 | H | H | N(CH₃)₂ | 0 | — | 1 | CH₃ | CH₃ | 1 | CO₂CH₃ | X1 |
| 3-30a | | | A2* | 1 | Ph | 0 | — | — | 0 | — | X1 |
| 3-30b | | | A2* | 1 | Ph | 0 | — | — | 0 | — | X1 |
| 3-31a | CH₃ | H | N(CH₃)₂ | 0 | — | 1 | CH₂(CH₂)₂CH₂ ring | | 1 | CO₂Et | X2 |
| 3-32a | Et | H | N(CH₃)₂ | 0 | — | 1 | CH₃ | CH₃ | 1 | CO₂CH₃ | X1 |
| 3-33a | CH₃ | H | N(CH₃)iPr | 0 | — | 1 | CH₂(CH₂)₂CH₂ ring | | 1 | CO₂Et | X2 | wherein A2* = R²R³G¹ taken together with the carbon atom to which they are attached form:

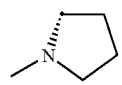

where • is the carbon to which they are attached.

General Synthetic Method D for the preparation of compounds of the Formula I: An acetonitrile solution (0.2M) of compound of Formula II (1 eq) was charged with 1,1'-carbonyldiimidazole or 1,1-carbonylditriazole (2 eq) and allowed to stir at 70° C. for 10 h. The reaction mixture was quenched with water and sat. NaHCO₃ and concentrated in vacuo to a slurry. The mixture was partitioned between CH₂Cl₂ and NaHCO₃ (sat) and the aqueous layer extracted with CH₂Cl₂ (5×). The combined organic layers were dried over Na₂SO₄, filtered, and concentrated in vacuo. The resulting residue was purified by silica gel chromatography (gradient of 2:1 CH₂Cl₂:4% CH₃OH in CH₂Cl₂ (1% ~7 N NH₃ in CH₃OH) to 4% CH₃OH in CH₂Cl₂ (1% ~7 N NH₃ in CH₃OH) to afford the desired compounds of Formula I.

EXAMPLE 3-1a (Compound of Formula I where X1=imidazol-1-yl, R²=CH₃, R³=H, G¹=N(CH₃)₂, n²=0, n³=1, R⁴ᵇ and R⁵ᵇ=CH₃, n⁴=1, and Q¹=CO₂CH₃): The title compound was prepared according to the General Synthetic Method D as described above wherein compound of Formula II, R²=CH₃, R³=H, G¹=N(CH₃)₂, n²=0, n³=1, R⁴ᵇ and R⁵ᵇ=CH₃, n⁴=1, and Q¹=CO₂CH₃. ¹H NMR (CDCl₃, 200 MHz) δ 0.79 (d, 3H, J=6.6 Hz), 1.35 (s, 6H), 2.27 (s, 6H), 3.46-3.55 (m, 1H), 3.70

(s, 3H), 4.07 (s, 2H), 5.05 (d, 1H, J=10.6 Hz), 7.00 (s, 2H), 7.11-7.14 (m, 1H), 7.17 (d, 1H, J=5.2 Hz), 7.26-7.30 (m, 1H), 7.65 (d, 2H, J=11.6 Hz), 7.72 (d, 2H, J=8.8 Hz); MS (ES) 410.0 (M+1).

EXAMPLE 3-1b (Compound of Formula I where X1=imidazol-1-yl, $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CO_2CH_3$): The title compound was prepared according to the General Synthetic Method D as described above wherein compound of Formula II, $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CO_2CH_3$. $^1H$ NMR (CDCl$_3$, 200 MHz) δ 0.90 (d, 3H, J=6.6 Hz), 1.35 (s, 6H), 2.21 (s, 6H), 3.55-3.63 (m, 1H), 3.70 (s, 3H), 4.07 (s, 2H), 5.09 (d, 1H, J=9.8 Hz), 7.01 (d, 2H, J=9.6 Hz), 7.10 (s, 1H), 7.15 (d, 1H, J=2.6 Hz), 7.40 (dd, 1H, J=1.4 Hz, 8.6 Hz), 7.67-7.71 (m, 4H); MS (ES) 410.0 (M+1).

EXAMPLE 3-2a (Compound of Formula I where X1=imidazol-1-yl, $R^2=CH_3$, $R^3=H$, $G^1=N(CH_3)_2$, $n^2=1$, Z=4-phenyl, $n^3=0$, $n^4=1$, and $Q^1=CO_2CH_3$): The title compound was prepared according to the General Synthetic Method D as described above wherein compound of Formula II, $R^2=CH_3$, $R^3=H$, $G^1=N(CH_3)_2$, $n^2=1$, Z=4-phenyl, $n^3=0$, $n^4=1$, and $Q^1=CO_2CH_3$. $^1HNMR$ (CDCl$_3$, 200 MHz) δ 0.81 (d, 3H, J=8.0 Hz), 2.28 (s, 6H), 3.49-3.53 (m, 1H), 3.93 (s, 3H), 5.06 (d, 1H, J=8.0 Hz), 5.24 (s, 2H), 7.00 (s, 2H), 7.16 (d, 1H, J=2.4 Hz), 7.27-7.31 (m, 2H), 7.55 (d, 2H, J=8.0 Hz), 7.65-7.75 (m, 4H), 8.07 (d, 2H, J=8.0 Hz); MS (ES) 375.9 (M+1).

EXAMPLE 3-2b (Compound of Formula I where X1=imidazol-1-yl, $R^2=CH_3$, $R^3=H$, $G^1=N(CH_3)_2$, $n^2=1$, Z=4-phenyl, $n^3=0$, $n^4=1$, and $Q^1=CO_2CH_3$): The title compound was prepared according to the General Synthetic Method D as described above wherein compound of Formula II, $R^2=CH_3$, $R^3=H$, $G^1=N(CH_3)_2$, $n^2=1$, Z=4-phenyl, $n^3=0$, $n^4=1$, and $Q^1=CO_2CH_3$. $^1H$ NMR (CDCl$_3$, 400 MHz) δ 0.90 (d, 3H, J=8.0 Hz), 2.23 (s, 6H), 3.58-3.62 (m, 1H), 3.93 (s, 3H), 5.09 (d, 1H, J=8.0 Hz), 5.24 (s, 2H), 7.01 (d, 2H, J=8.0 Hz), 7.15 (d, 1H, J=2.4 Hz), 7.23-7.25 (m, 2H), 7.41-7.43 (m, 1H), 7.55 (d, 2H, J=8.0 Hz), 7.65-7.74 (m, 3H), 8.07 (d, 2H, J=8.0 Hz); MS (ES) 375.9 (M+1).

EXAMPLE 3-3a (Compound of Formula I where X1=imidazol-1-yl, $R^2=CH_3$, $R^3=H$, $G^1=N(CH_3)_2$, $n^2=1$, Z=3-phenyl, $n^3=0$, $n^4=1$, and $Q^1=CO_2CH_3$): The title compound was prepared according to the General Synthetic Method D as described above wherein compound of Formula II, $R^2=CH_3$, $R^3=H$, $G^1=N(CH_3)_2$, $n^2=1$, Z=3-phenyl, $n^3=0$, $n^4=1$, and $Q^1=CO_2CH_3$. $^1H$ NMR (CDCl$_3$, 200 MHz) δ 0.80 (d, 3H, J=6.6 Hz), 2.28 (s, 6H), 3.47-3.55 (m, 1H), 3.92 (s, 3H), 5.06 (d, 1H, J=10.6 Hz), 5.21 (s, 2H), 6.75 (s, 1H), 7.21-7.27 (m, 1H), 7.36-7.45 (m, 3H), 7.59 (d, 2H, J=7.2 Hz), 7.73-7.87 (m, 4H), 7.93 (s, 1H), 8.01 (s, 1H); MS (ES) 443.9 (M+1).

EXAMPLE 3-3b (Compound of Formula I where X1=imidazol-1-yl, $R^2=CH_3$, $R^3=H$, $G^1=N(CH_3)_2$, $n^2=1$, Z=3-phenyl, $n^3=0$, $n^4=1$, and $Q^1=CO_2CH_3$): The title compound was prepared according to the General Synthetic Method D as described above wherein compound of Formula II, $R^2=CH_3$, $R^3=H$, $G^1=N(CH_3)_2$, $n^2=1$, Z=3-phenyl, $n^3=0$, $n^4=1$, and $Q^1=CO_2CH_3$. $^1H$ NMR (CDCl$_3$, 200 MHz) δ 0.91 (d, 3H, J=6.6 Hz), 2.21 (s, 6H), 3.55-3.65 (m, 1H), 3.93 (s, 3H), 5.08 (d, 1H, J=10.2 Hz), 5.21 (s, 2H), 6.83 (s, 1H), 7.23 (dd, 1H, J=2.6, 8.8 Hz), 7.37-7.38 (m, 2H), 7.51 (t, 1H, J=7.4 Hz), 7.68-7.91 (m, 7H), 8.05 (s, 1H); MS (ES) 443.89.

EXAMPLE 3-4a (Compound of Formula I where X1=imidazol-1-yl, $R^2=CH_3$, $R^3=H$, $G^1=N(CH_3)_2$, $n^2=1$, Z=4-phenyl, $n^3=1$, $R^{4b}$ and $R^{5b}=H$, $n^4=1$, and $Q^1=CO_2CH_3$): The title compound was prepared according to the General Synthetic Method D as described above wherein compound of Formula II, $R^2=CH_3$, $R^3=H$, $G^1=N(CH_3)_2$, $n^2=1$, Z=4-phenyl, $n^3=1$, $R^{4b}$ and $R^{5b}=H$, $n^4=1$, and $Q^1=CO_2CH_3$. $^1H$ NMR (CDCl$_3$, 200 MHz) δ 0.80 (d, 3H, J=6.6 Hz), 2.28 (s, 6H), 3.43-3.58 (m, 1H), 3.64 (s, 2H), 3.70 (s, 3H), 5.05 (d, 1H, J=10.0 Hz), 5.15 (s, 2H), 6.99 (s, 2H), 7.17-7.33 (m, 5H), 7.42 (s, 1H), 7.46 (s, 1H), 7.65-7.73 (m, 4H); MS (ES) 458.0 (M+1).

EXAMPLE 3-4b (Compound of Formula I where X1=imidazol-1-yl, $R^2=CH_3$, $R^3=H$, $G^1=N(CH_3)_2$, $n^2=1$, Z=4-phenyl, $n^3=1$, $R^{4b}$ and $R^{5b}=H$, $n^4=1$, and $Q^1=CO_2CH_3$): The title compound was prepared according to the General Synthetic Method C as described above wherein compound of Formula II, $R^2=CH_3$, $R^3=H$, $G^1=N(CH_3)_2$, $n^2=1$, Z=4-phenyl, $n^3=1$, $R^{4b}$ and $R^{5b}=H$, $n^4=1$, and $Q^1=CO_2CH_3$. $^1H$ NMR (CDCl$_3$, 200 MHz) δ 0.90 (d, 3H, J=6.6 Hz), 2.21 (s, 6H), 3.53-3.65 (m, 1H), 3.64 (s, 2H), 3.69 (s, 3H), 5.10 (d, 1H, J=10.0 Hz), 5.15 (s, 2H), 7.01 (d, 2H, J=4.4 Hz), 7.18-7.26 (m, 3H), 7.29 (s, 1H), 7.33 (s, 1H), 7.41-7.45 (m, 2H), 7.65-7.73 (m, 4H); MS (ES) 458.0 (M+1).

EXAMPLE 3-5a (Compound of Formula I where X1=imidazol-1-yl, $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CH_3$): The title compound was prepared according to the General Synthetic Method D as described above wherein compound of Formula II, $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CH_3$. $^1H$ NMR (CDCl$_3$, 200 MHz) δ 0.80 (d, 3H, J=6.4 Hz), 3.69 (s, 9H), 2.28 (s, 6H), 3.49-3.53 (m, 1H), 3.70 (s, 2H), 5.05 (d, 1H, J=10.4 Hz), 7.00 (d, 2H, J=4.8 Hz), 7.09 (d, 1H, J=2.0 Hz), 7.19 (dd, 1H, J=2.4 Hz, 8.8 Hz) 7.29 (d, 1H, J=1.6 Hz), 7.63-7.74 (m, 4H); MS (ES) 366.0 (M+1).

EXAMPLE 3-5b (Compound of Formula I where X1=imidazol-1-yl, $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CH_3$): The title compound was prepared according to the General Synthetic Method D as described above wherein compound of Formula II, $R^2=CH_3$, $R^3=H$, $G^1=N(CH_3)_2$, $n^2=0$, $n^3=1$, $R^{4b}$ and $R^{5b}=CH_3$, $n^4=1$, and $Q^1=CH_3$. $^1H$ NMR (CDCl$_3$, 200 MHz) δ 0.90 (d, 3H, J=6.0 Hz), 1.07 (s, 9H), 2.12 (s, 6H), 3.57-3.61 (m, 1H), 3.69 (s, 2H), 5.10 (d, 1H, J=10 Hz), 7.00 (bs, 1H), 7.03 (bs, 1H), 7.08 (d, 1H, J=2.0 Hz), 7.17 (dd, 1H, J=2.4 Hz, 9.2 Hz), 7.40 (dd, 1H, J=1.0, 4.2 Hz), 7.66-7.70 (m, 4H); MS (ES) 366.02 (M+1).

EXAMPLE 3-6a (Compound of Formula I where X1=imidazol-1-yl, $R^2$=$CH_3$, $R^3$=H, $G^1$=$N(CH_3)_2$, $n^2$=1, Z=4-phenyl, $n^3$=0, $n^4$=1, and $Q^1$=OtBu): The title compound was prepared according to the General Synthetic Method D as described above wherein compound of Formula II, $R^2$=$CH_3$, $R^3$=H, $G^1$=$N(CH_3)_2$, $n^2$=1, Z=4-phenyl, $n^3$=0, $n^4$=1, and $Q^1$=OtBu. $^1$H NMR (CDCl$_3$, 200 MHz) δ 0.81 (d, 3H, J=6.0 Hz), 1.36 (s, 9H), 2.21 (s, 6H), 3.47-3.63 (m, 1H), 5.06 (d, 1H, J=6.0 Hz), 5.11 (s, 2H), 7.00-7.04 (m, 4H), 7.19-7.39 (m, 5H), 7.64-7.74 (m, 4H); MS (ES) 458.0 (M+1).

EXAMPLE 3-6b (Compound of Formula I where X1=imidazol-1-yl, $R^2$=$CH_3$, $R^3$=H, $G^1$=$N(CH_3)_2$, $n^2$=1, Z=4-phenyl, $n^3$=0, $n^4$=1, and $Q^1$=OtBu): The title compound was prepared according to the General Synthetic Method D as described above wherein compound of Formula II, $R^2$=$CH_3$, $R^3$=H, $G^1$=$N(CH_3)_2$, $n^2$=1, Z=4-phenyl, $n^3$=0, $n^4$=1, and $Q^1$=OtBu. $^1$H NMR (CDCl$_3$, 200 MHz) δ 0.91 (d, 3H, J=6.0 Hz), 1.36 (s, 9H), 2.21 (s, 6H), 3.47-3.63 (m, 1H), 5.06 (d, 1H, J=6.0 Hz), 5.11 (s, 2H), 7.00-7.04 (m, 4H), 7.19-7.39 (m, 5H), 7.64-7.74 (m, 4H); MS (ES) 458.0 (M+1).

EXAMPLE 3-7a (Compound of Formula I where X1=imidazol-1-yl, $R^2$=$CH_3$, $R^3$=H, $G^1$=$N(CH_3)_2$, $n^2$=1, Z=4-PhO, $n^3$=1, $R^{4b}$ and $R^{5b}$=H, $n^4$=1, and $Q^1$=$CO_2CH_3$): The title compound was prepared according to the General Synthetic Method D as described above wherein compound of Formula II, $R^2$=$CH_3$, $R^3$=H, $G^1$=$N(CH_3)_2$, $n^2$=1, Z=4-PhO, $n^3$=1, $R^{4b}$ and $R^{5b}$=H, $n^4$=1, and $Q^1$=$CO_2CH_3$. $^1$H NMR (CDCl$_3$, 200 MHz) δ 0.80 (d, 3H, J=6.6 Hz), 2.73 (s, 6H), 3.46-3.55 (m, 1H), 3.80 (s, 3H), 4.64 (s, 2H), 5.05 (d, 1H, J=10.6 Hz), 5.09 (s, 2H), 6.90-7.00 (m, 4H), 7.17-7.31 (m, 2H), 7.36-7.44 (m, 3H), 7.64-7.73 (m, 4H); MS (ES) 474.0 (M+1).

EXAMPLE 3-7b (Compound of Formula I where X1=imidazol-1-yl, $R^2$=$CH_3$, $R^3$=H, $G^1$=$N(CH_3)_2$, $n^2$=1, Z=4-PhO, $n^3$=1, $R^{4b}$ and $R^{5b}$=H, $n^4$=1, and $Q^1$=$CO_2CH_3$): The title compound was prepared according to the General Synthetic Method D as described above wherein compound of Formula II, $R^2$=$CH_3$, $R^3$=H, $G^1$=$N(CH_3)_2$, $n^2$=1, Z=4-PhO, $n^3$=1, $R^{4b}$ and $R^{5b}$=H, $n^4$=1, $CO_2CH_3$. $^1$H NMR (CDCl$_3$, 200 MHz) δ 0.89 (d, 3H, J=6.6 Hz), 2.73 (s, 6H), 3.46-3.55 (m, 1H), 3.80 (s, 3H), 4.64 (s, 2H), 5.05 (d, 1H, J=10.6 Hz), 5.09 (s, 2H), 6.90-7.00 (m, 4H), 7.17-7.31 (m, 2H), 7.36-7.44 (m, 3H), 7.64-7.73 (m, 4H); MS (ES) 474.0 (M+1).

EXAMPLE 3-8a (Compound of Formula I where X1=imidazol-1-yl, $R^2$=$CH_3$, $R^3$=H, $G^1$=$N(CH_3)_2$, $n^2$=0, $n^3$=2, $R^{4b}$ and $R^{5b}$=H, $n^4$=1, and $Q^1$=$OCH_3$): The title compound was prepared according to the General Synthetic Method D as described above wherein compound of Formula II, $R^2$=$CH_3$, $R^3$=H, $G^1$=$N(CH_3)_2$, $n^2$=0, $n^3$=2, $R^{4b}$ and $R^{5b}$=H, $n^4$=1, and $Q^1$=$OCH_3$. MS (ES) 354.3 (M+1).

EXAMPLE 3-8b (Compound of Formula I where X1=imidazol-1-yl, $R^2$=$CH_3$, $R^3$=H, $G^1$=$N(CH_3)_2$, $n^2$=0, $n^3$=2, $R^{4b}$ and $R^{5b}$=H, $n^4$=1, and $Q^1$=$OCH_3$): The title compound was prepared according to the General Synthetic Method D as described above wherein compound of Formula II, $R^2$=$CH_3$, $R^3$=H, $G^1$=$N(CH_3)_2$, $n^2$=0, $n^3$=2, $R^{4b}$ and $R^{5b}$=H, $n^4$=1, and $Q^1$=$OCH_3$. MS (ES) 354.3 (M+1).

EXAMPLE 3-9a (Compound of Formula I where X1=imidazol-1-yl, $R^2$=$CH_3$, $R^3$=H, $G^1$=$N(CH_3)_2$, $n^2$=1, Z=4-phenyl, $n^3$=0, $n^4$=1, and $Q^1$=$OCH_3$): The title compound was prepared according to the General Synthetic Method D as described above wherein compound of Formula II, $R^2$=$CH_3$, $R^3$=H, $G^1$=$N(CH_3)_2$, $n^2$=1, Z=4-phenyl, $n^3$=0, $n^4$=1, and $Q^1$=$OCH_3$.

EXAMPLE 3-10a (Compound of Formula I where X1=imidazol-1-yl, $R^2$=$CH_3$, $R^3$=H, $G^1$=$N(CH_3)_2$, $n^2$=1, Z equals trans-CH=CHPh, $n^3$ and $n^4$=0): The title compound was prepared according to the General Synthetic Method D as described above wherein compound of Formula II, $R^2$=$CH_3$, $R^3$=H, $G^1$=$N(CH_3)_2$, $n^2$=1, Z equals trans-CH=CHPh, $n^3$ and $n^4$=0. MS (ES) 412.3 (M+1).

EXAMPLE 3-10b (Compound of Formula I where X1=imidazol-1-yl, $R^2$=$CH_3$, $R^3$=H, $G^1$=$N(CH_3)_2$, $n^2$=1, Z equals trans-CH=CHPh, $n^3$ and $n^4$=0): The title compound was prepared according to the General Synthetic Method D as described above wherein compound of Formula II, $R^2$=$CH_3$, $R^3$=H, $G^1$=$N(CH_3)_2$, $n^2$=1, Z equals trans-CH=CHPh, $n^3$ and $n^4$=0. MS (ES) 412.3 (M+1).

EXAMPLE 3-11a (Compound of Formula I where X1=imidazol-1-yl, $R^2$=$CH_3$, $R^3$=H, $G^1$=$N(CH_3)_2$, $n^2$=1, Z=4-phenyl, $n^3$=0, $n^4$=1, and $Q^1$=CN): The title compound was prepared according to the General Synthetic Method D as described above wherein compound of Formula II, $R^2$=$CH_3$, $R^3$=H, $G^1$=$N(CH_3)_2$, $n^2$=1, Z=4-phenyl, $n^3$=0, $n^4$=1, and $Q^1$=CN. $^1$H NMR (CDCl$_3$, 400 MHz) δ 0.80 (d, 3H, J=6.4 Hz), 2.28 (s, 6H), 3.48-3.53 (m, 1H), 5.06 (d, 1H, J=10.4 Hz), 5.24 (s, 2H), 7.00 (s, 2H), 7.14 (d, 1H, J=2.4 Hz), 7.24 (d, 1H, J=2.4 Hz), 7.29-7.31 (m, 1H), 7.59 (d, 2H, J=8.4 Hz), 7.62 (d, 2H, J=2.4 Hz), 7.69 (d, 2H, J=1.6 Hz), 7.71-7.76 (m, 2H).

EXAMPLE 3-11b (Compound of Formula I where X1=imidazol-1-yl, $R^2$=$CH_3$, $R^3$=H, $G^1$=$N(CH_3)_2$, $n^2$=1, Z=4-phenyl, $n^3$=0, $n^4$=1, and $Q^1$=CN): The title compound was prepared according to the General Synthetic Method D as described above wherein compound of Formula II, $R^2$=$CH_3$, $R^3$=H, $G^1$=$N(CH_3)_2$, $n^2$=1, Z=4-phenyl, $n^3$=0, $n^4$=1, and $Q^1$=CN. $^1$H NMR (CDCl$_3$, 400 MHz) δ 0.91 (d, 3H, J=6.4 Hz), 2.22 (s, 6H), 3.58-3.63 (m, 1H), 5.10 (d, 1H, J=10.0 Hz), 5.28 (s, 2H), 7.01 (d, 2H, J=12.0 Hz), 7.14 (s, 1H), 7.23 (s, 1H), 7.43 (d, 1H, J=8.8 Hz) 7.64-7.76 (m, 6H), 8.26 (d, 2H, J=7.2 Hz).

EXAMPLE 3-12a (Compound of Formula I where X1=imidazol-1-yl, $R^2$=$CH_3$, $R^3$=H, $G^1$=$N(CH_3)_2$, $n^2$=1, Z=4-phenyl, $n^3$=0, $n^4$=1, and $Q^1$=$NO_2$): The title compound was prepared according to the General Synthetic Method D as described above wherein compound of Formula II, $R^2$=$CH_3$, $R^3$=H, $G^1$=$N(CH_3)_2$, $n^2$=1, Z=4-phenyl, $n^3$=0, $n^4$=1, and $Q^1$=$NO_2$. $^1$H NMR ($CDCl_3$, 400 MHz) δ 0.80 (d, 3H, J=6.4 Hz), 2.28 (s, 6H), 3.48-3.53 (m, 1H), 5.06 (d, 1H, J=10.4 Hz), 5.24 (s, 2H), 7.13 (s, 1H), 7.22 (dd, 1H, J=2.4, 8.8 Hz), 7.42 (d, 1H, J=8.4 Hz), 7.57-7.59 (m, 2H), 7.67-7.75 (m, 8H).

EXAMPLE 3-13a (Compound of Formula I where X1=imidazol-1-yl, $R^2$=$CH_3$, $R^3$=H, $G^1$=$N(CH_3)_2$, $n^2$=0, $n^3$=1, $R^{4b}$ and $R^{5b}$=$CH_2CH_3$, $n^4$=1, and $Q^1$=$CO_2Et$): The title compound was prepared according to the General Synthetic Method D as described above wherein compound of Formula II, $R^2$=$CH_3$, $R^3$=H, $G^1$=$N(CH_3)_2$, $n^2$=0, $n^3$=1, $R^{4b}$ and $R^{5b}$=$CH_2CH_3$, $n^4$=1, and $Q^1$=$CO_2Et$. MS (ES) 452.3 (M+1).

EXAMPLE 3-14a (Compound of Formula I where X1=imidazol-1-yl, $R^2$=$CH_3$, $R^3$=H, $G^1$=$N(CH_3)_2$, $n^2$=0, $n^3$=1, $R^{4b}$ and $R^{5b}$ are taken together with the carbon to which they are attached to equal a cyclopropyl ring, $n^4$=1, and $Q^1$=$CO_2Et$): The title compound was prepared according to the General Synthetic Method D as described above wherein compound of Formula II, $R^2$=$CH_3$, $R^3$=H, $G^1$=$N(CH_3)_2$, $n^2$=0, $n^3$=1, $R^{4b}$ and $R^{5b}$ are taken together with the carbon to which they are attached to equal a cyclopropyl ring, $n^4$=1, and $Q^1$=$CO_2Et$. MS (ES) 422.3 (M+1).

EXAMPLE 3-15a (Compound of Formula I where X1=imidazol-1-yl, $R^2$=$CH_3$, $R^3$=H, $G^1$=$N(CH_3)_2$, $n^2$=0, $n^3$=1, $R^{4b}$ and $R^{5b}$ are taken together with the carbon to which they are attached to equal a cyclobutyl ring, $n^4$=1, and $Q^1$=$CO_2Et$): The title compound was prepared according to the General Synthetic Method D as described above wherein compound of Formula II, $R^2$=$CH_3$, $R^3$=H, $G^1$=$N(CH_3)_2$, $n^2$=0, $n^3$=1, $R^{4b}$ and $R^{5b}$ are taken together with the carbon to which they are attached to equal a cyclobutyl ring, $n^4$=1, and $Q^1$=$CO_2Et$. MS (ES) 436.3 (M+1).

EXAMPLE 3-16a (Compound of Formula I where X1=imidazol-1-yl, $R^2$=$CH_3$, $R^3$=H, $G^1$=$N(CH_3)_2$, $n^2$=0, $n^3$=1, $R^{4b}$ and $R^{5b}$ are taken together with the carbon to which they are attached to equal a 4-pyranyl ring, $n^4$=1, and $Q^1$=$CO_2CH_3$): The title compound was prepared according to the General Synthetic Method D as described above wherein compound of Formula II, $R^2$=$CH_3$, $R^3$=H, $G^1$=$N(CH_3)_2$, $n^2$=0, $n^3$=1, $R^{4b}$ and $R^{5b}$ are taken together with the carbon to which they are attached to equal a 4-pyranyl ring, $n^4$=1, and $Q^1$=$CO_2CH_3$. MS (ES) 452.3 (M+1).

EXAMPLE 3-17a (Compound of Formula I where X1=imidazol-1-yl, $R^2$=$CH_3$, $R^3$=H, $G^1$=$N(CH_3)_2$, $n^2$=0, $n^3$=1, $R^{4b}$ and $R^{5b}$ are taken together with the carbon to which they are attached to equal a cyclohexyl ring, $n^4$=1, and $Q^1$=$CO_2Et$): The title compound was prepared according to the General Synthetic Method D as described above wherein compound of Formula II, $R^2$=$CH_3$, $R^3$=H, $G^1$=$N(CH_3)_2$, $n^2$=0, $n^3$=1, $R^{4b}$ and $R^{5b}$ are taken together with the carbon to which they are attached to equal a cyclohexyl ring, $n^4$=1, and $Q^1$=$CO_2Et$. MS (ES) 464.2 (M+1).

EXAMPLE 3-18a (Compound of Formula I where X1=imidazol-1-yl, $R^2$=$CH_3$, $R^3$=H, $G^1$=$N(CH_3)_2$, $n^2$=0, $n^3$=1, $R^{4b}$ and $R^{5b}$ are taken together with the carbon to which they are attached to equal a cyclopentyl ring, $n^4$=1, and $Q^1$=$CO_2Et$): The title compound was prepared according to the General Synthetic Method D as described above wherein compound of Formula II, $R^2$=$CH_3$, $R^3$=H, $G^1$=$N(CH_3)_2$, $n^2$=0, $n^3$=1, $R^{4b}$ and $R^{5b}$ are taken together with the carbon to which they are attached to equal a cyclopentyl ring, $n^4$=1, and $Q^1$=$CO_2Et$. MS (ES) 450.3 (M+1).

EXAMPLE 3-19a (Compound of Formula I where X1=imidazol-1-yl, $R^2$=$CH_3$, $R^3$=H, $G^1$=$N(CH_3)_2$, $n^2$=1, Z=Ph, $n^3$ and $n^4$=0): The title compound was prepared according to the General Synthetic Method D as described above wherein compound of Formula II, $R^2$=$CH_3$, $R^3$=H, $G^1$=$N(CH_3)_2$, $n^2$=1, Z=Ph, $n^3$ and $n^4$=0. $^1$H NMR ($CDCl_3$, 200 MHz) δ 0.80 (d, 3H, J=6.0 Hz), 2.21 (s, 6H), 3.47-3.55 (m, 1H), 5.03 (d, 1H, J=6.0 Hz), 5.17 (s, 2H), 7.00-7.74 (m, 14H); MS (ES) 386.1 (M+1).

EXAMPLE 3-19b (Compound of Formula I where X1=imidazol-1-yl, $R^2$=$CH_3$, $R^3$=H, $G^1$=$N(CH_3)_2$, $n^2$=1, Z=Ph, $n^3$ and $n^4$=0): The title compound was prepared according to the General Synthetic Method D as described above wherein compound of Formula II, $R^2$=$CH_3$, $R^3$=H, $G^1$=$N(CH_3)_2$, $n^2$=1, Z=Ph, $n^3$ and $n^4$=0. $^1$H NMR ($CDCl_3$, 200 MHz) δ 0.91 (d, 3H, J=6.0 Hz), 2.21 (s, 6H), 3.47-3.55 (m, 1H), 5.03 (d, 1H, J=6.0 Hz), 5.17 (s, 2H), 7.00-7.74 (m, 14H); MS (ES) 386.1 (M+1).

EXAMPLE 3-20a (Compound of Formula I where X1=imidazol-1-yl, $R^2$=$CH_3$, $R^3$=H, $G^1$=$N(CH_2)_2O(CH_2)_2$ ring, $n^2$=0, $n^3$=1, $R^{4b}$ and $R^{5b}$=$CH_3$, $n^4$=1, and $Q^1$=$CO_2CH_3$): The title compound was prepared according to the General Synthetic Method D as described above wherein compound of Formula II, $R^2$=$CH_3$, $R^3$=H, $G^1$=$N(CH_2)_2O(CH_2)_2$ ring, $n^2$=0, $n^3$=1, $R^{4b}$ and $R^{5b}$=$CH_3$, $n^4$=1, and $Q^1$=$CO_2CH_3$. MS (ES) 452.3 (M+1).

EXAMPLE 3-21a (Compound of Formula I where X1=imidazol-1-yl, $R^2$=$CH_3$, $R^3$=H, $G^1$=$N(Et)_2$, $n^2$=0, $n^3$=1, $R^{4b}$ and $R^{5b}$=$CH_3$, $n^4$=1, and $Q^1$=$CO_2CH_3$): The title compound was prepared according to the General Synthetic Method D as described above wherein compound of Formula II, $R^2$=$CH_3$, $R^3$=H, $G^1$=$N(Et)_2$, $n^2$=0, $n^3$=1, $R^{4b}$ and $R^{5b}$=$CH_3$, $n^4$=1, and $Q^1$=$CO_2CH_3$. MS (ES) 438.3 (M+1).

EXAMPLE 3-22a (Compound of Formula I where X1=imidazol-1-yl, $R^2$=$CH_3$, $R^3$=H, $G^1$=$N(CH_3)$cyclohexyl, $n^2$=0, $n^3$=1, $R^{4b}$ and $R^{5b}$=$CH_3$, $n^4$=1, and $Q^1$=$CO_2CH_3$): The title compound was prepared according to the General Synthetic Method D as described above wherein compound of Formula II, $R^2$=$CH_3$,

EXAMPLE 3-23a (Compound of Formula I where X1=imidazol-1-yl, $R^2=CH_3$, $R^3=H$, $G^1=N(CH_3)$n-butyl, $n^2=0$, $n^3=1$, $R^{4b}$ and $R^{5b}=CH_3$, $n^4=1$, and $Q^1=CO_2CH_3$): The title compound was prepared according to the General Synthetic Method D as described above wherein compound of Formula II, $R^2=CH_3$, $R^3=H$, $G^1=N(CH_3)$n-butyl, $n^2=0$, $n^3=1$, $R^{4b}$ and $R^{5b}=CH_3$, $n^4=1$, and $Q^1=CO_2CH_3$. MS (ES) 425.2 (M+1).

EXAMPLE 3-24a (Compound of Formula I where X1=imidazol-1-yl, $R^2=CH_3$, $R^3=H$, $G^1=N(CH_3)$iPr, $n^2=0$, $n^3=1$, $R^{4b}$ and $R^{5b}=CH_3$, $n^4=1$, and $Q^1=CO_2CH_3$): The title compound was prepared according to the General Synthetic Method D as described above wherein compound of Formula II, $R^2=CH_3$, $R^3=H$, $G^1=N(CH_3)$iPr, $n^2=0$, $n^3=1$, $R^{4b}$ and $R^{5b}=CH_3$, $n^4=1$, and $Q^1CO_2CH_3$. MS (ES) 438.2 (M+1).

EXAMPLE 3-25a (Compound of Formula I where X1=imidazol-1-yl, $R^2=CH_3$, $R^3=H$, $G^1=N(CH_2)_4$, $n^2=0$, $n^3=1$, $R^{4b}$ and $R^{5b}=CH_3$, $n^4=1$, and $Q^1=CO_2CH_3$): The title compound was prepared according to the General Synthetic Method D as described above wherein compound of Formula II, $R^2=CH_3$, $R^3=H$, $G^1=N(CH_2)_4$, $n^2=0$, $n^3=1$, $R^{4b}$ and $R^{5b}=CH_3$, $n^4=1$, and $Q^1=CO_2CH_3$. MS (ES) 436.3 (M+1).

EXAMPLE 3-26a (Compound of Formula I where X1=imidazol-1-yl, $R^2=CH_3$, $R^3=H$, $G^1=N(CH_3)$Et, $n^2=0$, $n^3=1$, $R^{4b}$ and $R^{5b}=CH_3$, $n^4=1$, and $Q^1=CO_2CH_3$): The title compound was prepared according to the General Synthetic Method D as described above wherein compound of Formula II, $R^2=CH_3$, $R^3=H$, $G^1=N(CH_3)$Et, $n^2=0$, $n^3=1$, $R^{4b}$ and $R^{5b}=CH_3$, $n^4=1$, and $Q^1=CO_2CH_3$. MS (ES) 424.3 (M+1).

EXAMPLE 3-27a (Compound of Formula I where X1=imidazol-1-yl, $R^2=CH_3$, $R^3=H$, $G^1=N(CH_3)_2$, $n^2=0$, $n^3=0$, $n^4=1$, and $Q^1=CO_2tBu$): The title compound was prepared according to the General Synthetic Method D as described above wherein compound of Formula II, $R^2=CH_3$, $R^3=H$, $G^1=N(CH_3)_2$, $n^2=0$, $n^3=0$, $n^4=1$, and $Q^1=CO_2tBu$. $^1$HNMR (CDCl$_3$, 200 MHz) δ 0.79 (d, 3H, J=6.6 Hz), 1.49 (s, 9H), 2.27 (s, 6H), 3.51-3.66 (m, 1H), 4.61 (s, 2H), 5.20 (d, 1H, J=4.0 Hz), 6.98-7.04 (m, 3H), 7.21 (dd, 1H, J=2.6, 9.2 Hz), 7.41 (dd, 1H, J=1.8, 8.4 Hz), 7.64-7.74 (m, 4H).

EXAMPLE 3-27b (Compound of Formula I where X1=imidazol-1-yl, $R^2=CH_3$, $R^3=H$, $G^1=N(CH_3)_2$, $n^2=0$, $n^3=0$, $n^4=1$, and $Q^1=CO_2tBu$): The title compound was prepared according to the General Synthetic Method D as described above wherein compound of Formula II, $R^2=CH_3$, $R^3=H$, $G^1=N(CH_3)_2$, $n^2=0$, $n^3=0$, $n^4=1$, and $Q^1=CO_2tBu$. $^1$HNMR (CDCl$_3$, 200 MHz) δ 0.89 (d, 3H, J=6.6 Hz), 1.49 (s, 9H), 2.20 (s, 6H), 3.51-3.66 (m, 1H), 4.61 (s, 2H), 5.60 (d, 1H, J=9.4 Hz), 6.98-7.04 (m, 3H), 7.21 (dd, 1H, J=2.6, 9.2 Hz), 7.41 (dd, 1H, J=1.8, 8.4 Hz), 7.64-7.74 (m, 4H).

EXAMPLE 3-28

(Compound of Formula I where X1=imidazol-1-yl, $R^2=CH_3$, $R^3=CH_3$, $G^1=N(CH_3)_2$, $n^2=0$, $n^3=1$, $R^{4b}$ and $R^{5b}=CH_3$, $n^4=1$, and $Q^1=CO_2CH_3$): The title compound was prepared according to the General Synthetic Method D as described above wherein compound of Formula II, $R^2=CH_3$, $R^3=CH_3$, $G^1=N(CH_3)_2$, $n^2=0$, $n^3=1$, $R^{4b}$ and $R^{5b}=CH_3$, $n^4=1$, and $Q^1=CO_2CH_3$. MS (ES) 424.3 (M+1).

EXAMPLE 3-29

(Compound of Formula I where X1=imidazol-1-yl, $R^2=H$, $R^3=H$, $G^1=N(CH_3)_2$, $n^2=0$, $n^3=1$, $R^{4b}$ and $R^{5b}=CH_3$, $n^4=1$, and $Q^1=CO_2CH_3$): The title compound was prepared according to the General Synthetic Method D as described above wherein compound of Formula II, $R^2=H$, $R^3=H$, $G^1=N(CH_3)_2$, $n^2=0$, $n^3=1$, $R^{4b}$ and $R^{5b}=CH_3$, $n^4=1$, and $Q^1=CO_2CH_3$. $^1$H NMR (CDCl$_3$, 400 MHz) δ 1.36 (s, 6H), 2.31 (s, 6H), 2.91-3.19 (m, 2H), 3.70 (s, 3H), 4.08 (s, 2H), 5.39-5.42 (m, 1H), 7.00-7.23 (m, 5H), 7.55 (s, 1H), 7.66-7.70 (m, 3H); MS (ES) 396.0 (M+1).

EXAMPLE 3-30a (Compound of Formula I where X1=imidazol-1-yl, $R^2$, $R^3$, and $G^1$ are taken together to equal A2* (see Table 3), $n^2=1$, Z=Ph, and $n^3$ and $n^4=0$): The title compound was prepared according to the General Synthetic Method D as described above wherein compound of Formula II, X1=imidazol-1-yl, $R^2$, $R^3$, and $G^1$ are taken together to equal A2*, $n^2=1$, Z=Ph, and $n^3$ and $n^4=0$. White solid, mp 124-126° C.; MS (ES) 398.18 (M+1).

EXAMPLE 3-30b (Compound of Formula I where X1=imidazol-1-yl, $R^2$, $R^3$, and $G^1$ are taken together to equal A2* (see Table 3), $n^2=1$, Z=Ph): The title compound was prepared according to the General Synthetic Method D as described above wherein compound of Formula II, X1=imidazol-1-yl, $R^2$, $R^3$, and $G^1$ are taken together to equal A2*, $n^2=1$, Z=Ph. White solid, mp 110-112° C.; MS (ES) 398.05 (M+1).

EXAMPLE 3-31a (Compound of Formula I where X2=triazol-1-yl, $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclopentyl ring, $n^4=1$, and $Q^1=CO_2Et$): The title compound was prepared according to the General Synthetic Method D as described above wherein compound of Formula II, $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclopentyl ring, $n^4=1$, and $Q^1=CO_2Et$. MS (ES) 451.2 (M+1).

EXAMPLE 3-32a (Compound of Formula I where X1=imidazol-1-yl, $R^2=CH_2CH_3$, $R^3=H$, $G^1=N(CH_3)_2$, $n^2=0$, $n^4=1$, $R^{4b}$ and $R^{5b}=CH_3$, $n^4=1$, and $Q^1=CO_2CH_3$): The title compound was prepared according to the General Synthetic Method D as described above wherein compound of Formula II, $R^2=CH_2CH_3$, $R^3=H$, $G^1=N(CH_3)_2$, $n^2=0$, $n^3=1$, $R^{4b}$ and $R^{5b}=CH_3$, $n^4=1$, and $Q^1=CO_2CH_3$. MS (ES) 424.2 (M+1). $^1H$ NMR (CDCl$_3$, 400 MHz) δ 0.74 (t, 3H, J=7.4 Hz), 1.19-1.27 (m, 1H), 1.36 (s, 6H), 1.45-1.56 (m, 1H), 2.33 (s, 6H), 3.25-3.31 (m, 1H), 3.70 (s, 3H), 4.07 (s, 2H), 5.12 (d, 1H, J=10.0 Hz), 7.00 (s, 1H), 7.05 (s, 1H), 7.11 (d, 1H, J=2.3 Hz), 7.16 (dd, 1H, J=2.5, 8.9 Hz), 7.37 (dd, 1H, J=1.8, 8.5 Hz), 7.68-7.70 (m, 4H).

EXAMPLE 3-33a (Compound of Formula I where X2=triazol-1-yl, $R^2=CH_3$, $R^3=H$, $G^1=N(CH_3)iPr$, $n^2=0$, $n^3=1$, $R^{4b}$ and $R^{5b}$ are taken together with the carbon to which they are attached to equal a cyclopentyl ring, $n^4=1$, and $Q^1=CO_2Et$): The title compound was prepared according to the General Synthetic Method D as described above wherein compound of Formula II, $R^2=CH_3$, $R^3=H$, $G^1=N(CH_3)iPr$, $n^2=0$, $n^3=1$, $R^{4b}$ and $R^{5b}$ are taken together with the carbon to which they are attached to equal a cyclopentyl ring, $n^4=1$, and $Q^1=CO_2Et$. MS (ES) 478.2 (M+1).

Following the general methods described hereinbefore, the following compounds of Formula I-B as listed in Table 4 were prepared. In the EXAMPLE numbers, "a" denotes the syn isomer and "b" denotes the anti isomer, with respect to X and $G^1$. X1=imidazol-1-yl, X2=triazol-1-yl, and X3=triazol-3-yl.

General Synthetic Method E for the preparation of compounds of the Formula I-B: A solution of compound of Formula I-C in THF was charged with 5 eq. NaOH in H$_2$O and allowed to stir at 45° C. for 3 h. The reaction mixture was concentrated in vacuo to solids, taken up in minimal water, neutralized to pH 7 with 6 M HCl, and extracted with CH$_2$Cl$_2$. The combined organic layers were dried over Na$_2$SO$_4$, filtered and concentrated in vacuo. The resulting solids were purified by silica gel chromatography with 10% CH$_3$OH in CHCl$_3$ to afford the desired compounds of Formula I-B.

EXAMPLE 4-1a (Compound of Formula I-B where X1=imidazol-1-yl, $R^2=CH_3$, $R^3=H$, $G^1=N(CH_3)_2$, $n^2=0$, $n^3=1$, $R^{4b}$ and $R^{5b}=CH_3$): The title compound was prepared according to the General Synthetic Method E as described above wherein compound of Formula I-C, X1=imidazol-1-yl, $R^2=CH_3$, $R^3=H$, $G^1=N(CH_3)_2$, $n^2=0$, $n^3=1$, $R^{4b}$ and $R^{5b}=CH_3$, and $R^7=CH_3$. $^1$HNMR (CD$_3$OD, 200 MHz) δ 0.85 (d, 3H, J=6.6 Hz), 1.32 (s, 6H), 2.30 (s, 6H), 3.81-3.98 (m, 1H), 4.07 (s, 2H), 5.43 (d, 1H, J=15 Hz), 6.97-7.22 (m, 3H), 7.35-7.60 (m, 2H), 7.23-7.96 (m, 3H), 8.20 (s, 1H); MS (ES) 395.9 (M+1).

EXAMPLE 4-1b (Compound of Formula I-B where X1=imidazol-1-yl, $R^2=CH_3$, $R^3=H$, $G^1=N(CH_3)_2$, $n^2=0$, $n^3=1$, and $R^{4b}$ and $R^{5b}=CH_3$): The title compound was prepared according to the General Synthetic Method E as described above wherein

TABLE 4

I-B

Listing of Compounds of Formula I-B

| EX. | $R^2$ | $R^3$ | $G^1$ | n2 | Z | n3 | $R^{4b}$ | $R^{5b}$ | X |
|---|---|---|---|---|---|---|---|---|---|
| 4-1a | CH$_3$ | H | N(CH$_3$)$_2$ | 0 | — | 1 | CH$_3$ | CH$_3$ | X1 |
| 4-1b | CH$_3$ | H | N(CH$_3$)$_2$ | 0 | — | 1 | CH$_3$ | CH$_3$ | X1 |
| 4-2a | CH$_3$ | H | N(CH$_3$)$_2$ | 1 | 4 Ph | 0 | — | — | X1 |
| 4-2b | CH$_3$ | H | N(CH$_3$)$_2$ | 1 | 4 Ph | 0 | — | — | X1 |
| 4-3a | CH$_3$ | H | N(CH$_3$)$_2$ | 1 | 3 Ph | 0 | — | — | X1 |
| 4-3b | CH$_3$ | H | N(CH$_3$)$_2$ | 1 | 3 Ph | 0 | — | — | X1 |
| 4-4a | CH$_3$ | H | N(CH$_3$)$_2$ | 1 | 4 Ph | 1 | H | H | X1 |
| 4-4b | CH$_3$ | H | N(CH$_3$)$_2$ | 1 | 4 Ph | 1 | H | H | X1 |
| 4-5a | CH$_3$ | H | N(CH$_3$)$_2$ | 0 | — | 1 | Et | Et | X1 |
| 4-6a | CH$_3$ | H | N(CH$_3$)$_2$ | 0 | — | 1 | CH$_2$CH$_2$ ring | | X1 |
| 4-7a | CH$_3$ | H | N(CH$_3$)$_2$ | 0 | — | 1 | CH$_2$CH$_2$CH$_2$ ring | | X1 |
| 4-8a | CH$_3$ | H | N(CH$_3$)$_2$ | 0 | — | 1 | CH$_2$CH$_2$OCH$_2$CH$_2$ ring | | X1 |
| 4-9a | CH$_3$ | H | N(CH$_3$)$_2$ | 0 | — | 1 | CH$_2$(CH$_2$)$_3$CH$_2$ ring | | X1 |
| 4-10a | CH$_3$ | H | N(CH$_3$)$_2$ | 0 | — | 1 | CH$_2$(CH$_2$)$_2$CH$_2$ ring | | X1 |
| 4-11a | CH$_3$ | H | N(CH$_2$)$_2$O(CH$_2$)$_2$ ring | 0 | — | 1 | CH$_3$ | CH$_3$ | X1 |
| 4-12a | CH$_3$ | H | N(Et)$_2$ | 0 | — | 1 | CH$_3$ | CH$_3$ | X1 |
| 4-13a | CH$_3$ | H | N(CH$_3$)cyclohexyl | 0 | — | 1 | CH$_3$ | CH$_3$ | X1 |
| 4-14a | CH$_3$ | H | N(CH$_3$)n-butyl | 0 | — | 1 | CH$_3$ | CH$_3$ | X1 |
| 4-15a | CH$_3$ | H | N(CH$_3$)iPr | 0 | — | 1 | CH$_3$ | CH$_3$ | X1 |
| 4-16a | CH$_3$ | H | N(CH$_2$)$_4$ ring | 0 | — | 1 | CH$_3$ | CH$_3$ | X1 |
| 4-17a | CH$_3$ | H | N(CH$_3$)Et | 0 | — | 1 | CH$_3$ | CH$_3$ | X1 |
| 4-18 | CH$_3$ | CH$_3$ | N(CH$_3$)$_2$ | 0 | — | 1 | CH$_3$ | CH$_3$ | X1 |
| 4-19 | H | H | N(CH$_3$)$_2$ | 0 | — | 1 | CH$_3$ | CH$_3$ | X1 |
| 4-20a | CH$_3$ | H | N(CH$_3$)$_2$ | 0 | — | 1 | CH$_2$(CH$_2$)$_2$CH$_2$ ring | | X2 |
| 4-21a | Et | H | N(CH$_3$)$_2$ | 0 | — | 1 | CH$_3$ | CH$_3$ | X1 |
| 4-22a | CH$_3$ | H | N(CH$_3$)iPr | 0 | — | 1 | CH$_2$(CH$_2$)$_2$CH$_2$ ring | | X1 | compound of Formula I-C, X1=imidazol-1-yl, $R^2$=$CH_3$, $R^3$=H, $G^1$=$N(CH_3)_2$, $n^2$=0, $n^3$=1, $R^{4b}$ and $R^{5b}$=$CH_3$, and $R^7$=$CH_3$. $^1$HNMR ($CD_3OD$, 200 MHz) δ 0.94 (d, 3H, J=6.6 Hz), 1.32 (s, 6H), 2.30 (s, 6H), 3.81-3.98 (m, 1H), 4.07 (s, 2H), 6.97-7.22 (m, 3H), 7.35-7.60 (m, 2H), 7.23-7.96 (m, 3H), 8.20 (s, 1H); MS (ES) 395.9 (M+1).

EXAMPLE 4-2a (Compound of Formula I-B where X1=imidazol-1-yl, $R^2$=$CH_3$, $R^3$=H, $G^1$=$N(CH_3)_2$, $n^2$=1, Z=4-phenyl, and $n^3$=0): The title compound was prepared according to the General Synthetic Method E as described above wherein compound of Formula I-C, X1=imidazol-1-yl, $R^2$=$CH_3$, $R^3$=H, $G^1$=$N(CH_3)_2$, $n^2$=1, Z=4-phenyl, $n^3$=0, and $R^7$=$CH_3$. $^1$H NMR (DMSO-$d_6$, 400 MHz) δ 0.85 (d, 3H, J=8.0 Hz), 2.39 (s, 6H), 4.15-4.40 (m, 1H), 5.31 (s, 2H), 5.83 (d, 1H, J=9.2 Hz), 7.30 (dd, 1H, J=9.2 Hz, 2.8 Hz), 7.15 (d, $^{H, J}$=2.0 Hz), 7.59 (d, 2H, J=8.4 Hz), 7.67 (d, 2H, J=8.8 Hz), 8.31 (d, 2H, J=8.8 Hz), 7.91-7.96 (m, 3H), 8.05 (s, 1H), 9.05 (s, 1H); MS (ES) 429.1 (M+1).

EXAMPLE 4-2b (Compound of Formula I-B where X1=imidazol-1-yl, $R^2$=$CH_3$, $R^3$=H, $G^1$=$N(CH_3)_2$, $n^2$=1, Z=4-phenyl, and $n^3$=0): The title compound was prepared according to the General Synthetic Method E as described above wherein compound of Formula I-C, X1=imidazol-1-yl, $R^2$=$CH_3$, $R^3$=H, $G^1$=$N(CH_3)_2$, $n^2$=1, Z=4-phenyl, $n^3$=0, and $R^7$=$CH_3$. $^1$H NMR ($CD_3OD$, 200 MHz) δ 0.71 (d, 3H, J=6.4 Hz), 2.10 (s, 6H), 3.74-3.82 (m, 1H), 5.27 (s, 2H), 5.34 (d, 1H, J=11.0 Hz), 6.82 (s, 1H), 7.23 (dd, 1H, J=9.2 Hz, 2.6 Hz), 7.36-7.39 (m, 2H), 7.55 (d, 2H, J=8.0 Hz), 7.69 (d, 2H, J=3.8 Hz), 7.75-7.80 (m, 2H), 7.91-7.95 (m, 3H); MS (ES) 361.8 (M+1).

EXAMPLE 4-3a (Compound of Formula I-B where X1=imidazol-1-yl, $R^2$=$CH_3$, $R^3$=H, $G^1$=$N(CH_3)_2$, $n^2$=1, Z=3-phenyl, and $n^3$=0): The title compound was prepared according to the General Synthetic Method E as described above wherein compound of Formula I-C, X1=imidazol-1-yl, $R^2$=$CH_3$, $R^3$=H, $G^1$=$N(CH_3)_2$, $n^2$=1, Z=3-phenyl, $n^3$=0, and $R^7$=$CH_3$. $^1$H NMR ($CDCl_3$, 200 MHz) δ 0.66 (d, 3H, J=6.2 Hz), 2.15 (s, 6H), 3.65-3.83 (m, 1H), 5.24 (s, 2H), 5.33 (d, 1H, J=11.4 Hz), 6.75 (s, 1H), 6.75 (s, 1H), 7.21-7.27 (m, 1H), 7.34-7.45 (m, 3H), 7.59 (d, 2H, J=7.2 Hz), 7.73-7.87 (m, 4H), 7.93 (s, 1H), 8.01 (s, 1H); MS (ES) 430.0 (M+1).

EXAMPLE 4-3b (Compound of Formula I-B where X1=imidazol-1-yl, $R^2$=$CH_3$, $R^3$=H, $G^1$=$N(CH_3)_2$, $n^2$=1, Z=3-phenyl, and $n^3$=0): The title compound was prepared according to the General Synthetic Method E as described above wherein compound of Formula I-C, X1=imidazol-1-yl, $R^2$=$CH_3$, $R^3$=H, $G^1$=$N(CH_3)_2$, $n^2$=1, Z=3-phenyl, $n^3$=0, and $R^7$=$CH_3$. $^1$H NMR ($CDCl_3$, 200 MHz) δ 0.71 (d, 3H, J=6.2 Hz), 2.09 (s, 6H), 3.74-3.83 (m, 1H), 5.28 (s, 2H), 5.34 (d, 1H, J=11.4 Hz), 6.83 (s, 1H), 7.21 (d, 1H, J=2.6 Hz), 7.25 (d, 1H, J=2.6 Hz), 7.37-7.91 (m, 9H), 8.05 (s, 1H); MS (ES) 430.0 (M+1).

EXAMPLE 4-4a (Compound of Formula I-B where X1=imidazol-1-yl, $R^2$=$CH_3$, $R^3$=H, $G^1$=$N(CH_3)_2$, $n^2$=1, Z=4-phenyl, and $R^{4b}$ and $R^{5b}$=H): The title compound was prepared according to the General Synthetic Method E as described above wherein compound of Formula I-C, X1=imidazol-1-yl, $R^2$=$CH_3$, $R^3$=H, $G^1$=$N(CH_3)_2$, $n^2$=1, Z=4-phenyl, $n^3$=1, $R^{4b}$ and $R^{5b}$=H, and $R^7$=$CH_3$. $^1$H NMR ($CDCl_3$, 400 MHz) δ 0.77 (d, 3H, J=6.2 Hz), 2.19 (s, 6H), 3.46-3.70 (m, 3H), 5.00-5.18 (m, 3H), 7.02 (m, 2H), 7.15-7.36 (m, 6H), 7.62-7.69 (m, 3H), 7.89 (s, 1H), 8.08 (s, 1H), 11.26 (bs, 1H).

EXAMPLE 4-4b (Compound of Formula I-B where X1=imidazol-1-yl, $R^2$=$CH_3$, $R^3$=H, $G^1$=$N(CH_3)_2$, $n^2$=1, Z=4-phenyl, $n^3$=1, and $R^{4b}$ and $R^{5b}$=H): The title compound was prepared according to the General Synthetic Method E as described above wherein compound of Formula I-C, X1=imidazol-1-yl, $R^2$=$CH_3$, $R^3$=H, $G^1$=$N(CH_3)_2$, $n^2$=1, Z=4-phenyl, $n^3$=1, $R^{4b}$ and $R^{5b}$=H, and $R^7$=$CH_3$. $^1$H NMR ($CDCl_3$, 400 MHz) δ 0.90 (d, 3H), 2.24 (s, 6H), 3.46-3.70 (m, 3H), 5.00-5.18 (m, 3H), 7.02 (m, 2H), 7.15-7.36 (m, 6H), 7.62-7.69 (m, 3H), 7.89 (s, 1H), 8.08 (s, 1H), 11.26 (bs, 1H).

EXAMPLE 4-5a (Compound of Formula I-B where X1=imidazol-1-yl, $R^2$=$CH_3$, $R^3$=H, $G^1$=$N(CH_3)_2$, $n^2$=0, $n^3$=1, and $R^{4b}$ and $R^{5b}$=$CH_2CH_3$): The title compound was prepared according to the General Synthetic Method E as described above wherein compound of Formula I-C, X1=imidazol-1-yl, $R^2$=$CH_3$, $R^3$=H, $G^1$=$N(CH_3)_2$, $n^2$=0, $n^3$=1, $R^{4b}$ and $R^{5b}$=$CH_2CH_3$, and $R^4$=Et. MS (ES) 424.2 (M+1).

EXAMPLE 4-6a (Compound of Formula I-B where X1=imidazol-1-yl, $R^2$=$CH_3$, $R^3$=H, $G^1$=$N(CH_3)_2$, $n^2$=0, $n^3$=1, and $R^{4b}$ and $R^{5b}$ are taken together with the carbon to which they are attached to equal a cyclopropyl ring): The title compound was prepared according to the General Synthetic Method E as described above wherein compound of Formula I-C, X1=imidazol-1-yl, $R^2$=$CH_3$, $R^3$=H, $G^1$=$N(CH_3)_2$, $n^2$=0, $n^3$=1, $R^{4b}$ and $R^{5b}$ are taken together with the carbon to which they are attached to equal a cyclopropyl ring, and $R^7$=Et. MS (ES) 394.2 (M+1).

EXAMPLE 4-7a (Compound of Formula I-B where X1=imidazol-1-yl, $R^2$=$CH_3$, $R^3$=H, $G^1$=$N(CH_3)_2$, $n^2$=0, $n^3$=1, and $R^{4b}$ and $R^{5b}$ are taken together with the carbon to which they are attached to equal a cyclobutyl ring): The title compound was prepared according to the General Synthetic Method E as described above wherein compound of Formula I-C, X1=imidazol-1-yl, $R^2$=$CH_3$, $R^3$=H, $G^1$=$N(CH_3)_2$, $n^2$=0, $n^3$=1, $R^{4b}$ and $R^{5b}$ are taken together with the carbon to which they are attached to equal a cyclobutyl ring, and $R^7$=Et. MS (ES) 408.6 (M+1).

EXAMPLE 4-8a (Compound of Formula I-B where X1=imidazol-1-yl, $R^2$=$CH_3$, $R^3$=H, $G^1$=$N(CH_3)_2$, $n^2$=0, $n^3$=1, and $R^{4b}$ and $R^{5b}$ are taken together with the carbon to which they are attached to equal a 4-pyranyl ring): The title compound was prepared according to the General Synthetic Method E as described above wherein compound of Formula I-C, X1=imidazol-1-yl, $R^2$=$CH_3$, $R^3$=H, $G^1$=$N(CH_3)_2$, $n^2$=0, $n^3$=1, $R^{4b}$ and $R^{5b}$ are taken together with the carbon to which they are attached to equal a 4-pyranyl ring, and $R^7=CH_3$. MS (ES) 438.3 (M+1).

EXAMPLE 4-9a (Compound of Formula I-B where X1=imidazol-1-yl, $R^2=CH_3$, $R^3=H$, $G^1=N(CH_3)_2$, $n^2=0$, $n^3=1$, and $R^{4b}$ and $R^{5b}$ are taken together with the carbon to which they are attached to equal a cyclohexyl ring): The title compound was prepared according to the General Synthetic Method E as described above wherein compound of Formula I-C, X1=imidazol-1-yl, $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclohexyl ring, and $R^7=Et$. MS (ES) 436.2 (M+1).

EXAMPLE 4-10a (Compound of Formula I-B where X1=imidazol-1-yl, $R^2=CH_3$, $R^3=H$, $G^1=N(CH_3)_2$, $n^2=0$, $n^3=1$, and $R^{4b}$ and $R^{5b}$ are taken together with the carbon to which they are attached to equal a cyclopentyl ring): The title compound was prepared according to the General Synthetic Method E as described above wherein compound of Formula I-C, X1=imidazol-1-yl, $R^2=CH_3$, $R^3=H$, $G^1=N(CH_3)_2$, $n^2=0$, $n^3=1$, $R^{4b}$ and $R^{5b}$ are taken together with the carbon to which they are attached to equal a cyclopentyl ring, and $R^7=Et$. MS (ES) 422.2 (M+1).

EXAMPLE 4-11a (Compound of Formula I-B where X1=imidazol-1-yl, $R^2=CH_3$, $R^3=H$, $G^1=N(CH_2)_2O(CH_2)_2$ ring, $n^2=0$, $n^3=1$, and $R^{4b}$ and $R^{5b}=CH_3$): The title compound was prepared according to the General Synthetic Method E as described above wherein compound of Formula I-C, X1=imidazol-1-yl, $R^2=CH_3$, $R^3=H$, $G^1=N(CH_2)_2O(CH_2)_2$ ring, $n^2=0$, $n^3=1$, $R^{4b}$ and $R^{5b}=CH_3$, and $R^7=CH_3$. $^1$HNMR (CD$_3$OD, 400 MHz) δ 0.92 (d, 3H, J=6.8 Hz), 1.36 (s, 6H), 2.45-2.52 (m, 2H), 2.75-2.80 (m, 2H), 3.48-3.69 (m, 4H), 3.69-3.73 (m, 1H), 4.12 (s, 2H), 5.42 (d, 1H, J=11.6 Hz), 6.99-7.00 (m, 1H), 7.18 (dd, 1H, J=9.2 Hz, 3.2 Hz), 7.25 (d, 1H, J=4.0 Hz), 7.36-7.39 (m, 1H), 7.55 (d, 1H, J=9.2 Hz), 7.73-7.83 (m, 2H), 7.89 (s, 1H), 8.04 (s, 1H).

EXAMPLE 4-12a (Compound of Formula I-B where X1=imidazol-1-yl, $R^2=CH_3$, $R^3=H$, $G^1=N(Et)_2$, $n^2=0$, $n^3=1$, and $R^{4b}$ and $R^{5b}=CH_3$): The title compound was prepared according to the General Synthetic Method E as described above wherein compound of Formula I-C, X1=imidazol-1-yl, $R^2=CH_3$, $R^3=H$, $G^1=N(Et)_2$, $n^2=0$, $n^3=1$, $R^{4b}$ and $R^{5b}=CH_3$, and $R^7=CH_3$. $^1$HNMR (CD$_3$OD, 400 MHz) δ 0.85 (d, 3H, J=6.8 Hz), 0.93 (t, 6H, J=6.8 Hz), 1.37 (s, 6H), 2.37-2.45 (m, 2H), 2.65-2.73 (m, 2H), 3.76-3.84 (m, 1H), 4.09 (s, 2H), 5.35 (d, 1H, J=11.2 Hz), 7.00 (s, 1H), 7.15 (dd, 1H, J=9.2 Hz, 2.4 Hz), 7.23 (d, 1H, J=2.0 Hz), 7.37 (s, 1H), 7.56 (d, 1H, J=8.4 Hz), 7.77 (m, 2H), 7.90 (s, 1H), 8.11 (s, 1H).

EXAMPLE 4-13a (Compound of Formula I-B where X1=imidazol-1-yl, $R^2=CH_3$, $R^3=H$, $G^1=N(CH_3)$cyclohexyl, $n^2=0$, $n^3=1$, and $R^{4b}$ and $R^{5b}=CH_3$): The title compound was prepared according to the General Synthetic Method E as described above wherein compound of Formula I-C, X1=imidazol-1-yl, $R^2=CH_3$, $R^3=H$, $G^1=N(CH_3)$cyclohexyl, $n^2=0$, $n^3=1$, $R^{4b}$ and $R^{5b}=CH_3$, and $R^7=CH_3$. MS (ES) 464.2 (M+1).

EXAMPLE 4-14a (Compound of Formula I-B where X1=imidazol-1-yl, $R^2=CH_3$, $R^3=H$, $G^1=N(CH_3)$n-butyl, $n^2=0$, $n^3=1$, and $R^{4b}$ and $R^{4b}=CH_3$): The title compound was prepared according to the General Synthetic Method E as described above wherein compound of Formula I-C, X1=imidazol-1-yl, $R^2=CH_3$, $R^3=H$, $G^1=N(CH_3)$n-butyl, $n^2=0$, $n^3=1$, $R^{4b}$ and $R^{5b}=CH_3$, and $R^7=CH_3$. MS (ES) 438.1 (M+1).

EXAMPLE 4-15a (Compound of Formula I-B where X1=imidazol-1-yl, $R^2=CH_3$, $R^3=H$, $G^1=N(CH_3)$iPr, $n^2=0$, $n^3=1$, and $R^{4b}$ and $R^{5b}=CH_3$): The title compound was prepared according to the General Synthetic Method E as described above wherein compound of Formula I-C, X1=imidazol-1-yl, $R^2=CH_3$, $R^3=H$, $G^1=N(CH_3)$iPr, $n^2=0$, $n^3=1$, $R^{4b}$ and $R^{5b}=CH_3$, and $R^7=CH_3$. MS (ES) 424.2 (M+1).

EXAMPLE 4-16a (Compound of Formula I-B where X1=imidazol-1-yl, $R^2=CH_3$, $R^3=H$, $G^1=N(CH_2)_4$ ring, $n^2=0$, $n^3=1$, and $R^{4b}$ and $R^{5b}=CH_3$): The title compound was prepared according to the General Synthetic Method E as described above wherein compound of Formula I-C, X1=imidazol-1-yl, $R^2=CH_3$, $R^3=H$, $G^1=N(CH_2)_4$ ring, $n^2=0$, $n^3=1$, $R^{4b}$ and $R^{5b}=CH_3$, and $R^7=CH_3$. MS (ES) 436.3 (M+1). MS (ES) 422.1 (M+1).

EXAMPLE 4-17a (Compound of Formula I-B where X1=imidazol-1-yl, $R^2=CH_3$, $R^3=H$, $G^1=N(CH_3)Et$, $n^2=0$, $n^3=1$, and $R^{4b}$ and $R^{5b}=CH_3$): The title compound was prepared according to the General Synthetic Method E as described above wherein compound of Formula I-C, X1=imidazol-1-yl, $R^2=CH_3$, $R^3=H$, $G^1=N(CH_3)Et$, $n^2=0$, $n^3=1$, $R^{4b}$ and $R^{5b}=CH_3$, and $R^7=CH_3$. $^1$HNMR (CD$_3$OD, 400 MHz) δ 0.83 (d, 3H, J=6.8 Hz), 0.96 (t, 3H, J=6.8 Hz), 1.32 (s, 6H), 2.28 (s, 3H), 2.42-2.47 (m, 1H), 2.60-2.65 (m, 1H), 3.79-3.82 (m, 1H), 4.08 (s, 2H), 5.39 (d, 1H, J=10.8 Hz), 6.99 (s, 1H), 7.14 (dd, 1H, J=9.2 Hz, 2.4 Hz), 7.22 (d, 1H, J=2.0 Hz), 7.36 (s, 1H), 7.50 (d, 1H, J=8.8 Hz), 7.73-7.77 (m, 2H), 7.86 (s, 1H), 8.11 (s, 1H).

EXAMPLE 4-18

(Compound of Formula I-B where X1=imidazol-1-yl, $R^2=CH_3$, $R^3=CH_3$, $G^1=N(CH_3)_2$, $n^2=0$, $n^3=1$, $R^{4b}$ and $R^{5b}=CH_3$): The title compound was prepared according to the General Synthetic Method E as described above wherein compound of Formula I-C, X1=imidazol-1-yl, $R^2=CH_3$, $R^3=CH_3$, $G^1=N(CH_3)_2$, $n^2=0$, $n^3=1$, $R^{4b}$ and $R^{5b}=CH_3$, and $R^7=CH_3$. MS (ES) 410.2 (M+1).

EXAMPLE 4-19

(Compound of Formula I-B where X1=imidazol-1-yl, $R^2=H$, $R^3=H$, $G^1=N(CH_3)_2$, $n^2=0$, $n^3=1$, and $R^{4b}$ and $R^{5b}=CH_3$): The title compound was prepared according to the General Synthetic Method E as described above wherein compound of Formula I-C, X1=imidazol-1-yl, $R^2=H$, $R^3=H$, $G^1=N(CH_3)_2$, $n^2=0$, $n^3=1$, $R^{4b}$ and $R^{5b}=CH_3$, and $R^7=CH_3$. $^1$H NMR (CDCl$_3$, 400 MHz) δ 1.37 (s, 6H), 2.29 (s, 6H), 2.99-3.20 (m, 2H), 4.06 (s, 2H), 5.44 (m, 1H), 7.05-7.21 (m, 5H), 7.44-7.52 (m, 2H), 7.63 (d, 1H, J=8.4 Hz), 7.74 (s, 1H); MS (ES) 382.0 (M+1).

EXAMPLE 4-20a (Compound of Formula I-B where X2=triazol-1-yl, $R^2$=$CH_3$, $R^3$=H, $G^1$=$N(CH_3)_2$, $n^2$=0, $n^3$=1, and $R^{4b}$ and $R^{5b}$= are taken together with the carbon to which they are attached to equal a cyclopentyl ring): The title compound was prepared according to the General Synthetic Method E as described above wherein compound of Formula I-C, X2=triazol-1-yl, $R^2$=$CH_3$, $R^3$=H, $G^1$=$N(CH_3)_2$, $n^2$=0, $n^3$=1, $R^{4b}$ and $R^{5b}$= are taken together with the carbon to which they are attached to equal a cyclopentyl ring, and $R^7$=Et. MS (ES) 423.3 (M+1).

EXAMPLE 4-21a (Compound of Formula I-B where X1=imidazol-1-yl, $R^2$=$CH_2CH_3$, $R^3$=H, $G^1$=$N(CH_3)_2$, $n^2$=0, $n^3$=1, $R^{4b}$ and $R^{5b}CH_3$): The title compound was prepared according to the General Synthetic Method E as described above wherein compound of Formula I-C, X1=imidazol-1-yl, $R^2$=$CH_2CH_3$, $R^3$=H, $G^1$=$N(CH_3)_2$, $n^2$=0, $n^3$=1, $R^{4b}$ and $R^{5b}$=$CH_3$, and $R^7$=$CH_3$. $^1$H NMR ($CDCl_3$, 400 MHz) δ 0.72 (t, 3H, J=7.4 Hz), 1.19-1.26 (m, 1H), 1.38 (s, 6H), 1.47-1.54 (m, 1H), 2.32 (s, 6H), 3.26-3.31 (m, 1H), 4.08 (m, 2H), 5.08 (d, 1H, J=10.1 Hz), 7.04 (d, 2H, J=8.2 Hz), 7.09 (d, 1H, J=2.3 Hz), 7.13 (dd, 1H, J=2.4, 8.9 Hz), 7.30 (dd, 1H, J=1.6 Hz, 8.6 Hz), 7.62 (t, 3H, J=11.0 Hz), 7.84 (s, 1H).

EXAMPLE 4-22a (Compound of Formula I-B where X1=imidazol-1-yl, $R^2$=$CH_3$, $R^3$=H, $G^1$=$N(CH_3)$iPr, $n^2$=0, $n^3$=1, and $R^{4b}$ and $R^{5b}$ are taken together with the carbon to which they are attached to equal a cyclopentyl ring): The title compound was prepared according to the General Synthetic Method E as described above wherein compound of Formula I-C, X1=imidazol-1-yl, $R^2$=$CH_3$, $R^3$=H, $G^1$=$N(CH_3)$iPr, $n^2$=0, $n^3$=1, $R^{4b}$ and $R^{5b}$ are taken together with the carbon to which they are attached to equal a cyclopentyl ring, and $R^7$=Et. MS (ES) 450.2 (M+1).

Following the general methods described hereinbefore, the following compounds of Formula I-$(HA^6)_{n7}$ (where $R^1$=H, Y=O, n1=1, $R^{4a}$ and $R^{5a}$=H, $R^{6a}$ and $R^{6b}$=H, n4=1) as listed in Table 5 were prepared. In the EXAMPLE numbers, "a" and "a'" denotes the syn isomer and "b" denotes the anti isomer with respect to X and $G^1$. X1=imidazol-1-yl, X2=triazol-1-yl, and X3=triazol-3-yl.

TABLE 5

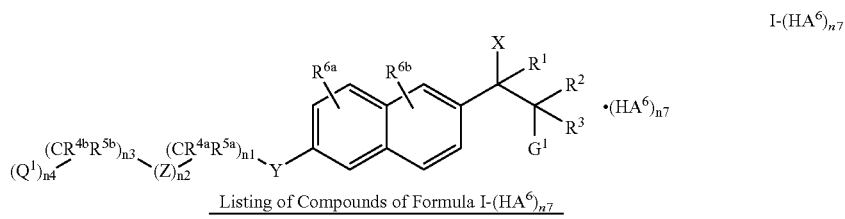

Listing of Compounds of Formula I-$(HA^6)_{n7}$

| EX. | $R^2$ | $R^3$ | $G^1$ | n2 | Z | n3 | $R^{4b}$ | $R^{5b}$ | $Q^1$ | X | $(HA^6)_{n7}$ |
|---|---|---|---|---|---|---|---|---|---|---|---|
| 5-1a | $CH_3$ | H | $N(CH_3)_2$ | 0 | — | 1 | $CH_3$ | $CH_3$ | $CO_2H$ | X1 | $HCO_2H$ |
| 5-1a' | $CH_3$ | H | $N(CH_3)_2$ | 0 | — | 1 | $CH_3$ | $CH_3$ | $CO_2H$ | X1 | $(HCl)_2$ |
| 5-1b | $CH_3$ | H | $N(CH_3)_2$ | 0 | — | 1 | $CH_3$ | $CH_3$ | $CO_2H$ | X1 | $HCO_2H$ |
| 5-2a | $CH_3$ | H | $N(CH_3)_2$ | 1 | 4 Ph | 1 | H | H | $CO_2H$ | X1 | $HCO_2H$ |
| 5-3a | $CH_3$ | H | $N(CH_3)_2$ | 0 | — | 1 | Et | Et | $CO_2H$ | X1 | $(HCl)_2$ |
| 5-4a | $CH_3$ | H | $N(CH_3)_2$ | 0 | — | 1 | $CH_2CH_2$ ring | | $CO_2H$ | X1 | $(HCl)_2$ |
| 5-5a | $CH_3$ | H | $N(CH_3)_2$ | 0 | — | 1 | $CH_2CH_2CH_2$ ring | | $CO_2H$ | X1 | $(HCl)_2$ |
| 5-6a | $CH_3$ | H | $N(CH_3)_2$ | 0 | — | 1 | $CH_2CH_2OCH_2CH_2$ ring | | $CO_2H$ | X1 | $(HCl)_2$ |
| 5-7a | $CH_3$ | H | $N(CH_3)_2$ | 0 | — | 1 | $CH_2(CH_2)_3CH_2$ ring | | $CO_2H$ | X1 | $(HCl)_2$ |
| 5-8a | $CH_3$ | H | $N(CH_3)_2$ | 0 | — | 1 | $CH_2(CH_2)_2CH_2$ ring | | $CO_2H$ | X1 | $(HCl)_2$ |
| 5-9a | $CH_3$ | H | $N(CH_3)$iPr | 0 | — | 1 | $CH_2(CH_2)_2CH_2$ ring | | $CO_2H$ | X1 | $(HCl)_2$ |
| 5-10a | $CH_3$ | H | $N(Et)_2$ | 0 | — | 1 | $CH_3$ | $CH_3$ | $CO_2H$ | X1 | $(HCl)_2$ |
| 5-11a | $CH_3$ | H | $N(CH_3)$cyclohexyl | 0 | — | 1 | $CH_3$ | $CH_3$ | $CO_2H$ | X1 | $(HCl)_2$ |
| 5-12a | $CH_3$ | H | $N(CH_3)$n-butyl | 0 | — | 1 | $CH_3$ | $CH_3$ | $CO_2H$ | X1 | $(HCl)_2$ |
| 5-13a | $CH_3$ | H | $N(CH_3)$iPr | 0 | — | 1 | $CH_3$ | $CH_3$ | $CO_2H$ | X1 | $(HCl)_2$ |
| 5-14a | $CH_3$ | H | $N(CH_3)$Et | 0 | — | 1 | $CH_3$ | $CH_3$ | $CO_2H$ | X1 | $(HCl)_2$ |
| 5-15a | $CH_3$ | H | $N(CH_3)_2$ | 1 | 4 PhO | 1 | H | H | $CO_2H$ | X1 | $HCO_2H$ |
| 5-16a | $CH_3$ | H | $N(CH_3)_2$ | 0 | — | 0 | — | — | $CO_2H$ | X1 | $(HCl)_2$ |
| 5-16b | $CH_3$ | H | $N(CH_3)_2$ | 0 | — | 0 | — | — | $CO_2H$ | X1 | $(HCl)_2$ |
| 5-17 | $CH_3$ | $CH_3$ | $N(CH_3)_2$ | 0 | — | 1 | $CH_3$ | $CH_3$ | $CO_2H$ | X1 | $(HCl)_2$ |
| 5-18a | $CH_3$ | H | $N(CH_3)_2$ | 0 | — | 1 | $CH_3$ | $CH_3$ | $CONH_2$ | X1 | $HCO_2H$ |
| 5-19a | $CH_3$ | H | $N(CH_3)_2$ | 0 | — | 1 | $CH_3$ | $CH_3$ | $CONHCH_3$ | X1 | $HCO_2H$ |
| 5-20a | $CH_3$ | H | $N(CH_3)_2$ | 0 | — | 1 | $CH_3$ | $CH_3$ | $CON(CH_3)_2$ | X1 | $HCO_2H$ |
| 5-21a | $CH_3$ | H | $N(CH_3)_2$ | 1 | 4 Ph | 0 | — | — | $CONH_2$ | X1 | $HCO_2H$ |
| 5-22a | $CH_3$ | H | $N(CH_3)_2$ | 1 | 4 Ph | 0 | — | — | $CONHCH_3$ | X1 | $HCO_2H$ |
| 5-23a | $CH_3$ | H | $N(CH_3)_2$ | 1 | 4 Ph | 0 | — | — | $CON(CH_3)_2$ | X1 | $HCO_2H$ |
| 5-24a | Et | H | $N(CH_3)_2$ | 0 | — | 1 | $CH_3$ | $CH_3$ | $CO_2H$ | X1 | $(HCl)_2$ |
| 5-25a | $CH_3$ | H | $N(CH_3)_2$ | 1 | 4 Ph | 0 | — | — | OH | X1 | $HCO_2H$ |

General Synthetic Method F for the preparation of compounds of the Formula I-(HA$^6$)$_{n7}$: Compounds of Formula I were charged with 5 eq. 2N HCl in water and concentrated in vacuo to solids to afford compounds of the Formula I-(HCl)$_2$. Compounds of Formula I could also be treated with formic acid in water followed by concentration in vacuo to afford compounds of Formula I-(HCO$_2$H). Additionally, Compounds of Formula I were charged with 3 eq. 2N HCl in ether and concentrated in vacuo to solids to afford compounds of the Formula I-(HCl)$_2$.

EXAMPLE 5-1a (Compound of Formula I-(HA$^6$)$_{n7}$ where X1=imidazol-1-yl, R$^2$=CH$_3$, R$^3$=H, G$^1$=N(CH$_3$)$_2$, n$^2$=0, n$^3$=1, R$^{4b}$ and R$^{5b}$=CH$_3$, Q$^1$=CO$_2$H, and (HA$^6$)$_{n7}$=HCO$_2$H: The title compound was prepared according to the General Synthetic Method F as described above wherein compound of Formula I, X1=imidazol-1-yl, R$^2$=CH$_3$, R$^3$=H, G$^1$=N(CH$_3$)$_2$, n$^2$=0, n$^3$=1, R$^{4b}$ and $^{5b}$=CH$_3$, and Q$^1$=CO$_2$H. $^1$H NMR (CD$_3$OD, 200 MHz) δ 0.89 (d, 3H, J=6.6 Hz), 1.33 (s, 6H), 2.38 (s, 6H), 3.86-4.01 (m, 1H), 4.09 (s, 2H), 5.42 (d, 1H, J=11.0 Hz), 7.11-8.46 (m, 9H); MS (ES) 396.0 (M+1).

EXAMPLE 5-1a'

(Compound of Formula I-(HA$^6$)$_{n7}$ where X1=imidazol-1-yl, R$^2$=CH$_3$, R$^3$=H, G$^1$=N(CH$_3$)$_2$, n$^2$=0, n$^3$=1, R$^{4b}$ and R$^{5b}$=CH$_3$, Q$^1$=CO$_2$H, and (HA$^6$)$_{n7}$=(HCl)$_2$: The title compound was prepared according to the General Synthetic Method F as described above wherein compound of Formula I, X1=imidazol-1-yl, R$^2$=CH$_3$, R$^3$=H, G$^1$=N(CH$_3$)$_2$, n$^2$=0, n$^3$=1, R$^{4b}$ and R$^{5b}$=CH$_3$, and Q$^1$=CO$_2$H. $^1$H NMR (CD$_3$OD, 400 MHz) δ 1.31 (d, 3H, J=6.7 Hz), 1.37 (s, 6H), 3.03 (s, 3H), 3.11 (s, 3H), 4.14 (s, 2H), 5.04-5.12 (m, 1H), 6.28 (d, 1H, J=11.3 Hz), 7.26 (dd, 1H, J=2.4 Hz, 9.0 Hz), 7.32 (d, 1H, J=2.2 Hz), 7.66 (dd, 1H, J=1.9 Hz, 8.7 Hz), 7.73 (t, 1H, J=1.7 Hz), 7.87 (d, 1H, J=9.0 Hz), 3.94 (d, 1H, J=8.6 Hz), 8.10 (s, 1H), 8.21 (t, 1H, J=1.8 Hz), 9.62 (s, 1H).

EXAMPLE 5-1b (Compound of Formula I-(HA$^6$)$_{n7}$ where X1=imidazol-1-yl, R$^2$=CH$_3$, R$^3$=H, G$^1$=N(CH$_3$)$_2$, n$^2$=0, n$^3$=1, R$^{4b}$ and R$^{5b}$=CH$_3$, Q$^1$=CO$_2$H, and (HA$^6$)$_{n7}$=HCO$_2$H: The title compound was prepared according to the General Synthetic Method F as described above wherein compound of Formula I, X1=imidazol-1-yl, R$^2$=CH$_3$, R$^3$=H, G$^1$=N(CH$_3$)$_2$, n$^2$=0, n$^3$=1, R$^{4b}$ and R$^{5b}$=CH$_3$, and Q$^1$=CO$_2$H. $^1$H NMR (CD$_3$OD, 200 MHz) δ 0.93 (d, 3H, J=6.6 Hz), 1.33 (s, 6H), 2.30 (s, 6H), 3.91-4.00 (m, 1H), 4.09 (s, 2H), 5.42 (d, 1H, J=10.6 Hz), 6.96 (s, 1H), 7.14 (dd, 1H, J=2.6 Hz, 9.1Hz), 7.22 (d, 1H, J=2.6 Hz), 7.35 (s, 1H), 7.58-7.94 (m, 5H); MS (ES) 395.9 (M+1).

EXAMPLE 5-2a (Compound of Formula I-(HA$^6$)$_{n7}$ where X1=imidazol-1-yl, R$^2$=CH$_3$, R$^3$=H, G$^1$=N(CH$_3$)$_2$, n$^2$=1, Z=4-Ph, n$^3$=1, R$^{4b}$ and R$^{5b}$=H, Q$^1$=CO$_2$H, and (HA$^6$)$_{n7}$=HCO$_2$H: The title compound was prepared according to the General Synthetic Method F as described above wherein compound of Formula I, X1=imidazol-1-yl, R$^2$=CH$_3$, R$^3$=H, G$^1$=N(CH$_3$)$_2$, n$^2$=1, Z=4-Ph, n$^3$=1, R$^{4b}$ and R$^{5b}$=H, and Q$^1$=CO$_2$H. $^1$H NMR (CD$_3$OD, 200 MHz) δ 0.93 (d, 3H, J=6.6 Hz), 2.42 (s, 6H), 3.90-3.99 (m, 1H), 4.54 (s, 2H), 5.14 (s, 2H), 5.52 (d, 1H, J=11.2 Hz), 6.97 (d, 2H, J=8.4 Hz), 6.90 (d, $^{H, J=}$1.4 Hz), 7.25 (dd, 1H, J=2.6 Hz, 6.6 Hz), 7.33-7.43 (m, 3H), 7.50-7.58 (m, 2H), 7.81 (d, 2H, J=8.8 Hz), 7.90-7.95 (m, 1H), 8.37 (s, 1H), 8.44 (s, 1H); MS (ES) 460.0 (M+1).

EXAMPLE 5-3a (Compound of Formula I-(HA$^6$)$_{n7}$ where X1=imidazol-1-yl, R$^2$=CH$_3$, R$^3$=H, G$^1$=N(CH$_3$)$_2$, n$^2$=0, n$^3$=1, R$^{4b}$ and R$^{5b}$=CH$_2$CH$_3$, Q$^1$=CO$_2$H, and (HA$^6$)$_{n7}$=(HCl)$_2$: The title compound was prepared according to the General Synthetic Method F as described above wherein compound of Formula I, X1=imidazol-1-yl, R$^2$=CH$_3$, R$^3$=H, G$^1$=N(CH$_3$)$_2$, n$^2$=0, n$^3$=1, R$^{4b}$ and R$^{5b}$=CH$_2$CH$_3$, and Q$^1$=CO$_2$H. $^1$H NMR (CD$_3$OD, 400 MHz) δ 0.89 (t, 6H, J=7.6 Hz), 1.29 (d, 3H, J=6.8 Hz), 1.81 (q, 4H, J=7.6 Hz), 3.01 (s, 3H), 3.09 (s, 3H), 3.30 (s, 2H), 5.06-5.11 (m, 1H), 6.28 (d, 1H, J=11.2 Hz), 7.23 (dd, 1H, J=2.8, 9.2 Hz), 7.34 (d, 1H, J=2.0 Hz), 7.67 (t, 2H, J=12.4 Hz), 7.85 (d, 1H, J=9.2 Hz), 7.93 (d, 1H, J=8.8 Hz), 8.10 (s, 1H), 8.20 (s, 1H), 9.62 (s, 1H).

EXAMPLE 5-4a (Compound of Formula I-(HA$^6$)$_{n7}$ where X1=imidazol-1-yl, R$^2$=CH$_3$, R$^3$=H, G$^1$=N(CH$_3$)$_2$, n$^2$=0, n$^3$=1, R$^{4b}$ and R$^{5b}$ are taken together with the carbon to which they are attached to equal a cyclopropyl ring, Q$^1$=CO$_2$H, and (HA$^6$)$_{n7}$=(HCl)$_2$: The title compound was prepared according to the General Synthetic Method F as described above wherein compound of Formula I, X1=imidazol-1-yl, R$^2$=CH$_3$, R$^3$=H, G$^1$=N(CH$_3$)$_2$, n$^2$=0, n$^3$=1, R$^{4b}$ and R$^{5b}$ are taken together with the carbon to which they are attached to equal a cyclopropyl ring, and Q$^1$=CO$_2$H. $^1$H NMR (DMSO-d$_6$, 400 MHz), δ 1.15-1.18 (m, 2H), 1.20 (d, 3H, J=6.5 Hz), 1.33-1.36 (m, 2H), 2.91 (s, 3H), 3.02 (s, 3H), 4.29 (s, 2H), 5.24-5.35 (m, 1H), 6.51 (d, 1H, J=11.3 Hz), 7.36 (dd, 1H, J=2.5, 8.9 Hz), 7.45 (d, 1H, J=2.4 Hz), 7.85-7.86 (m, 2H), 7.92 (d, 1H, J=9.1Hz), 8.00 (d, 1H, J=8.9 Hz), 8.24 (s, 1H), 8.39 (s, 1H), 9.97 (s, 1H), 10.39 (s, 1H).

EXAMPLE 5-5a (Compound of Formula I-(HA$^6$)$_{n7}$ where X1=imidazol-1-yl, R$^2$=CH$_3$, R$^3$=H, G$^1$=N(CH$_3$)$_2$, n$^2$=0, n$^3$=1, R$^{4b}$ and R$^{5b}$ are taken together with the carbon to which they are attached to equal a cyclobutyl ring, Q$^1$=CO$_2$H, and (HA$^6$)$_{n7}$=(HCl)$_2$: The title compound was prepared according to the General Synthetic Method F as described above wherein compound of Formula I, X1=imidazol-1-yl, R$^2$=CH$_3$, R$^3$=H, G$^1$=N(CH$_3$)$_2$, n$^2$=0, n$^3$=1, R$^{4b}$ and R$^{5b}$ are taken together with the carbon to which they are attached to equal a cyclobutyl ring, and Q$^1$=CO$_2$H. $^1$H NMR (DMSO-d$_6$, 400 MHz), δ 1.10 (d, 3H, J=7.61), 1.85-2.10 (m, 4H), 2.37-2.45 (m, 2H), 2.82 (s, 3H), 2.92 (s, 3H), 4.33 (s, 2H), 5.23-5.27 (m, 1H), 6.46 (d, 1H, J=11.0 Hz), 7.23 (dd, 1H, J=2.5, 9.0 Hz), 7.44 (d, 1H, J=2.4 Hz), 7.75 (s, 1H), 7.78-7.83 (m, 2H), 7.91 (d, 1H, J=8.7 Hz), 8.17 (s, 1H), 8.33 (s, 1H), 9.93 (s, 1H), 10.36 (s, 1H).

EXAMPLE 5-6a (Compound of Formula I-(HA$^6$)$_{n7}$ where X1=imidazol-1-yl, R$^2$=CH$_3$, R$^3$=H, G$^1$=N(CH$_3$)$_2$, n$^2$=0, n$^3$=1, R$^{4b}$ and R$^{5b}$ are taken together with the carbon to which they are attached to equal a 4-pyranyl ring, Q$^1$=CO$_2$H, and (HA$^6$)$_{n7}$=(HCl)$_2$: The title compound was prepared according to the General Synthetic Method F as described above wherein compound of Formula I, X1=imidazol-1-yl, R$^2$=CH$_3$, R$^3$=H, G$^1$=N(CH$_3$)$_2$, n$^2$=0, n$^3$=1, R$^{4b}$ and R$^{5b}$ are taken together with the carbon to which they are attached to equal a 4-pyranyl ring, and $Q^1$=CO$_2$H. $^1$H NMR (DMSO-d$_6$, 400 MHz), δ 1.10 (d, 3H, J=6.8 Hz), 1.63-1.71 (m, 2H), 2.03 (d, 2H, J=13.6 Hz), 2.82 (s, 3H), 2.93 (s, 3H), 3.49 (t, 2H, J=10.4 Hz), 3.77-3.81 (m, 2H), 4.17 (s, 2H), 5.24-5.28 (m, 1H), 6.47 (d, 1H), 7.21 (d, 1H, J=2.4, 8.8 Hz), 7.42 (d, 1H, J=2.4 Hz), 7.75-7.84 (m, 2H), 7.91 (d, 1H, J=8.4 Hz), 8.18 (s, 1H), 8.33 (s, 1H), 9.94 (s, 1H), 10.38 (s, 1H).

EXAMPLE 5-7a (Compound of Formula I-(HA$^6$)$_{n7}$ where X1=imidazol-1-yl, $R^2$=CH$_3$, $R^3$=H, $G^1$=N(CH$_3$)$_2$, $n^2$=0, $n^3$=1, $R^{4b}$ and $R^{5b}$ are taken together with the carbon to which they are attached to equal a cyclohexyl ring, $Q^1$=CO$_2$H, and (HA$^6$)$_{n7}$=(HCl)$_2$: The title compound was prepared according to the General Synthetic Method F as described above wherein compound of Formula I, X1=imidazol-1-yl, $R^2$=CH$_3$, $R^3$=H, $G^1$=N(CH$_3$)$_2$, $n^2$=0, $n^3$=1, $R^{4b}$ and $R^{5b}$ are taken together with the carbon to which they are attached to equal a cyclohexyl ring, and $Q^1$=CO$_2$H. $^1$H NMR (CD$_3$OD, 400 MHz) δ 1.34 (d, 3H, J=6.7 Hz), 1.54-1.69 (m, 8H), 2.18-2.26 (m, 2H), 3.06 (s, 3H), 3.14 (s, 3H), 4.18 (s, 2H), 5.05-5.14 (m, 1H), 6.31 (d, 1H), 7.28 (dd, 1H, J=2.3, 9.1 Hz), 7.34 (s, 1H), 7.69 (d, 1H, J=8.7 Hz), 7.76 (s, 1H), 7.89 (d, 1H, J=8.9 Hz), 7.97 (d, 1H, J=8.8 Hz), 8.13 (s, 1H), 8.24 (s, 1H), 9.65 (s, 1H).

EXAMPLE 5-8a (Compound of Formula I-(HA$^6$)$_{n7}$ where X1=imidazol-1-yl, $R^2$=CH$_3$, $R^3$=H, $G^1$=N(CH$_3$)$_2$, $n^2$=0, $n^3$=1, $R^{4b}$ and $R^{5b}$ are taken together with the carbon to which they are attached to equal a cyclopentyl ring, $Q^1$=CO$_2$H, and (HA$^6$)$_{n7}$=(HCl)$_2$: The title compound was prepared according to the General Synthetic Method F as described above wherein compound of Formula I, X1=imidazol-1-yl, $R^2$=CH$_3$, $R^3$=H, $G^1$=N(CH$_3$)$_2$, $n^2$=0, $n^3$=1, $R^{4b}$ and $R^{5b}$ are taken together with the carbon to which they are attached to equal a cyclopentyl ring, and $Q^1$=CO$_2$H. $^1$H NMR (CD$_3$OD, 400 MHz) δ 1.29 (d, 3H, J=6.8 Hz), 1.75-1.83 (m, 6H), 2.14-2.23 (m, 2H), 3.00 (s, 3H), 3.07 (s, 3H), 4.19 (s, 2H), 5.01-5.09 (m, 1H), 6.25 (d, 1H, J=11.2 Hz), 7.22 (dd, 1H, J=2.4, 8.8 Hz), 7.30 (d, 1H, J=2.4 Hz), 7.63 (d, 1H, J=8.8 Hz), 7.70 (s, 1H), 7.84 (d, 1H, J=9.2 Hz), 7.91 (d, 1H, J=8.4 Hz), 8.07 (d, 1H, J=1.6 Hz), 8.18 (d, 1H, J=1.2 Hz), 9.59 (s, 1H).

EXAMPLE 5-9a (Compound of Formula I-(HA$^6$)$_{n7}$ where X1=imidazol-1-yl, $R^2$=CH$_3$, $R^3$=H, $G^1$=N(CH$_3$)iPr, $n^2$=0, $n^3$=1, $R^{4b}$ and $R^{5b}$ are taken together with the carbon to which they are attached to equal a cyclopentyl ring, $Q^1$=CO$_2$H, and (HA$^6$)$_{n7}$=(HCl)$_2$: The title compound was prepared according to the General Synthetic Method F as described above wherein compound of Formula I, X1=imidazol-1-yl, $R^2$=CH$_3$, $R^3$=H, $G^1$=N(CH$_3$)iPr, $n^2$=0, $n^3$=1, $R^{4b}$ and $R^{5b}$ are taken together with the carbon to which they are attached to equal a cyclopentyl ring, and $Q^1$=CO$_2$H. $^1$H NMR (CD$_3$OD, 400 MHz) δ 1.12-1.16 (m, 3H), 1.31-1.76 (m, 8H), 2.08 (s, 3H), 2.92-2.98 (m, 1H), 3.61-3.73 (m, 1H), 4.09 (s, 2H), 6.27 (d, 1H, J=7.5 Hz), 7.12 (dd, 1H, J=2.3, 9.0 Hz), 7.20 (s, 1H), 7.62 (s, 2H), 7.75 (d, 1H, J=9.1 Hz), 7.80-7.82 (m, 1H), 8.04 (s, 1H), 8.19 (s, 1H), 9.39 (s, 1H).

EXAMPLE 5-10a (Compound of Formula I-(HA$^6$)$_{n7}$ where X1=imidazol-1-yl, $R^2$=CH$_3$, $R^3$=H, $G^1$=N(CH$_2$CH$_3$)$_2$, $n^2$=0, $n^3$=1, $R^{4b}$ and $R^{5b}$=CH$_3$, $Q^1$=CO$_2$H, and (HA$^6$)$_{n7}$=(HCl)$_2$: The title compound was prepared according to the General Synthetic Method F as described above wherein compound of Formula I, X1=imidazol-1-yl, $R^2$=CH$_3$, $R^3$=H, $G^1$=N(CH$_2$CH$_3$)$_2$, $n^2$=0, $n^3$=1, $R^{4b}$ and $R^{5b}$=CH$_3$, and $Q^1$=CO$_2$H. $^1$HNMR (CD$_3$OD, 400 MHz) δ 1.29 (d, 3H, J=6.8 Hz), 1.37 (s, 6H), 1.48-1.54 (m, 6H), 3.25-3.29 (m, 1H), 3.61-3.66 (m, 1H), 3.77-3.82 (m, 1H), 4.14 (s, 2H), 5.00-5.04 (m, 1H), 6.47 (d, 1H, J=10.4 Hz), 7.25 (dd, 1H, J=2.8, 9.2 Hz), 7.32 (d, 1H, J=2.4 Hz), 7.72-7.76 (m, 2H), 7.88 (d, 1H, J=9.2 Hz), 7.93 (d, 1H, J=8.4 Hz), 8.19 (d, 1H, J=1.6 Hz), 8.28-8.29 (m, 1H), 9.67 (s, 1H).

EXAMPLE 5-11a (Compound of Formula I-(HA$^6$)$_{n7}$ where X1=imidazol-1-yl, $R^2$=CH$_3$, $R^3$=H, $G^1$=N(CH$_3$)cyclohexyl, $n^2$=0, $n^3$=1, $R^{4b}$ and $R^{5b}$=CH$_3$, $Q^1$=CO$_2$H, and (HA$^6$)$_{n7}$=(HCl)$_2$: The title compound was prepared according to the General Synthetic Method F as described above wherein compound of Formula I, X1=imidazol-1-yl, $R^2$=CH$_3$, $R^3$=H, $G^1$=N(CH$_3$)cyclohexyl, $n^2$=0, $n^3$=1, $R^{4b}$ and $R^{5b}$=CH$_3$, and $Q^1$=CO$_2$H. $^1$HNMR (CD$_3$OD, 400 MHz) δ 1.26-1.28 (m, 4H), 1.37 (s, 6H), 1.45-1.47 (m, 3H), 1.73-1.76 (m, 2H), 1.94-2.01 (m, 2H), 2.11-2.13 (m, 1H), 2.49-2.57 (m, 1H), 3.06 (s, 3H), 3.43-3.45 (m, 1H), 4.13 (s, 2H), 5.08-5.11 (m, 1H), 6.41 (d, 1H, J=11.2 Hz), 7.25 (dd, 1H, J=2.4, 8.8 Hz), 7.31 (d, 1H, J=2.4 Hz), 7.72-7.75 (m, 2H), 7.87 (d, 1H, J=9.2 Hz), 7.92 (d, 1H, J=9.2 Hz), 8.12 (s, 1H), 8.31 (s, 1H), 9.51 (s, 1H).

EXAMPLE 5-12a (Compound of Formula I-(HA$^6$)$_{n7}$ where X1=imidazol-1-yl, $R^2$=CH$_3$, $R^3$=H, $G^1$=N(CH$_3$)n-Bu, $n^2$=0, $n^3$=1, $R^{4b}$ and $R^{5b}$=CH$_3$, $Q^1$=CO$_2$H, and (HA$^6$)$_{n7}$=(HCl)$_2$: The title compound was prepared according to the General Synthetic Method F as described above wherein compound of Formula I, X1=imidazol-1-yl, $R^2$=CH$_3$, $R^3$=H, $G^1$=N(CH$_3$)n-Bu, $n^2$=0, $n^3$=1, $R^{4b}$ and $R^{5b}$=CH$_3$, and $Q^1$=CO$_2$H. $^1$HNMR (CD$_3$OD, 400 MHz) δ 1.06 (t, 3H, J=7.2 Hz), 1.29-1.32 (m, 4H), 1.37 (s, 6H), 1.45-1.53 (m, 3H), 1.70-1.72 (m, 1H), 3.07 (s, 3H), 3.04-3.09 (m, 1H), 3.35-3.46 (m, 1H), 4.13 (s, 2H), 6.36 (d, 1H, J=11.2 Hz), 7.25 (dd, 1H, J=2.4, 8.8 Hz), 7.32 (d, 1H, J=2.4 Hz), 7.71-7.73 (m, 2H), 7.87 (d, 1H, J=8.8 Hz), 7.93 (d, 1H, J=8.4 Hz), 8.16 (s, 1H), 8.28 (s, 1H), 9.60 (s, 1H).

EXAMPLE 5-13a (Compound of Formula I-(HA$^6$)$_{n7}$ where X1=imidazol-1-yl, $R^2$=CH$_3$, $R^3$=H, $G^1$=N(CH$_3$)iPr, $n^2$=0, $n^3$=1, $R^{4b}$ and $R^{5b}$=CH$_3$, $Q^1$=CO$_2$H, and (HA$^6$)$_{n7}$=(HCl)$_2$: The title compound was prepared according to the General Synthetic Method F as described above wherein compound of Formula I, X1=imidazol-1-yl, $R^2$=CH$_3$, $R^3$=H, $G^1$=N(CH$_3$)iPr, $n^2$=0, $n^3$=1, $R^{4b}$ and $R^{5b}$=CH$_3$, and $Q^1$=CO$_2$H. $^1$HNMR (CD$_3$OD, 400 MHz) δ 1.28 (d, 3H, J=6.4 Hz), 1.37 (s, 6H), 1.51 (d, 3H, J=6.8 Hz), 1.58 (d, 3H, J=6.8 Hz), 3.08 (s, 3H), 3.76-3.83 (m, 1H), 4.14 (s, 2H), 5.02-5.10 (m, 1H), 6.42 (d, 1H, J=10.8 Hz), 7.25 (dd, 1H, J=2.4, 8.8 Hz), 7.31 (d, 1H, J=2.4 Hz), 7.73-7.77 (m, 2H), 7.87 (d, 1H, J=8.8 Hz), 7.92 (d, 1H, J=8.8 Hz), 8.18 (s, 1H), 8.34 (s, 1H), 9.54 (s, 1H).

EXAMPLE 5-14a (Compound of Formula I-(HA$^6$)$_{n7}$ where X1=imidazol-1-yl, $R^2$=CH$_3$, $R^3$=H, $G^1$=N(CH$_3$)Et, $n^2$=0, $n^3$=1, $R^{4b}$ and $R^{5b}$=CH$_3$, $Q^1$=CO$_2$H, and (HA$^6$))$_{n7}$=(HCl)$_2$: The title compound was prepared according to the General Synthetic Method F as described above wherein compound of Formula I, X1=imidazol-1-yl, $R^2$=$CH_3$, $R^3$=H, $G^1$=$N(CH_3)$Et, $n^2$=0, $n^3$=1, $R^{4b}$ and $R^{5b}$=$CH_3$, and $Q^1$=$CO_2H$. $^1$HNMR ($CD_3OD$, 400 MHz) δ 1.26 (d, 3H, J=6.8 Hz), 1.33 (s, 6H), 1.48 (t, 3H, J=7.2 Hz), 3.03 (s, 3H), 3.36-3.41 (m, 1H), 3.52-3.57 (m, 1H), 4.11 (s, 2H), 5.06-5.10 (m, 1H), 6.47 (d, 1H, J=10.8 Hz), 7.20 (dd, 1H, J=2.4, 8.8 Hz), 7.27 (s, 1H), 7.68-7.77 (m, 2H), 7.84-7.90 (m, 2H), 8.21-8.34 (m, 2H), 9.68 (s, 1H).

EXAMPLE 5-15a (Compound of Formula I-$(HA^6)_{n7}$ where X1=imidazol-1-yl, $R^2$=$CH_3$, $R^3$=H, $G^1$=$N(CH_3)_2$, $n^2$=1, Z=4-PhO, $n^3$=1, $R^{4a}$ and $R^{5b}$=H, $Q^1$=$CO_2H$, and $(HA^6)_{n7}$=$HCO_2H$: The title compound was prepared according to the General Synthetic Method E followed by General Synthetic Method F as described above wherein compound of Formula I, X1=imidazol-1-yl, $R^2$=$CH_3$, $R^3$=H, $G^1$=$N(CH_3)_2$, $n^2$=1, Z=4-PhO, $n^3$=1, $R^{4a}$ and $R^{5b}$=H, $Q^1$=$CO_2H$, compound of Formula I-B, X1=imidazol-1-yl, $R^2$=$CH_3$, $R^3$=H, $G^1$=$N(CH_3)_2$, $n^2$=1, Z=4-PhO, $n^3$=1, $R^{4a}$ and $R^{5b}$=H, and compound of Formula I-C, X1=imidazol-1-yl, $R^2$=$CH_3$, $R^3$=H, $G^1$=$N(CH_3)_2$, $n^2$=1, Z=4-PhO, $n^3$=1, $R^{4a}$ and $R^{5b}$=H, and $R^7$=$CH_3$. $^1$H NMR ($CD_3OD$, 200 MHz) δ 0.93 (d, 3H, J=6.6 Hz), 2.42 (s, 6H), 3.90-3.99 (m, 1H), 4.54 (s, 2H), 5.14 (s, 2H), 5.52 (d, 1H, J=11.2 Hz), 6.97 (d, 2H, J=8.4 Hz), 6.90 (s, 1H, J=1.4 Hz), 7.25 (dd, 1H, J=2.6 Hz, 6.6 Hz), 7.33-7.43 (m, 3H), 7.50-7.58 (m, 2H), 7.81 (d, 2H, J=8.8 Hz), 7.90-7.95 (m, 1H), 8.37 (s, 1H), 8.44 (s, 1H); MS (ES) 460.0 (M+1).

EXAMPLE 5-16a (Compound of Formula I-$(HA^6)_{n7}$ where X1=imidazol-1-yl, $R^2$=$CH_3$, $R^3$=H, $G^1$=$N(CH_3)_2$, $n^2$=0, $n^3$=0, $Q^1$=$CO_2H$, and $(HA^6)_{n7}$=$(HCl)_2$: The title compound was prepared as follows: Compound 3-27a (100 mg, 0.24 mmol) in THF (500 μL) was charged with 2M HCl (610 μL, 1.22 mmol) and allowed to stir at rt for 4 h. The mixture was concentrated in vacuo to afford compound 5-16a. $^1$HNMR ($D_2O$, 200 MHz) δ 1.20 (d, 3H, J=6.6Hz), 2.90 (s, 6H), 4.80 (s, 2H), 6.05 (d, 1H, J=10.0 Hz), 7.17-7.22 (m, 2H), 7.5 (s, 1H), 7.79-7.83 (m, 2H), 7.94 (d, 2H, J=6.0 Hz), 9.18 (s, 1H); MS (ES) 354.2 (M+1).

EXAMPLE 5-16b (Compound of Formula I-$(HA^6)_{n7}$ where X1=imidazol-1-yl, $R^2$=$CH_3$, $R^3$=H, $G^1$=$N(CH_3)_2$, $n^2$=0, $n^3$=0, $Q^1$=$CO_2H$, and $(HA^6)_{n7}$=$(HCl)_2$: The title compound was prepared according to the procedures listed for compound 5-16a above except for the substitution of compound 3-27b for compound 3-27a. $^1$HNMR ($D_2O$, 200 MHz) δ 1.32 (d, 3H, J=7.4 Hz), 2.90 (s, 6H), 4.80 (s, 2H), 7.17-7.22 (m, 2H), 7.5 (s, 1H), 7.79-7.83 (m, 2H), 7.94 (d, 2H, J=6.0 Hz), 9.18 (s, 1H); MS (ES) 354.3 (M+1).

EXAMPLE 5-17

(Compound of Formula I-$(HA^6)_{n7}$ where X1=imidazol-1-yl, $R^2$=$CH_3$, $R^3$=$CH_3$, $G^1$=$N(CH_3)_2$, $n^2$=0, $n^3$=1, $R^{4b}$ and $R^{5b}$=$CH_3$, $Q^1$=$CO_2H$, and $(HA^6)_{n7}$=$(HCl)_2$: The title compound was prepared according to the General Synthetic Method F as described above wherein compound of Formula I, X1=imidazol-1-yl, $R^2$=$CH_3$, $R^3$=$CH_3$, $G^1$=$N(CH_3)_2$, $n^2$=0, $n^3$=1, $R^{4b}$ and $R^{5b}$=$CH_3$, and $Q^1$=$CO_2H$. MS (ES) 424.3 (M+1).

General Synthetic Method G for the preparation of compounds of the Formula I-$(HA^6)_{n7}$ (Compound of Formula I where $R^1$ equals H, $R^2$=$CH_3$, $R^3$=H, $G^1$=$N(CH_3)_2$, $n^1$=1, $R^{4a}$, $R^{5a}$, $R^{6a}$ and $R^{6b}$ equal H, Y equals O, $n^2$=0, $n^3$=1, $R^{4b}$ and $R^{5b}$=$CH_3$, $n^4$=1, and $Q^1$=$CONR^7R^8$): An acetonitrile solution (0.3M) of compound of Formula I (1 eq) and 1,1'-carbonyldiimidazole (2 eq) was refluxed at 80° C. for 16 h. $HNR^7R^8$ (solution in THF, 1.0 mmol) was added dropwise to the reaction mixture. After stirring for 3 h, the reaction mixture was concentrated in vacuo, partitioned between sat. $NaHCO_3$ and $CH_2Cl_2$, and the aqueous layer extracted with $CH_2Cl_2$ (5×). The combined organic layers were washed with brine, dried over $Na_2SO_4$, filtered, and concentrated in vacuo. The resulting residue was purified by Gilson HLPC to afford compounds of Formula I-$(HA^6)_{n7}$.

EXAMPLE 5-18a (Compound of Formula I-$(HA^6)_{n7}$ where X1=imidazol-1-yl, $R^2$=$CH_3$, $R^3$=H, $G^1$=$N(CH_3)_2$, $n^2$=0, $n^3$=1, $R^{4b}$ and $R^{5b}$=$CH_3$, $Q^1$=$CONH_2$, and $(HA^6)_{n7}$=$HCO_2H$: The title compound was prepared according to the General Synthetic Method G as described above wherein compound of Formula I, X1=imidazol-1-yl, $R^2$=$CH_3$, $R^3$=H, $G^1$=$N(CH_3)_2$, $n^2$=0, $n^3$=1, $R^{4b}$ and $R^{5b}$=$CH_3$, and $Q^1$=$CO_2H$ and $HNR^7R^8$=$NH_3$. MS (ES) 395.3 (M+1).

EXAMPLE 5-19a (Compound of Formula I-$(HA^6)_{n7}$ where X1=imidazol-1-yl, $R^2$=$CH_3$, $R^3$=H, $G^1$=$N(CH_3)_2$, $n^2$=0, $n^3$=1, $R^{4b}$ and $R^{5b}$=$CH_3$, $Q^1$=$CONHCH_3$, and $(HA^6)_{n7}$=$HCO_2H$: The title compound was prepared according to the General Synthetic Method G as described above wherein compound of Formula I, X1=imidazol-1-yl, $R^2$=$CH_3$, $R^3$=H, $G^1$=$N(CH_3)_2$, $n^2$=0, $n^3$=1, $R^{4b}$ and $R^{5b}$=$CH_3$, and $Q^1$=$CO_2H$ and $HNR^7R^8$=$NH_2CH_3$. $^1$H NMR ($CD_3OD$, 400 MHz) δ0.90 (d, 3H, J=6.4Hz), 1.32 (s, 6H), 2.40 (s, 6H), 2.74 (s, 3H), 3.90-3.98 (m, 1H), 4.07 (s, 2H), 5.06 (d, 1H, J=10.4 Hz), 7.17 (dd, 1H, J=6.4 Hz, 2.4 Hz), 7.24 (d, 1H, J=2.4 Hz), 7.51 (d, 1H, J=8.8 Hz), 7.76-7.81 (m, 3H), 7.89 (s, 1H), 8.39 (s, 1H); MS (ES) 409.2 (M+1).

EXAMPLE 5-20a (Compound of Formula I-$(HA^6)_{n7}$ where X1=imidazol-1-yl, $R^2$=$CH_3$, $R^3$=H, $G^1$=$N(CH_3)_2$, $n^2$=0, $n^3$=1, $R^{4b}$ and $R^{5b}$=$CH_3$, $Q^1$=$CON(CH_3)_2$, and $(HA^6)_{n7}$=$HCO_2H$: The title compound was prepared according to the General Synthetic Method G as described above wherein compound of Formula I, X1=imidazol-1-yl, $R^2$=$CH_3$, $R^3$=H, $G^1$=$N(CH_3)_2$, $n^2$=0, $n^3$=1, $R^{4b}$ and $R^{5b}$=$CH_3$, and $Q^1$=$CO_2H$ and $HNR^7R^8$=$NH(CH_3)_2$. MS (ES) 423.3 (M+1).

General Synthetic Method H for the preparation of compounds of the Formula I-$(HA^6)_{n7}$ (Compound of Formula I where $R^1$ equals H, $R^2$=$CH_3$, $R^3$=H, $G^1$=$N(CH_3)_2$, $n^1$=1, $R^{4a}$, $R^{5a}$, $R^{6a}$ and $R^{6b}$ equal H, Y equals O, $n^2$=0, $n^3$=1, $R^{4b}$ and $R^{5b}$=$CH_3$, $n^4$=1, and $Q^1$=$CONR^7R^8$): A DMF solution of compound of Formula I (1 eq), 1-(3-dimethylaminopropyl)-3-ethylcarbodiimide hydrochloride (1.5 eq), $HNR^7R^8$ HCl (1.5 eq), and 1-hydroxy-7-azabenzotriazole (0.5 eq) was charged with diisopropylethylamine (1.5 eq) dropwise and stirred at rt for 16 h. Upon completion, the reaction mixture was concentrated in vacuo, partitioned between sat. $NaHCO_3$ and $CH_2Cl_2$, and the aqueous layer extracted with $CH_2Cl_2$ (5×). The combined organic layers were washed with brine, dried over $Na_2SO_4$, filtered, and concentrated in vacuo. The resulting residue was purified by Gilson HLPC to afford compounds of Formula I-$(HA^6)_{n7}$.

EXAMPLE 5-21a (Compound of Formula I-$(HA^6)_{n7}$ where X1=imidazol-1-yl, $R^2=CH_3$, $R^3=H$, $G^1=N(CH_3)_2$, $n^2=1$, Z=4-Ph, $n^3=0$, $Q^1=CONH_2$, and $(HA^6)_{n7}=HCO_2H$: The title compound was prepared according to the General Synthetic Method H as described above wherein compound of Formula I, X1=imidazol-1-yl, $R^2=CH_3$, $R^3=H$, $G^1=N(CH_3)_2$, $n^2=1$, Z=4-Ph, $n^3=0$, and $Q^1=CO_2H$ and $HNR^7R^8=NH_3$. MS (ES) 429.3 (M+1).

EXAMPLE 5-22a (Compound of Formula I-$(HA^6)_{n7}$ where X1=imidazol-1-yl, $R^2=CH_3$, $R^3=H$, $G^1=N(CH_3)_2$, $n^2=1$, Z=4-Ph, $n^3=0$, $Q^1=CONHCH_3$, and $(HA^6)_{n7}=HCO_2H$: The title compound was prepared according to the General Synthetic Method H as described above wherein compound of Formula I, X1=imidazol-1-yl, $R^2=CH_3$, $R^3=H$, $G^1=N(CH_3)_2$, $n^2=1$, Z=4-Ph, $n^3=0$, $Q^1=CO_2H$ and $HNR^7R^8=NH_2CH_3$ MS (ES) 443.3 (M+1).

EXAMPLE 5-23a (Compound of Formula I-$(HA^6)_{n7}$ where X1=imidazol-1-yl, $R^2=CH_3$, $R^3=H$, $G^1=N(CH_3)_2$, $n^2=1$, Z=4-Ph, $n^30$, $Q^1=CON(CH_3)_2$, and $(HA^6)_{n7}=HCO_2H$: The title compound was prepared according to the General Synthetic Method H as described above wherein compound of Formula I, X1=imidazol-1-yl, $R^2=CH_3$, $R^3=H$, $G^1=N(CH_3)_2$, $n^2=1$, Z=4-Ph, $n^3=0$, and $Q^1=CO_2H$ and $HNR^7R^8=NH(CH_3)_2$. $^1H$ NMR ($CD_3OD$, 400 MHz) δ 0.91 (d, 3H, J=6.8 Hz), 2.41 (s, 6H), 2.96 (s, 1H), 3.09 (s, 1H), 3.90-4.10 (m, 1H), 5.26 (s, 2H), 5.53 (d, 1H, J=11.6 Hz), 7.19 (s, 1H), 7.27 (dd, 1H, J=2.4, 6.4 Hz), 7.33 (d, 1H, J=2.8 Hz), 7.37 (d, 1H, J=7.6 Hz), 7.47-7.54 (m, 4H), 7.60 (d, 1H, J=7.6 Hz), 7.78-7.82 (m, 2H), 7.91 (s, 1H), 8.46 (s, 1H); MS (ES) 457.3 (M+1).

EXAMPLE 5-24a (Compound of Formula I-$(HA^6)_{n7}$ where X1=imidazol-1-yl, $R^2=CH_2CH_3$, $R^3=H$, $G^1=N(CH_3)_2$, $n^2=0$, $n^3=1$, $R^{4b}$ and $R^{5b}=CH_3$, $Q^1=CO_2H$, and $(HA^6)_{n7}=(HCl)_2$: The title compound was prepared according to the General Synthetic Method F as described above wherein compound of Formula I, X1=imidazol-1-yl, $R^2=CH_2CH_3$, $R^3=H$, $G^1=N(CH_3)_2$, $n^2=0$, $n^3=1$, $R^{4b}$ and $R^{5b}=CH_3$, and $Q^1=CO_2H$. $^1H$ NMR ($CD_3OD$, 400 MHz) δ 0.81 (t, 3H, J=7.6 Hz), 1.37 (s, 6H), 1.63-1.75 (m, 1H), 1.85-1.94 (m, 1H), 3.02 (s, 3H), 3.10 (s, 3H), 4.11 (s, 2H), 5.06-5.11 (m, 1H), 6.59 (d, 1H, J=11.6 Hz), 7.17 (d, 1H, J=2.8 Hz), 7.23 (dd, 1H, J=2.4, 9.2 Hz), 7.42 (s, 1H), 7.47 (s, 1H), 7.74 (dd, 1H, J=2.0, 8.8 Hz), 7.82-7.85 (m, 2H), 8.19 (s, 1H), 8.35 (s, 1H), 9.91 (s, 1H).

EXAMPLE 5-25a (Compound of Formula I-$(HA^6)_{n7}$ where X1=imidazol-1-yl, $R^2=CH_3$, $R^3=H$, $G^1=N(CH_3)_2$, $n^2=1$, Z=4-Ph, $n^3=0$, $Q^1=OH$, and $(HA^6)_{n7}=HCO_2H$: A methylene chloride solution (1 mL) of compound 3-6a (20 mg, 0.044 mmol) was charged with trifluoroacetic acid and allowed to stir at rt for 16 h. Upon completion, the reaction mixture was concentrated in vacuo to solids, taken up in minimal water, and neutralized to pH 7 with sat. $NaHCO_3$. The white solid that precipitated out of solution was filtered, washed with water, and purified on Gilson HPLC to afford the desired product as a white solid; $^1H$ NMR ($CD_3OD$, 200 MHz) δ0.83 (d, 3H, J=6.6 Hz), 2.30 (s, 6H), 3.70-3.79 (m, 1H), 4.32 (s, 2H), 5.32 (d, 1H, J=10.6 Hz), 6.63 (d, 2H, J=8.4 Hz), 6.90 (s, 1H), 7.02 (d, 2H, J=8.8 Hz), 7.21 (d, 1H, J=9.2 Hz), 7.28-7.31 (m, 1H), 7.42 (d, 1H, J=8.4 Hz), 7.68 (d, 1H, J=9.2 Hz), 7.81-7.89 (m, 2H), 8.58 (s, 2H); MS (ES) 402.0 (M+1).

What is claimed is:
1. A compound represented by Formula I

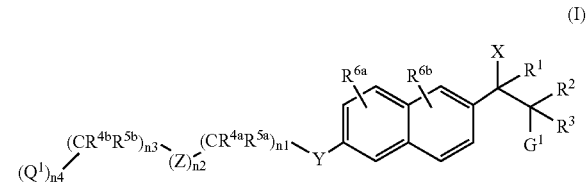

(I)

or a pharmaceutically acceptable salt thereof, wherein:

X is an unsaturated heterocycle selected from pyrrolyl, pyrazolyl, imidazolyl, triazolyl, tetrazolyl, thiazole, or pyridinyl, any of which is optionally substituted with one or more independent $R^{66}$ substituents; X is imidazolyl or triazolyl, any of which is optionally substituted with one or more independent $R^{66}$ substituents $R^1$ is a $C_{0-6}$alkyl, $-OR^7$, $-SR^7$, or $-NR^7R^8$;

$R^2$ and $R^3$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, $-SO_2NR^{71}R^{81}$, or $-NR^{71}R^{81}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, $-OR^{71}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CONR^{71}R^{81}$, $-SO_2NR^{71}R^{81}$ or $-NR^{71}R^{81}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, $-OR^{71}$, $C_{1-10}$alkyl, $C_{2-10}$alkenyl, $C_{2-10}$alkynyl, halo$C_{1-10}$alkyl, halo$C_{2-10}$alkenyl, $-COOH$, $C_{1-4}$alkoxycarbonyl, $-CONR^{71}R^{81}$, $-SO_2NR^{71}R^{81}$ substituents;

or $R^2$ and $R^3$ taken together with the carbon atom to which they are attached form a 3-10 membered saturated ring, unsaturated ring, heterocyclic saturated ring, or heterocyclic unsaturated ring, wherein said ring is optionally substituted with one or more independent $C_{1-6}$alkyl, halo, cyano, nitro, $-OR^{71}$, $-SO_2NR^{71}R^{81}$ or $-NR^{71}R^{81}$ substituents;

$G^1$ is $-NR^{72}$, $R^{82}(R^9)_{n5}$ wherein $R^{72}$, and $R^{82}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, $-SO_2NR^{73}R^{83}$ or $-NR^{73}R^{83}$ substituents;

Y is an oxygen atom;

Z is -aryl-, -arylalkyl-, -aryloxy-, -oxyaryl-, -arylalkenyl-, -alkenylaryl-, -hetaryl-, -hetarylalkyl-, -alkylhetaryl-, -hetarylalkenyl-, -alkenylhetaryl-, or -aryl-, any of which is optionally substituted with $R^{68}$;

$Q^1$ is $C_{0-6}$alkyl, $-OR^{75}$, $-NR^{75}R^{85}(R^{95})_{n6}$, $-CO_2R^{75}$, $-CONR^{75}R^{85}$, $-(C=S)OR^{75}$, $-(C=O)SR^{75}$, $-NO_2$, $-CN$, halo, $-S(O)_{n6}R^{75}$, $-SO_2NR^{75}R^{85}$, $-NR^{75}(C=NR^{775})NR^{7775}R^{85}$, $-NR^{75}(C=NR^{775})OR^{7775}$, $-NR^{75}(C=NR^{775})SR^{7775}$, $-O(C=O)OR^{75}$, $-O(C=O)NR^{75}R^{85}$, $-O(C=O)SR^{75}$, $-S(C=O)OR^{75}$, $-S(C=O)NR^{75}R^{85}$, $-S(C=O)SR^{75}$, $-NR^{75}(C=O)NR^{775}R^{85}$, or $-NR^{75}(C=S)NR^{775}R^{85}$; in the case of $-NR^{75}R^{85}(R^{95})_{n6}$, $R^{75}$ and $R^{85}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, $-SO_2NR^{76}R^{86}$ or $-NR^{76}R^{86}$ substituents;

$R^{4a}$, $R^{4b}$, $R^{4c}$, $R^{5a}$, $R^{5b}$ and $R^{5c}$ are each independently a $C_{0-10}$alkyl, $C_{2-10}$alkenyl, $C_{2-10}$alkynyl, $C_{1-10}$alkoxy $C_{1-10}$alkyl, $C_{1-10}$alkoxy$C_{2-10}$alkenyl, $C_{1-10}$alkoxy $C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo $C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl $C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, $-OR^{77}$, $-SO_2NR^{77}R^{87}$ or $-NR^{77}R^{87}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, $-OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CONR^{77}R^{87}$, $-SO_2NR^{77}R^{87}$ or $-NR^{77}R^{87}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, $-OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CONR^{77}R^{87}$, $-SO_2NR^{77}R^{87}$ or $-NR^{77}R^{87}$ substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or $-N(C_{1-6}$alkyl)-$C_{1-6}$alkyl-aryl, any of which is optionally substituted with one or more independent halo, cyano, nitro, $-OR^{77}$, $C_{1-10}$alkyl, $C_{2-10}$alkenyl, $C_{2-10}$alkynyl, halo$C_{1-10}$alkyl, halo $C_{2-10}$alkenyl, halo$C_{2-10}$alkynyl, $-COOH$, $C_{1-4}$alkoxycarbonyl, $-CONR^{77}R^{87}$, $-SO_2NR^{77}R^{87}$ or $-NR^{77}R^{87}$ substituents; or $R^{4a}$ with $R^{5a}$, or $R^{4b}$ with $R^{5b}$, or $R^{4c}$ with $R^{5c}$, taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$, or $R^{4c}$ with $R^{5c}$, taken together with the respective carbon atom to which they are attached, form a 3-10 membered saturated or unsaturated heterocyclic ring, wherein said ring is optionally substituted with $R^{69}$;

n1, n2, n3, n4, n5, n6, and n7 are each independently equal to 0, 1 or 2;

$R^{6a}$, $R^{6b}$, $R^{66}$, $R^{67}$, $R^{68}$, and $R^{69}$ are each independently halo, $-OR^{78}$, $-NR^{78}R^{88}(R^{98})_{n7}$, $-CO_2R^{78}$, $-CONR^{78}R^{88}$, $-NO_2$, $-CN$, $-S(O)_{n7}R^{78}$, $-SO_2NR^{78}R^{88}$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo $C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl $C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, $-OR^{778}$, $-SO_2NR^{778}R^{888}$ or $-NR^{778}R^{888}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, $-OR^{778}$, $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, $-COOH$, $C_{1-4}$alkoxycarbonyl, $-CONR^{778}R^{888}$, $-SO_2NR^{778}R^{888}$ or $-NR^{778}R^{888}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, $-OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, $-COOH$, $C_{1-4}$alkoxycarbonyl, $-CONR^{778}R^{888}$, $-SO_2NR^{778}R^{888}$ or $-NR^{778}R^{888}$ substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, $-N(C_{1-6}$alkyl)-$C_{1-6}$alkyl-aryl, any of which is optionally substituted with one or more independent halo, cyano, nitro, $-OR^{778}$, $C_{1-10}$alkyl, $C_{2-10}$alkenyl, $C_{2-10}$alkynyl, halo$C_{1-10}$alkyl, halo $C_{2-10}$alkenyl, halo$C_{2-10}$alkynyl, $-COOH$, $C_{1-4}$alkoxycarbonyl, $-CONR^{778}R^{888}$, $-SO_2NR^{778}R^{888}$ or $-NR^{778}R^{888}$ substituents; or in the case of $-NR^{78}R^{88}(R^{98})_{n7}$, $R^{78}$ and $R^{88}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, $-SO_2NR^{778}R^{888}$ or $-NR^{778}R^{888}$ substituents;

$R^7$, $R^{71}$, $R^{72}$, $R^{73}$, $R^{74}$, $R^{75}$, $R^{775}$, $R^{7775}$, $R^{76}$, $R^{77}$, $R^{78}$, $R^{778}$, $R^8$, $R^{81}$, $R^{82}$, $R^{83}$, $R^{84}$, $R^{85}$, $R^{86}$, $R^{87}$, $R^{88}$, $R^{888}$, $R^9$, $R^{95}$, and $R^{98}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo $C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo $C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$ alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —$SO_2N(C_{0-4}$alkyl$)(C_{0-4}$alkyl$)$ or —$N(C_{0-4}$alkyl$)$ ($C_{0-4}$alkyl$)$ substituents; aryl-$C_{0-10}$alkyl, aryl-$C_{2-10}$alkenyl, or aryl-$C_{2-10}$alkynyl, any of which is optionally substituted with one or more independent halo, cyano, nitro, —$O(C_{0-4}$alkyl$)$, $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, $C_{1-4}$alkoxycarbonyl, —CON($C_{0-4}$alkyl$)(C_{0-10}$alkyl$)$, —$SO_2N(C_{0-4}$alkyl$)(C_{0-4}$alkyl$)$ or —$N(C_{0-4}$alkyl$)(C_{0-4}$alkyl$)$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$O(C_{0-4}$alkyl$)$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CON($C_{0-4}$alkyl$)(C_{0-4}$alkyl$)$, —$SO_2N(C_{0-4}$alkyl$)(C_{0-4}$alkyl$)$ or —$N(C_{0-4}$alkyl$)$ ($C_{0-4}$alkyl$)$ substituents; or mono($C_{1-6}$alkyl)amino $C_{1-6}$alkyl, di($C_{1-6}$alkyl)amino$C_{1-6}$alkyl, mono(aryl) amino$C_{1-6}$alkyl, di(aryl)amino$C_{1-6}$alkyl, or —$N(C_1$-alkyl)-$C_{1-6}$alkyl-aryl, any of which is optionally substituted with one or more independent halo, cyano, nitro, —$O(C_{0-4}$alkyl$)$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CON($C_{0-4}$alkyl$)$ ($C_{0-4}$alkyl$)$, —$SO_2N(C_{0-4}$alkyl$)(C_{0-4}$alkyl$)$ or —N ($C_{0-4}$alkyl$)(C_{0-4}$alkyl$)$ substituents.

2. The compound of claim 1 wherein X is imidazolyl or triazolyl, any of which is optionally substituted with one or more independent $R^{66}$ substituents.

3. The compound of claim 2 wherein X is imidazolyl or triazolyl.

4. The compound of claim 2 wherein $Q^1$ is —$CO_2H$ or —$CO_2R^{75}$.

5. The compound of claim 1 wherein X is imidazolyl or triazolyl, any of which is optionally substituted with one or more independent $R^{66}$ substituents.

6. The compound of claim 1 wherein X is imidazolyl or triazolyl.

7. The compound of claim 1 wherein $Q^1$ is —$CO_2H$ or —$CO_2R^{75}$.

8. The compound of claim 1 wherein $R^{4a}$ and $R^{5a}$ are each hydrogen.

9. The compound of claim 2 wherein $R^1$, $R^2$ and $R^3$ are each independently $C_{0-10}$alkyl;
$Q^1$ is $CO_{0-6}$alkyl, —$CO_2R^{75}$, or —$CONR^{75}R^{85}$;
$R^{4a}$, $R^{4b}$, $R^{5a}$, and $R^{5b}$ are each independently a $C_{0-10}$ alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5b}$ or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and $R^{6a}$ and $R^{6b}$ are each independently halo, —$OR^{78}$, —$NR^{78}R^{88}(R^{98})_{n7}$, —$CO_2R^{78}$, —$CONR^{78}R^{88}$, —$NO_2$, —CN, —$S(O)_{n7}R^{78}$, —$SO_2NR^{78}R^{88}$, or $C_{0-10}$alkyl.

10. The compound of claim 9 wherein
X is imidazolyl or triazolyl;
$R^1$ is hydrogen;
$R^2$ and $R^3$ are each independently $C_{0-10}$alkyl;
$Q^1$ is —$CO_2R^{75}$ or —$CONR^{75}R^{85}$; and
$R^{6a}$ and $R^{6b}$ are each independently a hydrogen atom.

11. The compound of claim 9 wherein
$R^{4a}$ and $R^{5a}$ are each hydrogen; and
$R^{4b}$ and $R^{5b}$ are each independently $C_{0-10}$alkyl; or $R^{4b}$ with $R^{5b}$ taken together with the respective carbon atom to which they are attached form a 3-10 membered saturated or unsaturated ring, wherein said ring is optionally substituted with $R^{69}$; or $R^{4b}$ with $R^{5b}$ taken together with the respective carbon atom to which they are attached form a 3-10 membered saturated or unsaturated heterocyclic ring, wherein said ring is optionally substituted with $R^{69}$.

12. The compound of claim 9 wherein $R^{4b}$ and $R^{5b}$ are each independently $C_{0-6}$alkyl, or $R^{4b}$ with $R^{5b}$ taken together with the respective carbon atom to which they are attached form a 3-10 membered saturated ring.

13. The compound of claim 12 wherein $R^{4b}$ with $R^{5b}$ taken together with the respective carbon atom to which they are attached form a cyclopropyl, cyclobutyl, cyclopentyl, or cyclohexyl ring.

14. The compound of claim 12 wherein $R^{4b}$ and $R^{5b}$ are both ethyl, or are both methyl.

15. The compound of claim 9 wherein $Q^1$ is —$CO_2R^{75}$.

16. The compound of claim 9 wherein $Q^1$ is —$CO_2H$.

17. The compound of claim 9 wherein $G^1$ is di($C_{1-6}$alkyl) amino.

18. The compound of claim 9 wherein $G^1$ is dimethylamino, ethylmethylamino, diethylamino, or isopropylmethylamino.

19. The compound of claim 9 wherein $R^2$ and $R^3$ are each independently hydrogen, methyl, or ethyl.

20. The compound of claim 3 wherein X is imidazole.

21. The compound of claim 10 wherein $R^2$ is hydrogen and $R^3$ is methyl.

22. The compound of claim 10 wherein $R^2$ is hydrogen and $R^3$ is ethyl.

23. The compound of claim 10 wherein $R^2$ and $R^3$ are both methyl.

24. The compound of claim 1 wherein Z is -aryl- or -aryloxy- or -oxyaryl-.

25. A compound selected from the group consisting of:
3-[6-(2-Dimethylamino-1-imidazol-1-yl-propyl)-naphthalen-2-yloxy]-2,2-dimethyl-propionic acid;
2-[6-(2-Dimethylamino-1-imidazol-1-yl-propyl)-naphthalen-2-yloxymethyl]-2-ethyl-butyric acid;
1-[6-(2-Dimethylamino-1-imidazol-1-yl-propyl)-naphthalen-2-yloxymethyl]-cyclopropanecarboxylic acid;
1-[6-(2-Dimethylamino-1-imidazol-1-yl-propyl)-naphthalen-2-yloxymethyl]-cyclobutanecarboxylic acid;
1-[6-(2-Dimethylamino-1-imidazol-1-yl-propyl)-naphthalen-2-yloxymethyl]-cyclopentanecarboxylic acid;
1-[6-(2-Dimethylamino-1-imidazol-1-yl-propyl)-naphthalen-2-yloxymethyl]-cyclohexanecarboxylic acid;
1-{6-[1-Imidazol-1-yl-2-(isopropylmethylamino)-propyl]-naphthalen-2-yloxymethyl}-cyclopentanecarboxylic acid;
3-[6-(2-Diethylamino-1-imidazol-1-yl-propyl)-naphthalen-2-yloxy]-2,2-dimethyl-propionic acid;
3-{6-[1-Imidazol-1-yl-2-(isopropylmethylamino)-propyl]-naphthalen-2-yloxy}-2,2-dimethyl-propionic acid;
3-{6-[2-(Ethyl-methyl-amino)-1-imidazol-1-yl-propyl]-naphthalen-2-yloxy}-2,2-dimethyl-propionic acid;

3-[6-(2-Dimethylamino-1-imidazol-1-yl-propyl)-naphthalen-2-yloxy]-2,2-dimethyl-propionamide;

3-[6-(2-Dimethylamino-1-imidazol-1-yl-propyl)-naphthalen-2-yloxy]-2,2,N-trimethyl-propionamide;

3-[6-(2-Dimethylamino-1-imidazol-1-yl-propyl)-naphthalen-2-yloxy]-2,2,N,N-tetramethyl-propionamide;

3-[6-(2-Dimethylamino-1-imidazol-1-yl-butyl)-naphthalen-2-yloxy]-2,2-dimethyl-propionic acid;

4-[6-(2-Dimethylamino-1-imidazol-1-yl-propyl)-naphthalen-2-yloxymethyl]-benzoic acid;

3-[6-(2-Dimethylamino-1-imidazol-1-yl-propyl)-naphthalen-2-yloxymethyl]-benzoic acid;

4-[6-(2-Dimethylamino-1-imidazol-1-yl-propyl)-naphthalen-2-yloxymethyl]-benzamide;

4-[6-(2-Dimethylamino-1-imidazol-1-yl-propyl)-naphthalen-2-yloxymethyl]-N-methyl-benzamide;

4-[6-(2-Dimethylamino-1-imidazol-1-yl-propyl)-naphthalen-2-yloxymethyl]-N,N-dimethyl-benzamide; and 1-[(6-Benzyloxy-naphthalen-2-yl)-(1-methyl-pyrrolidin-2-yl)-methyl]-1H-imidazole.

26. A compound represented by Formula II:

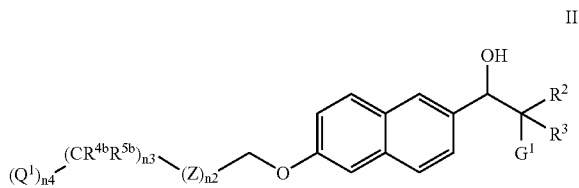

or a pharmaceutically acceptable salt thereof, wherein:

$R^2$ and $R^3$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy $C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl $C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —$SO_2NR^{71}R^{81}$, or —$NR^{71}R^{81}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —$OR^{71}$, $C_{1-10}$alkyl, $C_{2-10}$alkenyl, $C_{2-10}$alkynyl, halo$C_{1-10}$alkyl, halo $C_{2-10}$alkenyl, halo$C_{2-10}$alkynyl, —COOH, $C_{1-4}$alkoxycarbonyl, —$CONR^{71}R^{81}$, —$SO_2NR^{71}R^{81}$ or —$NR^{71}R^{81}$ substituents; or heteroaryl-$C_{0-10}$alkyl, heteroaryl-$C_{2-10}$alkenyl, or heteroaryl-$C_{2-10}$alkynyl, any of which is optionally substituted with one or more independent halo, cyano, nitro, —$OR^{71}$, $C_{1-10}$alkyl, $C_{2-10}$alkenyl, $C_{2-10}$alkynyl, halo$C_{1-10}$alkyl, halo $C_{2-10}$alkenyl, halo$C_{2-10}$alkynyl, —COOH, $C_{1-4}$alkoxycarbonyl, —$CONR^{71}R^{81}$, —$SO_2NR^{71}R^{81}$ or —$NR^{71}R^{81}$ substituents;

or $R^2$ and $R^3$ taken together with the carbon atom to which they are attached form a 3-10 membered saturated ring, unsaturated ring, heterocyclic saturated ring, or heterocyclic unsaturated ring, any of which is optionally substituted with one or more independent $C_{1-6}$alkyl, halo, cyano, nitro, —$OR^{71}$, —$SO_2NR^{71}R^{81}$ or —$NR^{71}R^{81}$ substituents;

$G^1$ is —$NR^{72}R^{82}(R^9)_{n5}$, wherein $R^{72}$ and $R^{82}$ taken together with the nitrogen atom to which they are attached form a 3-10 membered saturated ring, heterocyclic saturated ring, or heterocyclic unsaturated ring, any of which is optionally substituted with one or more independent halo, cyano, hydroxy, nitro, $C_{1-10}$alkoxy, —$SO_2NR^{73}$ or —$NR^{73}R^{83}$ substituents;

Z is -aryl-, -arylalkyl-, -aryloxy-, -oxyaryl-, -arylalkenyl-, -alkenylaryl-, -hetaryl-, -hetarylalkyl-, -alkylhetaryl-, -hetarylalkenyl-, -alkenylhetaryl-, or -aryl-, any of which is optionally substituted with $R^{68}$;

$Q^1$ is $C_{0-6}$alkyl, —$OR^{75}$, —$NR^{75}R^{85}(R^{95})_{n6}$, —$CO_2R^{75}$, —$CONR^{75}R^{85}$, —(C=S)$OR^{75}$, —(C=O)$SR^{75}$, —$NO_2$, —CN, halo, —$S(O)_{n6}R^{75}$, —$SO_2NR^{75}R^{85}$, —$NR^{75}(C=NR^{775})NR^{7775}R^{85}$, —$NR^{75}(C=NR^{775})OR^{7775}$, —$NR^{75}(C=NR^{775})SR^{7775}$, —$O(C=O)OR^{75}$, —$O(C=O)NR^{75}R^{85}$, —$O(C=O)SR^{75}$, —$S(C=O)OR^{75}$, —$S(C=O)NR^{75}R^{85}$, —$S(C=O)SR^{75}$, —$NR^{75}(C=O)NR^{775}R^{85}$, or —$NR^{75}(C=S)NR^{775}R^{85}$; in the case of —$NR^{75}R^{85}(R^{95})_{n6}$, $R^{75}$ and $R^{85}$ taken together with the nitrogen atom to which they are attached form a 3-10 membered saturated ring, unsaturated ring, heterocyclic saturated ring, or heterocyclic unsaturated ring, any of which is optionally substituted with one or more independent halo, cyano, hydroxy, nitro, $C_{1-10}$alkoxy, —$SO_2NR^{76}R^{86}$ or —$NR^{76}R^{86}$ substituents;

$R^{4b}$ and $R^{5b}$ are each independently a $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo $C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo $C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, —$OR^{77}$, —$SO_2NR^{77}R^{87}$ or —$NR^{77}R^{87}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —$OR^{77}$, $C_{1-10}$alkyl, $C_{2-10}$alkenyl, $C_{2-10}$alkynyl, halo$C_{1-10}$alkyl, halo $C_{2-10}$alkenyl, halo$C_{2-10}$alkynyl, —COOH, $C_{1-4}$alkoxycarbonyl, —$CONR^{77}R^{87}$, —$SO_2NR^{77}R^{87}$ or —$NR^{77}R^{87}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$OR^{77}$, $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, $C_{1-4}$alkoxycarbonyl, —$CONR^{77}R^{87}$, —$SO_2NR^{77}R^{87}$ or —$NR^{77}R^{87}$ substituents; or mono($C_{1-6}$alkyl)amino$C_{1-6}$alkyl, di($C_{1-6}$alkyl) amino$C_{1-6}$alkyl, mono(aryl)amino$C_{1-6}$alkyl, di(aryl) amino$C_{1-6}$alkyl, or —$N(C_{1-6}$alkyl)-$C_{1-6}$alkyl-aryl, any of which is optionally substituted with one or more independent halo, cyano, nitro, —$OR^{77}$, $C_{1-10}$alkyl, $C_{2-10}$alkenyl, $C_{2-10}$alkynyl, halo$C_{1-10}$alkyl, halo $C_{2-10}$alkenyl, halo$C_{2-10}$alkynyl, —COOH, $C_{1-4}$alkoxycarbonyl, —$CONR^{77}R^{87}$, —$SO_2NR^{77}R^{87}$ or —$NR^{77}R^{87}$ substituents; or $R^{4a}$ with $R^{5a}$, or $R^{4b}$ with $R^{5b}$, or $R^{4c}$ with $R^{5c}$, taken together with the respective carbon atom to which they are attached, form a 3-10 membered saturated or unsaturated ring, any of which is optionally substituted with $R^{69}$; or $R^{4a}$ with $R^{5a}$, or $R^{4b}$ with $R^{5b}$, or $R^{4c}$ with $R^{5c}$, taken together with the respective carbon atom to which they are attached, form a 3-10 membered saturated or unsaturated heterocyclic ring, any of which is optionally substituted with $R^{69}$;

n1, n2, n3, n4, n5, n6, and n7 are each independently equal to 0, 1 or 2;

$R^7$, $R^{71}$, $R^{72}$, $R^{73}$, $R^{74}$, $R^{75}$, $R^{775}$, $R^{7775}$, $R^{76}$, $R^{77}$, $R^{78}$, $R^{778}$, $R^8$, $R^{81}$, $R^{82}$, $R^{83}$, $R^{85}$, $R^{86}$, $R^{87}$, $R^{88}$, $R^{888}$, $R^9$, $R^{95}$, and $R^{98}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —SO$_2$N(C$_{0-4}$alkyl)(C$_{0-4}$alkyl) or —N(C$_{0-4}$alkyl)(C$_{0-4}$alkyl) substituents; aryl-$C_{1-10}$alkyl, aryl-$C_{2-10}$alkenyl, or aryl-$C_{2-10}$alkynyl, any of which is optionally substituted with one or more independent halo, cyano, nitro, —O(C$_{0-4}$alkyl), $C_{1-10}$alkyl, $C_{2-10}$alkenyl, $C_{2-10}$alkynyl, haloC$_{1-10}$alkyl, haloC$_{2-10}$alkenyl, halo C$_{2-10}$alkynyl, —COOH, C$_{1-4}$alkoxycarbonyl, —CON(C$_{0-4}$alkyl)(C$_{0-10}$alkyl), —SO$_2$N(C$_{0-4}$alkyl)(C$_{0-4}$alkyl) or —N(C$_{0-4}$alkyl)(C$_{0-4}$alkyl) substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —O(C$_{0-4}$alkyl), $C_{1-10}$alkyl, $C_{2-10}$alkenyl, $C_{2-10}$alkynyl, haloC$_{1-10}$alkyl, haloC$_{2-10}$alkenyl, haloC$_{2-10}$alkynyl, —COOH, C$_{1-4}$alkoxycarbonyl, —CON(C$_{0-4}$alkyl)(C$_{0-4}$alkyl), —SO$_2$N(C$_{0-4}$alkyl)(C$_{0-4}$alkyl) or —N(C$_{0-4}$alkyl)(C$_{0-4}$alkyl) substituents; or mono(C$_{1-6}$alkyl)amino C$_{1-6}$alkyl, di(C$_{1-6}$alkyl)aminoC$_{1-6}$alkyl, mono(aryl)aminoC$_{1-6}$alkyl, di(aryl)aminoC$_{1-6}$alkyl, or —N(C$_{1-6}$alkyl)-C$_{1-6}$alkyl-aryl, any of which is optionally substituted with one or more independent halo, cyano, nitro, —O(C$_{0-4}$alkyl), C$_{1-10}$alkyl, C$_{2-10}$alkenyl, C$_{2-10}$alkynyl, haloC$_{1-10}$alkyl, haloC$_{2-10}$alkenyl, halo C$_{2-10}$alkynyl, —COOH, C$_{1-4}$alkoxycarbonyl, —CON(C$_{0-4}$alkyl)(C$_{0-4}$alkyl), —SO$_2$N(C$_{0-4}$alkyl)(C$_{0-4}$alkyl) or —N(C$_{0-4}$alkyl)(C$_{0-4}$alkyl) substituents.

27. A compound represented by Formula I-B:

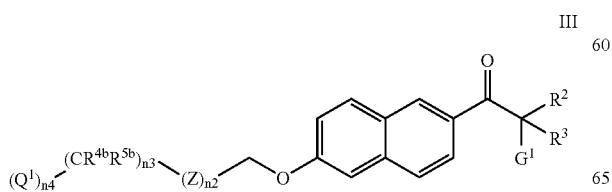

III or a pharmaceutically acceptable salt thereof, wherein:

$R^2$ and $R^3$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —SO$_2$NR$^{71}$R$^{81}$, or —NR$^{71}$R$^{81}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —OR$^{71}$, $C_{1-10}$alkyl, $C_{2-10}$alkenyl, $C_{2-10}$alkynyl, haloC$_{1-10}$alkyl, halo C$_{2-10}$alkenyl, haloC$_{2-10}$alkynyl, —COOH, C$_{1-4}$alkoxycarbonyl, —CONR$^{71}$R$^{81}$, —SO$_2$NR$^{71}$R$^{81}$ or —NR$^{71}$R$^{81}$ substituents; or heteroaryl-$C_{0-10}$alkyl, heteroaryl-$C_{2-10}$alkenyl, or heteroaryl-$C_{2-10}$alkynyl, any of which is optionally substituted with one or more independent halo, cyano, nitro, —OR$^{71}$, $C_{1-10}$alkyl, $C_{2-10}$alkenyl, $C_{2-10}$alkynyl, haloC$_{1-10}$alkyl, halo C$_{2-10}$alkenyl, haloC$_{2-10}$alkynyl, —COOH, C$_{1-4}$alkoxycarbonyl, —CONR$^{71}$R$^{81}$, —SO$_2$NR$^{71}$R$^{81}$ or —NR$^{71}$R$^{81}$ substituents;

or $R^2$ and $R^3$ taken together with the carbon atom to which they are attached form a 3-10 membered saturated ring, unsaturated ring, heterocyclic saturated ring, or heterocyclic unsaturated ring, any of which is optionally substituted with one or more independent $C_{1-6}$alkyl, halo, cyano, nitro, —OR$^{71}$, —SO$_2$NR$^{71}$R$^{81}$ or —NR$^{71}$R$^{81}$ substituents;

or $R^2$ and $R^3$ taken together with the carbon atom to which they are attached form a 3-10 membered saturated ring, unsaturated ring, heterocyclic saturated ring, or heterocyclic unsaturated ring, any of which is optionally substituted with one or more independent $C_{1-6}$alkyl, halo, cyano, nitro, —OR$^{71}$, —SO$_2$NR$^{71}$R$^{81}$ substituents;

$G^1$ is —NR$^{72}$R$^{82}$(R$^9$)$_{n5}$, wherein $R^{72}$ and $R^{82}$ taken together with the nitrogen atom to which they are attached form a 3-10 membered saturated ring, unsaturated ring, heterocyclic saturated ring, or heterocyclic unsaturated ring, any of which is optionally substituted with one or more independent halo, cyano, hydroxy, nitro, C$_{1-10}$alkoxy, —SO$_2$NR$^{73}$R$^{83}$ or —NR$^{73}$R$^{83}$ substituents;

Z is -aryl-, -arylalkyl-, -aryloxy-, -oxyaryl-, -arylalkenyl-, -alkenylaryl-, -hetaryl-, -hetarylalkyl-, -alkylhetaryl-, -hetarylalkenyl-, -alkenylhetaryl-, or -aryl-, any of which is optionally substituted with R$^{68}$;

$Q^1$ is C$_{0-6}$alkyl, —OR$^{75}$, —NR$^{75}$R$^{85}$(R$^{95}$)$_{n6}$, —CO$_2$R$^{75}$, —CONR$^{75}$R$^{85}$, —(C=S)OR$^{75}$, —(C=O)SR$^{75}$, —NO$_2$, —CN, halo, —S(O)$_{n6}$R$^{75}$, —SO$_2$NR$^{75}$R$^{85}$, —NR$^{75}$(C=NR$^{775}$)NR$^{7775}$R$^{85}$, —NR$^{75}$(C=NR$^{775}$)OR$^{7775}$, —NR$^{75}$(C=NR$^{775}$)SR$^{7775}$, —O(C=O)OR$^{75}$, —O(C=O)NR$^{75}$R$^{85}$, —O(C=O)SR$^{85}$, —S(C=O)O)NR$^{75}$R$^{85}$, —S(C=O)NR$^{75}$R$^{85}$, —S(C=O)SR$^{75}$, —NR$^{75}$(C=O)NR$^{775}$R$^{85}$, or —NR$^{75}$(C=S)NR$^{775}$R$^{85}$; in the case of —NR$^{75}$R$^{85}$(R$^{95}$)$_{n6}$, R$^{75}$ and R$^{85}$ taken together with the nitrogen atom to which they are attached form a 3-10 membered saturated ring, unsaturated ring, heterocyclic saturated ring, or heterocyclic unsaturated ring, any of which is optionally substituted with one or more independent halo, cyano, hydroxy, nitro, $C_{1-10}$alkoxy, —$SO_2NR^{76}R^{86}$ or —$NR^{76}R^{86}$ substituents;

$R^{4b}$ and $R^{5b}$ are each independently a $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, —$OR^{77}$, —$SO_2NR^{77}R^{87}$ or —$NR^{77}R^{87}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —$OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{77}R^{87}$, —$SO_2NR^{77}R^{87}$ or —$NR^{77}R^{87}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{77}R^{87}$, —$SO_2NR^{77}R^{87}$ or —$NR^{77}R^{87}$ substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or —N($C_{1-6}$alkyl)-$C_{1-6}$alkyl-aryl, any of which is optionally substituted with one or more independent halo, cyano, nitro, —$OR^{77}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{77}R^{87}$, —$SO_2NR^{77}R^{87}$ or —$NR^{77}R^{87}$ substituents; or $R^{4a}$ with $R^{5a}$ or $R^{4b}$ with $R^{5b}$, or $R^{4c}$ with $R^{5c}$, taken together with the respective carbon atom to which they are attached, form a 3-10 membered saturated or unsaturated ring, any of which is optionally substituted with $R^{69}$; or $R^{4a}$ with $R^{5a}$, or $R^{4b}$ with $R^{5b}$, or $R^{4c}$ with $R^{5c}$, taken together with the respective carbon atom to which they are attached, form a 3-10 membered saturated or unsaturated heterocyclic ring, any of which is optionally substituted with $R^{69}$;

n1, n2, n3, n4, n5, n6, and n7 are each independently equal to 0, 1 or 2;

$R^{67}$, $R^{68}$, and $R^{69}$ is a halo, —OR , —$NR^{78}R^{88}(R^{98})_{n7}$, —$CO_2R^{78}$, —$CONR^{78}R^{88}$, —$NO_2$, —CN, —S$(O)_{n7}R^{78}$, —$SO_2NR^{78}R^{88}$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, or heterocyclyl-$C_{2-10}$alkynyl, any of which is optionally substituted with one or more independent halo, cyano, nitro, —$OR^{778}$, —$SO_2NR^{778}R^{888}$ or —$NR^{778}R^{888}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{778}R^{888}$, —$SO_2NR^{778}R^{888}$ or —$NR^{778}R^{888}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{778}R^{888}$, —$SO_2NR^{778}R^{888}$ or —$NR^{778}R^{888}$ substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, —N($C_{1-6}$alkyl)-$C_{1-6}$alkyl-aryl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{778}R^{888}$, —$SO_2NR^{778}R^{888}$ or —$NR^{778}R^{888}$ substituents; or in the case of —$NR^{78}R^{88}$ $(R^{98})_{n7}$, $R^{78}$ and $R^{88}$ taken together with the nitrogen atom to which they are attached form a 3-10 membered saturated ring, unsaturated ring, heterocyclic saturated ring, or heterocyclic unsaturated ring, any of which is optionally substituted with one or more independent halo, cyano, hydroxy, nitro, $C_{1-10}$alkoxy, —$SO_2NR^{778}R^{888}$ or —$NR^{778}R^{888}$ substituents;

$R^7$, $R^{71}$, $R^{72}$, $R^{73}$, $R^{74}$, $R^{75}$, $R^{775}$, $R^{7775}$, $R^{76}$, $R^{77}$, $R^{78}$, $R^{778}$, $R^8$, $R^{81}$, $R^{82}$, $R^{83}$, $R^{85}$, $R^{86}$, $R^{87}$, $R^{88}$, $R^{888}$, $R^9$, $R^{95}$, and $R^{98}$ are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl$C_{2-10}$alkynyl, heterocyclyl-$C_{0-10}$alkyl, heterocyclyl-$C_{2-10}$alkenyl, heterocyclyl-$C_{2-10}$alkynyl, $C_{1-10}$alkylcarbonyl, $C_{2-10}$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —$SO_2N(C_{0-4}$alkyl$)(C_{0-4}$alkyl$)$ or —N$(C_{0-4}$alkyl$)(C_{0-4}$alkyl$)$ substituents; aryl-$C_{0-10}$alkyl, aryl-$C_{2-10}$alkenyl, or aryl-$C_{2-10}$alkynyl, any of which is optionally substituted with one or more independent halo, cyano, nitro, —O$(C_{0-4}$alkyl$)$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CON$(C_{0-4}$alkyl$)(C_{0-10}$alkyl$)$, —$SO_2N(C_{0-4}$alkyl$)(C_{0-4}$alkyl$)$ or —N$(C_{0-4}$alkyl$)(C_{0-4}$alkyl$)$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —O$(C_{0-4}$alkyl$)$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CON$(C_{0-4}$alkyl$)(C_{0-4}$alkyl$)$, —$SO_2N(C_{0-4}$alkyl$)(C_{0-4}$alkyl$)$ or —N$(C_{0-4}$alkyl$)(C_{0-4}$alkyl$)$ substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or —N($C_{1-6}$alkyl)-$C_{1-6}$alkyl-aryl, any of which is optionally substituted with one or more independent halo, cyano, nitro, —O($C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, $C_{1-4}$alkoxycarbonyl, —CON($C_{0-4}$alkyl)($C_{0-4}$alkyl), —$SO_2$N($C_{0-4}$alkyl)($C_{0-4}$alkyl) or —N($C_{0-4}$alkyl)($C_{0-4}$alkyl) substituents.

28. A pharmaceutical composition comprising a therapeutically effective amount of a compound of claim 1, or a pharmaceutically acceptable salt thereof, and a pharmaceutically acceptable carrier.

29. The pharmaceutical composition of claim 1 wherein the pharmaceutical composition is adapted for oral, rectal, topical, or parenteral administration.

30. The pharmaceutical composition of claim 1 wherein the pharmaceutical composition is in the form of tablet, capsule, cachets, aerosol, cream, ointment, lotion, powder, or suppository.

31. The compound of claim 1 having a ratio of the $IC_{50}$ value of Cyp3A4 activity to the $IC_{50}$ value of Cyp26 activity is 10:1 or greater.

32. The compound of claim 1 having a ratio of the $IC_{50}$ value of Cyp3A4 activity to the $IC_{50}$ value of Cyp26 activity is 100:1 or greater.

33. A compound represented by Formula I

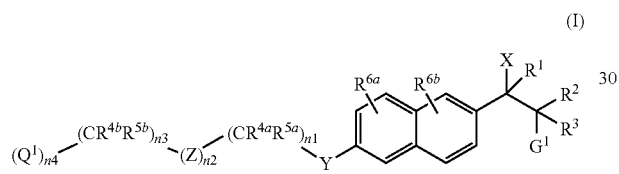

(I)

or a pharmaceutically acceptable salt thereof, wherein:
X is imidazolyl or triazolyl, any of which is optionally substituted with one or more independent $R^{66}$ substituents;
$R^1$, $R^2$ and $R^3$ are each independently $C_{0-10}$alkyl;
$G^1$ is di($C_{1-6}$alkyl)amino;
Y is oxygen;
Z is -aryl-, -arylalkyl-, -aryloxy-, -oxyaryl-, -arylalkenyl-, -alkenylaryl-, -hetaryl-, -hetarylalkyl-, -alkylhetaryl-, -hetarylalkenyl-, -alkenylhetaryl-, or -aryl-, any of which is optionally substituted with $R^{68}$;
$Q^1$ is $C_{0-6}$alkyl, —$CO_2R^{75}$, or —$CONR^{75}R^{85}$;
$R^{4a}$, $R^{4b}$, $R^{5a}$, and $R^{5b}$ are each independently a $C_{0-10}$alkyl, any of which is optionally substituted with one or more independent halo, cyano, nitro, —$OR^{77}$, —$SO_2NR^{77}R^{87}$ or —$NR^{77}R^{87}$ substituents; or $R^{4a}$ with $R^{5a}$ or $R^{4b}$ with $R^{5b}$ taken together with the respective carbon atom to which they are attached, form a 3-10 membered saturated or unsaturated ring, wherein said ring is optionally substituted with $R^{69}$; or $R^{4a}$ with $R^{5a}$, or $R^{4b}$ with $R^{5b}$ taken together with the respective carbon atom to which they are attached form a 3-10 membered saturated or unsaturated heterocyclic ring, wherein said ring is optionally substituted with $R^{69}$; and
$R^{6a}$ and $R^{6b}$ are each independently halo, —$OR^{78}$, $NR^{78}R^{88}(R^{98})_{n7}$, —$CO_2R^{78}$, —$CONR^{78}R^{88}$, —$NO_2$, —CN, —$S(O)_{n7}R^{78}$, —$SO_2NR^{78}R^{88}$, or $C_{0-10}$alkyl;
n1, n2, n3, n4, n5, n6, and n7 are each independently equal to 0, 1 or 2;
$R^{66}$, $R^{67}$, $R^{68}$, and $R^{69}$ are each independently halo, —$OR^{78}$, —$NR^{78}R^{88}(R^{98})_{n7}$, —$CO_2R^{78}$, —$CONR^{78}R^{88}$, —$NO_2$, —CN, —$S(O)_{n7}R^{78}$, —$SO_2NR^{78}R^{88}$, $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$alkynyl, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl $C_{1-10}$alkyl, cyclo$C_{3-8}$alkenyl$C_{1-10}$alkyl, cyclo $C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl $C_{2-10}$alkynyl, heterocyclyl$C_{0-10}$alkyl, heterocyclyl $C_{2-10}$alkenyl, or heterocyclyl$C_{2-10}$alkynyl, any of which is optionally substituted with one or more independent halo, cyano, nitro, —$OR^{778}$, —$SO_2NR^{778}R^{888}$ or —$NR^{778}R^{888}$ substituents; or aryl-$C_{0-10}$alkyl, aryl-$C_{2-10}$alkenyl, or aryl-$C_{2-10}$alkynyl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, $C_{1-4}$alkoxycarbonyl, —$CONR^{778}R^{888}$, —$SO_2NR^{778}R^{888}$ or —$NR^{778}R^{888}$ substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —$CONR^{778}R^{888}$, —$SO_2NR^{778}R^{888}$ or —$NR^{778}R^{888}$ substituents; or mono($C_{1-6}$alkyl)amino$C_{1-6}$alkyl, di($C_{1-6}$alkyl)amino $C_{1-6}$alkyl, mono(aryl)amino$C_{1-6}$alkyl, di(aryl)amino $C_{1-6}$alkyl, —N($C_{1-6}$alkyl)-$C_{1-6}$alkyl-aryl, any of which is optionally substituted with one or more independent halo, cyano, nitro, —$OR^{778}$, $C_{1-10}$alkyl, $C_{2-10}$alkenyl, $C_{2-10}$alkynyl, halo$C_{1-10}$alkyl, halo$C_{2-10}$alkenyl, halo $C_{2-10}$alkynyl, —COOH, $C_{1-4}$alkoxycarbonyl, —$CONR^{778}R^{888}$, —$SO_2NR^{778}R^{888}$ or —$NR^{778}R^{888}$ substituents; or in the case of —$NR^{78}R^{88}(R^{98})_{n7}$, $R^{78}$ and $R^{88}$ taken together with the nitrogen atom to which they are attached form a 3-10 membered saturated ring, unsaturated ring, heterocyclic saturated ring, or heterocyclic unsaturated ring, wherein said ring is optionally substituted with one or more independent halo, cyano, hydroxy, nitro, $C_{1-10}$alkoxy, —$SO_2NR^{778}R^{888}$ or —$NR^{778}R^{888}$ substituents;
$R^7$, $R^{71}$, $R^{72}$, $R^{73}$, $R^{74}$, $R^{75}$, $R^{775}$, $R^{7775}$, $R^{76}$, $R^{77}$, $R^{78}$, $R^{778}$, $R^8$, $R^{81}$, $R^{82}$, $R^{83}$, $R^{84}$, $R^{85}$, $R^{86}$, $R^{87}$, $R^{88}$, $R^{888}$, $R^9$, $R^{95}$, and $R^{98}$, are each independently $C_{0-10}$alkyl, $C_{2-10}$alkenyl, $C_{2-10}$alkynyl, $C_{1-10}$alkoxy$C_{1-10}$alkyl, $C_{1-10}$alkoxy$C_{2-10}$alkenyl, $C_{1-10}$alkoxy$C_{2-10}$, $C_{1-10}$alkylthio$C_{1-10}$alkyl, $C_{1-10}$alkylthio$C_{2-10}$alkenyl, $C_{1-10}$alkylthio$C_{2-10}$alkynyl, cyclo$C_{3-8}$alkyl, cyclo$C_{3-8}$alkenyl, cyclo$C_{3-8}$alkyl$C_{1-10}$alkyl, cyclo$C_{3-8}$alkenyl$C_{1-10}$alkyl, cyclo$C_{3-8}$alkyl$C_{2-10}$alkenyl, cyclo$C_{3-8}$alkenyl$C_{2-10}$alkenyl, cyclo$C_{3-8}$alkyl$C_{2-10}$alkynyl, cyclo$C_{3-8}$alkenyl $C_{2-10}$alkynyl, heterocyclyl$C_{0-10}$alkyl, heterocyclyl $C_{2-10}$alkenyl, heterocyclyl$C_{2-10}$alkynyl, $C_{1-10}$alkylcarbonyl, $C_2$alkenylcarbonyl, $C_{2-10}$alkynylcarbonyl, $C_{1-10}$alkoxycarbonyl, $C_{1-10}$alkoxycarbonyl$C_{1-10}$alkyl, mono$C_{1-6}$alkylaminocarbonyl, di$C_{1-6}$alkylaminocarbonyl, mono(aryl)aminocarbonyl, di(aryl)aminocarbonyl, or $C_{1-10}$alkyl(aryl)aminocarbonyl, any of which is optionally substituted with one or more independent halo, cyano, hydroxy, nitro, $C_{1-10}$alkoxy, —$SO_2N$($C_{0-4}$alkyl)($C_{0-4}$alkyl) or —N($C_{0-4}$alkyl)($C_{0-4}$alkyl) substituents; aryl-$C_{0-10}$alkyl, aryl-$C_{2-10}$alkenyl, or aryl-$C_{2-10}$alkynyl, any of which is optionally substituted with one or more independent halo, cyano, nitro, —O($C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CON($C_{0-4}$alkyl)($C_{0-10}$alkyl), —SO$_2$N($C_{0-4}$alkyl)($C_{0-4}$alkyl) or —N($C_{0-4}$alkyl)($C_{0-4}$alkyl) substituents; or hetaryl-$C_{0-10}$alkyl, hetaryl-$C_{2-10}$alkenyl, or hetaryl-$C_{2-10}$alkynyl, any of which is optionally substituted with one or more independent halo, cyano, nitro, —O($C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, CON($C_{0-4}$alkyl)($C_{0-4}$alkyl), SO$_2$N($C_{0-4}$alkyl)($C_{0-4}$alkyl) or —N($C_{0-4}$alkyl)($C_{0-4}$alkyl) substituents; or mono($C_{1-6}$alkyl)amino$C_{1-6}$alkyl, di($C_{1-6}$alkyl)amino$C_{1-6}$alkyl, mono(aryl)amino$C_{1-6}$alkyl, di(aryl)amino$C_{1-6}$alkyl, or —N($C_{1-6}$alkyl)$C_{1-6}$alkylaryl, any of which is optionally substituted with one or more independent halo, cyano, nitro, —O($C_{0-4}$alkyl), $C_{1-10}$alkyl, $C_{2-10}$alkenyl, $C_{2-10}$alkynyl, halo$C_{1-10}$alkyl, halo$C_{2-10}$alkenyl, halo$C_{2-10}$alkynyl, —COOH, $C_{1-4}$alkoxycarbonyl, —CON($C_{0-4}$alkyl)($C_{0-4}$alkyl), —SO$_2$N($C_{0-4}$alkyl)($C_{0-4}$alkyl) or —N($C_{0-4}$alkyl)($C_{0-4}$alkyl) substituents.

\* \* \* \* \*

UNITED STATES PATENT AND TRADEMARK OFFICE
CERTIFICATE OF CORRECTION

PATENT NO. : 7,662,844 B2 Page 1 of 1
APPLICATION NO. : 10/889520
DATED : February 16, 2010
INVENTOR(S) : Smith et al.

It is certified that error appears in the above-identified patent and that said Letters Patent is hereby corrected as shown below:

In the Title, item (54) and column 1, line 1, the term "NAPHTHYLENE" should be replaced with -- NAPHTHALENE --;

On the cover page, (*) Notice: Subject to any disclaimer, the term of this patent is extended or adjusted under 35 USC 154(b) by 0 days.

Delete the phrase "by 0 days" and insert -- by 1028 days --;

In the claims, column 125, line 1, the term "–$NR^{72}$, $R^{82}(R^9)_{n5}$," should be replaced with -- –$NR^{72}R^{82}(R^9)_{n5}$ --; and In the claims, column 132, lines 41-46, the paragraph "or $R^2$ and $R^3$ taken together with the carbon atom to which they are attached form a 3-10 membered saturated ring, unsaturated ring, heterocyclic saturated ring, or heterocyclic unsaturated ring, any of which is optionally substituted with one or more independent $C_{1-6}$alkyl, halo, cyano, nitro, -$OR^{71}$, -$SO_2NR^{71}R^{81}$ substituents;" should be deleted.

Signed and Sealed this

Fifteenth Day of June, 2010

David J. Kappos
*Director of the United States Patent and Trademark Office*